(12) United States Patent
Sucheck et al.

(10) Patent No.: US 11,053,236 B2
(45) Date of Patent: Jul. 6, 2021

(54) SUBSTITUTED ISOSELENAZOLONE ANTI-INFECTIVE, ANTI-INFLAMMATORY, ANTI-CANCER, CYTOPROTECTIVE, NEUROPROTECTIVE, AND ANTI-OXIDANT AGENTS

(71) Applicant: The University of Toledo, Toledo, OH (US)

(72) Inventors: Steven Sucheck, Toledo, OH (US); Sandeep Thanna, Toledo, OH (US); Donald Ronning, Toledo, OH (US); Alexander Landgraf, Toledo, OH (US)

(73) Assignee: The University of Toledo, Toledo, OH (US)

( * ) Notice: Subject to any disclaimer, the term of this patent is extended or adjusted under 35 U.S.C. 154(b) by 0 days.

(21) Appl. No.: 16/312,024

(22) PCT Filed: Jun. 21, 2017

(86) PCT No.: PCT/US2017/038467
§ 371 (c)(1),
(2) Date: Dec. 20, 2018

(87) PCT Pub. No.: WO2017/223160
PCT Pub. Date: Dec. 28, 2017

(65) Prior Publication Data
US 2019/0161482 A1 May 30, 2019

Related U.S. Application Data

(60) Provisional application No. 62/352,712, filed on Jun. 21, 2016.

(51) Int. Cl.
| | |
|---|---|
| *C07D 421/04* | (2006.01) |
| *C07D 421/06* | (2006.01) |
| *C07D 293/10* | (2006.01) |
| *A61P 31/06* | (2006.01) |
| *A61P 31/00* | (2006.01) |
| *A61P 27/00* | (2006.01) |
| *A61P 29/00* | (2006.01) |
| *A61P 35/00* | (2006.01) |
| *A61P 27/16* | (2006.01) |

(52) U.S. Cl.
CPC ............ *C07D 421/04* (2013.01); *A61P 27/00* (2018.01); *A61P 27/16* (2018.01); *A61P 29/00* (2018.01); *A61P 31/00* (2018.01); *A61P 31/06* (2018.01); *A61P 35/00* (2018.01); *C07D 293/10* (2013.01); *C07D 421/06* (2013.01)

(58) Field of Classification Search
CPC .............................. C07D 421/04; A61P 27/16
See application file for complete search history.

(56) References Cited

U.S. PATENT DOCUMENTS

| | | | |
|---|---|---|---|
| 8,901,158 B2* | 12/2014 | Churchill | A61K 31/416 514/373 |
| 2003/0220337 A1 | 11/2003 | Ko et al. | |
| 2011/0288130 A1 | 11/2011 | Holmgren et al. | |

FOREIGN PATENT DOCUMENTS

WO 2004047925 A2 6/2004

OTHER PUBLICATIONS

Welter et al (1986): STN International HCAPLUS database, (Columbus, Ohio), Accession No. 1986: 553070.*
Inglot et al (1996): STN International HCAPLUS database, (Columbus, Ohio), Accession No. 1996: 373467.*
Dakova et al (1990): STN International HCAPLUS database, (Columbus, Ohio), Accession No. 1990: 640012.*
Welter et al (1987): STN International HCAPLUS database, (Columbus, Ohio), Accession No. 1987: 84181.*
Li et al (2012): STN International HCAPLUS database, (Columbus, Ohio), Accession No. 2012: 1399572.*
Luo et al (2014): STN International HCAPLUS database, (Columbus, Ohio), Accession No. 2014: 110102.*
Beilhartz, et al., "Comment on A small-molecule antivirulence agent for treating Clostridium difficile infection", Sci. Transl. Med. 8, 370tc2 (2016), pp. 1-3.
Dallacker, et al, "Organische Selenverbindungen, 1. Mitteilung Darstellung von 2-substituierten 1,2-Benzoisoselenazol-3(2H)-onen", Chemiker-Zeitung, 115, Jahrgeng (1991) Nr. 5, pp. 135-139.
Pietka-Ottlik, et al., "New Organoselenium Compounds Active against Pathogenic Bacteria, Fungi and Viruses", Chem. Pharm. Bull. 56(10), (2008), pp. 1423-1427.
PCT International Search Report and Written Opinion, Application No. PCT/US17/38467, dated Oct. 31, 2017.
Rafique, et al., "Synthesis and Biological Evaluation of 2-Picolylamide-Based Diselenides with Non-Bonded Interactions", Molecules 2015, 20, pp. 10095-10109.
Thanna, et al., "Thermal and Photoinduced Copper-Promoted C—Se Bond Formation: Synthesis of 2-Alkyl-1,2-benzisoselenazol-3(2H)-ones and Evaluation against *Mycobacterium tuberculosis*", The Journal of Organic Chemistry, 2017, pp. 1-2.
Wójtowicz et al., "Azaanalogues of ebselen as antimicrobial and antiviral agents: synthesis and properties", Elsevier, IL Farmaco, 2004, vol. 59, pp. 863-868.

* cited by examiner

*Primary Examiner* — Golam M Shameem
(74) *Attorney, Agent, or Firm* — MacMillan, Sobanski & Todd, LLC

(57) ABSTRACT

Compounds, compositions, and methods for the treatment of infections, inflammation, cancers, tinnitus, Meniere's disease, hearing loss, or bipolar disorder, or for providing cytoprotection against *Clostridium difficile* toxins, are disclosed.

2 Claims, 90 Drawing Sheets
(46 of 90 Drawing Sheet(s) Filed in Color)

| MIC under aerobic conditions | Task Summary | | | |
|---|---|---|---|---|
| | Compound | MIC (µM) | $IC_{50}$ (µM) | $IC_{90}$ (µM) |
| | 506a | 88 | 56 | 64 |
| | 506c | 70 | 54 | 68 |
| | 506b | 93 | 70 | 77 |
| | 506d | 86 | 73 | 79 |
| All compounds had activity against *M. tuberculosis* under aerobic conditions | 506e | 70 | 61 | 68 |
| | 506f | 88 | 54 | 63 |
| | 506g | 58 | 52 | 55 |
| | 506h | 67 | 58 | 64 |
| | 506i | 83 | 55 | 63 |
| | 506k | 66 | 60 | 67 |
| | 506j | 95 | 70 | 73 |
| | 506l | 99 | 69 | 92 |
| | 506m | 92 | 63 | 79 |
| | 506n | 98 | 81 | 88 |

| Control Compounds | | | | | |
|---|---|---|---|---|---|
| Control Compound ID | Strain ID | MIC (µM) | $IC_{50}$ (µM) | $IC_{90}$ (µM) | Replicates |
| Rifampicin | H37Rv | 0.0062 | 0.0048 | 0.0062 | n = 2 |
| Rifampicin | H37Rv | 0.0068 | | | |
| Rifampicin | H37Rv | 0.0056 | 0.0035 | 0.0057 | n = 1 |

FIG. 7 – Table 1

| MIC Against Other Disease Relevant Mycobacteria | Task Summary | | |
|---|---|---|---|
| | Compound | MIC (µM) | Species |
| | 506a | 93 | *M. abscessus* |
| | 506c | 87 | *M. abscessus* |
| | 506b | 91 | *M. abscessus* |
| | 506d | 63 | *M. abscessus* |
| | 506e | 88 | *M. abscessus* |
| | 506f | 86 | *M. abscessus* |
| | 506g | 64 | *M. abscessus* |
| | 506h | 106 | *M. abscessus* |
| compounds had activity against other mycobacterial species | 506i | 56 | *M. abscessus* |
| | 506k | 73 | *M. abscessus* |
| | 506l | 90 | *M. abscessus* |
| | 506m | 88 | *M. abscessus* |
| | 506n | 88 | *M. abscessus* |
| | 506a | 200 | *M. avium* |
| | 506c | 100 | *M. avium* |
| | 506b | 100 | *M. avium* |
| | 506d | 200 | *M. avium* |
| | 506e | 200 | *M. avium* |
| | 506f | 100 | *M. avium* |
| | 506g | 100 | *M. avium* |
| | 506h | 200 | *M. avium* |
| | 506i | 200 | *M. avium* |
| | 506k | 100 | *M. avium* |
| | 506l | 100 | *M. avium* |
| | 506m | 100 | *M. avium* |
| | 506n | 100 | *M. avium* |

FIG. 8 – Table 2

Test Compounds

| Compound ID | Species | MIC (µM) | IC$_{50}$ (µM) | IC$_{90}$ (µM) |
|---|---|---|---|---|
| 506a | M. abscessus | 93 | 72 | 76 |
| 506c | M. abscessus | 87 | 58 | 66 |
| 506b | M. abscessus | 91 | 65 | 78 |
| 506d | M. abscessus | 63 | 62 | 75 |
| 506e | M. abscessus | 88 | 59 | 66 |
| 506f | M. abscessus | 86 | 54 | 61 |
| 506g | M. abscessus | 64 | 56 | 61 |
| 506h | M. abscessus | 106 | 98 | 110 |
| 506i | M. abscessus | 56 | 58 | 64 |
| 506k | M. abscessus | 73 | 61 | 67 |
| 506j | M. abscessus | > 200 | > 200 | > 200 |
| 506l | M. abscessus | 90 | 62 | 78 |
| 506m | M. abscessus | 88 | 59 | 68 |
| 506n | M. abscessus | 88 | 58 | 67 |

Control Compounds

| Control Compound ID | Species | MIC (µM) | IC$_{50}$ (µM) | IC$_{90}$ (µM) |
|---|---|---|---|---|
| Rifampicin | M. abscessus | 5.4 | 2.8 | 5.5 |

FIG. 11A – Table 3

Test Compounds

| Compound ID | Species | MIC (µM) |
| --- | --- | --- |
| 506a | *M. avium* | 200 |
| 506c | *M. avium* | 100 |
| 506b | *M. avium* | 100 |
| 506d | *M. avium* | 200 |
| 506e | *M. avium* | 200 |
| 506f | *M. avium* | 100 |
| 506g | *M. avium* | 100 |
| 506h | *M. avium* | 200 |
| 506i | *M. avium* | 200 |
| 506k | *M. avium* | 100 |
| 506j | *M. avium* | > 200 |
| 506l | *M. avium* | 100 |
| 506m | *M. avium* | 100 |
| 506n | *M. avium* | 100 |

Control Compounds

| Control Compound ID | Species | MIC (µM) |
| --- | --- | --- |
| Rifampicin | *M. avium* | 0.078 |

FIG. 11B – Table 4

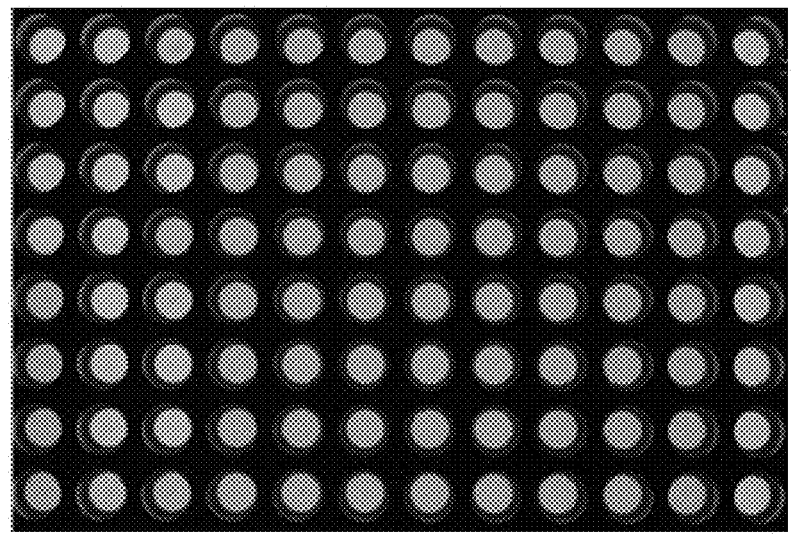
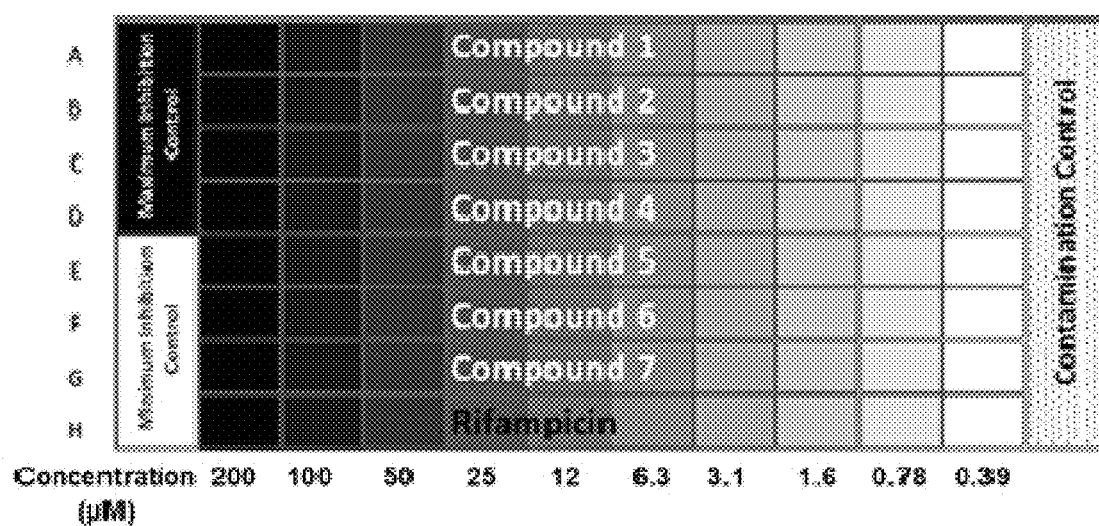
FIG. 13A

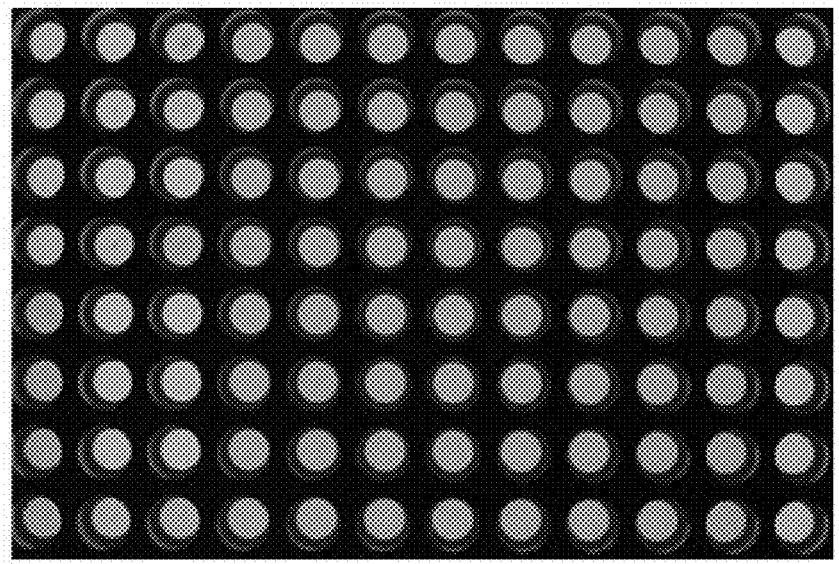
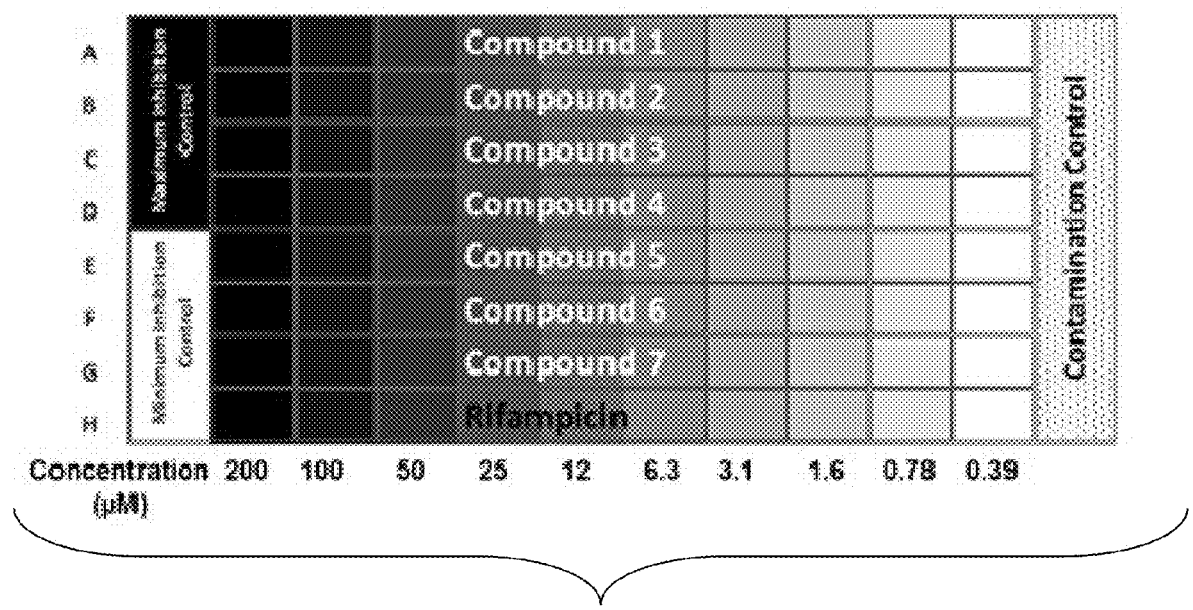
FIG. 13B

| Compound | Structure | Name/Formula/Exact Mass | Example numbers in Example I |
|---|---|---|---|
| 506a | 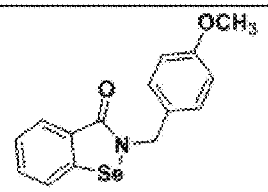 | 2-(4-methoxybenzyl)benzo[d][1,2]selenazol-3(2H)-one<br><br>Chemical Formula: $C_{15}H_{13}NO_2Se$<br><br>Exact Mass: 319.0112 | 1 |
| 506c | 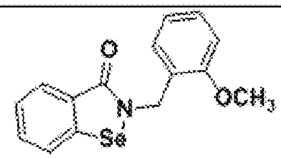 | 2-(2-methoxybenzyl)benzo[d][1,2]selenazol-3(2H)-one<br><br>Chemical Formula: $C_{15}H_{13}NO_2Se$<br><br>Exact Mass: 319.0112 | 3 |
| 506b | 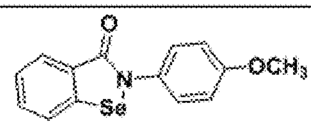 | 2-(4-methoxyphenyl)benzo[d][1,2]selenazol-3(2H)-one<br><br>Chemical Formula: $C_{14}H_{11}NO_2Se$<br><br>Exact Mass: 304.9955 | 2 |
| 506d | 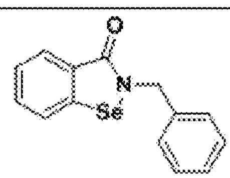 | 2-benzylbenzo[d][1,2]selenazol-3(2H)-one<br><br>Chemical Formula: $C_{14}H_{11}NOSe$<br><br>Exact Mass: 289.0006 | 4 |
| 506e | 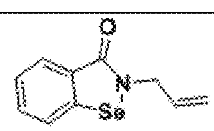 | 2-allylbenzo[d][1,2]selenazol-3(2H)-one<br><br>Chemical Formula: $C_{10}H_9NOSe$<br><br>Exact Mass: 238.9849 | 5 |

FIG. 15A – Table 5, Part I

| | | | |
|---|---|---|---|
| 506f | 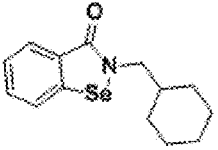 | 2-(cyclohexylmethyl)benzo[d][1,2]selenazol-3(2H)-one<br><br>Chemical Formula: $C_{14}H_{17}NOSe$<br><br>Exact Mass: 295.0475 | 6 |
| 506g | 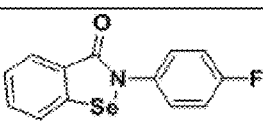 | 2-(4-fluorophenyl)benzo[d][1,2]selenazol-3(2H)-one<br><br>Chemical Formula: $C_{13}H_8FNOSe$<br><br>Exact Mass: 292.9755 | 7 |
| 506h | 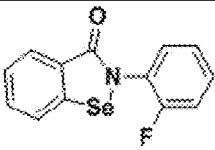 | 2-(2-fluorophenyl)benzo[d][1,2]selenazol-3(2H)-one<br><br>Chemical Formula: $C_{13}H_8FNOSe$<br><br>Exact Mass: 292.9755 | 8 |
| 506i | 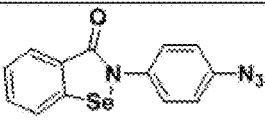 | 2-(4-azidophenyl)benzo[d][1,2]selenazol-3(2H)-one<br><br>Chemical Formula: $C_{13}H_8N_4OSe$<br><br>Exact Mass: 315.9863 | 9 |
| 506k | 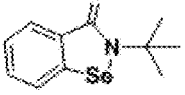 | 2-(tert-butyl)benzo[d][1,2]selenazol-3(2H)-one<br><br>Chemical Formula: $C_{11}H_{13}NOSe$<br><br>Exact Mass: 255.0162 | 10 |
| 506j | 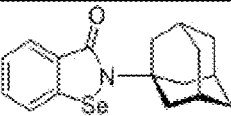 | 2-((3R,5S)-adamantan-1-yl)benzo[d][1,2]selenazol-3(2H)-one<br><br>Chemical Formula: $C_{17}H_{19}NOSe$<br><br>Exact Mass: 333.0632 | 11 |

FIG. 15B – Table 5, Part II

| | | | |
|---|---|---|---|
| 506l | (structure) | 2-cyclopentylbenzo[d][1,2]selenazol-3(2H)-one<br>Chemical Formula: C₁₂H₁₃NOSe<br>Exact Mass: 267.0162 | 12 |
| 506m | (structure) | 2-cyclohexylbenzo[d][1,2]selenazol-3(2H)-one<br>Chemical Formula: C₁₃H₁₅NOSe<br>Exact Mass: 281.0319 | 13 |
| 506n | (structure) | 2-isobutylbenzo[d][1,2]selenazol-3(2H)-one<br>Chemical Formula: C₁₁H₁₃NOSe<br>Exact Mass: 255.02 | 14 |
| 506o | (structure) | 2-(pyridin-2-yl)benzo[d][1,2]selenazol-3(2H)-one<br>Chemical Formula: C₁₂H₈N₂OSe<br>Molecular Weight: 275.17 | 15 |
| 506p | (structure) | 2-(pyridin-3-yl)benzo[d][1,2]selenazol-3(2H)-one<br>Chemical Formula: C₁₂H₈N₂OSe<br>Molecular Weight: 275.17 | 16 |
| 506q | (structure) | 2-(quinolin-2-yl)benzo[d][1,2]selenazol-3(2H)-one<br>Chemical Formula: C₁₆H₁₀N₂OSe<br>Molecular Weight: 325.23 | 17 |
| 506r | (structure) | 2-(furan-2-ylmethyl)benzo[d][1,2]selenazol-3(2H)-one<br>Chemical Formula: C₁₂H₉NO₂Se<br>Molecular Weight: 278.17 | 18 |

FIG. 15C – Table 5, Part III

| 506s | 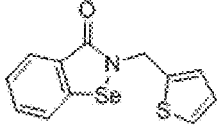 | 2-(thiophen-2-ylmethyl)benzo[d][1,2]selenazol-3(2H)-one<br><br>Chemical Formula: $C_{12}H_9NOSSe$<br><br>Molecular Weight: 294.23 | 19 |
|---|---|---|---|
| 506t | 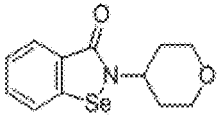 | 2-(tetrahydro-2H-pyran-4-yl)benzo[d][1,2]selenazol-3(2H)-one<br><br>Chemical Formula: $C_{12}H_{13}NO_2Se$<br><br>Molecular Weight: 282.20 | 20 |
FIG. 15D – Table 5, Part IV

| Compound | Structure | Name/Formula/Exact Mass | Example numbers in Example I |
|---|---|---|---|
| 600 | 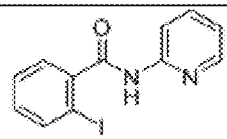 | 2-iodo-N-(pyridin-2-yl)benzamide<br>Chemical Formula: $C_{12}H_9IN_2O$<br>Exact Mass: 323.98<br>Molecular Weight: 324.12 | 21 |
| 602 | 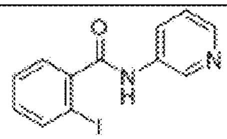 | 2-iodo-N-(pyridin-3-yl)benzamide<br>Chemical Formula: $C_{12}H_9IN_2O$<br>Exact Mass: 323.98<br>Molecular Weight: 324.12 | 22 |
| 604 | 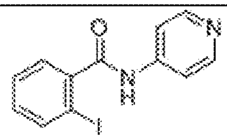 | 2-iodo-N-(pyridin-4-yl)benzamide<br>Chemical Formula: $C_{12}H_9IN_2O$<br>Exact Mass: 323.98<br>Molecular Weight: 324.12 | 23 |
| 606 | 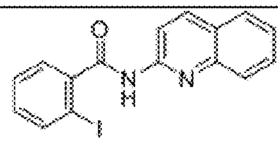 | 2-iodo-N-(quinolin-2-yl)benzamide<br>Chemical Formula: $C_{16}H_{11}IN_2O$<br>Exact Mass: 373.99<br>Molecular Weight: 374.18 | 24 |
| 608 | 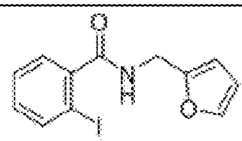 | N-(furan-2-ylmethyl)-2-iodobenzamide<br>Chemical Formula: $C_{12}H_{10}INO_2$<br>Molecular Weight: 327.12 | 25 |
| 610 | 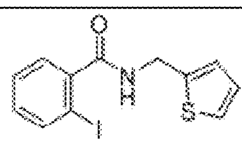 | 2-iodo-N-(thiophen-2-ylmethyl)benzamide<br>Chemical Formula: $C_{12}H_{10}INOS$<br>Molecular Weight: 343.18 | 26 |
| 612 | 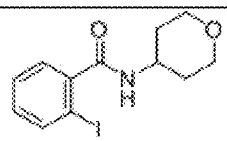 | 2-iodo-N-(tetrahydro-2H-pyran-4-yl)benzamide<br>Chemical Formula: $C_{12}H_{14}INO_2$<br>Molecular Weight: 331.15 | 27 |

FIG. 16 – Table 6

| entry | aryl halide | phen-CuI (equiv) | solvent | temp (°C) | time (h) | yield (%) |
|---|---|---|---|---|---|---|
| 1[b] | 4a | 0.25 | DMF | 110 | 30 | 20 |
| 2 | 4b | 0.2 | DMF | 100 | 12 | 30 |
| 3 | 4b | 0.3 | DMF | 100 | 1 | 34 |
| 4 | 4b | 0.3 | DMF | 100 | 12 | 53 |
| 5 | 4b | 1.0 | DMF | 100 | 1 | 71 |
| 6 | 4a | 1.0 | DMF | 100 | 1.5 | 33 |
| 7 | 4c | 1.0 | DMF | 100 | 0.6 | 75 |
| 8 | 4a | 1.0 | $CH_3CN$ | 80 | 1 | 48 |
| 9 | 4b | 1.0 | $CH_3CN$ | 82 | 12 | 89 |
| 10 | 4c | 1.0 | $CH_3CN$ | 80 | 12 | 91 |
| 11 | 4b | 1.0 | DMSO | 100 | 1.5 | 44 |
| 12[c] | 4b | 1.0 | $CH_3CN$ | 82 | 12 | 41 |

FIG. 26 – Table 7

FIG. 27 – Table 8

FIG. 28 – Table 9

FIG. 36 – Table 10

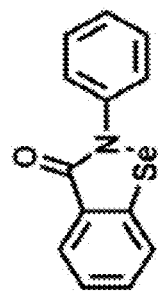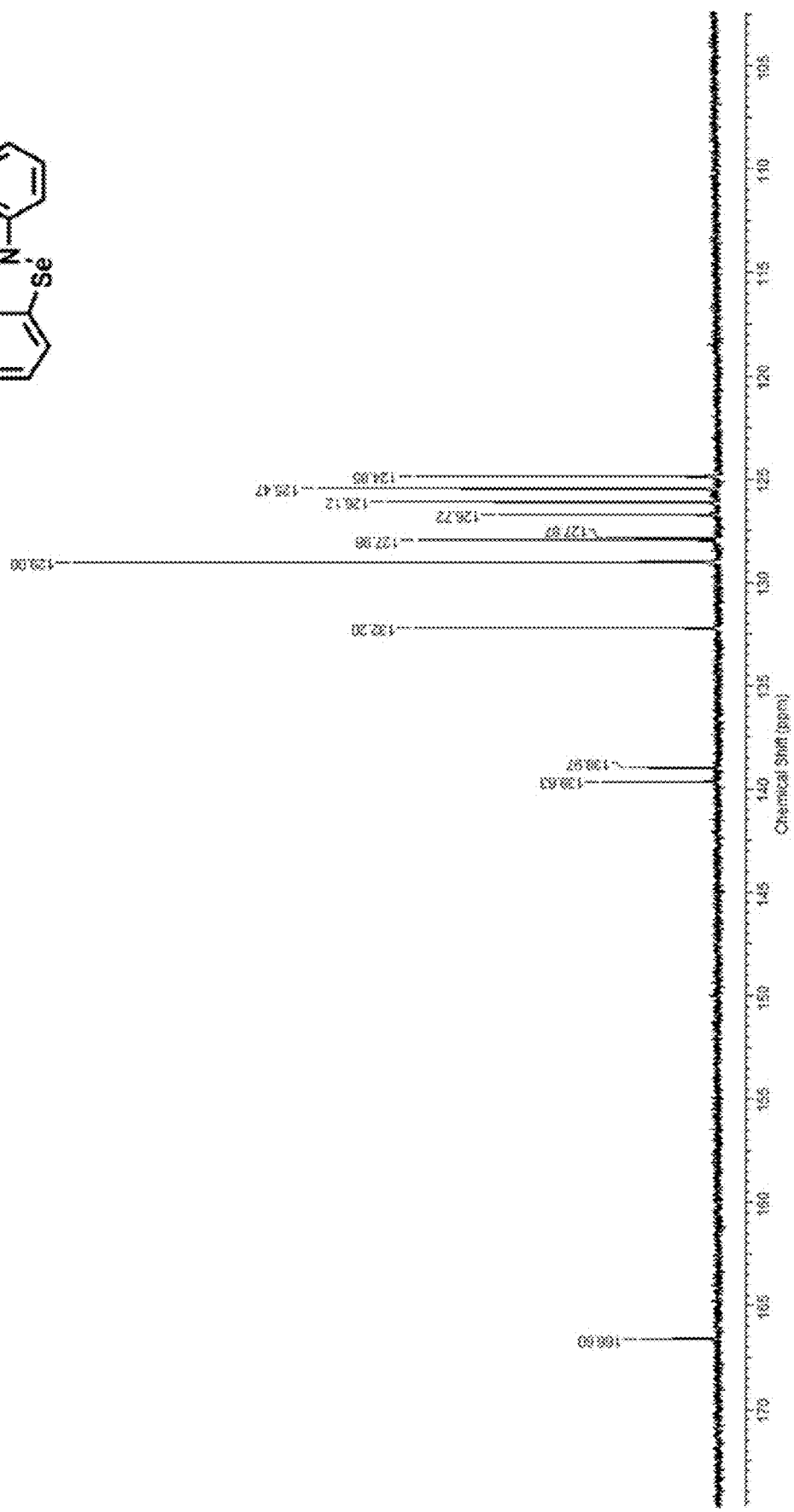
FIG. 39B

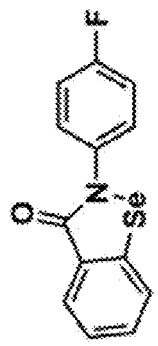
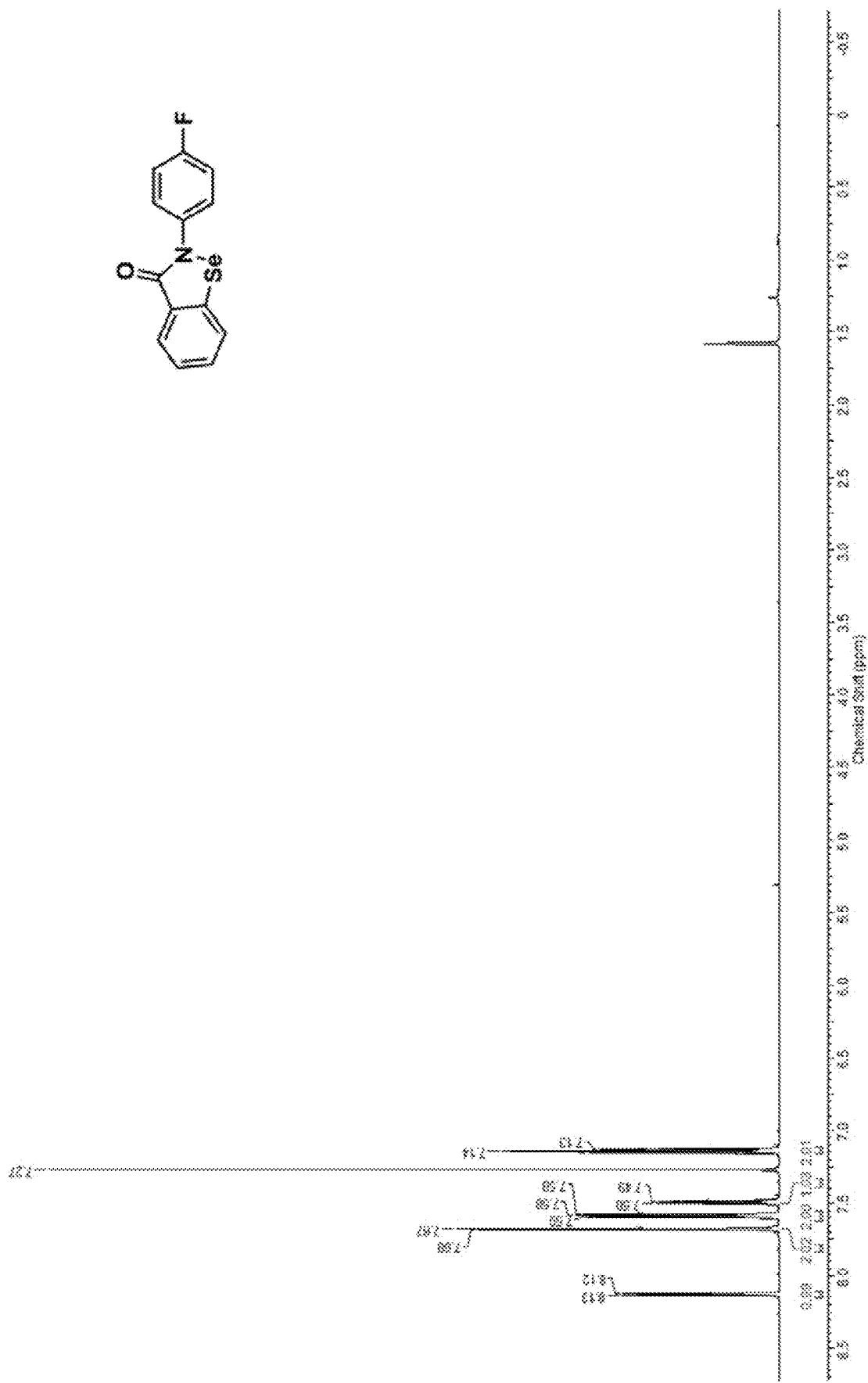
FIG. 46A

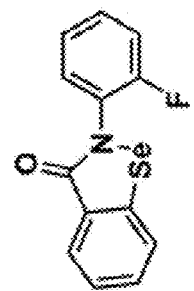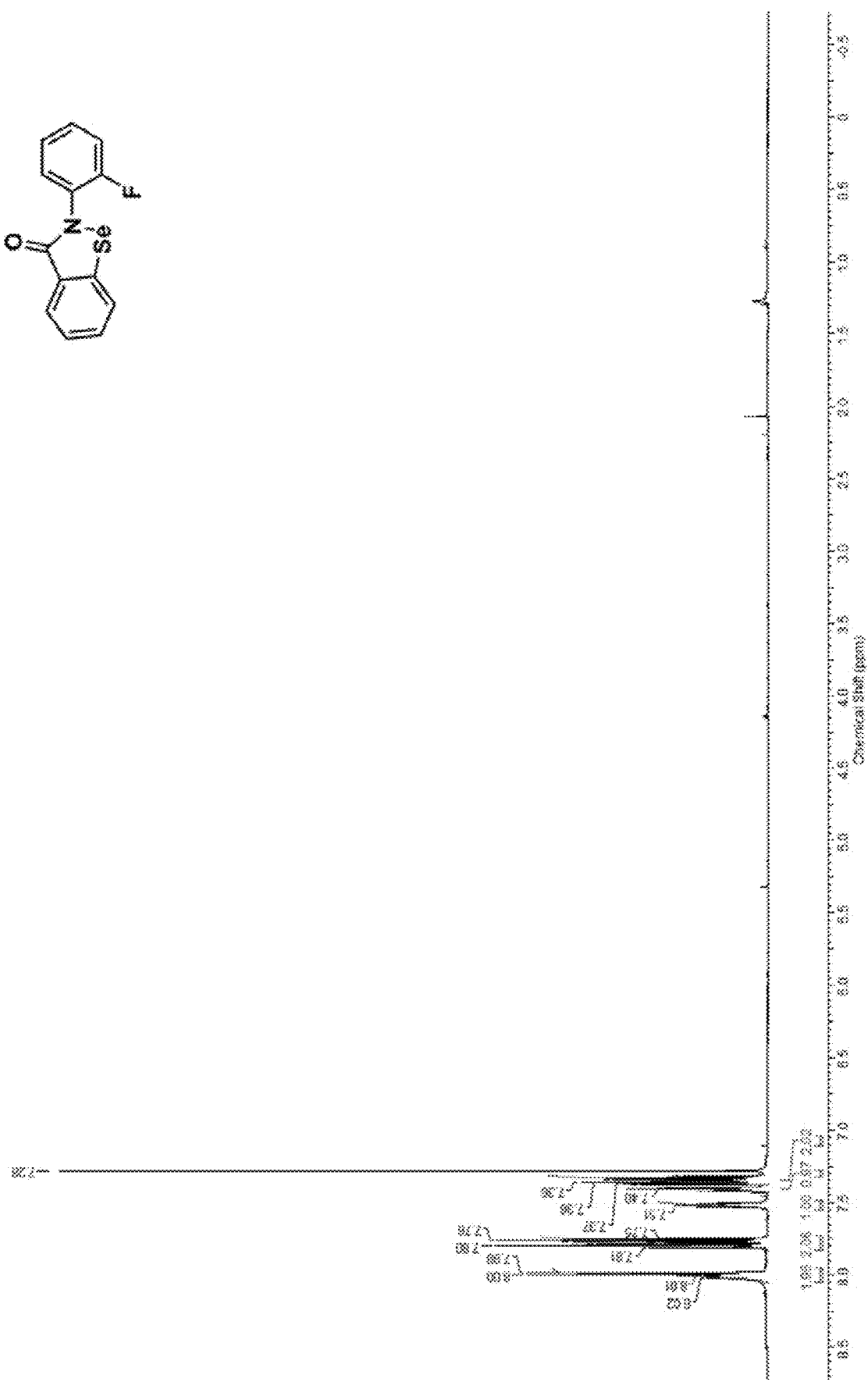
FIG. 47A

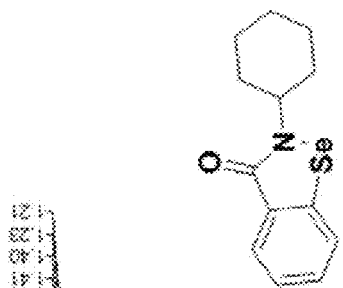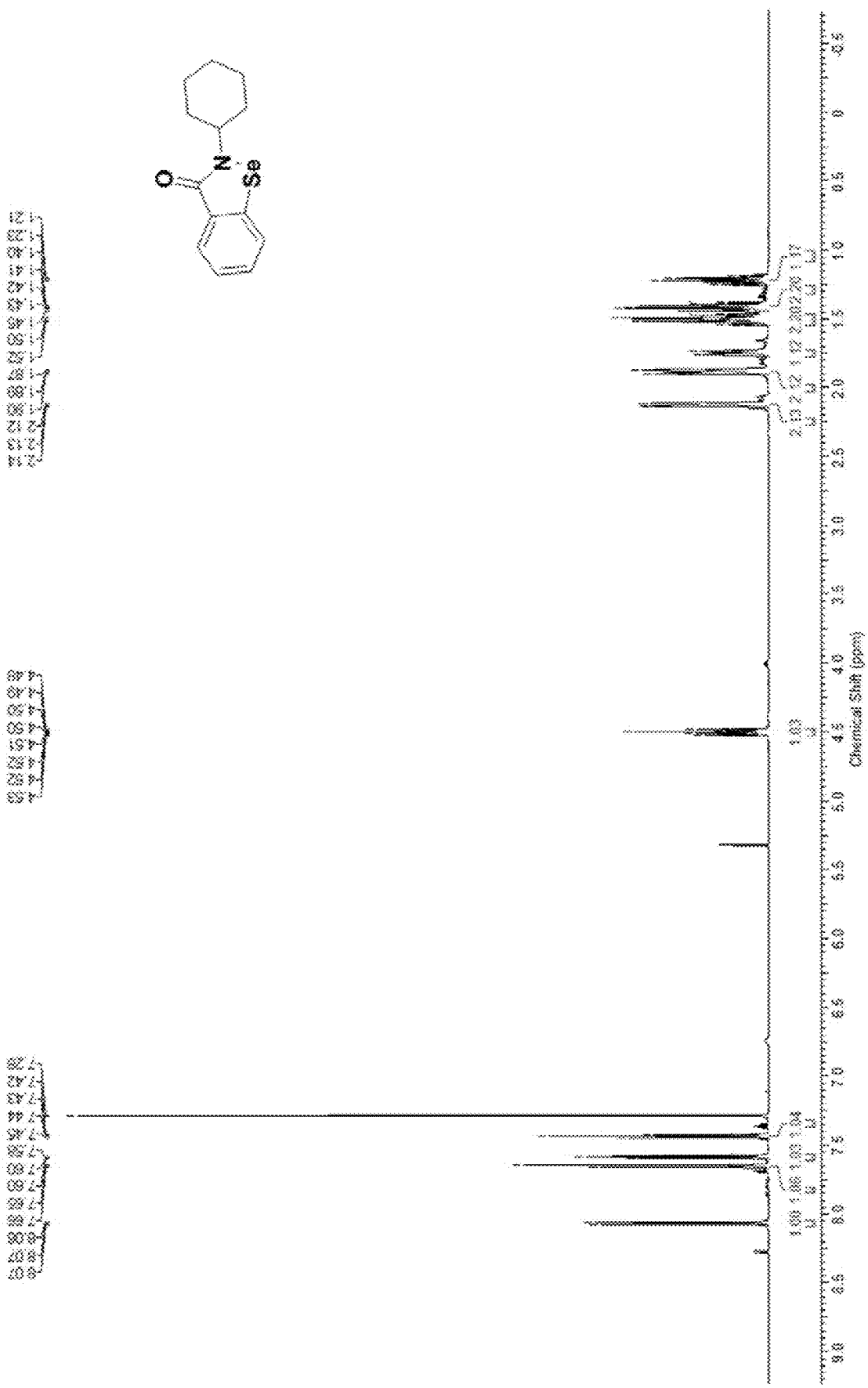
FIG. 52A

SUBSTITUTED ISOSELENAZOLONE ANTI-INFECTIVE, ANTI-INFLAMMATORY, ANTI-CANCER, CYTOPROTECTIVE, NEUROPROTECTIVE, AND ANTI-OXIDANT AGENTS

CROSS-REFERENCE TO RELATED APPLICATIONS

This application is a national stage application filed under 35 U.S.C. § 371 of international application PCT/US2017/038467, filed under the authority of the Patent Cooperation Treaty on Jun. 21, 2017, which claims priority to U.S. Provisional Application No. 62/352,712 filed under 35 U.S.C. § 111(b) on Jun. 21, 2016. The disclosures of all the aforementioned applications are expressly incorporated herein by reference in their entirety.

STATEMENT REGARDING FEDERALLY SPONSORED RESEARCH

This invention was made with government support under Grant Number AI105084 awarded by the National Institutes of Health. The government has certain rights in this invention.

BACKGROUND OF THE INVENTION

Ebselen, or 2-phenyl-1,2-benzisoselenazol-3(2H)-one (also called PZ 51 or DR3305), is a mimic of glutathione peroxidase (GPx) and can also react with peroxynitrite. GPx catalyzes the reduction of hazardous peroxides and their by-products to water or alcohols. It is a selenoenzyme which protects biomembranes and other cellular components from damage caused by reactive oxygen species (ROS). Several diseases, including neurodegenerative diseases such as Alzheimer's and Parkinson's disease, as well as other physiological and inflammatory processes, are linked to the activity of ROS.

Ebselen forms a reversible covalent complex with Ag85C that inhibits enzyme activity. Ebselen is a known anti-infective against gram-positive bacteria, gram-negative bacteria, yeast, and fungi, and also posseses anti-viral activity. Ebselen is also a potent scavenger of hydrogen peroxide as well as hydroperoxides including membrane-bound phospholipid and cholesterylester hydroperoxides. Ebselen is being investigated as a possible treatment for repferusion injury and stroke, hearing loss and tinnitus, and bipolar disorder.

It would be advantageous to discover compounds which have activity similar to ebselen.

SUMMARY OF THE INVENTION

Provided are various isoselenazolone derivatives which are useful as anti-inflammatory, anti-artheroscleroitc, anti-oxidant, cytoprotective, neuroprotective, and anti-cancer agents.

Provided is a compound comprising Formula I:

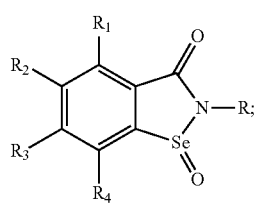

Formula I where R is (a) $C_1$-$C_8$ alkyl optionally substituted with one or more of the following: F, Cl, $N_3$, hydroxy, $C_1$-$C_5$ alkoxy, $C_1$-$C_8$ acyloxy, amino, $C_1$-$C_8$ alkylamino, $C_1$-$C_8$ dialkylamino, O—$CH_2$-Ph, Ph, or vinyl; $C_3$-$C_6$ cycloalkyl, or Ph optionally substituted with one or more of the following: F, Cl, $N_3$, 1,2,3-triazole, hydroxy, $C_1$-$C_8$ alkyl, $C_1$-$C_8$ alkoxy, $C_1$-$C_8$ acyloxy, amino, $C_1$-$C_8$ alkylamino, $C_1$-$C_8$ dialkylamino, O—$CH_2$-Ph, Ph, vinyl, CN, $CO_2H$, $CO_2R_6$, or $CH_2mR_5$, where m is 1 or 2; (b) $C_1$-$C_8$ alkenyl optionally substituted with one or more of the following: F, Cl, $N_3$, 1,2,3-triazole, hydroxy, $C_1$-$C_8$ alkyl, $C_1$-$C_8$ alkoxy, $C_1$-$C_8$ acyloxy, amino, $C_1$-$C_8$ alkylamino, $C_1$-$C_8$ dialkylamino, O—$CH_2$-Ph, Ph, or vinyl; (c) Ph optionally substituted with one or more of the following: F, Cl, $N_3$, 1,2,3-triazole, hydroxy, $C_1$-$C_8$ alkyl, $C_1$-$C_8$ alkoxy, $C_1$-$C_8$ acyloxy, amino, $C_1$-$C_8$ alkylamino, $C_1$-$C_8$ dialkylamino, O—$CH_2$-Ph, Ph, vinyl, CN, $CO_2H$, $CO_2R_6$ or $CH_2mR_5$, where m is 1 or 2; (d) $C_3$-$C_6$ cycloalkyl; or (e) a pyridine group, quinoline group, or 5-8-membered heterocyclyl group linked via n number of carbons or directly to a heteroatom with 1-4 heteroatoms selected from O, N, and S, wherein the pyridine or heterocyclyl group optionally carries up to 5 substituents on an available carbon atom selected from F, Cl, $N_3$, 1,2,3-triazole, hydroxy, $C_1$-$C_8$ alkyl, $C_1$-$C_8$ alkoxy, $C_1$-$C_8$ acyloxy, amino, $C_1$-$C_8$ alkylamino, $C_1$-$C_8$ dialkylamino, O—$CH_2$-Ph, Ph, vinyl, CN, $CO_2H$, $CO_2R_6$, and $CH_2mR_5$ where m is 1 or 2; $R_1$ is independently H, F, Cl, $N_3$, 1,2,3-triazole, hydroxy, $C_1$-$C_8$ alkyl, $C_1$-$C_8$ alkoxy, $C_1$-$C_8$ acyloxy, amino, $C_1$-$C_8$ alkylamino, $C_1$-$C_8$ dialkylamino, O—$CH_2$-Ph, $C_1$-$C_8$ alkoxy Ph, Ph, vinyl, CN, $CO_2H$, $CO_2R_6$, or $CH_2mR_5$, where m is 1 or 2; $R_2$ is independently H, F, Cl, $N_3$, 1,2,3-triazole, hydroxy, $C_1$-$C_8$ alkyl, $C_1$-$C_8$ alkoxy, $C_1$-$C_8$ acyloxy, amino, $C_1$-$C_8$ alkylamino, $C_1$-$C_8$ dialkylamino, O—$CH_2$-Ph, Ph, vinyl, CN, $CO_2H$, $CO_2R_6$, or $CH_2mR_5$, where m is 1 or 2; $R_3$ is independently H, F, Cl, $N_3$, 1,2,3-triazole, hydroxy, $C_1$-$C_8$ alkyl, $C_1$-$C_8$ alkoxy, $C_1$-$C_8$ acyloxy, amino, $C_1$-$C_8$ alkylamino, $C_1$-$C_8$ dialkylamino, O—$CH_2$-Ph, Ph, vinyl, CN, $CO_2H$, $CO_2R_6$ or $CH_2mR_5$, where m is 1 or 2; $R_4$ is independently H, F, Cl, $N_3$, 1,2,3-triazole, hydroxy, $C_1$-$C_8$ alkyl, $C_1$-$C_8$ alkoxy, $C_1$-$C_8$ acyloxy, amino, $C_1$-$C_8$ alkylamino, $C_1$-$C_8$ dialkylamino, O—$CH_2$-Ph, Ph, vinyl, CN, $CO_2H$, $CO_2R_6$, or $CH_2mR_5$, where m is 1 or 2; $R_5$ is independently Ph, or $C_1$-$C_8$ alkyl optionally substituted with one or more of the following: F, Cl, hydroxy, $C_1$-$C_8$ alkoxy, $C_1$-$C_8$ acyloxy, amino, $C_1$-$C_8$ alkylamino, $C_1$-$C_8$ dialkylamino, O—$CH_2$-Ph, Ph, or vinyl; $R_6$ is independently Ph, or $C_1$-$C_8$ alkyl optionally substituted with one or more of the following: hydroxy, $C_1$-$C_8$ alkoxy, $C_1$-$C_8$ acyloxy, amino, $C_1$-$C_8$ alkylamino, $C_1$-$C_8$ dialkylamino, Ph, or vinyl; and X is O or a lone pair of electrons; provided, however, that the compound is not ebselen (that is, when each of $R_1$, $R_2$, $R_3$, and $R_4$ is H, and X is a lone pair of electrons, then R is not Ph). Also provided a/re salts, stereoisomers, hydrates, solvates, racemates, prodrugs, and polymorphs thereof.

In some embodiments of Formula I, R is a substituted or unsubstituted $C_1$-$C_8$ alkyl, $C_3$-$C_6$ cycloalkyl, Ph, $C_1$-$C_8$ alkenyl, $C_3$-$C_6$ cycloalkyl, or heterocyclic group; each of $R_1$, $R_2$, $R_3$, and $R_4$ is independently H, F, Cl, $N_3$, 1,2,3-triazole, $C_1$-$C_8$ alkyl, $C_1$-$C_8$ alkoxy, $C_1$-$C_8$ acyloxy, amino, $C_1$-$C_8$ alkylamino, $C_1$-$C_8$ dialkylamino, O—$CH_2$-Ph, $C_1$-$C_8$ alkoxy Ph, Ph, vinyl, CN, $CO_2H$, $CO_2R_6$, or $CH_2mR_5$, wherein m is 1 or 2; and X is either a lone pair of electrons or O. In particular embodiments, the heterocyclic group comprises a pyridine group, quinoline group, or 5-8-membered heterocyclic group linked via n number of carbons or directly to a heteroatom with 1-4 heteroatoms selected from O, N, and S, wherein the pyridine or heterocyclic group optionally carries up to 5 substituents on an available carbon atom selected from F, Cl, $N_3$, 1,2,3-triazole, hydroxy, $C_1$-$C_8$ alkyl, $C_1$-$C_8$ alkoxy, $C_1$-$C_8$ acyloxy, amino, $C_1$-$C_8$ alkylamino, $C_1$-$C_8$ dialkylamino, O—$CH_2$-Ph, Ph, vinyl, CN, $CO_2H$, $CO_2R_6$, and $CH_2mR_5$ where m is 1 or 2.

In certain embodiments, each of $R_1$, $R_2$, $R_3$, and $R_4$ is H. In certain embodiments, X is a lone pair of electrons. In certain embodiments, X is a lone pair of electrons, and each of $R_1$, $R_2$, $R_3$, and $R_4$ is H.

In certain embodiments, one of R, $R_1$, $R_2$, $R_3$, $R_4$, $R_5$, or $R_6$ comprises a 1,2,3-triazole group or a 1,2,3-triazole group substituted with one or more of the following: $C_1$-$C_8$ alkyl, $C_1$-$C_8$ alkoxy, $C_1$-$C_8$ acyloxy, amino, $C_1$-$C_8$ alkylamino, $C_1$-$C_8$ dialkylamino, O—$CH_2$-Ph, Ph, vinyl, CN, $CO_2H$, $CO_2R_6$, $CH_2mR_5$, where m is 1 or 2, or a linker group (L) linked to a biotin group. In particular embodiments, the linker group is selected from the group consisting of: substituted or unsubstituted $C_1$-$C_{20}$ alkyl; substituted or unsubstituted $C_1$-$C_{20}$ alkenyl; substituted or unsubstituted Ph; cycloalkyl; or a polyethylene glycol moiety. In particular embodiments, the polyethylene glycol moiety comprises Formula IIg:

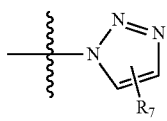

Formula IIg where n ranges from 0 to 100,000.

In certain embodiments, one of R, $R_1$, $R_2$, $R_3$, $R_4$, $R_5$, or $R_6$ comprises a substituent selected from the group consisting of Formulas IIa-IIf:

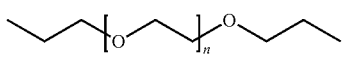

Formula IIa

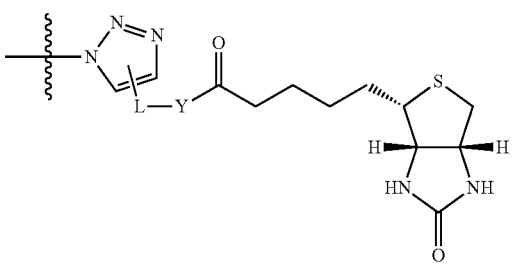

Formula IIb

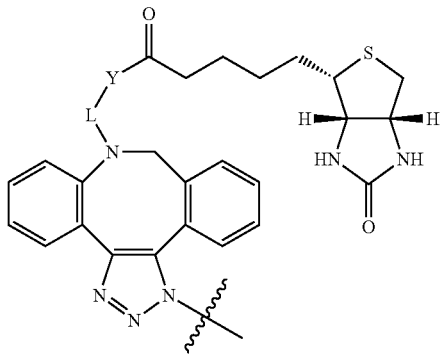

Formula IIc

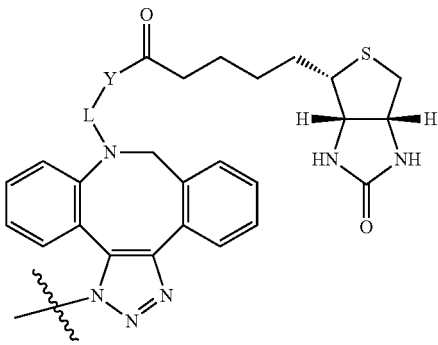

Formula IId

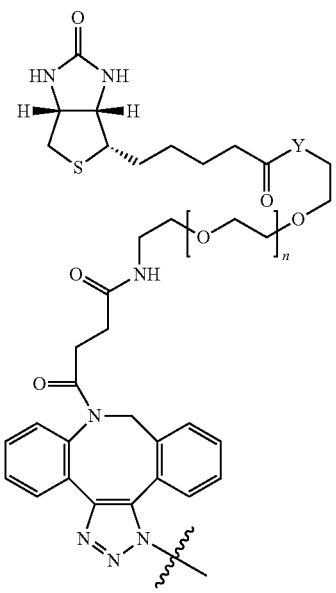

Formula IIe

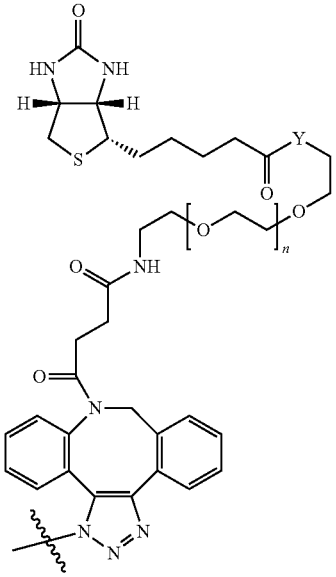

Formula IIf where n=0-100,000; Y is NH or O; $R_7$ is: (a) $C_1$-$C_8$ alkyl optionally substituted with one or more of the following: F, Cl, hydroxy, $C_1$-$C_8$ alkoxy, $C_1$-$C_8$ acyloxy, amino, $C_1$-$C_8$ alkylamino, $C_1$-$C_8$ dialkylamino, O—$CH_2$-Ph, Ph, or vinyl; or $C_3$-$C_6$ cycloalkyl or Ph optionally substituted with one or more of the following: F, Cl, hydroxy, $C_1$-$C_8$ alkyl, $C_1$-$C_8$ alkoxy, $C_1$-$C_8$ acyloxy, amino, $C_1$-$C_8$ alkylamino, $C_1$-$C_8$ dialkylamino, O—$CH_2$-Ph, Ph, vinyl, CN, $CO_2H$, $CO_2R_6$; or $CH_2mR_5$, where m is 1 or 2; (b) $C_1$-$C_8$ alkenyl optionally substituted with one or more of the following: F, Cl, hydroxy, $C_1$-$C_8$ alkyl, $C_1$-$C_8$ alkoxy, $C_1$-$C_8$ acyloxy, amino, $C_1$-$C_8$ alkylamino, $C_1$-$C_8$ dialkylamino, O—$CH_2$-Ph, Ph, or vinyl; (c) Ph optionally substituted with one or more of the following: F, Cl, hydroxy, $C_1$-$C_8$ alkyl, $C_1$-$C_8$ alkoxy, $C_1$-$C_8$ acyloxy, amino, $C_1$-$C_8$ alkylamino, $C_1$-$C_8$ dialkylamino, O—$CH_2$-Ph, Ph, vinyl, CN, $CO_2H$, $CO_2R_6$, or $CH_2mR_5$, where m is 1 or 2; (d) $C_3$-$C_6$ cycloalkyl; and L is a linker group comprising one of: (a) substituted or unsubstituted $C_1$-$C_{20}$ alkyl; (b) substituted or unsubstituted $C_1$-$C_{20}$ alkenyl; (c) substituted or unsubstituted Ph; (d) cycloalkyl; or (e) a polyethylene glycol moiety. In particular embodiments, the polyethylene glycol moiety comprises Formula IIg:

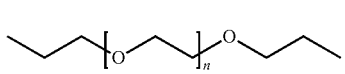

Formula IIg where n ranges from 0 to 100,000.

In certain embodiments, R is (b) $C_1$-$C_8$ alkenyl optionally substituted with one or more of the following: F, Cl, $N_3$, 1,2,3-triazole, hydroxy, $C_1$-$C_8$ alkyl, $C_1$-$C_8$ alkoxy, $C_1$-$C_8$ acyloxy, amino, $C_1$-$C_8$ alkylamino, $C_1$-$C_8$ dialkylamino, O—$CH_2$-Ph, Ph, or vinyl; (c) Ph optionally substituted with one or more of the following: F, Cl, $N_3$, 1,2,3-triazole, hydroxy, $C_1$-$C_8$ alkyl, $C_1$-$C_8$ alkoxy, $C_1$-$C_8$ acyloxy, amino, $C_1$-$C_8$ alkylamino, $C_1$-$C_8$ dialkylamino, O—$CH_2$-Ph, Ph, vinyl, CN, $CO_2H$, $CO_2R_6$ or $CH_2mR_5$, where m is 1 or 2; or (d) $C_3$-$C_6$ cycloalkyl. In particular embodiments, R is Ph substituted with F or $N_3$. In particular embodiments, R is $C_3$-$C_6$ cycloalkyl. In particular embodiments, R is $C_1$-$C_8$ alkenyl. In particular embodiments, X is a lone pair of electrons, and each of $R_1$, $R_2$, $R_3$, and $R_4$ is H.

In certain embodiments, the compound comprises Formula III:

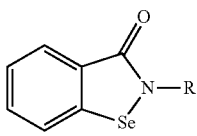

Formula III where R is as defined above in Formula I. In particular embodiments, R comprises a pyridine, a quinoline, or a furan group. In particular embodiments, R is a substituted or unsubstituted Ph or 5-8-membered heterocyclic group. In particular embodiments, R is selected from the following groups:

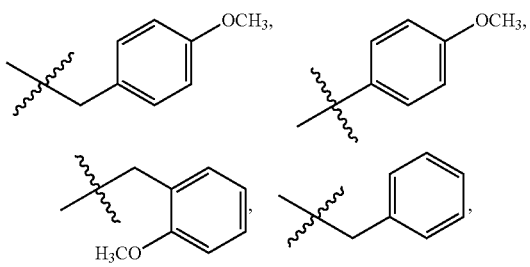

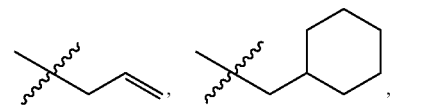

-continued

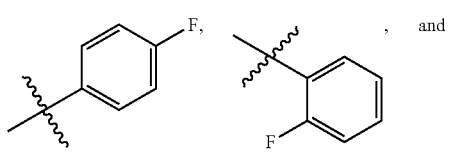

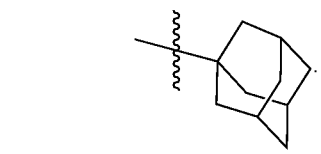

In certain embodiments, the compound comprises compound 506a:

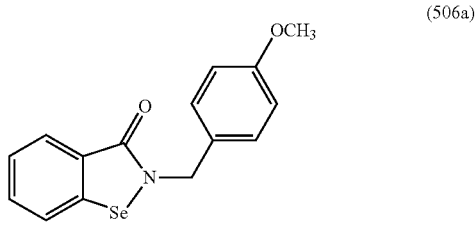 [SMILES: COc1ccc(Cn2[se]c3ccccc3c2=O)cc1]

(506a)

In certain embodiments, the compound comprises compound 506b:

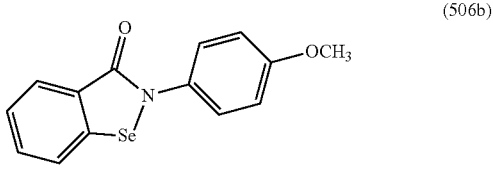 [SMILES: COc1ccc(-n2[se]c3ccccc3c2=O)cc1]

(506b)

In certain embodiments, the compound comprises compound 506c:

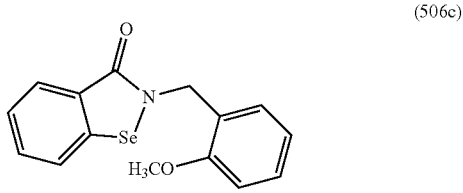 [SMILES: COc1ccccc1Cn1[se]c2ccccc2c1=O]

(506c)

In certain embodiments, the compound comprises compound 506d:

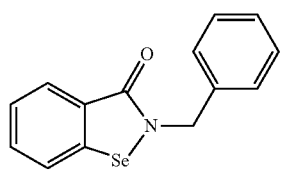
(506d)

In certain embodiments, the compound comprises compound 506e:

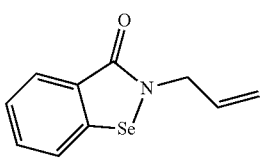
(506e)

In certain embodiments, the compound comprises compound 506f:

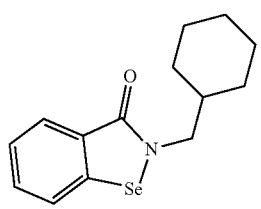
(506f)

In certain embodiments, the compound comprises compound 506g:

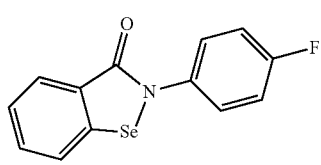
(506g)

In certain embodiments, the compound comprises compound 506h:

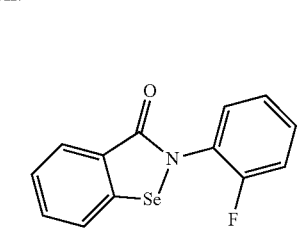
(506h)

In certain embodiments, the compound comprises compound 506i:

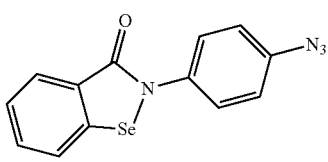
(506i)

In certain embodiments, the compound comprises compound 506j:

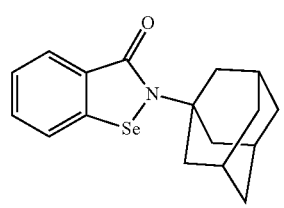
(506j)

In certain embodiments, the compound comprises compound 506k:

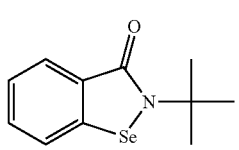
(506k)

In certain embodiments, the compound comprises compound 506l:

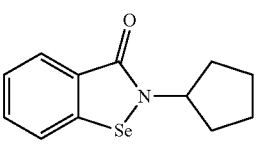
(506l)

In certain embodiments, the compound comprises compound 506m:

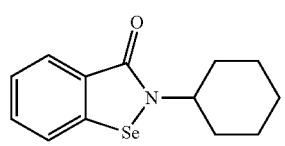
(506m)

In certain embodiments, the compound comprises compound 506n:

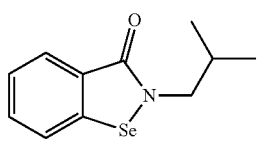

(506n)

In certain embodiments, the compound comprises compound 506o:

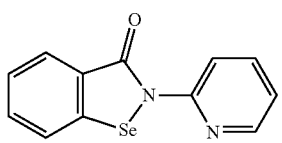

(506o)

In certain embodiments, the compound comprises compound 506p:

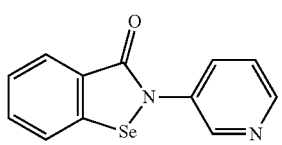

(506p)

In certain embodiments, the compound comprises compound 506q:

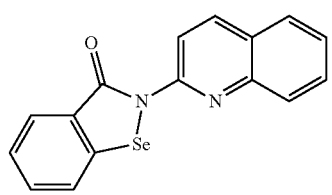

(506q)

In certain embodiments, the compound comprises compound 506r:

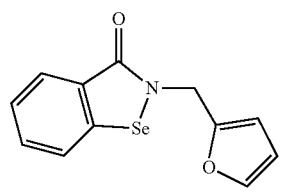

(506r)

In certain embodiments, the compound comprises compound 506s:

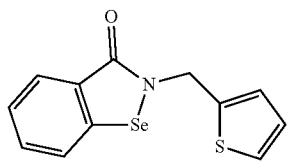

(506s)

In certain embodiments, the compound comprises compound 506t:

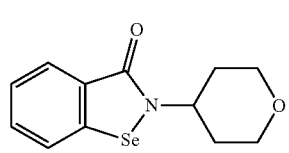

(506t)

In certain embodiments, the compound comprises compound 506u:

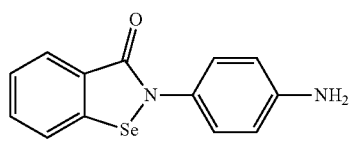

(506u)

In certain embodiments, the compound includes an azide group. In certain embodiments, the compound includes an azide group linked to a ligand. In particular embodiments, the ligand comprises biotin or a fluorophore.

In certain embodiments, the compound is selected from the group consisting of: 2-(4-methoxybenzyl)benzo[d][1,2]selenazol-3(2H)-one; 2-(4-methoxyphenyl)benzo[d][1,2]selenazol-3(2H)-one; 2-(2-methoxybenzyl)benzo[d][1,2]selenazol-3(2H)-one; 2-benzylbenzo[d][1,2]selenazol-3(2H)-one; 2-allylbenzo[d][1,2]selenazol-3(2H)-one; 2-(cyclohexylmethyl)benzo[d][1,2]selenazol-3(2H)-one; 2-(4-fluorophenyl)benzo[d][1,2]selenazol-3(2H)-one; 2-(2-fluorophenyl)benzo[d][1,2]selenazol-3(2H)-one; and 2-(4-azidophenyl)benzo[d][1,2]selenazol-3(2H)-one.

Further provided is a pharmaceutical composition comprising an effective amount of a compound of Formula I, and a pharmaceutically acceptable carrier, diluent, or adjuvant. In certain embodiments, the pharmaceutical composition further includes an additional active ingredient. In particular embodiments, the additional active ingredient is a glutathione peroxidase (GPx) mimic.

Further provided is a method of making a compound of Formula I, the method comprising reacting an acid chloride with an amine to produce an ortho-haloamide, and reacting the ortho-haloamide with a nitrogenous ligand and a selenium source to produce a selenylamide. In certain embodiments, the selenium source comprises KSeCN or NaSeCN. In certain embodiments, the selenylamide contains an azide, and the method further includes reacting the azide-containing selenylamide with an alkyne and a catalyst to produce a 1,4-substituted or 1,5-substituted 1,2,3-triazole. In certain embodiments, the selenylamide contains an azide, and the method further includes reacting the azide-containing selenylamide with a strained alkyne to produce a 4,5-disubstituted 1,2,3-triazole. In particular embodiments, the strained alkyne comprises DBCO-PEG4-biotin.

Further provided is a method of treating, preventing, or ameliorating an infection, the method comprising administering an effective amount of a compound of Formula I to a subject in need thereof and treating, preventing, or ameliorating an infection in the subject. In certain embodiments, the infection is a bacterial infection. In certain embodiments, the infection is a fungal infection. In certain embodiments, the infection is a viral infection. In certain embodiments, the infection is caused by *Staphylococcus aureus*, methicillin-resistant *Staphylococcus aureus*, vancomycin-resistant *Staphylococcus aureus*, *Staphylococcus simulans*, *Helicobacter pylori*, *Haemophilus influenza*, *Escherichia coli*, *Pseudomonas aeruginosa*, *Klebsiella pneumonia*, *Mycobacterium tuberculosis*, *Clostridium difficile*, *Saccharomyces cerevisiae*, *Candida albicans*, *Aspergillus niger*, herpes simplex virus type-I (HSV-1), encephalomyocarditis virus, or vesicular stomatitis virus. In certain embodiments, the infection is caused by a *Mycobacterium* species.

Further provided is a method of treating tuberculosis, the method comprising administering an effective amount of a compound of Formula I to a subject in need thereof and treating tuberculosis.

Further provided is a method of treating a cancer, the method comprising administering an effective amount of a compound of Formula I to a subject in need thereof and treating a cancer. In certain embodiments, the cancer is lung cancer, or head and neck cancer.

Further provided is a method of reducing inflammation, the method comprising administering an effective amount of a compound of Formula I to a subject in need thereof and reducing inflammation in the subject.

Further provided is a method of treating reperfusion injury, Meniere's disease, hearing loss, ototoxicity, neuropathy, stroke, tinnitus, hearing loss, or bipolar disorder, the method comprising administering an effective amount of a compound Formula I to a subject in need thereof and treating reperfusion injury, Meniere's disease, ototoxicity, neuropathy, stroke, tinnitus, hearing loss, or bipolar disorder.

Further provided is a method of making a compound, the method comprising thermally inducing or photoinducing a copper-mediated cross-coupling between KSeCN and a N-substituted ortho-halobenzamide to form a 2-alkyl-1,2-benzisoselenazol-3(2H)-one containing a C—Se—N bond. In certain embodiments, the 2-alkyl-1,2-benzisoselenazol-3 (2H)-one containing a C—Se—N bond is ebselen or an ebselen derivative.

Further provided is a method of providing cytoprotection against a *Clostridium difficile* toxin, the method comprising administering to a cell an effective amount of a compound of Formula I to provide cytoprotection to the cell against *Clostridium difficile* toxin. In certain embodiments, the *Clostridium difficile* toxin comprises TcdB or TcdA. In certain embodiments, the compound comprises compound 506o.

Further provided is a kit comprising a first container housing either (i) an ortho-haloamide, or (ii) an acid chloride and an amine; and a second container housing a selenium source. In certain embodiment, the kit further includes a ligand.

BRIEF DESCRIPTION OF THE DRAWINGS

The patent or application file may contain one or more drawings executed in color and/or one or more photographs. Copies of this patent or patent application publication with color drawing(s) and/or photograph(s) will be provided by the U.S. Patent and Trademark Office upon request and payment of the necessary fees.

FIG. 7: Table 1, displaying the MICs under aerobic conditions for compounds 506a-506n.

FIG. 8: Table 2, displaying MICs against other disease relevant mycobacteria for compounds 506a-506n.

FIG. 10A shows the dose-response curve for compound 506a. FIG. 10N shows the dose-response curve for compound 506n.

FIG. 11A: Table 3, summarizing the activity of compounds 506a-506n, and the control rifampicin, against *M. abscessus*.

FIG. 11B: Table 4, summarizing activity of compounds 506a-506n, and the control rifampicin, against *M. avium*.

FIG. 12A shows the dose-response curve for compound 506a.

FIG. 12N shows the dose-response curve for compound 506n.

FIGS. 13A-13B: Raw plate images for activity of compounds 506a-506g (FIG. 13A) and compounds 506h-506n (FIG. 13B) against *Mycobacterium avium*.

FIGS. 15A-15D: Table 5, depicted in Parts I-IV, displaying example compounds by compound number, structure, chemical name, and example number within Example I herein.

FIG. 16: Table 6, showing non-limiting example benzamides.

FIG. 36: Table 10, showing activity of 2-alkyl-1,2benzisoselenazol-3(2H)-ones against Mtb H$_{37}$Rv and Mtb Ag85C.

FIGS. 39A-39B: $^1$H (600 MHz, CDCl$_3$, FIG. 39A) and $^{13}$C NMR (600 MHz, MeOD, FIG. 39B) spectra of 2-phenylbenzo[d][1,2]selenazol-3(2H)-one (201a).

FIGS. 46A-46B: $^1$H (FIG. 46A) and $^{13}$C NMR (FIG. 46B) spectra of 2-(4-fluorophenyl)benzo[d][1,2]selenazol-3(2H)-one (506g).

FIGS. 47A-47B: $^1$H (FIG. 47A) and $^{13}$C NMR (FIG. 47B) spectra of 2-(2-fluorophenyl)benzo[d][1,2]selenazol-3(2H)-one (506h).

FIGS. 52A-52B: $^1$H (FIG. 52A) and $^{13}$C NMR (FIG. 52B) spectra of 2-cyclohexylbenzo[d][1,2]selenazol-3(2H)-one (506m).

DETAILED DESCRIPTION

Figure 1:
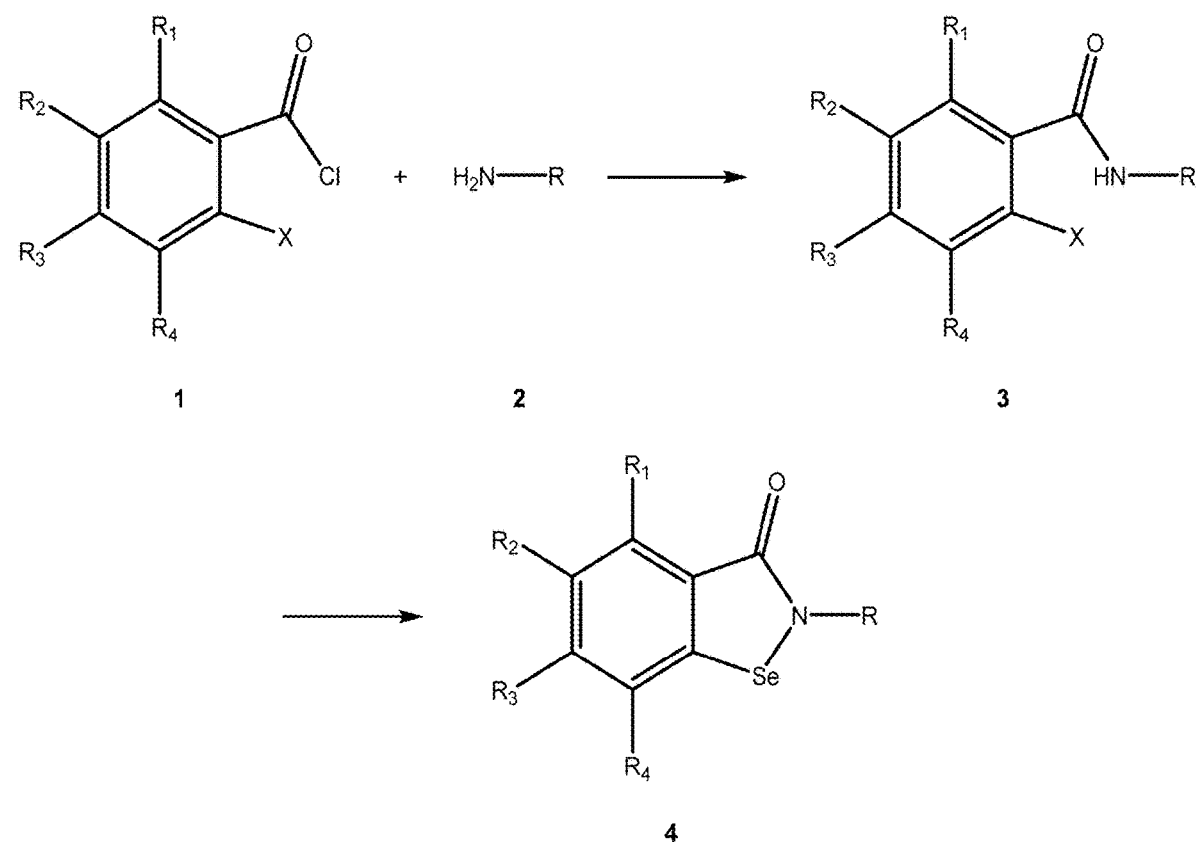
FIG. 1: Non-limiting example scheme showing the production of isoselenazolone derivatives 4.

Throughout this disclosure, various publications, patents, and published patent specifications are referenced by an identifying citation. The disclosures of these publications, patents, and published patent specifications are hereby incorporated by reference into the present disclosure in their entirety to more fully describe the state of the art to which this invention pertains.

For convenience, various terms and concepts are defined prior to further description of the present disclosure.

It will be appreciated that any of the compounds described herein may be substituted with any number of substituents or functional moieties. In general, the term "substituted" whether preceded by the term "optionally" or not, and substituents contained in formulas, refer to the replacement of hydrogen atoms in a given structure with a specified substituent. When more than one position in any given structure may be substituted with more than one substituent selected from a specified group, the substituent may be either the same or different at every position.

It will also be appreciated by one of ordinary skill in the art that asymmetric centers may exist in any of the compounds disclosed herein. Thus, the compounds and pharmaceutical compositions thereof may be in the form of an individual enantiomer, diastereomer, or geometric isomer, or may be in the form of a mixture of stereoisomers. In certain embodiments, the compounds are enantiopure compounds. In certain other embodiments, mixtures of stereoisomers or diastereomers are provided. Additionally, the compounds encompass both (Z) and (E) double bond isomers (or cis and trans isomers) unless otherwise specifically designated. Thus, compounds generally depicted in structures herein encompass those structures in which double bonds are (Z) or (E).

The term "solvate" refers to a pharmaceutically acceptable solid form of a specified compound containing solvent molecules as part of the crystal structure. A solvate typically retains at least some of the biological effectiveness of such compound. Solvates can have different solubilities, hygroscopicities, stabilities, and other properties. Examples of solvates include, but are not limited to, compounds in combination with water, isopropanol, ethanol, methanol, DMSO, ethyl acetate, acetic acid, or ethanolamine. Solvates are sometimes termed "pseudopolymorphs."

The term "hydrate" refers to a solvate with water.

The term "racemate" refers to a mixture that contains an equal amount of enantiomers.

The term "polymorph" means a crystalline form of a substance that is distinct from another crystalline form of the substance but that shares the same chemical formula.

The term "prodrug" refers to a precursor or derivative of a particular compound which, when consumed, generates the pharmacologically active compound by action of natural processes or biological conditions. For example, a prodrug can be cleaved, hydrolyzed, or oxidized by enzymes in vivo to produce the pharmacologically active compound.

The carbon content of various hydrocarbon containing moieties is indicated by a prefix designating the minimum and maximum number of carbon atoms in the moiety, i.e., the prefix $C_i$—$C_j$ defines the number of carbon atoms present from the integer "i" to the integer "j" inclusive. Thus, $C_1$-$C_3$ alkyl refers to alkyl of 1-3 carbon atoms, inclusive, or methyl, ethyl, propyl, and isopropyl; $C_1$-$C_8$ alkyl is methyl, ethyl, propyl, butyl, pentyl, hexyl, heptyl, octyl, and isomeric forms thereof.

The term "alkyl" means a functional group or substituent derived from an alkane missing one hydrogen. "Alkyl" can be a straight or branched alkyl such as, but not limited to, methyl, ethyl, propyl, tert-butyl, or sec-butyl. The number of carbons in alkyl may be specified. For example, "$C_1$-$C_6$ alkyl" means an alkyl as described above containing from 1 to 6 carbon atoms.

The term "haloalkyl" means an alkyl as described above wherein one or more hydrogens are replaced by halo. The term "halo" means fluoro, chloro, bromo, or iodo.

The term "aryl" refers to a functional group containing, or derived from, an aromatic ring. Aryl groups include, but are not limited to, phenyl, naphthyl, thienyl, indolyl, or any of the preceding functional groups substituted by $C_1$-$C_6$ alkyl, one or more halogens, trifluoromethyl, or lower alkyl or lower alkoxy moieties.

The term "acyl" refers to a functional group derived from an oxoacid having one or more hydroxyl groups removed. An acyl group contains a double bonded oxygen atom and an alkyl group. The number of carbons in acyl may be specified. For example, "$C_n$-acyl" refers to a radical having a single carbon atom of a carbonyl group as the point of attachment, further having a linear or branched, cyclic or acyclic structure, further having a total of n carbons, 1 or more hydrogen atoms, and a total of one oxygen atom.

The term "aryloxy" means an aryl group singular bonded to oxygen. A non-limiting example of an aryloxy group is phenoxy, $C_6H_5O$—.

The term "alkoxy" means an alkyl group singular bonded to oxygen.

The term "aralkyl" refers to a radical derived from an alkyl radical by replacing one or more hydrogen atoms with one or more aryl groups. In other words, an aralkyl group is an aryl-substituted alkyl group.

The term "Ph" refers to phenyl. The term "Bn" refers to benzyl.

The term $C_1$-$C_8$ alkylamino means an amino moiety (—NH—) containing one alkyl moiety having 1 to 8 carbon atoms. The term $C_1$-$C_8$ dialkylamino means an amino moiety containing two alkyl moieties having 1 to 8 carbon atoms, for example, propylamino and dipropylamino, respectively. The $C_1$-$C_5$ alkyl or $C_1$-$C_4$ alkyl groups can be optionally substituted with fluoro, chloro, azido, hydroxy, $C_1$-$C_8$ alkyl, $C_1$-$C_8$ alkoxy, amino, $C_1$-$C_8$ alkylamino, $C_1$-$C_8$ dialkylamino, or —O—$CH_2$Ph, where "Ph" is phenyl. The term "vinyl" refers to —CH=$CH_2$. "Acyloxy" are groups such as methylcarbamate, ethylcarbamate, etc. Such optionally substituted $C_1$-$C_8$ alkyl groups can include 1-chloropropyl, 1-fluoropropyl, 3-chloropropyl, 3-fluoropropyl, 1-hydroxybutyl, 2-hydroxybutyl, 1-methoxypropyl, 1-octyloxypropyl, 1-aminopropyl, 1-aminooctyl, 1-butylaminopropyl, 1-dibutylaminopropyl, and the like.

The term "heterocyclyl" or "heterocyclic" includes aromatic or non-aromatic rings, for example containing from 4 to 20, suitably from 5 to 8 ring atoms, at least one of which, and preferably from 1-4 of which, is a heteroatom such as oxygen, sulfur, or nitrogen. Examples of such groups include furyl, thienyl, pyrrolyl, pyridinyl, pyrrolidinyl, imidazolyl, triazolyl, thiazolyl, tetrazolyl, oxazolyl, isoxazolyl, pyrazolyl, pyridyl, pyrimidinyl, pyrazinyl, pyridazinyl, triazinyl, quinolinyl, isoquinolinyl, quinoxalinyl, benzothiazolyl, benzoxazolyl, benzothienyl, or benzofuryl. Examples of non-aromatic heterocyclyl groups include morpholino, piperidino, azetidine, tetrahydrofuryl, tetrahydropyridyl. In the case of bicyclic rings, these may comprise an aromatic and non-aromatic portion.

The term "TcdB" refers to *Clostridium difficile* toxin B, and the term "TcdA" refers to *Clostridium difficile* toxin A.

The term "MRHF" refers a human foreskin fibroblast cell line.

The term "pharmaceutically acceptable salts," as used herein, refers to salts of compounds of the present disclosure that are substantially non-toxic to living organisms. Typical pharmaceutically acceptable salts include those salts prepared by reaction of a compound of the present disclosure with an inorganic or organic acid, or an organic base, depending on the substituents present on the compounds. Pharmaceutically acceptable salts includes acid addition salts useful for administering the compounds of the present disclosure. Non-limiting examples of pharmaceutically acceptable salts are hydrochloride, hydrobromide, hydroiodide, sulfate, phosphate, acetate, propionate, lactate, mesylate, maleate, malate, succinate, tartrate, citric acid, 2-hydroxyethyl sulfonate, fumarate, and the like when a basic group is present. These salts may be in hydrated form.

Examples of inorganic acids which may be used to prepare pharmaceutically acceptable salts include: hydrochloric acid, phosphoric acid, sulfuric acid, hydrobromic acid, hydroiodic acid, phosphorous acid, and the like. Examples of organic acids which may be used to prepare pharmaceutically acceptable salts include: aliphatic mono- and dicarboxylic acids, such as oxalic acid, carbonic acid, citric acid, succinic acid, phenyl-heteroatom-substituted alkanoic acids, aliphatic and aromatic sulfuric acids, and the like. Pharmaceutically acceptable salts prepared from inorganic or organic acids thus include hydrochloride, hydrobromide, nitrate, sulfate, pyrosulfate, bisulfate, sulfite, bisulfate, phosphate, monohydrogenphosphate, dihydrogenphosphate, metaphosphate, pyrophosphate, hydroiodide, hydrofluoride, acetate, propionate, formate, oxalate, citrate, lactate, p-toluenesulfonate, methanesulfonate, maleate, and the like.

Suitable pharmaceutically acceptable salts may also be formed by reacting the compounds of the present disclosure with an organic base such as methylamine, ethylamine, ethanolamine, lysine, ornithine, and the like. Other suitable salts are known to one of ordinary skill in the art.

It should be recognized that the particular anion or cation forming a part of any salt is not critical, so long as the salt, as a whole, is pharmacologically acceptable and as long as the anion or cation does not contribute undesired qualities or effects. Further, additional pharmaceutically acceptable salts are known to those skilled in the art, and may be used within the scope of the invention. Additional examples of pharmaceutically acceptable salts and their methods of preparation and use are presented in Pharmaceutical Salts: Properties, Selection and Use-A Handbook, by C. G. Wermuth and P. H. Stahl, Verlag Helvetica Chimica Acta, 2002, which is incorporated herein by reference for all purposes.

General Description

Provided are various isoselenazolone derivatives that possess GPx-like activity. The isoselenazolone derivatives are compounds useful as anti-inflammatory, anti-artherosclerotic, anti-oxidant, cytoprotective, neuroprotective, and anti-cancer agents. These compounds have the general structural formula of Formula I:

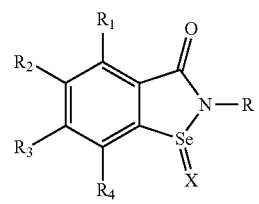

Formula I where R is (a) $C_1$-$C_8$ alkyl optionally substituted with one or more of the following: F, Cl, $N_3$, hydroxy, $C_1$-$C_8$ alkoxy, $C_1$-$C_8$ acyloxy, amino, $C_1$-$C_8$ alkylamino, $C_1$-$C_8$ dialkylamino, O—$CH_2$-Ph, Ph or vinyl, $C_3$-$C_6$ cycloalkyl, Ph optionally substituted with one or more of the following: F, Cl, $N_3$, 1,2,3-triazole, hydroxy, $C_1$-$C_8$ alkyl, $C_1$-$C_8$ alkoxy, $C_1$-$C_8$ acyloxy, amino, $C_1$-$C_8$ alkylamino, $C_1$-$C_8$ dialkylamino, O—$CH_2$-Ph, Ph, vinyl, CN, $CO_2H$, $CO_2R_6$, or $CH_2mR_5$ (m is 1 or 2); (b) $C_1$-$C_8$ alkenyl optionally substituted with one or more of the following: F, Cl, $N_3$, 1,2,3-triazole, hydroxy, $C_1$-$C_8$ alkyl, $C_1$-$C_8$ alkoxy, $C_1$-$C_8$ acyloxy, amino, $C_1$-$C_8$ alkylamino, $C_1$-$C_8$ dialkylamino, O—$CH_2$-Ph, Ph or vinyl; (c) Ph optionally substituted with one or more of the following: F, Cl, $N_3$, 1,2,3-triazole, hydroxy, $C_1$-$C_8$ alkyl, $C_1$-$C_8$ alkoxy, $C_1$-$C_8$ acyloxy, amino, $C_1$-$C_8$ alkylamino, $C_1$-$C_8$ dialkylamino, O—$CH_2$-Ph, Ph, vinyl, CN, $CO_2H$, $CO_2R_6$ or $CH_2mR_5$ (m is 1 or 2); (d) $C_3$-$C_6$ cycloalkyl; or (e) a pyridine group, quinoline group, or 5-8-membered heterocyclyl group linked via n number of carbons or directly to a heteroatom with 1-4 heteroatoms selected from O, N, and S, wherein the pyridine or heterocyclyl group optionally carries up to 5 substituents on an available carbon atom selected from F, Cl, $N_3$, 1,2,3-triazole, hydroxy, $C_1$-$C_8$ alkyl, $C_1$-$C_8$ alkoxy, $C_1$-$C_8$ acyloxy, amino, $C_1$-$C_8$ alkylamino, $C_1$-$C_8$ dialkylamino, O—$CH_2$-Ph, Ph, vinyl, CN, $CO_2H$, $CO_2R_6$, and $CH_2mR_5$ where m is 1 or 2; $R_1$ is independently H, F, Cl, $N_3$, 1,2,3-triazole, hydroxy, $C_1$-$C_8$ alkyl, $C_1$-$C_8$ alkoxy, $C_1$-$C_8$ acyloxy, amino, $C_1$-$C_8$ alkylamino, $C_1$-$C_8$ dialkylamino, O—$CH_2$-Ph, $C_1$-$C_8$ alkoxy Ph, Ph, vinyl, CN, $CO_2H$, $CO_2R_6$ or $CH_2mR_5$ (m is 1 or 2); $R_2$ is independently H, F, Cl, $N_3$, 1,2,3-triazole, hydroxy, $C_1$-$C_8$ alkyl, $C_1$-$C_8$ alkoxy, $C_1$-$C_8$ acyloxy, amino, $C_1$-$C_8$ alkylamino, $C_1$-$C_8$ dialkylamino, O—$CH_2$-Ph, Ph, vinyl, CN, $CO_2H$, $CO_2R_6$ or $CH_2mR_5$ (m is 1 or 2); $R_3$ is independently H, F, Cl, $N_3$, 1,2,3-triazole, hydroxy, $C_1$-$C_8$ alkyl, $C_1$-$C_8$ alkoxy, $C_1$-$C_8$ acyloxy, amino, $C_1$-$C_8$ alkylamino, $C_1$-$C_8$ dialkylamino, O—$CH_2$-Ph, Ph, vinyl, CN, $CO_2H$, $CO_2R_6$ or $CH_2mR_5$ (m is 1 or 2); $R_4$ is independently H, F, Cl, $N_3$, 1,2,3-triazole, hydroxy, $C_1$-$C_8$ alkyl, $C_1$-$C_8$ alkoxy, $C_1$-$C_8$ acyloxy, amino, $C_1$-$C_8$ alkylamino, $C_1$-$C_8$ dialkylamino, O—$CH_2$-Ph, Ph, vinyl, CN, $CO_2H$, $CO_2R_6$ or $CH_2mR_5$ (m is 1 or 2); $R_5$ is independently Ph, $C_1$-$C_8$ alkyl optionally substituted with one or more of the following: F, Cl, hydroxy, $C_1$-$C_8$ alkoxy, $C_1$-$C_8$ acyloxy, amino, $C_1$-$C_8$ alkylamino, $C_1$-$C_8$ dialkylamino, O—$CH_2$-Ph, Ph, vinyl; $R_6$ is independently Ph, $C_1$-$C_8$ alkyl optionally substituted with one or more of the following: hydroxy, $C_1$-$C_8$ alkoxy, $C_1$-$C_8$ acyloxy, amino, $C_1$-$C_8$ alkylamino, $C_1$-$C_8$ dialkylamino, Ph or vinyl; and X is O or a lone pair of electrons.

In some embodiments of Formula I, R is a substituted or unsubstituted $C_1$-$C_8$ alkyl, $C_3$-$C_6$ cycloalkyl, Ph, $C_1$-$C_8$ alkenyl, $C_3$-$C_6$ cycloalkyl, or heterocyclic group; each of $R_1$, $R_2$, $R_3$, and $R_4$ is independently H, F, Cl, $N_3$, 1,2,3-triazole, $C_1$-$C_8$ alkyl, $C_1$-$C_8$ alkoxy, $C_1$-$C_8$ acyloxy, amino, $C_1$-$C_8$ alkylamino, $C_1$-$C_8$ dialkylamino, O—$CH_2$-Ph, $C_1$-$C_8$ alkoxy Ph, Ph, vinyl, CN, $CO_2H$, $CO_2R_6$, or $CH_2mR_5$, wherein m is 1 or 2; and X is either a lone pair of electrons or O.

In certain embodiments, any of the R, $R_1$, $R_2$, $R_3$, $R_4$, $R_5$, or $R_6$ group can also contain a 1,2,3-triazole group, or a 1,2,3-triazole group optionally substituted with one or more of the following: $C_1$-$C_8$ alkyl, $C_1$-$C_8$ alkoxy, $C_1$-$C_8$ acyloxy, amino, $C_1$-$C_8$ alkylamino, $C_1$-$C_8$ dialkylamino, O—$CH_2$-Ph, Ph, vinyl, CN, $CO_2H$, $CO_2R_6$, $CH_2mR_5$ (m is 1 or 2), or a Linker group (L) linked to a biotin group. Non-limiting examples of these substituents include the following structures, Formulas IIa-IIf:

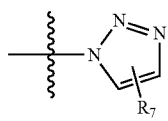
Formula IIa

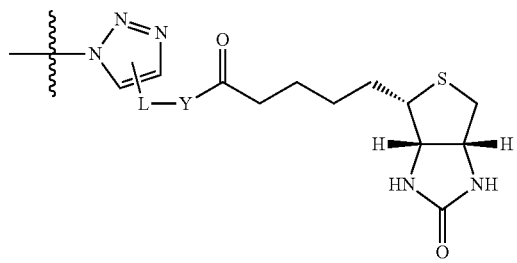
Formula IIb

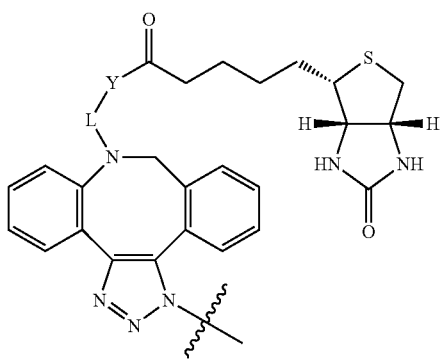
Formula IIc

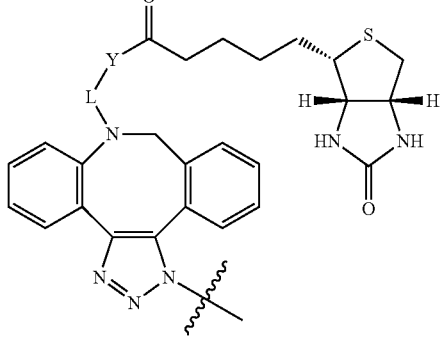
Formula IId

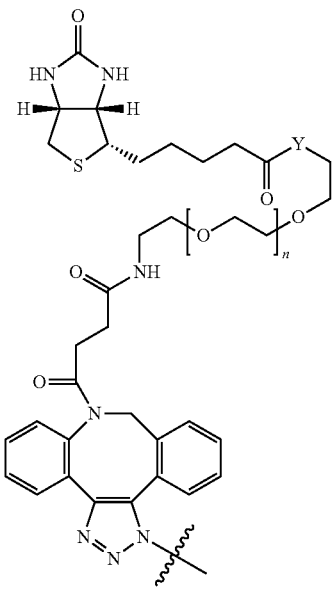
Formula IIe

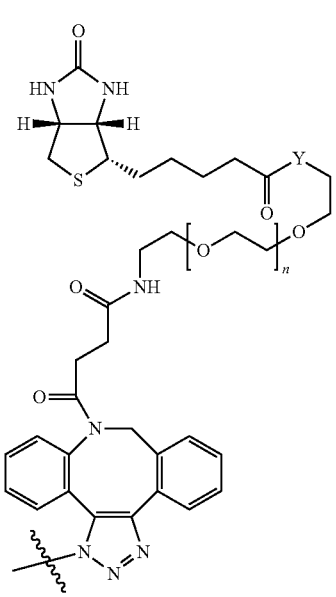
Formula IIf where n=0-100,000; Y is NH or O; $R_7$ is (a) $C_1$-$C_8$ alkyl optionally substituted with one or more of the following: F, Cl, hydroxy, $C_1$-$C_8$ alkoxy, $C_1$-$C_8$ acyloxy, amino, $C_1$-$C_8$ alkylamino, $C_1$-$C_8$ dialkylamino, O—$CH_2$-Ph, Ph, or vinyl; $C_3$-$C_6$ cycloalkyl or Ph optionally substituted with one or more of the following: F, Cl, hydroxy, $C_1$-$C_8$ alkyl, $C_1$-$C_8$ alkoxy, $C_1$-$C_8$ acyloxy, amino, $C_1$-$C_8$ alkylamino, $C_1$-$C_8$ dialkylamino, O—$CH_2$-Ph, Ph, vinyl, CN, $CO_2H$ $CO_2R_6$, or $CH_2mR_5$ (m is 1 or 2); (b) $C_1$-$C_8$ alkenyl optionally substituted with one or more of the following: F, Cl, hydroxy, $C_1$-$C_8$ alkyl, $C_1$-$C_8$ alkoxy, $C_1$-$C_8$ acyloxy, amino, $C_1$-$C_8$ alkylamino, $C_1$-$C_8$ dialkylamino, O—$CH_2$-Ph, Ph, or vinyl; (c) Ph optionally substituted with one or more of the following: F, Cl, hydroxy, $C_1$-$C_8$ alkyl, $C_1$-$C_8$ alkoxy, $C_1$-$C_8$ acyloxy, amino, $C_1$-$C_8$ alkylamino, $C_1$-$C_8$ dialkylamino, O—$CH_2$-Ph, Ph, vinyl, CN, $CO_2H$ $CO_2R_6$, or $CH_2mR_5$ (m is 1 or 2); (d) $C_3$-$C_6$ cycloalkyl; L is linker group and comprising: (a) $C_1$-$C_{20}$ alkyl, optionally substituted; (b) $C_1$-$C_{20}$ alkenyl, optionally substituted; (c) Ph, optionally substituted; (d) cycloalkyl; or (e) a polyethylene glycol moiety. In one non-limiting example, the polyethylene glycol moiety is Formula IIg:

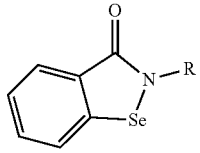

Formula IIg where n=0-100,000.

In some embodiments, the compounds have structural Formula III:

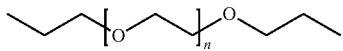

Formula III where R is a substituted or unsubstituted $C_1$-$C_8$ alkyl, $C_3$-$C_6$ cycloalkyl, Ph, $C_1$-$C_8$ alkenyl, $C_3$-$C_6$ cycloalkyl, or heterocyclic group, or is selected from the following groups:

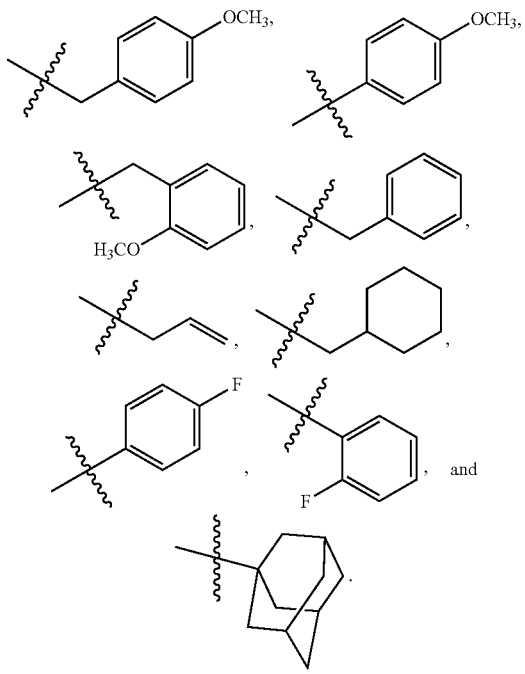

Non-limiting examples of compounds of Formula I include 2-(4-methoxybenzyl)benzo[d][1,2]selenazol-3(2H)-one, 2-(4-methoxyphenyl)benzo[d][1,2]selenazol-3(2H)-one, 2-(2-methoxybenzyl)benzo[d][1,2]selenazol-3(2H)-one, 2-benzylbenzo[d][1,2]selenazol-3(2H)-one, 2-allylbenzo[d][1,2]selenazol-3(2H)-one, 2-(cyclohexylmethyl)benzo[d][1,2]selenazol-3(2H)-one, 2-(4-fluorophenyl)benzo[d][1,2]selenazol-3(2H)-one, 2-(2-fluorophenyl)benzo[d][1,2]selenazol-3(2H)-one, and 2-(4-azidophenyl)benzo[d][1,2]selenazol-3(2H)-one.

2-(4-Methoxybenzyl)benzo[d][1,2]selenazol-3(2H)-one (506a) has the following structural formula:

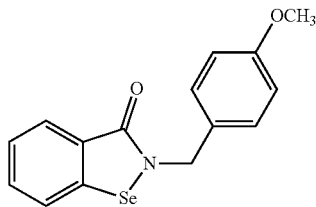

(506a)

2-(4-Methoxyphenyl)benzo[d][1,2]selenazol-3(2H)-one (506b) has the following structural formula:

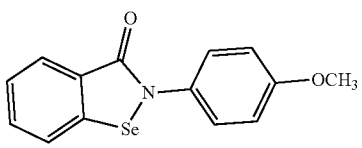

(506b)

2-(2-Methoxybenzyl)benzo[d][1,2]selenazol-3(2H)-one (506c) has the following structural formula:

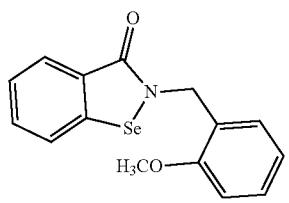

(506c)

2-Benzylbenzo[d][1,2]selenazol-3(2H)-one (506d) has the following structural formula:

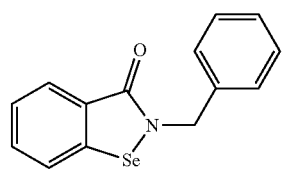

(506d)

2-Allylbenzo[d][1,2]selenazol-3(2H)-one (506e) has the following structural formula:

(506e)

2-(Cyclohexylmethyl)benzo[d][1,2]selenazol-3(2H)-one (506f) has the following structural formula:

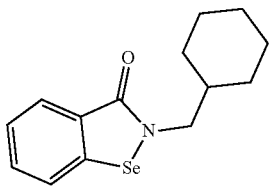
(506f)

2-(4-Fluorophenyl)benzo[d][1,2]selenazol-3(2H)-one (506g) has the following structural formula:

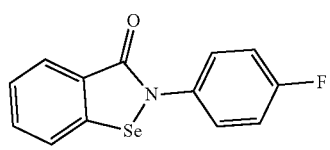
(506g)

2-(2-Fluorophenyl)benzo[d][1,2]selenazol-3(2H)-one (506h) has the following structural formula:

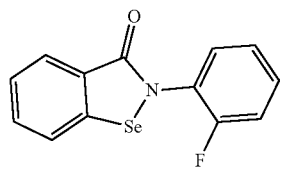
(506h)

2-(4-Azidophenyl)benzo[d][1,2]selenazol-3(2H)-one (506i) has the following structural formula:

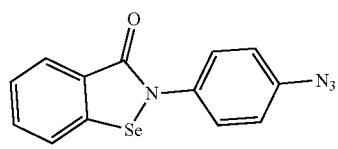
(506i)

Another non-limiting example of a compound of Formula I is the adamantyl derivative compound 506j:

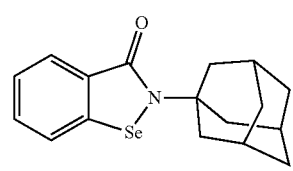
(506j)

Another non-limiting example of a compound of Formula I is compound 506k:

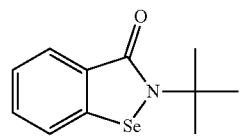
(506k)

Another non-limiting example of a compound of Formula I is compound 506l:

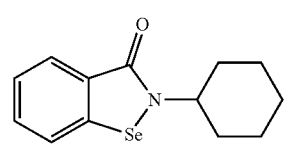
(506l)

Another non-limiting example of a compound of Formula I is compound 506m:

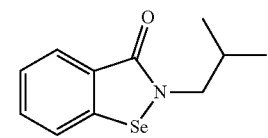
(506m)

Another non-limiting example of a compound of Formula I is compound 506n:

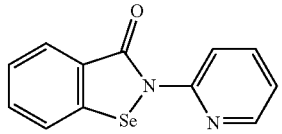
(506n)

Another non-limiting example of a compound of Formula I is compound 506o:

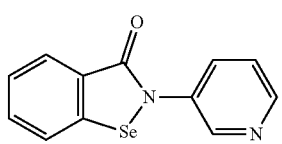
(506o)

Another non-limiting example of a compound of Formula I is compound 506p:

(506p)

Another non-limiting example of a compound of Formula I is compound 506q:

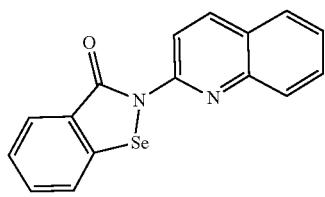
(506q)

Another non-limiting example of a compound of Formula I is compound 506r:

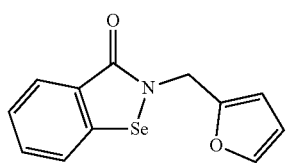
(506r)

Another non-limiting example of a compound of Formula I is compound 506s:

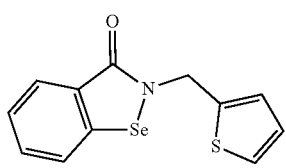
(506s)

Another non-limiting example of a compound of Formula I is compound 506t:

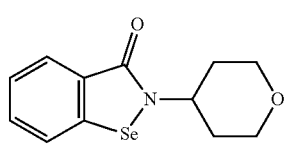
(506t)

Another non-limiting example of a compound of Formula I is compound 506u:

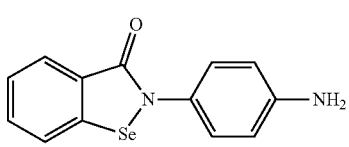
(506u)

Included in the compounds of Formula I are pharmaceutically acceptable salts, which means acid addition salts useful for administering the compounds herein and include hydrochloride, hydrobromide, hydroiodide, sulfate, phosphate, acetate, propionate, lactate, mesylate, maleate, malate, succinate, tartrate, citric acid, 2-hydroxyethyl sulfonate, fumarate, and the like when a basic group is present. These salts may be in hydrated form. The benzene ring, in addition to being unsubstituted, can be substituted with one or more halogen atoms in the series fluorine or chlorine. Thus, the $R_1$ through $R_4$ groups of Formula I can be independently either hydrogen atoms or halogen atoms in a variety of substitution patterns.

The synthesis of the compounds of Formula I can be relatively quick. In one example, the synthesis can be completed in only one to two hours. The synthesis of Formula I compounds generally involves KSeCN or NaSeCN as a selenium source, though other selenium sources can be utilized.

Figure 3:
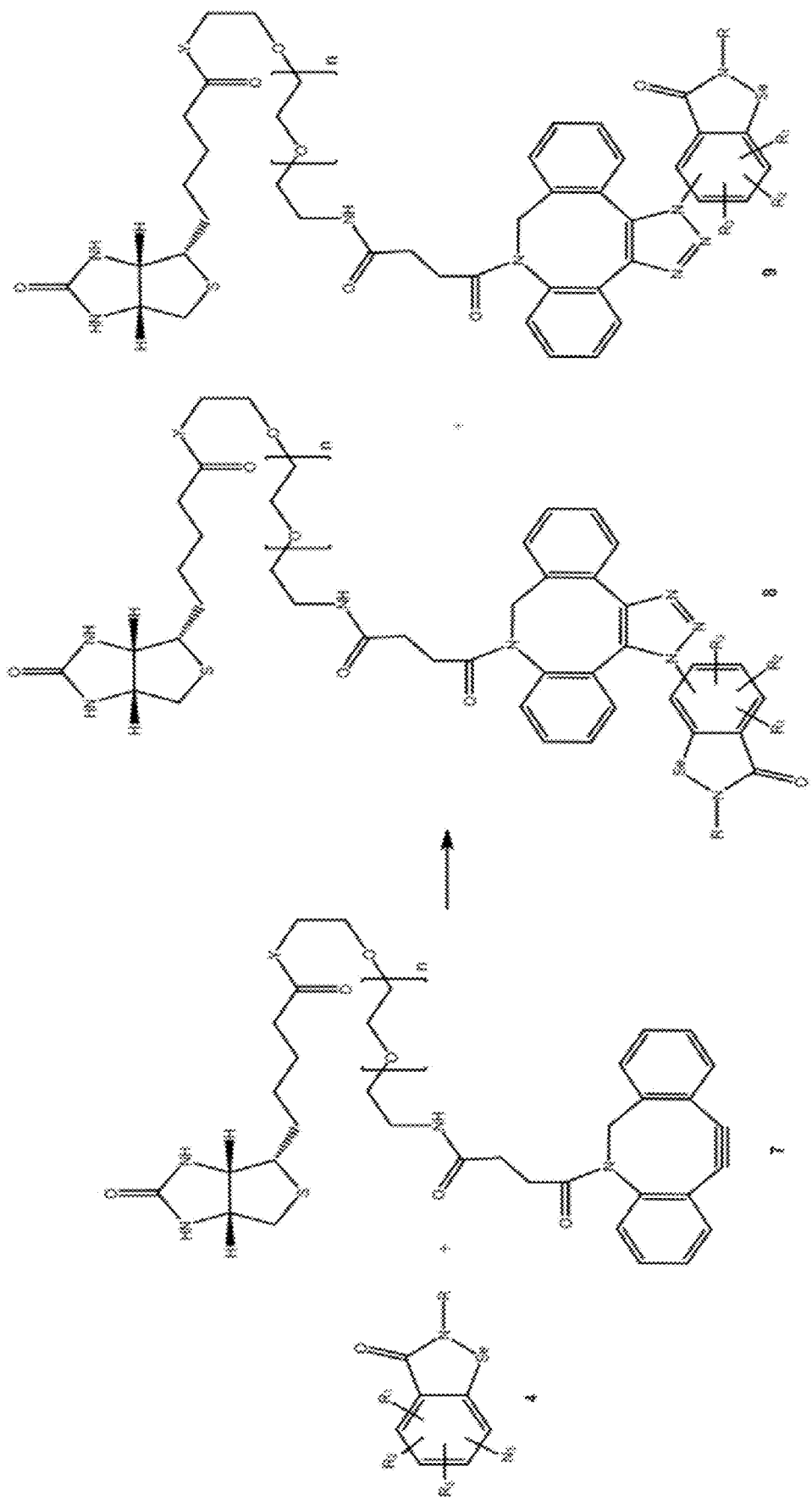
FIG. 3: Non-limiting example scheme showing the production of isoselenazolone derivatives 8, 9 having 4,5-disubstituted 1,2,3-triazoles.
Figure 4:
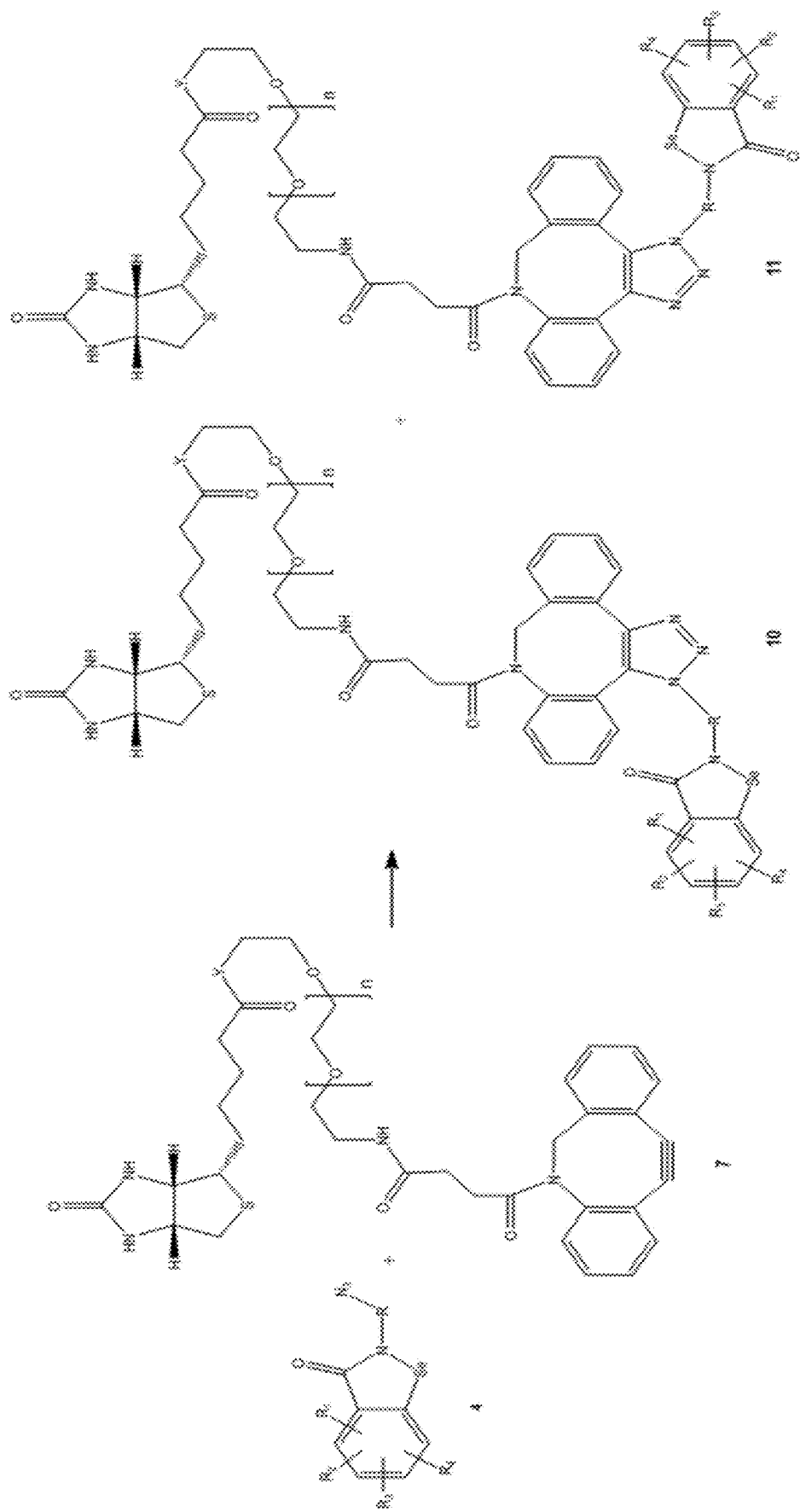
FIG. 4: Non-limiting example scheme showing the production of isoselenazolone derivatives 10, 11.
Figure 5:
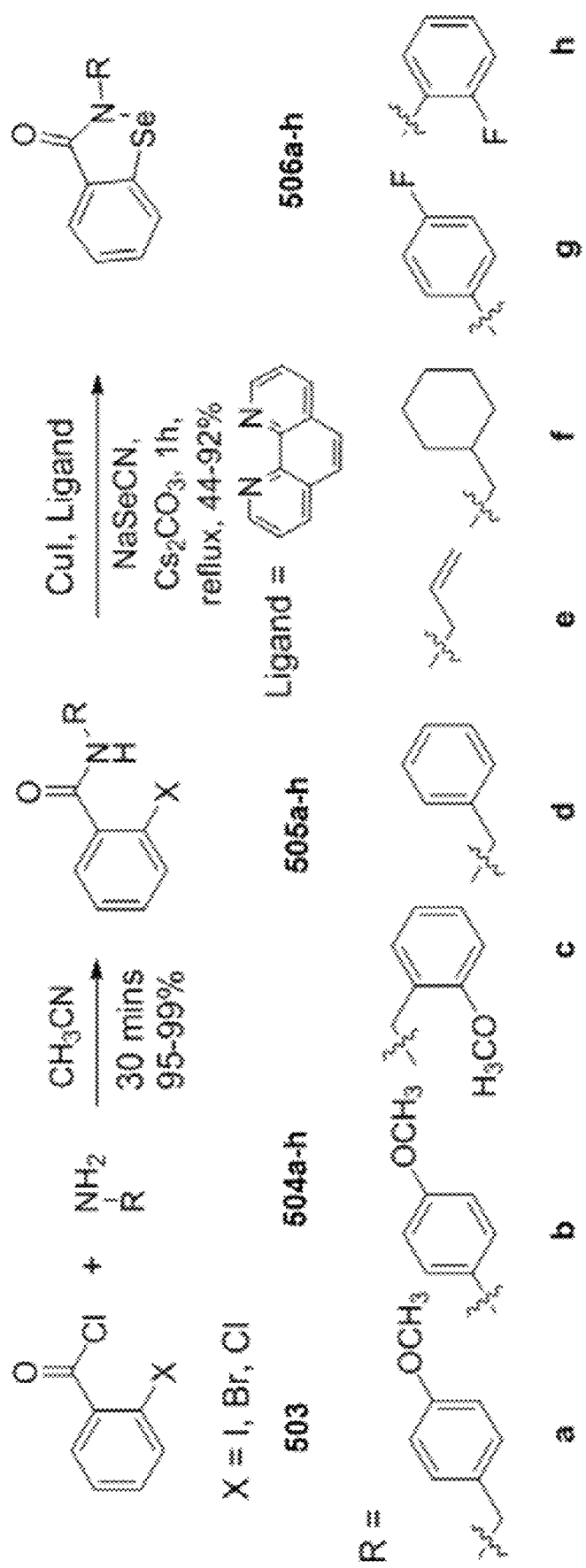
FIG. 5: Non-limiting example scheme showing the synthesis of 2-(4-methoxybenzyl)benzo[d][1,2]selenazol-3 (2H)-one (506a), 2-(4-methoxyphenyl)benzo[d][1,2]selenazol-3(2H)-one (506b), 2-(2-methoxybenzyl)benzo[d][1,2]selenazol-3(2H)-one (506c), 2-benzylbenzo[d][1,2]selenazol-3 (2H)-one (506d), 2-allylbenzo[d][1,2]selenazol-3(2H)-one (506e), 2-(cyclohexylmethyl)benzo[d][1,2]selenazol-3(2H)-one (506f), 2-(4-fluorophenyl)benzo[d][1,2]selenazol-3(2H)-one (506g), and 2-(2-fluorophenyl)benzo[d][1,2]selenazol-3(2H)-one (506h).

FIGS. 1-5 show schemes depicting the synthesis of various example compounds of Formula I. In general, the compounds of Formula I can be prepared by reacting an acid chloride with an amine to produce an ortho-haloamide, and reacting the ortho-haloamide with a ligand and a selenium source to produce a selenylamide. FIG. 5 depicts the synthesis of eight non-limiting example compounds 506a-h using this method.

As shown in FIG. 1, substituted 2-halo benzoyl chloride (X=halogen), where $R_1$, $R_2$, $R_3$, and $R_4$ of structure 1 are independently H, F, Cl, $N_3$, hydroxy, $C_1$-$C_8$ alkyl, $C_1$-$C_8$ alkoxy, $C_1$-$C_8$ acyloxy, amino, $C_1$-$C_8$ alkylamino, $C_1$-$C_8$ dialkylamino, O—$CH_2$-Ph, Ph, vinyl, CN, $CO_2H$ $CO_2R_6$, or $CH_2mR_5$ (m is 1 or 2), reacts with functionalized amines where R in structure 2 is (a) $C_1$-$C_8$ alkyl optionally substituted with one or more of the following: F, Cl, $N_3$, hydroxy, $C_1$-$C_8$ alkoxy, $C_1$-$C_8$ acyloxy, amino, $C_1$-$C_8$ alkylamino, $C_1$-$C_8$ dialkylamino, O—$CH_2$-Ph, Ph, vinyl, $C_3$-$C_6$ cycloalkyl, or Ph optionally substituted with one or more of the following: F, Cl, $N_3$, hydroxy, $C_1$-$C_8$ alkyl, $C_1$-$C_8$ alkoxy, $C_1$-$C_8$ acyloxy, amino, $C_1$-$C_8$ alkylamino, $C_1$-$C_8$ dialkylamino, O—$CH_2$-Ph, Ph, vinyl, CN, $CO_2H$ $CO_2$ $R_6$, or $CH_2mR_5$ (m is 1 or 2), (b) $C_1$-$C_8$ alkenyl optionally substituted with one or more of the following: F, Cl, $N_3$, hydroxy, $C_1$-$C_8$ alkyl, $C_1$-$C_8$ alkoxy, $C_1$-$C_8$ acyloxy, amino, $C_1$-$C_8$ alkylamino, $C_1$-$C_8$ dialkylamino, O—$CH_2$-Ph, Ph, or vinyl, (c) Ph optionally substituted with one or more of the following: F, Cl, $N_3$, hydroxy, $C_1$-$C_8$ alkyl, $C_1$-$C_8$ alkoxy, $C_1$-$C_8$ acyloxy, amino, $C_1$-$C_8$ alkylamino, $C_1$-$C_8$ dialkylamino, O—$CH_2$-Ph, Ph, vinyl, CN, $CO_2H$, $CO_2$ $R_6$ or $CH_2mR_5$ (m is 1 or 2), or (d) $C_3$-$C_6$ cycloalkyl, in acetonitrile to get respectively functionalized 2-halobenzamide structure 3. The functionalized 2-halobenzamide structure 3 in the presence of a suitable catalyst, such as copper(I) iodide, suitable ligand such as 1,10-phenanthroline, suitable base such as cesium carbonate, in the presence of a suitable selenium source such as potassium selenocyanate, and a suitable solvent such as acetonitrile, N,N-dimethylformamide, and dimethyl sulfoxide under reflux, forms respective isoselenazolone derivatives 4 in 1-2 hours.

Figure 2:
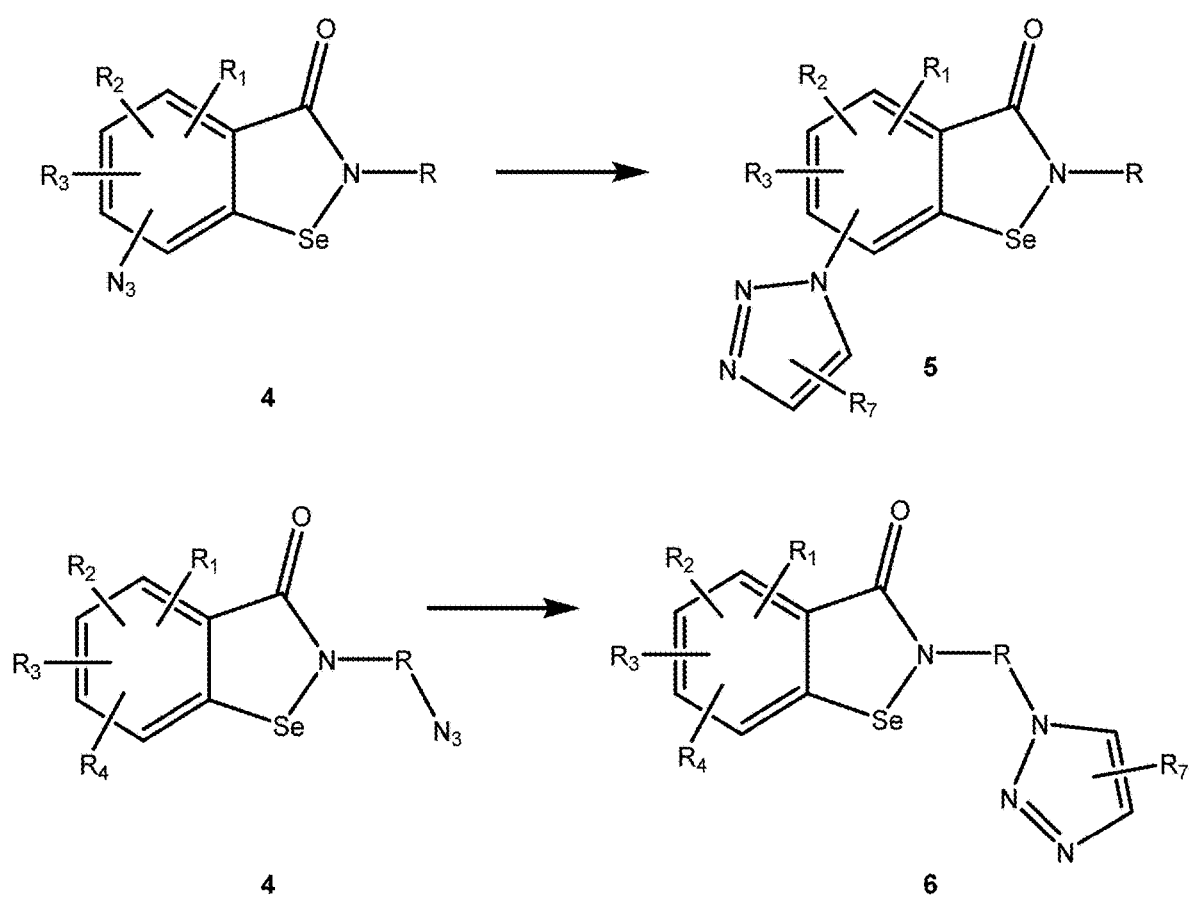
FIG. 2: Non-limiting example scheme showing the production of isoselenazolone derivatives 5, 6 containing 1,2,3-triazole.

As shown in FIGS. 2-4, isoselenazolone derivatives 4 that contain azides can be converted into 1,4-substituted or 1,5-substituted 1,2,3-triazoles by reaction with an alkyne and catalyst. When an isoselenazolone derivative 4 contains an azide group, that group is converted into a 1,2,3-triazole 5 or 1,2,3-triazole 6, which can be substituted at N-1 and either C-4, C-5, or both C-4 and C-5. The substituent at C-4 or C-5 can independently be H or $R_7$.

As shown in FIG. 3, isoselenazolone derivatives 4 that contain azides can be converted into 4,5-disubstituted 1,2,3-triazoles by reaction with a strained alkyne such as DBCO-PEG4-biotin (n=2) 7, also known as ADIBO-PEG4-biotin and as DIBACA-PEG4-biotin. When an isoselenazolone derivative 4 contains an azide group, that group is converted into 4,5-disubstituted 1,2,3-triazoles 8 and 9 as a mixture of regioisomers.

The compounds of Formula I are useful antimicrobial agents, effective against a number of human and veterinary pathogens, including Gram-positive and acid-fast organisms such as *Mycobacterium tuberculosis*. The compounds are active against a number of human pathogens and are antibacterial, anti-fungal, anti-yeast, and anti-viral agents. The compounds show activity against Gram-positive bacterial such as *Staphylococcus aureus*, methicillin-resistant *Staphylococcus aureus*, vancomycin-resistant *Staphylococcus aureus*, *Staphylococcus simulans*, and *Helicobacter pylori*. The compounds show activity against Gram-negative bacteria such as *Haemophilus* influenza, *Escherichia coli*, *Pseudomonas aeruginosa*, and *Klebsiella pneumonia*. The compounds show activity against acid-fast bacteria such as *Mycobacterium tuberculosis* and other *Mycobacterium* species. The compounds are also active against yeast and fungi such as *Saccharomyces cerevisiae*, *Candida albicans*, and *Aspergillus niger*. The compounds of Formula I also have anti-viral activity and are active against herpes simplex virus type-I (HSV-1), encephalomycoarditis virus, and vesicular stomatitis virus. The compounds of Formula I also provide cytoprotection against *Clostridium difficile* toxins A and B.

Without wishing to be bound by theory, it is believed that the compounds of Formula I have glutathione peroxidase (GPx)-like activity. GPx mimics reduce inflammation-causing molecules, such as hydrogen peroxide, hydroperoxides (including membrane-bound phospholipid and cholesterylester hydroperoxides), and peroxynitrites. The compounds in this class chemically modify thiol-containing enzymes, in many cases leading to inhibition of these enzymes. Some examples of such enzymes include, lipoxygenases, NO synthases, NADPH oxidase, protein kinase C, $H^+/K^+$-ATPase, viral helicases, and cysteine proteases. Ebselen, an organoselenium compound that is a known GPx mimic, inhibits multiple enzymes such as lipoxygenases (anti-inflammatory), NO synthases (anti-inflammatory), NADPH oxidase (anti-atherosclerosis), protein kinase C, $H^+/K^+$-ATPases, viral helicases, and cysteine proteases. The compounds of Formula I are analogues of ebselen.

Ebselen has anti-inflammatory, anti-oxidant, and cytoprotective properties. The compounds described herein are distinct from ebselen yet retain some of the pharmaceutically important properties of ebselen. For example, the Formula I compounds 2-allylbenzo[d][1,2]selenazol-3(2H)-one (506e) and 2-(2-methoxybenzyl)benzo[d][1,2]selenazol-3(2H)-one (506c) show MIC values against *Mycobacterium tuberculosis* that are lower than ebselen. The compounds of Formula I differ structurally from ebselen at least in that R can be substituted forms of alkyl, alkenyl, phenyl, and cyclohexyl. While the Examples herein show that the compounds are useful as anti-*Mycobacterium tuberculosis* agents, it is believed that the compounds retain the anti-inflammatory, anti-oxidant, and cytoprotective activity of ebselen. The compounds provide compositions which are unique from ebselen but which may have improved pharmacokinetics, dynamics, or safety profiles. For example, compounds containing the bioorthogonal azide group can form 1,2,3-triazoles with strained alkynes. This allows for reversible labeling of thiols via the formation and reductive reversal of a selenocystine bond with a variety of widely used ligands such as biotin or flurophores linked through the 1,2,3-triazole. Furthermore, without wishing to be bound by theory, it is believed that the compounds sensitize cancer cells to radiation and chemotherapy as well as reduce the toxicity of some anti-tumor compounds, inhibit some kinases involved in cancer progression, prevent inflammation-associated carcinogensis, and inhibit glutaminase, which is involved in cancer and HIV-associated dementia.

Pharmaceutical compositions of the present disclosure comprise an effective amount of a compound of Formula I (an "active" ingredient), and/or additional agents, dissolved or dispersed in a pharmaceutically acceptable carrier. The pharmaceutically acceptable composition of compounds of Formula I may be prepared by combining the solid or liquid of pharmaceutically acceptable carrier and optionally with pharmaceutically acceptable adjuvants and excipients by using standard and conventional techniques. The preparation of a pharmaceutical composition that contains at least one compound or additional active ingredient will be known to those of skill in the art in light of the present disclosure, as exemplified by Remington's Pharmaceutical Sciences, 2003, incorporated herein by reference. Moreover, for animal (e.g., human) administration, it is understood that preparations should meet sterility, pyrogenicity, general safety, and purity standards as required by FDA Office of Biological Standards.

A composition disclosed herein may comprise different types of carriers depending on whether it is to be administered in solid, liquid, or aerosol form, and whether it needs to be sterile for such routes of administration as injection. Compositions disclosed herein can be administered orally, intravenously, intranasally, intradermally, transdermally, intrathecally, intraarterially, intraperitoneally, intravaginally, intrarectally, intraosseously, periprosthetically, topically, intramuscularly, subcutaneously, mucosally, intraosseosly, periprosthetically, in utero, topically, locally, via inhalation (e.g., aerosol inhalation), by injection, by infusion, by continuous infusion, by localized perfusion bathing target cells directly, via a catheter, via a lavage, in cremes, in lipid compositions (e.g., liposomes), or by other method or any combination of the foregoing as would be known to one of ordinary skill in the art (see, for example, Remington's Pharmaceutical Sciences, 2003, incorporated herein by reference).

For oral administration, the compound of Formula I and its salts can be formulated as solids as well as liquids. Solid medications include pills, tablets, dispersible granules, capsules, powder, cachets, and suppositories. A solid carrier which can be at least one substance of which may also function as flavoring agent, solubilizer, lubricant, suspending agent, binder, tablet disintegrating agent, and encapsulating agent, which includes lactose, sucrose, cornstarch, gelatin, magnesium carbonate, magnesium stearate, sugar, pectin, dextrin, cellulosic materials, low melting wax, cocoa butter, and the like. For liquid medicaments, the composition may include aqueous solutions such as syrups, flavored syrups, aqueous or suspensions, emulsions with edible oils, and elixirs. In one non-limiting example, a compound of Formula I is suspended or dispersed in synthetic agents such as tragacanth, acacia, dextran, sodium carboxymethylcellouse, methylcellouse, and gelatin.

For intravenous-administered medicaments, the compound is formulated with suitable liquid injection vehicle, which includes water, saline, dextrose, water-miscible solvents such as ethanol, polyethylene glycol and propylene glycol, and non-aqueous vehicles such as animal and plant oil. The buffer, such as citrate, acetate, or phosphate, can be present to maintain pH, optionally between 6-8, and preferably between pH 6.5-7.5. Antioxidants such as ascorbic acid and sodium bisulphite can be present. The solubilizing agents and stabilizers such as cyclodextrin, lysolectin, oleic acid, stearic acid, and dextrin can be present.

Preferably, the compound is administrated in unit dosage form which contain an appropriate amount of active compound. The quantity of active compound (that is, compound of Formula I) in a dose, is varied or adjusted depending upon its potency and its particular application. In some embodiments, quantity ranges between 0.5% to 90% composition weight. In some embodiments, the suitable dosage of compound ranges about 0.1 to 5000 mg per human patient per day, for example from 50 to 2000 mg per human patient per day. In some embodiments, the dosage of compounds of Formula I can be divided into 2-4 doses per day.

The actual dosage amount of a composition disclosed herein administered to an animal or human patient can be determined by physical and physiological factors such as body weight, severity of condition, the type of disease being treated, previous or concurrent therapeutic interventions, idiopathy of the patient, and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active ingredient. In other embodiments, an active ingredient may comprise between about 2% to about 75% of the weight of the unit, or between about 25% to about 60%, for example, and any range derivable therein. Naturally, the amount of active ingredient(s) in each therapeutically useful composition may be prepared in such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In certain embodiments, a composition herein and/or additional agent is formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsules, they may be compressed into tablets, or they may be incorporated directly with the food of the diet.

In further embodiments, a composition described herein may be administered via a parenteral route. As used herein, the term "parenteral" includes routes that bypass the alimentary tract. Specifically, the pharmaceutical compositions disclosed herein may be administered, for example but not limited to, intravenously, intradermally, intramuscularly, intraarterially, intrathecally, subcutaneous, or intraperitoneally (U.S. Pat. Nos. 6,753,514, 6,613,308, 5,466,468, 5,543,158, 5,641,515, and 5,399,363 are each specifically incorporated herein by reference in their entirety).

Solutions of the compositions disclosed herein as free bases or pharmacologically acceptable salts may be prepared in water suitably mixed with a surfactant, such as hydroxypropylcellulose. Dispersions may also be prepared in glycerol, liquid polyethylene glycols and mixtures thereof, and in oils. Under ordinary conditions of storage and use, these preparations may contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In some cases, the form should be sterile and should be fluid to the extent that easy injectability exists. It should be stable under the conditions of manufacture and storage and should be preserved against the contaminating action of microorganisms, such as bacteria and fungi. The carrier can be a solvent or dispersion medium containing, for example, water, ethanol, polyol (i.e., glycerol, propylene glycol, liquid polyethylene glycol, and the like), suitable mixtures thereof, and/or vegetable oils. Proper fluidity may be maintained, for example, by the use of a coating, such as lecithin, by the maintenance of the required particle size in the case of dispersion, and/or by the use of surfactants. The prevention of the action of microorganisms can be brought about by various antibacterial and antifungal agents, such as, but not limited to, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption such as, for example, aluminum monostearate or gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

Sterile injectable solutions are prepared by incorporating the compositions in the required amount in the appropriate solvent with various other ingredients enumerated above, as required, followed by filtered sterilization. Generally, dispersions are prepared by incorporating the various sterilized compositions into a sterile vehicle which contains the basic dispersion medium and the required other ingredients from those enumerated above. In the case of sterile powders for the preparation of sterile injectable solutions, some methods of preparation are vacuum-drying and freeze-drying techniques which yield a powder of the active ingredient plus any additional desired ingredient from a previously sterile-filtered solution thereof. A powdered composition is combined with a liquid carrier such as, but not limited to, water or a saline solution, with or without a stabilizing agent.

In other embodiments, the compositions may be formulated for administration via various miscellaneous routes, for example, topical (i.e., transdermal) administration, mucosal administration (intranasal, vaginal, etc.) and/or via inhalation.

Pharmaceutical compositions for topical administration may include the compositions formulated for a medicated application such as an ointment, paste, cream, or powder. Ointments include all oleaginous, adsorption, emulsion, and water-soluble based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones, and luarocapram. Possible bases for compositions for topical application include polyethylene glycol, lanolin, cold cream, and petrolatum, as well as any other suitable absorption, emulsion, or water-soluble ointment base. Topical preparations may also include emulsifiers, gelling agents, and antimicrobial preservatives as necessary to preserve the composition and provide for a homogenous mixture. Transdermal administration of the compositions may also comprise the use of a "patch." For example, the patch may supply one or more compositions at a predetermined rate and in a continuous manner over a fixed period of time.

In certain embodiments, the compositions may be delivered by eye drops, intranasal sprays, inhalation, and/or other aerosol delivery vehicles. Methods for delivering compositions directly to the lungs via nasal aerosol sprays has been described in U.S. Pat. Nos. 5,756,353 and 5,804,212 (each specifically incorporated herein by reference in their entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts and could be employed to deliver the compositions described herein. Likewise, transmucosal drug delivery in the form of a polytetrafluoroetheylene support matrix is described in U.S. Pat. No. 5,780,045 (specifically incorporated herein by reference in its entirety), and could be employed to deliver the compositions described herein.

It is further envisioned the compositions disclosed herein may be delivered via an aerosol. The term aerosol refers to a colloidal system of finely divided solid or liquid particles dispersed in a liquefied or pressurized gas propellant. The typical aerosol for inhalation consists of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight, and the severity and response of the symptoms.

In particular embodiments, the compounds and compositions described herein are useful for treating, preventing, or ameliorating a bacterial infection. Thus, provided herein is a method for treating microbial infections in patients by administering to a patient in need thereof an effective amount of a compound of Formula I. In some embodiments, the compound is administered in a pharmaceutical composition orally, parenterally, or topically. The treatment is not limited to microbial infections. The compounds and compositions can be used to treat, prevent, or ameliorate diseases such as, but not limited to, Meniere's disease, lung cancer, head and neck cancer, hearing loss, ototoxicity, tinnitus, neuropathy, and bipolar disorder.

Furthermore, the compounds and compositions herein can be used in combination therapies. That is, the compounds or compositions can be administered concurrently with, prior to, or subsequent to one or more other desired therapeutic or medical procedures or drugs. The particular combination of therapies and procedures in the combination regimen will take into account compatibility of the therapies and/or procedures and the desired therapeutic effect to be achieved. Combination therapies include sequential, simultaneous, and separate administration of the active ingredient in a way that the therapeutic effects of the first administered procedure or drug is not entirely disappeared when the subsequent procedure or drug is administered.

In certain embodiments, the compounds herein are useful in combination with other anti-infectives, such as antibacterial agents. Suitable other antibacterial agents include, but are not limited to: soniazid, rifampin, pyrazinamide, fluoroquinolone, streptomycin, ethambutol, capreomycin, ethionamide, cycloserine, levofloxacin, ciprofloxacin, amikacin, moxifloxacin, p-amino salicylic acid, kanamycin, viomycin, prothionamide, rifabutin, clarithromycin, linezolid, Chioasetazon, arginine, vitamin B, or a corticosteroid.

In other embodiments, the compounds herein are useful in combination with other GPx mimics such as, but not limited to, ebselen.

It is further envisioned that the compositions and methods described herein can be embodied in the form of a kit or kits. A non-limiting example of such a kit is a kit for making a compound of Formula I, the kit comprising an ortho-haloamide (or an acid chloride and an amine for making an ortho-haloamide), a ligand, and a selenium source in two or more separate containers, where the containers may or may not be present in a combined configuration. Many other kits are possible, such as kits for making a pharmaceutical composition that further comprise a pharmaceutically acceptable carrier, diluent, or excipient. The kits may further include instructions for using the components of the kit to practice the subject methods. The instructions for practicing the subject methods are generally recorded on a suitable recording medium. For example, the instructions may be present in the kits as a package insert or in the labeling of the container of the kit or components thereof. In other embodiments, the instructions are present as an electronic storage data file present on a suitable computer readable storage medium, such as a flash drive or CD-ROM. In other embodiments, the actual instructions are not present in the kit, but means for obtaining the instructions from a remote source, such as via the internet, are provided. An example of this embodiment is a kit that includes a web address where the instructions can be viewed and/or from which the instructions can be downloaded. As with the instructions, this means for obtaining the instructions is recorded on a suitable substrate.

Further provided is a method of determining coverage of health insurance reimbursement or payments, the method

EXAMPLES

Example 1—Compounds 506a-506t, 600, 602, 604, 606, 608, 610, 612

General Procedure for Synthesis of Isoselenazoles

Compounds 506a-506t were synthesized according to the process depicted in FIG. 5. Starting material (1 eq) was taken into a round bottom flask to which copper(I) iodide (1 eq), 1,10-phenanthroline (1 eq), cesium carbonate (2.5 eq), and potassium selenocyanate (1.2 eq) were added. The flask with the reaction mixture was purged with nitrogen, solvent (N,N-dimethylformamide, acetonitrile) was added, and the flask was heated to 95-100° C. and maintained until the reaction was complete. The reaction mixture was filtered to remove dark brown solid. The residue was washed with ethyl acetate. Cold water was added to the filtrate which was further extracted with ethyl acetate three times. The ethyl acetate layers were combined and dried with anhydrous sodium sulfate and concentrated under reduced pressure to obtain crude product. The crude product was purified by column chromatography on silica gel to obtain pure isoselenazolone derivatives using ethyl acetate in hexanes as the mobile phase.

Example 1: 2-(4-methoxybenzyl)benzo[d][1,2]selenazol-3(2H)-one (506a)

2-iodo-N-(4-methoxybenzyl)benzamide (400 mg, 1.08 mmol) was taken into a 50.0 mL round bottom flask. Copper(I) iodide (207 mg, 1.08 mmol), 1,10-phenanthroline (196 mg, 1.08 mmol), cesium carbonate (888 mg, 2.72 mmol), and potassium selenocyanate (188 mg, 1.30 mmol) were added. The flask was purged with nitrogen and N,N-dimethylformamide (4.0 mL) was added to obtain a turbid solution. The reaction mixture was stirred and heated to 100° C. The reaction was maintained at that temperature for 1 h. The solution was cooled and the workup was performed using the general procedure. The product was purified using 35% ethyl acetate in hexanes to obtain 2-(4-methoxybenzyl)benzo[d][1,2]selenazol-3(2H)-one (506a). Yield 63% (221 mg); silica gel TLC $R_f$=0.1 (3:7 ethyl acetate-hexanes); mass spectrum (ESIMS), m/z=342.3 (M+23)$^+$, $C_{15}H_{13}NO_2Se$ requires 342.00 (M+23)$^+$; $^1H$ NMR (600 MHz, CDCl$_3$) δ 8.08 (d, J=7.89 Hz, 1H), 7.57 (m, 2H), 7.43 (m, 1H), 7.32 (d, 8.62 Hz, 2H), 6.91 (d, 8.62 Hz, 4H), 4.96 (s, 1H), 3.82 (s, 3H).

Example 2: 2-(4-methoxyphenyl)benzo[d][1,2]selenazol-3(2H)-one (506b)

2-Iodo-N-(4-methoxyphenyl)benzamide (400 mg, 1.13 mmol) was added to a 50.0 mL round bottom flask. Copper (I) iodide (216 mg, 1.13 mmol), 1,10-phenanthroline (204 mg, 1.33 mmol), cesium carbonate (922 mg, 2.83 mmol), and potassium selenocyanate (196 mg, 1.30 mmol) were added to the flask. The flask was purged with nitrogen and N,N-dimethylformamide (4.0 mL) was added to obtain a turbid solution. The reaction mixture was stirred and heated to 100° C. The reaction was maintained at that temperature for 1 h. The solution was cooled and the workup was performed using the general procedure. The product was purified using 25% ethyl acetate in hexanes to afford 2-(4-methoxyphenyl)benzo[d][1,2]selenazol-3(2H)-one (506b). Yield 67% (231 mg); silica gel TLC $R_f$=0.25 (3:7 ethyl acetate-hexanes); mass spectrum (ESIMS), m/z=328.2 (M+23)$^+$, $C_{14}H_{11}NO_2Se$ requires 327.9 (M+23)$^+$; $^1H$ NMR (600 MHz, CDCl$_3$) δ 8.13 (d, J=7.70 Hz, 1H), 7.66 (m, 2H), 7.51-7.47 (d, J=7.49 Hz, 3H), 6.97 (d, 2H), 3.85 (s, 3H).

Example 3: 2-(2-methoxybenzyl)benzo[d][1,2]selenazol-3(2H)-one (506c)

2-Iodo-N-(2-methoxybenzyl)benzamide (370 mg, 1.01 mmol) was taken into 50.0 mL round bottom flask. Copper (I) iodide (192 mg, 1.01 mmol), 1,10-phenanthroline (182 mg, 1.01 mmol), cesium carbonate (821 mg, 2.52 mmol), and potassium selenocyanate (174 mg, 1.20 mmol) were added to the flask. The flask was purged with nitrogen and N,N-dimethylformamide (4.0 mL) was added to obtain a turbid solution. The reaction mixture was stirred and heated to 100° C. The reaction was maintained at that temperature for 1 h. The solution was cooled and the workup was performed using general procedure. The product was purified using 25% ethyl acetate in hexanes to obtain 2-(2-methoxybenzyl)benzo[d][1,2]selenazol-3(2H)-one (506c). Yield 44% (141 mg); silica gel TLC $R_f$=0.24 (3:7 ethyl acetate-hexanes); mass spectrum (ESIMS), m/z=342.2 (M+23)$^+$, $C_{15}H_{13}NO_2Se$ requires 327.9 (M+23)$^+$; $^1H$ NMR (600 MHz, CDCl$_3$) δ 8.08 (d, J=7.89 Hz, 1H), 7.57 (m, 2H), 7.42 (m, 2H), 7.34 (m, 1H), 6.95 (m, 2H), 5.07 (s, 2H), 3.93 (s, 3H).

Example 4: 2-benzylbenzo[d][1,2]selenazol-3(2H)-one (506d)

N-Benzyl-2-iodobenzamide (276 mg, 0.88 mmol) was taken into a 50.0 mL round bottom flask. Copper(I) iodide (156 mg, 0.82 mmol), 1,10-phenanthroline (148 mg, 0.82 mmol), cesium carbonate (667 mg, 2.04 mmol), and potassium selenocyanate (142 mg, 1.20 mmol) were added to the flask. The flask was purged with nitrogen and N,N-dimethylformamide (4.0 mL) was added to obtain a turbid solution. The reaction mixture was stirred and heated to 100° C. The reaction was maintained at that temperature for 1 h. The solution was cooled and the workup was performed using the general procedure. The product was purified using 25% ethyl acetate in hexanes to obtain 2-benzylbenzo[d][1,2]selenazol-3(2H)-one (506d). Yield 39% (90 mg); silica gel TLC $R_f$=0.28 (3:7 ethyl acetate-hexanes); mass spectrum (ESIMS), m/z=312.2 (M+23)$^+$, $C_{15}H_{13}NO_2Se$ requires 311.99 (M+23)$^+$; $^1HNMR$ (600 MHz, CDCl$_3$) δ 8.10 (d, J=7.89, 1H), 7.58 (m, 2H), 7.44 (m, 1H), 7.37 (m, 5H), 5.03 (s, 2H).

Example 5: 2-allylbenzo[d][1,2]selenazol-3(2H)-one (506e)

2-Iodo-N-allylbenzamide (400 mg, 1.39 mmol) was taken into a 50.0 mL round bottom flask. Copper(I) iodide (267 mg, 1.39 mmol), 1,10-phenanthroline (251 mg, 1.39 mmol), cesium carbonate (1.14 g, 3.48 mmol), and potassium selenocyanate (241 mg, 1.67 mmol) were added to the flask. The flask was purged with nitrogen and N,N-dimethylformamide (4.0 mL) was added to obtain a turbid solution. The reaction mixture was stirred and heated to 100° C. The reaction was maintained at that temperature for 1.5 h. The solution was cooled and the workup was performed using the general procedure. The product was purified using 25% ethyl acetate in hexanes to obtain 2-allylbenzo[d][1,2]selenazol-3(2H)- one (506e). Yield 39% (90 mg); silica gel TLC $R_f$=0.28 (3:7 ethyl acetate-hexanes); mass spectrum (ESIMS), m/z=261.9 (M+23)$^+$, $C_{10}H_9NOSe$ requires 261.97 (M+23)$^+$; $^1HNMR$ (600 MHz, CDCl$_3$) δ 8.07 (d, J=7.70, 1H), 7.64 (d, J=8.07, 1H), 7.60 (t, J=8.07, 1H), 5.78 (m, 1H), 5.78 (m, 1H), 5.39 (dd, J=17.06, J=1.28, 1H), 5.33 (dd, J=10.09, J=0.92, 1H), 4.49 (d, J=6.42, 2H).

Example 6: 2-(cyclohexylmethyl)benzo[d][1,2]selenazol-3(2H)-one (506f)

N-(cyclohexylmethyl)-2-iodobenzamide (200 mg, 0.58 mmol) was taken into a 50.0 mL round bottom flask. Copper(I) iodide (110 mg, 0.58 mmol), 1,10-phenanthroline (105 mg, 0.58 mmol), cesium carbonate (474 mg, 1.45 mmol), and potassium selenocyanate (101 mg, 0.70 mmol) were added to the flask. The flask was purged with nitrogen and N,N-dimethylformamide (4.0 mL) was added to obtain a turbid solution. The reaction mixture was stirred and heated to 100° C. The reaction was maintained at that temperature for 1.5 h. The solution was cooled and the workup was performed using general procedure. The product was purified using 20% ethyl acetate in hexanes to obtain 2-(cyclohexylmethyl)benzo[d][1,2]selenazol-3(2H)-one (506f). Yield 63% (110 mg); silica gel TLC $R_f$=0.59 (1:1 ethyl acetate-hexanes); mass spectrum (ESIMS), m/z=318.04 (M+23)$^+$, $C_{14}H_{17}NOSe$ requires 318.03 (M+23)$^+$; $^1H$ NMR (600 MHz, CDCl$_3$) δ 8.06 (d, J=7.70, 1H), 7.63 (d, J=7.7, 1H), 7.59 (m, 1H), 7.43 (m, 1H), 3.72 (d, J=6.92, 2H), 1.78-1.87 (m, 6H), 1.26-1.20 (M, 5H).

Example 7: 2-(4-fluorophenyl)benzo[d][1,2]selenazol-3(2H)-one (506g)

N-(4-fluorophenyl)-2-iodobenzamide (400 mg, 1.17 mmol) was taken into a 50.0 mL round bottom flask. Copper(I) iodide (335 mg, 1.76 mmol), 1,10-phenanthroline (317 mg, 1.79 mmol), cesium carbonate (996 mg, 2.93 mmol), and potassium selenocyanate (203 mg, 1.40 mmol) were added to the flask. The flask was purged with nitrogen and N,N-dimethylformamide (4.0 mL) was added to obtain a turbid solution. The reaction mixture was stirred and heated to 100° C. The reaction was maintained at that temperature for 1 h. The solution was cooled and the workup was performed using the general procedure. The product was purified using 20% ethyl acetate in hexanes to obtain 2-(4-fluorophenyl)benzo[d][1,2]selenazol-3(2H)-one (506g). Yield 52% (180 mg); silica gel TLC $R_f$=0.15 (3:7 ethyl acetate-hexanes); mass spectrum (ESIMS), m/z=315.96 (M+23)$^+$, $C_{13}H_8FNOSe$ requires 315.9653 (M+23)$^+$; $^1H$ NMR (600 MHz, CDCl$_3$) δ 8.13 (d, J=7.70, 1H), 7.68-7.67 (m, 2H), 7.60-7.57 (m, 2H), 7.51-7.49 (m, 1H).

Example 8: 2-(2-fluorophenyl)benzo[d][1,2]selenazol-3(2H)-one (506h)

N-(2-fluorophenyl)-2-iodobenzamide (400 mg, 1.17 mmol) was taken into a 50.0 mL round bottom flask. Copper(I) iodide (335 mg, 1.76 mmol), 1,10-phenanthroline (317 mg, 1.79 mmol), cesium carbonate (995 mg, 2.93 mmol), and potassium selenocyanate (203 mg, 1.40 mmol) were added to the flask. The flask was purged with nitrogen and N,N-dimethylformamide (4.0 mL) was added to obtain a turbid solution. The reaction mixture was stirred and heated to 100° C. The reaction was maintained at that temperature for 1 h. The solution was cooled and the workup was performed using the general procedure. The product was purified using 20% ethyl acetate in hexanes to obtain 2-(2-fluorophenyl)benzo[d][1,2]selenazol-3(2H)-one (506h). Yield 35% (120 mg); silica gel TLC $R_f$=0.24 (3:7 ethyl acetate-hexanes); mass spectrum (ESIMS), m/z=315.96 (M+23)$^+$, $C_{13}H_8FNOSe$ requires 315.9653 (M+23)$^+$; $^1H$ NMR (600 MHz, CDCl$_3$) δ 7.55-7.52 (m, 1H), 7.51-7.48 (m, 1H), 7.41-7.37 (m, 1H), 7.26-7.22 (m, 1H).

Example 9: 2-(4-azidophenyl)benzo[d][1,2]selenazol-3(2H)-one (506i)

N-(4-azidophenyl)-2-iodobenzamide (500 mg, 1.37 mmol) was taken into a 50.0 mL round bottom flask. Copper(I) iodide (262 mg, 1.37 mmol), 1,10-phenanthroline (247 mg, 1.37 mmol), cesium carbonate (1.12 g, 3.43 mmol), and potassium selenocyanate (237 mg, 1.40 mmol) were added to the flask. The flask was purged with nitrogen and N,N-dimethylformamide (4.0 mL) was added to obtain a turbid solution. The reaction mixture was stirred and heated to 100° C. The reaction was maintained at that temperature for 1 h. The solution was cooled and the workup was performed using the general procedure. The product was purified using 20% ethyl acetate in hexanes to obtain 2-(4-azidophenyl)benzo[d][1,2]selenazol-3(2H)-one (506i). Yield 20% (90 mg); silica gel TLC $R_f$=0.24 (3:7 ethyl acetate-hexanes); mp 169-170° C.; $^1H$ NMR (600 MHz, CDCl$_3$) δ 8.14 (td, J=0.9, 7.9 Hz, 1H), 7.71-7.67 (m, 2H), 7.66-7.63 (m, J=8.8 Hz, 2H), 7.51 (ddd, J=3.7, 4.5, 7.9 Hz, 1H), 7.14-7.09 (m, J=8.8 Hz, 2H); $^{13}C$ NMR (150.2 MHz, CDCl$_3$) δ 165.8, 138.4, 137.4, 135.9, 132.7, 129.5, 127.2, 127.0, 126.7, 123.8, 119.8; HRMS (ESI-TOF) m/z: [M+Na]+ Calcd for $C_{13}H_8N_4OSeNa$ 338.9756; Found 338.9763.mass spectrum (ESIMS), m/z=338.97 (M+23)$^+$, $C_{13}H_8N_4OSe$ requires 338.9761 (M+23)$^+$.

Example 10: 2-(Tert-Butyl)benzo[d][1,2]selenazol-3(2H)-one (506k)

N-(tert-Butyl)-2-iodobenzamide (200.0 mg, 0.66 mmol), copper(I) iodide (126 mg, 0.66 mmol), 1,10-phenanthroline (119 mg, 0.66 mmol), cesium carbonate (538 mg, 1.65 mmol), potassium selenocyanate (114 mg, 0.79 mmol), and N,N-dimethylmethanamide (2.0 mL), 1 h, 90° C. After flash column chromatography on silica gel using 20% ethyl acetate in hexanes as mobile phase, pure product 2-(tert-butyl)benzo[d][1,2]selenazol-3(2H)-one (506k) was obtained. Yield 75% (125 mg), white solid; silica gel TLC Rf=0.43 (3:7 ethyl acetate-hexanes); mp 137-139° C.; $^1H$ NMR (600 MHz, CDCl$_3$) δ 7.97 (td, J=1.1, 7.8 Hz, 1H), 7.56-7.60 (m, 2H), 7.40 (ddd, J=1.7, 6.3, 8.0 Hz, 1H), 1.69 (s, 9H); $^{13}C$ NMR (151 MHz, CDCl$_3$) δ 167.1, 137.0, 131.7, 130.2, 128.5, 126.1, 123.3, 59.0, 29.2; HRMS (ESI-TOF) m/z: [M+H]+ Calcd for $C_{11}H_{14}NOSe$ 256.0235; Found 256.0233.

Example 11: 2-((3R,5S)-Adamantan-1-yl)benzo[d][1,2]-selenazol-3(2H)-one (506j)

N-((3R,5S)-Adamantan-1-yl)-2-iodobenzamide (400.0 mg, 1.04 mmol), copper(I) iodide (200 mg, 1.04 mmol), 1,10-phenanthroline (189 mg, 1.04 mmol), cesium carbonate (855 mg, 2.62 mmol), potassium selenocyanate (182 mg, 1.26 mmol), and N,N-dimethylmethanamide (4.0 mL), 1 h, 90° C. After flash column chromatography on silica gel using 20% ethyl acetate in hexanes as mobile phase, pure product 2-((3R,5S)-adamantan-1-yl)benzo[d][1,2]selenazol-3(2H)-one (506j) was obtained. Yield 72% (250 mg), white solid; silica gel TLC Rf=0.51 (3:7 ethyl acetate-hexanes); mp 215-217° C.; $^1$H NMR (600 MHz, CDCl$_3$) δ 7.97 (d, J=7.9 Hz, 1H), 7.59-7.58 (m, 1H), 7.57-7.54 (m, 1H), 7.41-7.38 (m, 1H), 2.43 (d, J=2.4 Hz, 6H), 2.19 (s, 3H), 1.81-1.79 (m, 3H), 1.75-1.73 (m, 3H); $^{13}$C NMR (150.2 MHz, CDCl$_3$) δ 166.8, 137.5, 131.5, 130.5, 128.5, 126.0, 123.4, 60.1, 41.7, 36.4, 30.3; HRMS (ESI-TOF) m/z: [M+H]+ Calcd for C$_{17}$H$_{20}$NOSe 334.0705; Found 334.0722.

Example 12: 2-Cyclopentylbenzo[d][1,2]selenazol-3 (2H)-one (506l)

N-Cyclopentyl-2-iodobenzamide (350.0 mg, 1.11 mmol), copper(I) iodide (211.6 mg, 1.11 mmol), 1,10-phenanthroline (200.2 mg, 1.11 mmol), cesium carbonate (905 mg, 2.77 mmol), potassium selenocyanate (192.1 mg, 1.33 mmol), and N,N-dimethylmethanamide (3.0 mL), 1 h, 90° C. After flash column chromatography on silica gel using 20% ethyl acetate in hexanes as mobile phase, pure product 2-cyclopentylbenzo[d][1,2]selenazol-3(2H)-one (506l) was obtained. Yield 78% (232 mg), white solid; silica gel TLC Rf=0.23 (3:7 ethyl acetate-hexanes); mp 119-120° C.; $^1$H NMR (600 MHz, CDCl$_3$) δ 8.03-8.05 (m, 1H), 7.62-7.64 (m, 1H), 7.57 (dt, J=1.4, 7.6 Hz, 1H), 7.42 (ddd, J=1.0, 7.1, 7.9 Hz, 1H), 4.98 (quin, J=7.8 Hz, 1H), 2.17-2.27 (m, J=1.6, 2.8 Hz, 2H), 1.81-1.90 (m, 1H), 1.69-1.75 (m, 2H), 1.61-1.68 (m, 2H); $^{13}$C NMR (151 MHz, CDCl$_3$) δ 167.2, 137.5, 133.2, 131.7, 128.6, 126.2, 123.8, 55.9, 33.5, 24.2; HRMS (ESI-TOF) m/z: [M+Na]+ Calcd for C$_{12}$H$_{13}$NOSeNa 290.0055; Found 290.0058.

Example 13: 2-Cyclohexylbenzo[d][1,2]selenazol-3 (2H)-one (506m)

N-Cyclohexyl-2-iodobenzamide (400.0 mg, 1.21 mmol), copper(I) iodide (231.6 mg, 1.22 mmol), 1,10-phenanthroline (219.1 mg, 1.21 mmol), cesium carbonate (990.3 mg, 3.04 mmol), potassium selenocyanate (210.2 mg, 1.45 mmol), and N,N-dimethylmethanamide (4.0 mL), 1 h, 90° C. After flash column chromatography on silica gel using 20% ethyl acetate in hexanes as mobile phase, pure product 2-cyclohexylbenzo[d][1,2]selenazol-3(2H)-one (506m) was obtained. Yield 85% (290 mg), white solid; silica gel TLC Rf=0.27 (3:7 ethyl acetate-hexanes); mp 157-158° C.; $^1$H NMR (600 MHz, CDCl$_3$) δ 8.10-7.99 (m, 1H), 7.64 (d, J=7.9 Hz, 1H), 7.57 (s, 1H), 7.42 (s, 1H), 4.53-4.45 (m, 1H), 2.11 (dd, J=2.0, 12.7 Hz, 2H), 1.87 (d, J=13.9 Hz, 2H), 1.77-1.70 (m, 1H), 1.50 (d, J=13.0 Hz, 2H), 1.40 (dd, J=3.7, 11.7 Hz, 2H), 1.25-1.16 (m, 1H); $^{13}$C NMR (151 MHz, CDCl$_3$) δ 166.6, 137.9, 137.9, 131.7, 128.8, 126.2, 124.0, 53.8, 34.4, 25.6. HRMS (ESI-TOF) m/z: [M+H]+ Calcd for C$_{13}$H$_{16}$NOSe 282.0392; Found 282.0392.

Example 14: 2-Isobutylbenzo[d][1,2]-selenazol-3 (2H)-one (506n)

2-Iodo-N-isobutylbenzamide (200 mg, 0.66 mmol), copper(I) iodide (126 mg, 0.66 mmol), cesium carbonate (258 mg, 0.79 mmol), potassium selenocyanate (237 mg, 1.65 mmol), and acetonitrile (3.0 mL), 32 h, 0° C. to room temperature. Purified by flash column chromatography on silica gel (30% ethyl acetate-hexane) to obtain pure 2-isobutylbenzo[d][1,2]selenazol-3(2H)-one (506n). Yield 85% (143.8 mg), white solid; silica gel TLC Rf=0.39 (3:7 ethyl acetate-hexanes); mp 114-116° C.; $^1$H NMR (600 MHz, CDCl$_3$) δ 8.06 (d, J=7.6 Hz, 1H), 7.62-7.66 (m, 1H), 7.57-7.62 (m, 1H), 7.43 (t, J=7.3 Hz, 1H), 3.70 (d, J=7.3 Hz, 2H), 2.05 (quind, J=6.8, 13.7 Hz, 1H), 1.00 (d, J=6.6 Hz, 6H); $^{13}$C NMR (151 MHz, CDCl$_3$) δ 167.5, 137.9, 132.0, 129.0, 127.6, 126.3, 124.0, 52.2, 30.1, 20.1; HRMS (ESI-MS) m/z: [M+Na]+ Calcd for C$_{11}$H$_{14}$NOSe 256.0235; Found 256.0240.

Example 15: 2-(Pyridin-2-yl)benzo[d][1,2]selenazol-3(2H)-one (506o)

2-Iodo-N-(pyridine-2-yl)benzamide (100 mg, 0.3085 mmol) was taken into 50.0 mL round bottom flask. Copper (I) iodide (93 mg, 0.4883 mmol), 1,10-phenanthroline (58 mg, 0.3218 mmol), cesium carbonate (235 mg, 0.721 mmol), and potassium selenocyanate (53 mg, 0.3702 mmol) were added to the flask. The flask was purged with nitrogen and N,N-dimethylformamide (5.0 mL) was added to obtain a turbid solution. The reaction mixture was stirred and heated to 100° C. The reaction was maintained at that temperature for 12 h. The solution was cooled and the workup was performed using general procedure. The product was purified using 20% ethyl acetate in hexanes to obtain 2-(pyridin-2-yl)benzo[d][1,2]selenazol-3(2H)-one (506o). Yield 35% (25 mg); silica gel TLC Rf=0.35 (3:7 ethyl acetate-hexanes); $^1$H NMR (600 MHz, CDCl$_3$) δ 8.73-8.72 (m, 1H), 8.34-8.08 (m, 1H), 8.07 (m, 1H), 7.783-7.781 (m, 1H), 7.778-7.682 (m, 1H), 7.670-7.435 (m, 1H), 7.132-7.111 (m, 1H).

Example 16: 2-(Pyridin-3-yl)benzo[d][1,2]selenazol-3(2H)-one (506p)

2-Iodo-N-(pyridine-3-yl)benzamide (100 mg, 0.3085 mmol) was taken into 50.0 mL round bottom flask. Copper (I) iodide (58.7 mg, 0.3085 mmol), 1,10-phenanthroline (56 mg, 0.3085 mmol), cesium carbonate (251 mg, 0.7712 mmol), and potassium selenocyanate (53 mg, 0.3702 mmol) were added to the flask. The flask was purged with nitrogen and N,N-dimethylformamide (5.0 mL) was added to obtain a turbid solution. The reaction mixture was stirred and heated to 100° C. The reaction was maintained at that temperature for 12 h. The solution was cooled and the workup was performed using general procedure. The product was purified using 20% ethyl acetate in hexanes to obtain 2-(pyridin-3-yl)benzo[d][1,2]selenazol-3(2H)-one (506p). Yield 79.76% (67 mg); silica gel TLC Rf=0.1 (1:1 ethyl acetate-hexanes); $^1$H NMR (600 MHz, CDCl$_3$) δ 8.14-8.16 (m, 2H), 7.70-7.71 (m, 2H), 7.50-7.52 (m, 1H), 7.39-7.41 (m, 1H).

Example 17: 2-(Quinolin-2-yl)benzo[d][1,2]selenazol-3(2H)-one (506q)

2-Iodo-N-(quinolin-2-yl)benzamide (100 mg, 0.267 mmol) was taken into 50.0 mL round bottom flask. Copper (I) iodide (50.85 mg, 0.266 mmol), 1,10-phenanthroline (48.12 mg, 0.267 mmol), cesium carbonate (217.48 mg, 0.667 mmol), and potassium selenocyanate (46.16 mg, 0.3203 mmol) were added to the flask. The flask was purged with nitrogen and N,N-dimethylformamide (5.0 mL) was added to obtain a turbid solution. The reaction mixture was stirred and heated to 100° C. The reaction was maintained at that temperature for 12 h. The solution was cooled and the workup was performed using the general procedure. A solid formed on the addition of ethyl acetate and the solid crystalline solid was removed via filtration and recrystallized obtain 2-(quinolin-2-yl)benzo[d][1,2]selenazol-3(2H)-one (506q). Yield 48.33% (42 mg); silica gel TLC Rf=0.75 (1:1 ethyl acetate-hexanes); $^1$H NMR (600 MHz, CDCl$_3$) δ 8.91 (d, 1H), 8.21 (d, 1H), 8.10 (d, 1H), 7.97 (d, 1H), 7.83 (d, 1H), 7.72 (t, 1H), 7.66 (m, 2H), 7.49 (t, 1H), 7.45 (m, 1H).

Example 18: 2-(Furan-2-ylmethyl)benzo[d][1,2]selenazol-3(2H)-one (506r)

N-(furan-2-ylmethyl)-2-iodobenzamide (100 mg, 0.305 mmol) was taken into 50.0 mL round bottom flask. Copper (I) iodide (58 mg, 0.305 mmol), 1,10-phenanthroline (54.9 mg, 0.305 mmol), cesium carbonate (248 mg, 0.7625 mmol), and potassium selenocyanate (52 mg, 0.367 mmol) were added to the flask. The flask was purged with nitrogen and N,N-dimethylformamide (7.0 mL) was added to obtain a turbid solution. The reaction mixture was stirred and heated to 100° C. The reaction was maintained at that temperature for 12 h. The solution was cooled and the workup was performed using general procedure. The product was purified using 20% ethyl acetate in hexanes to obtain 2-(furan-2-ylmethyl)benzo[d][1,2]selenazol-3(2H)-one (506r). Yield 67% (57 mg); silica gel TLC Rf=0.56 (1:1 ethyl acetate-hexanes); $^1$H NMR (600 MHz, CDCl$_3$) δ 8.06-8.08 (m, 1H), 7.58-7.59 (m, 2H), 7.41-7.44 (m, 2H), 6.43-6.37 (m, 1H), 5.03 (s, 2H).

Example 19: 2-(Thiophen-2-ylmethyl)benzo[d][1,2]selenazol-3(2H)-one (506s)

N-(thiophen-2-ylmethyl)-2-iodobenzamide (100 mg, 0.291 mmol) was taken into 50.0 mL round bottom flask. Copper(I) iodide (55 mg, 0.291 mmol), 1,10-phenanthroline (52 mg, 0.291 mmol), cesium carbonate (237 mg, 0.7275 mmol), and potassium selenocyanate (50 mg, 0.350 mmol) were added to the flask. The flask was purged with nitrogen and N,N-dimethylformamide (7.0 mL) was added to obtain a turbid solution. The reaction mixture was stirred and heated to 100° C. The reaction was maintained at that temperature for 12 h. The solution was cooled and the workup was performed using general procedure. The product was purified using 20% ethyl acetate in hexanes to obtain 2-(thiophen-2-ylmethyl)benzo[d][1,2]selenazol-3(2H)-one (506s). Yield 32.35% (70 mg); silica gel TLC Rf=0.63 (1:1 ethyl acetate-hexanes); $^1$H NMR (600 MHz, CDCl$_3$) δ 8.08-8.06 (m, 1H), 7.58-7.57 (m, 2H), 7.44-7.41 (m, 1H), 7.33-7.31 (m, 1H) 7.14-7.13 (m, 1H), 7.01-7.00 (m, 1H).

Example 20: 2-(Tetrahydro-2H-pyran-4-yl)benzo[d][1,2]selenazol-3(2H)-one (506t)

2-Iodo-N-(tetrahydro-2H-Pyran-4-yl)benzamide (612) (100 mg, 0.3019 mmol) was taken into 50.0 mL round bottom flask. Copper(I) iodide (57 mg, 0.299 mmol), 1,10-phenanthroline (54 mg, 0.298 mmol), cesium carbonate (246 mg, 0.764 mmol), and potassium selenocyanate (52 mg, 0.361 mmol) were added to the flask. The flask was purged with nitrogen and N,N-dimethylformamide (8.0 mL) was added to obtain a turbid solution. The reaction mixture was stirred and heated to 100° C. The reaction was maintained at that temperature for 12 h. The solution was cooled and the workup was performed using general procedure. The product was purified using 20% ethyl acetate in hexanes to obtain 2-(tetrahydro-2H-pyran-4-yl)benzo[d][1,2]selenazol-3(2H)-one (506t). Yield 88% (75 mg); silica gel TLC Rf=0.26 (1:1 ethyl acetate-hexanes); $^1$H NMR (600 MHz, CDCl$_3$) δ 8.056 (m, 1H), 7.657 (m, 1H), 7.592 (m, 1H), 7.435 (m, 1H), 4.08 (m, 2H), 3.582 (m, 2H), 2.026 (m, 2H), 1.789 (m, 2H).

FIGS. 26-31 show the $^1$H NMR spectra of compounds 506o-506t.

General Procedure for Synthesis of Benzamides (FIG. 16, Table 6)

Starting material (1 eq) was taken into a round bottom flask to which secondary amine (1.2 eq) was added. The flask with reaction mixture was purged with nitrogen and added solvent (dichloromethane). Triethylamine (1 eq) was added to the reaction mixture. The reaction mixture was stirred at room temperature for 1-12 hrs. The solution was concentrated under reduced pressure to obtain crude product. The crude product was purified by column chromatography on silica gel to obtain pure benzamides derivatives using ethyl acetate in hexanes as the mobile phase.

Example 21: 2-Iodo-N-(pyridin-2-yl)benzamide (600)

2-Iodobenzoyl chloride (300 mg, 1.126 mmol) was taken into 50.0 mL round bottom flask. Pyridin-2-amine (130 mg, 1.35 mmol) added to the flask. The flask was purged with nitrogen and dichloromethane (5.0 mL) was added to obtain a clear solution. Triethylamine (0.156 mL, 1.126 mmol) was added to the reaction mixture. The reaction mixture was stirred and kept at room temperature. The reaction was maintained in this state for 12 h. The solution was concentrated under vacuum. The product was purified by column chromatography using 25% ethyl acetate in hexanes to obtain 2-iodo-N-(pyridin-2-yl)benzamide (600). Yield 79.20% (289 mg); silica gel TLC Rf=0.15 (1:1 ethyl acetate-hexanes); $^1$H NMR (600 MHz, CDCl$_3$) δ 8.47 (s, 1H), 7.78-7.77 (m, 2H), 7.60-7.58 (m, 2H), 7.33-7.30 (m, 1H), 7.21-7.20 (m, 1H), 7.02-7.01 (m, 1H).

Example 22: 2-Iodo-N-(pyridine-3yl)benzamide (602)

2-Iodobenzoyl chloride (300 mg, 1.126 mmol) was taken into 50.0 mL round bottom flask. Pyridin-3-amine (140 mg, 1.49 mmol) added to the flask. The flask was purged with nitrogen and dichloromethane (5.0 mL) was added to obtain a clear solution. Triethylamine (0.156 mL, 1.126 mmol) was added to the reaction mixture. The reaction mixture was stirred and kept at room temperature. The reaction was maintained in this state for 12 h. The solution was concentrated under vacuum. The product was purified by column chromatography using 25% ethyl acetate in hexanes to obtain 2-iodo-N-(pyridine-3-yl)benzamide (602). Yield 90.10% (338 mg); silica gel TLC Rf=0.15 (1:1 ethyl acetate-hexanes); $^1$H NMR (600 MHz, CDCl$_3$) δ 8.65 (s, 1H), 8.39-8.34 (m, 2H), 7.95-7.94 (m, 1H), 7.57-7.55 (m, 1H), 7.49-7.46 (m, 1H), 7.37-7.35 (m, 1H), 7.21-7.18 (m, 1H).

Example 23: 2-Iodo-N-(pyridin-4-yl)benzamide (604)

2-Iodobenzoyl chloride (300 mg, 1.126 mmol) was taken into 50.0 mL round bottom flask. Pyridin-4-amine (172 mg, 1.49 mmol) added to the flask. The flask was purged with nitrogen and dichloromethane (5.0 mL) was added to obtain a clear solution. Triethylamine (0.156 mL, 1.126 mmol) was added to the reaction mixture. The reaction mixture was stirred and kept at room temperature. The reaction was maintained in this state for 12 h. The solution was concentrated under vacuum. The product was purified by column chromatography using 25% ethyl acetate in hexanes to obtain 2-iodo-N-(pyridine-4-yl)benzamide (604). Yield 94.5% (345 mg); silica gel TLC Rf=0.15 (1:1 ethyl acetate-hexanes); $^1$H NMR (600 MHz, CDCl$_3$) δ 8.56 (s, 2H), 7.952-7.951 (m, 2H), 7.93 (s, 2H), 7.93-7.55 (m, 1H), 7.54-7.46 (m, 1H), 7.22-7.19 (m, 1H).

Example 24: 2-Iodo-N-(quinolin-2-yl)benzamide (606)

2-Iodobenzoyl chloride (300 mg, 1.126 mmol) was taken into 50.0 mL round bottom flask. Quinolin-2-amine (195 mg, 1.35 mmol) added to the flask. The flask was purged with nitrogen and dichloromethane (5.0 mL) was added to obtain a clear solution. Triethylamine (0.156 mL, 1.126 mmol) was added to the reaction mixture. The reaction mixture was stirred and kept at room temperature. The reaction was maintained in this state for 12 h. The solution was concentrated under vacuum. The product was purified by column chromatography using 25% ethyl acetate in hexanes to obtain 2-iodo-N-(quinolin-2-yl)benzamide (606). Yield 83.78% (0.353 mg); silica gel TLC Rf=0.25 (1:1 ethyl acetate-hexanes); $^1$H NMR (600 MHz, CDCl$_3$) δ 8.70 (s, 1H), 8.27-8.25 (m, 1H), 7.91-7.90 (m, 1H), 7.82-7.79 (m, 3H), 7.69-7.65 (m, 1H), 7.56-7.54 (m, 1H), 7.49-7.46 (m, 1H), 7.41-7.39 (m, 1H), 7.14-7.11 (m, 1H).

Example 25: 2-Iodo-N-(furan-2-ylmethyl)benzamide (608)

2-Iodobenzoyl chloride (300 mg, 1.126 mmol) was taken into 50.0 mL round bottom flask. The flask was purged with nitrogen and dichloromethane (5.0 mL) was added to obtain a clear solution. Furan-2-ylmethanamine (0.119 mL, 1.23 mmol) was added to the flask. Triethylamine (0.156 mL, 1.126 mmol) was added to the reaction mixture. The reaction mixture was stirred and kept at room temperature. The reaction was maintained in this state for 12 h. The solution was concentrated under vacuum. The product was purified by column chromatography using 25% ethyl acetate in hexanes to obtain 2-iodo-N-(furan-2-ylmethyl)benzamide (608). Yield 99.18% (0.365 mg); silica gel TLC Rf=0.16 (1:1 ethyl acetate-hexanes); $^1$H NMR (600 MHz, CDCl$_3$) δ 7.87-7.86 (m, 1H), 7.43-7.37 (m, 3H), 7.12-7.09 (m, 1H), 6.36 (s, 2H), 6.05 (s, 1H), 4.66-4.65 (m, 2H).

Example 26: 2-Iodo-N-(thiophen-2-ylmethyl)benzamide (610)

2-Iodobenzoyl chloride (300 mg, 1.126 mmol) was taken into 50.0 mL round bottom flask. The flask was purged with nitrogen and dichloromethane (5.0 mL) was added to obtain a clear solution. Thiophen-2-ylmethanamine (0.139 mL, 1.35 mmol) added to the flask. Triethylamine (0.156 mL, 1.126 mmol) was added to the reaction mixture. The reaction mixture was stirred and kept at room temperature. The reaction was maintained in this state for 12 h. The solution was concentrated under vacuum. The product was purified by column chromatography using 25% ethyl acetate in hexanes to obtain 2-iodo-N-(thiophen-2-ylmethyl)benzamide (610). Yield 77.20% (0.298 mg); silica gel TLC Rf=0.67 (1:1 ethyl acetate-hexanes); $^1$H NMR (600 MHz, CDCl$_3$) δ 7.87-7.86 (m, 1H), 7.42-7.38 (m, 2H), 7.11-7.09 (m, 2H), 6.99-6.98 (m, 2H), 6.05 (s, 1H), 4.84-4.83 (m, 2H).

Example 27: 2-Iodo-N-(tetrahydro-2H-pyran-4-yl)benzamide (612)

2-Iodobenzoyl chloride (300 mg, 1.126 mmol) was taken into 50.0 mL round bottom flask. The flask was purged with nitrogen and dichloromethane (5.0 mL) was added to obtain a clear solution. Tetrahydro-2H-pyran-4-amine (0.140 mL, 1.35 mmol) added to the flask. Triethylamine (0.156 mL, 1.126 mmol) was added to the reaction mixture. The reaction mixture was stirred and kept at room temperature. The reaction was maintained in this state for 12 h. The solution was concentrated under vacuum. The product was purified by column chromatography using 25% ethyl acetate in hexanes to obtain 2-iodo-N-(tetrahydro-2H-pyran-4-yl)benzamide (612). Yield 86.44% (0.322 mg); silica gel TLC Rf=0.32 (1:1 ethyl acetate-hexanes); $^1$H NMR (600 MHz, CDCl$_3$) δ 7.86-7.85 (m, 1H), 7.43-7.37 (m, 2H), 7.12-7.09 (m, 1H), 4.27-4.21 (m, 1H), 4.02-3.99 (m, 2H), 3.56-3.52 (m, 2H), 2.09-2.06 (m, 2H), 1.64-1.59 (m, 2H).

Antimicrobial Activity

The synthesized compounds were shown to be active against clinical strains of Mycobacterium tuberculosis. The antimicrobial activity of these compounds was demonstrated by determining the minimum inhibitory concentration for the Mycobacterium tuberculosis H37Rv strain. All of the compounds from Examples 1-6 showed good MIC values, as displayed in Table A below.

TABLE A

Activity of compounds 506a-506f on Mycobacterium tuberculosis

| Compound Example No. | Strain Mtb | MIC µg/ml | MIC$_{50}$ µg/ml |
|---|---|---|---|
| 1 (506a) | H37Rv | 25 | 18.33 |
| 2 (506b) | H37Rv | 25 | 19.29 |
| 3 (506c) | H37Rv | 12.5 | 10.36 |
| 4 (506d) | H37Rv | 25 | 15.04 |
| 5 (506e) | H37Rv | 12.5 | 10.36 |
| 6 (506f) | H37Rv | 50 | 36.25 |
| Ebselen | H37Rv | 12.5 | 9.59 |

Figure 6A:
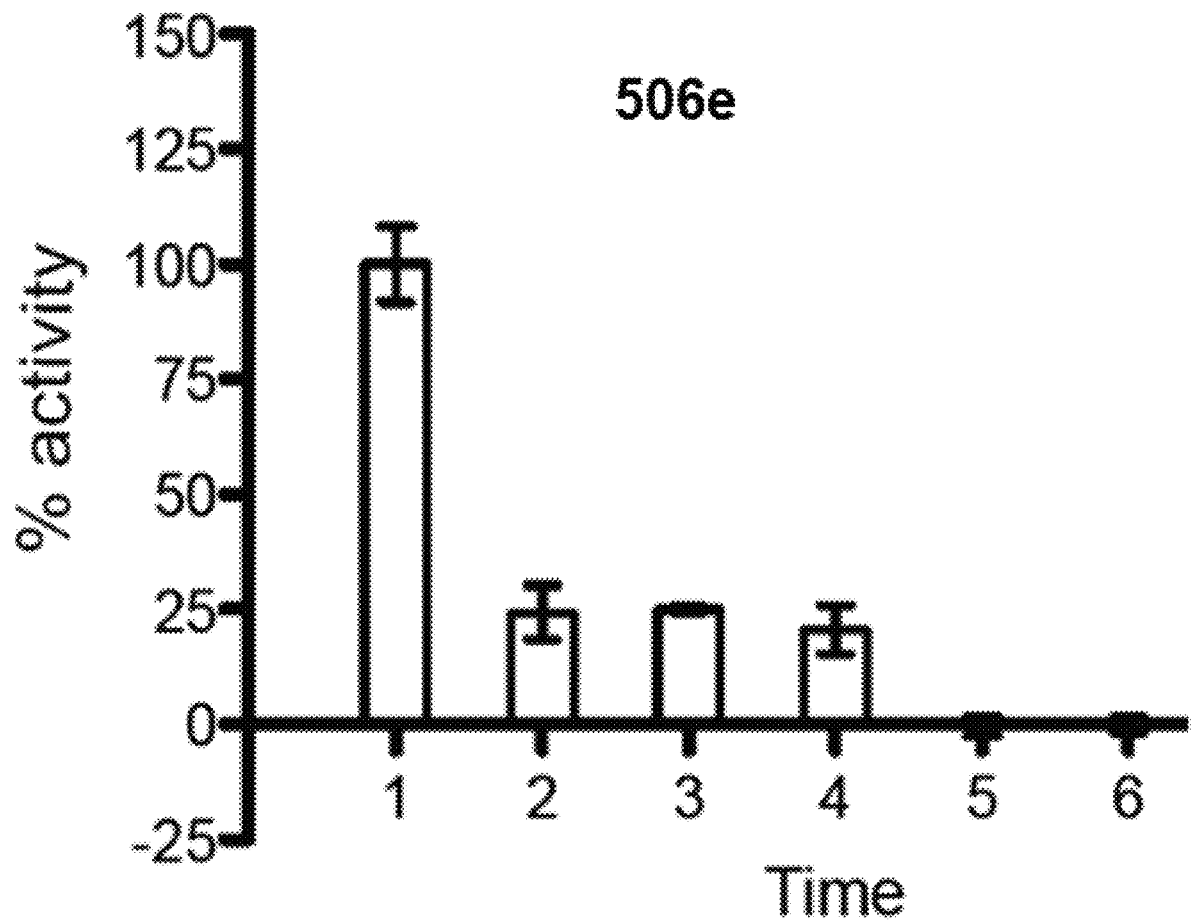
FIGS. 6A-6B: Activity of Ag85C modified by compounds 506e (FIG. 6A) and 506f (FIG. 6B) over time.
Figure 6B:
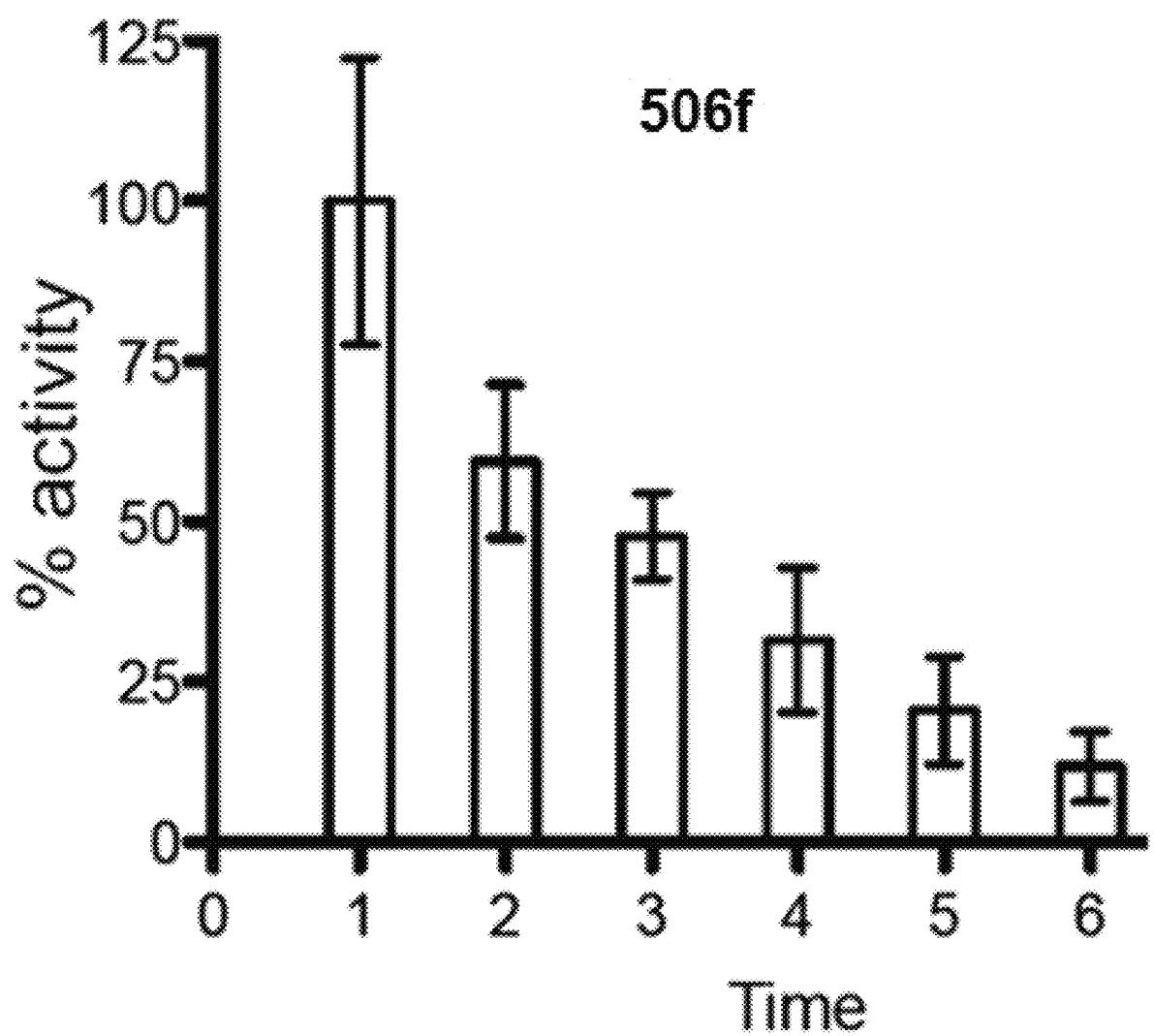

FIGS. 6A-6B show the activity of Ag85C modified by compounds 506e and 506f over time. As seen from these figures, both compounds 506e and 506f caused a decrease in the activity of Ag85C, indicating the compounds inhibit enzyme activity similar to ebselen.

In Vitro Characterization of Anti-Mycobacterial Activity

Compounds 506a-506n were evaluated for activity against mycobacteria. FIG. 7 shows Table 1, displaying a summary of the MICs under aerobic conditions for compounds 506a-506n. FIG. 8 shows Table 2, displaying a summary of the MICs against other disease relevant mycobacteria for compounds 506a-506n.

Compounds were solubilized in DMSO to a final concentration of 10 mM unless otherwise stated, aliquotted into matrix tubes and stored at −20° C. Assays were initiated within 7 days of solubilization. Compounds were dispensed from matrix tubes into mass spectrometer sample vials for assessing purity, solubility, fluorescence, aerobic MIC, and other disease-relevant mycobacteria MIC. Two-fold serial dilutions in DMSO were prepared from matrix tubes and reformatted into 96-well assay plates using MultiMek and BioMek 3000 liquid handlers.

The antimicrobial activity of compounds against Mycobacterium tuberculosis H37Rv grown under aerobic conditions was assessed by determining the minimum inhibitory concentration (MIC) of compound, i.e., the concentration required to prevent growth. The assay was based on measurement of growth in liquid medium of a fluorescent reporter strain of H37Rv where the readout is either optical density (OD) or fluorescence. The use of two readouts minimizes problems caused by compound precipitation or autofluoresence. A linear relationship between OD and fluorescence readout has been established justifying the use of fluorescence as a measure of bacterial growth. MICs generated from the OD are reported in the summary data in FIG. 7. The strain has been fully characterized and is equivalent to the parental strain in microbiological phenotypes and virulence.

Figure 9A:
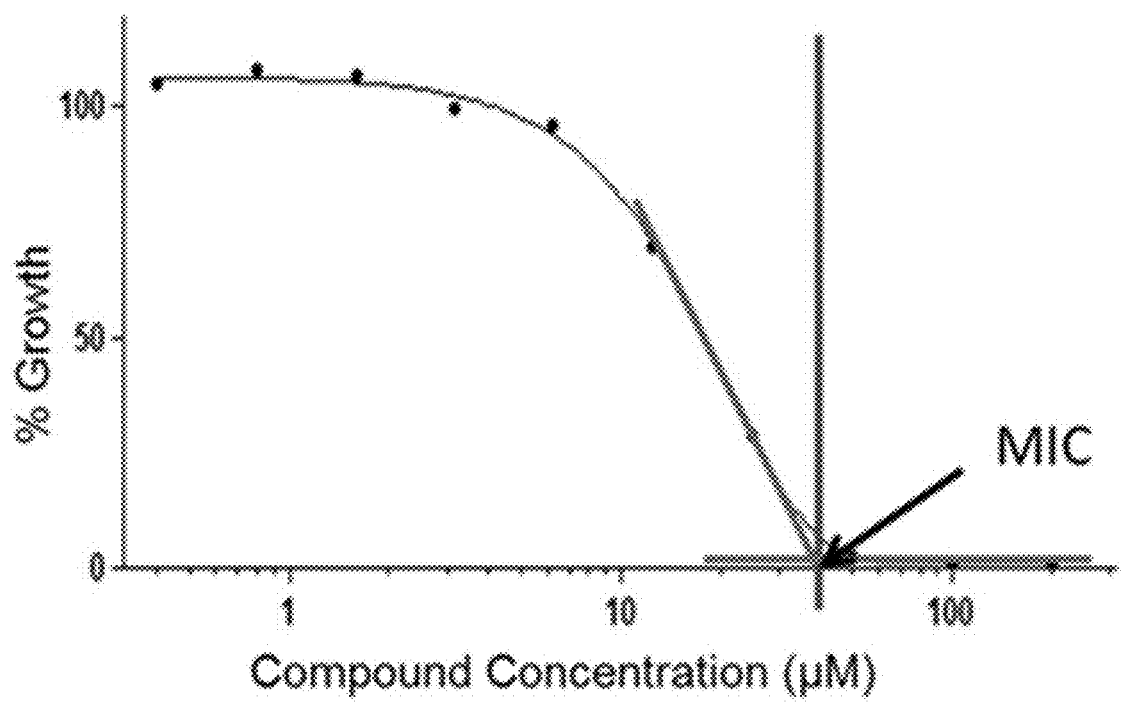
FIGS. 9A-9B: Dose response curves used to calculate MIC, $IC_{50}$, and $IC_{90}$. Data points obtained from a dose response growth inhibition assay were curve-fitted using the Gompertz model to calculate MIC (FIG. 9A), and the LEvenberg-Marquardt algorithm to calculate $IC_{50}$ and $IC_{90}$ (FIG. 9B). The MIC is the concentration at which complete inhibition of growth is seen and is derived from the point of inflection at which the curve meets the lower asymptote. $IC_{50}$ and $IC_{90}$ are points at which growth is inhibited by 50% and 90%, respectively. Orange line=MIC. Green line=$IC_{50}$. Blue line=$IC_{90}$.
Figure 9B:
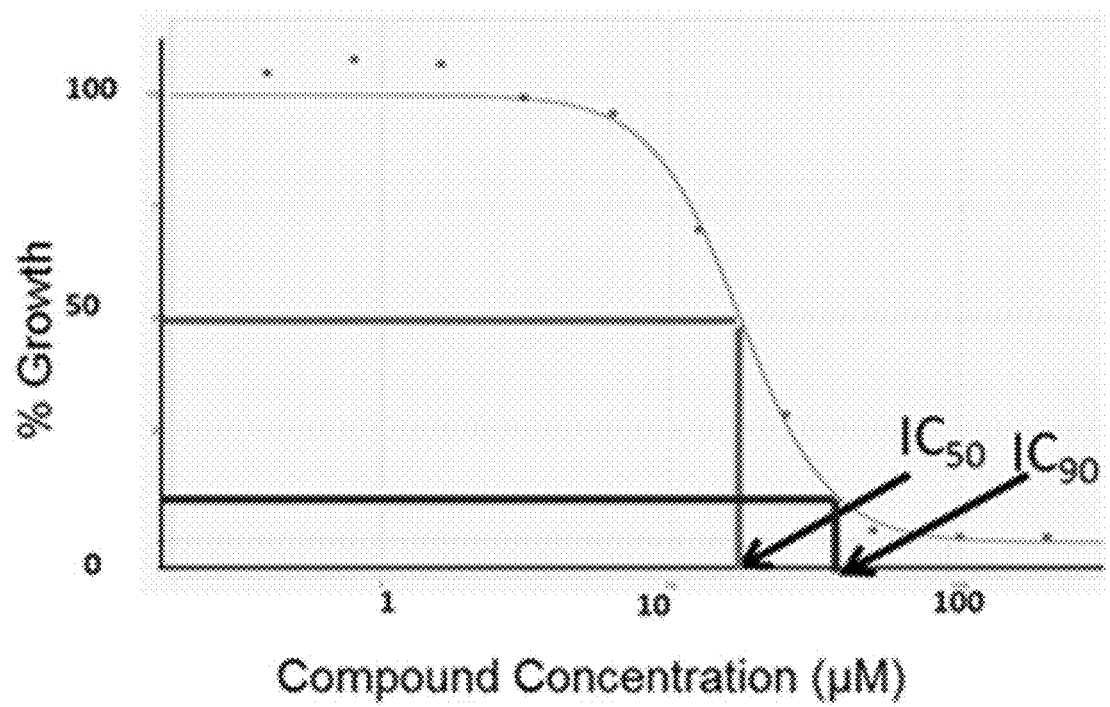

The MIC of compound was determined by measuring bacterial growth after 5 d in the presence of test compounds. Compounds were prepared as 10-point two-fold serial dilutions in DMSO and diluted into 7H9-Tw-OADC medium in 96-well plates with a final DMSO concentration of 2%. The highest concentration of compound was 200 M where compounds were soluble in DMSO at 10 mM. For compounds with limited solubility, the highest concentration was 50× less than the stock concentration, e.g., 100 μM for 5 mM DMSO stock, 20 M for 1 mM DMSO stock. For potent compounds, assays were repeated at lower starting concentrations. Each plate included assay controls for background (medium/DMSO only, no bacterial cells), zero growth (2 μM rifampicin), and maximum growth (DMSO only), as well as a rifampicin dose response curve. Plates were inoculated with $M.$ $tuberculosis$ and incubated for 5 days. Growth was measured by $OD_{590}$ and fluorescence (Ex 560/Em 590) using a BioTek™ Synergy H4 plate reader. Growth was calculated separately for $OD_{590}$ and RFU. To calculate the MIC, the dose response curve was plotted as % growth and fitted to the Gompertz model using GraphPad Prism 6. The MIC was defined as the minimum concentration at which growth was completely inhibited and was calculated from the inflection point of the fitted curve to the lower asymptote (FIG. 9A). In addition, dose response curves were generated using the Levenberg-Marquardt algorithm and the concentrations that resulted in 50% and 90% inhibition of growth were determined ($IC_{50}$ and $IC_{90}$ respectively) (FIG. 9B).

Figure 10A:
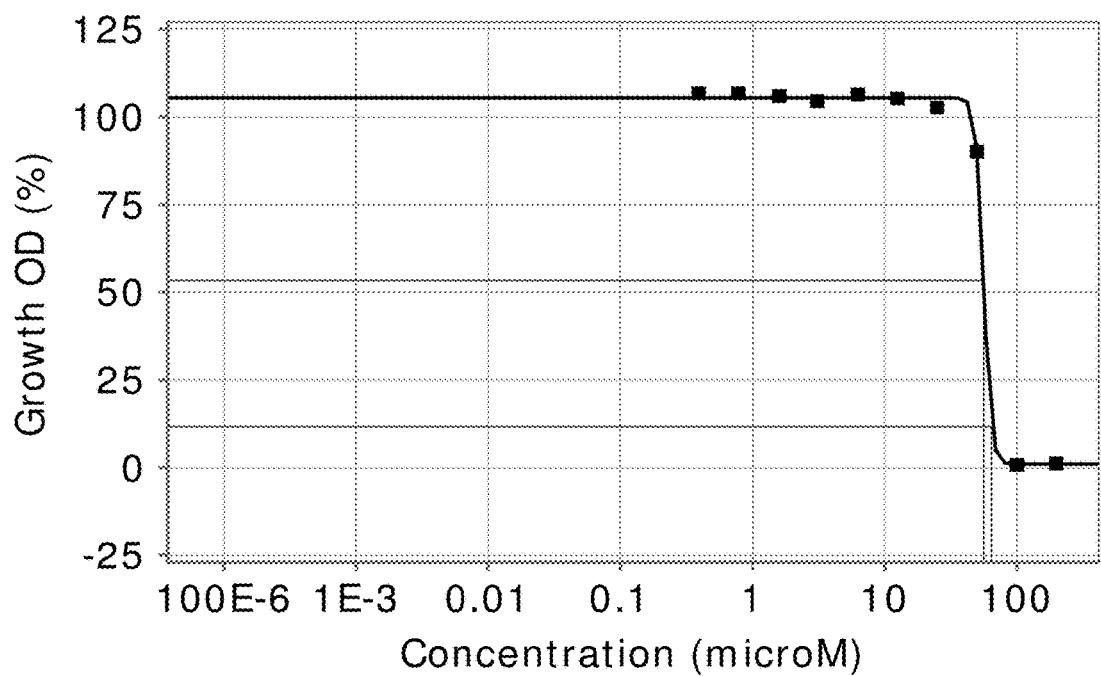
FIGS. 10A-10N: Dose-response curves for compounds 506a-506n against *Mycobacterium tuberculosis*.
Figure 10B:
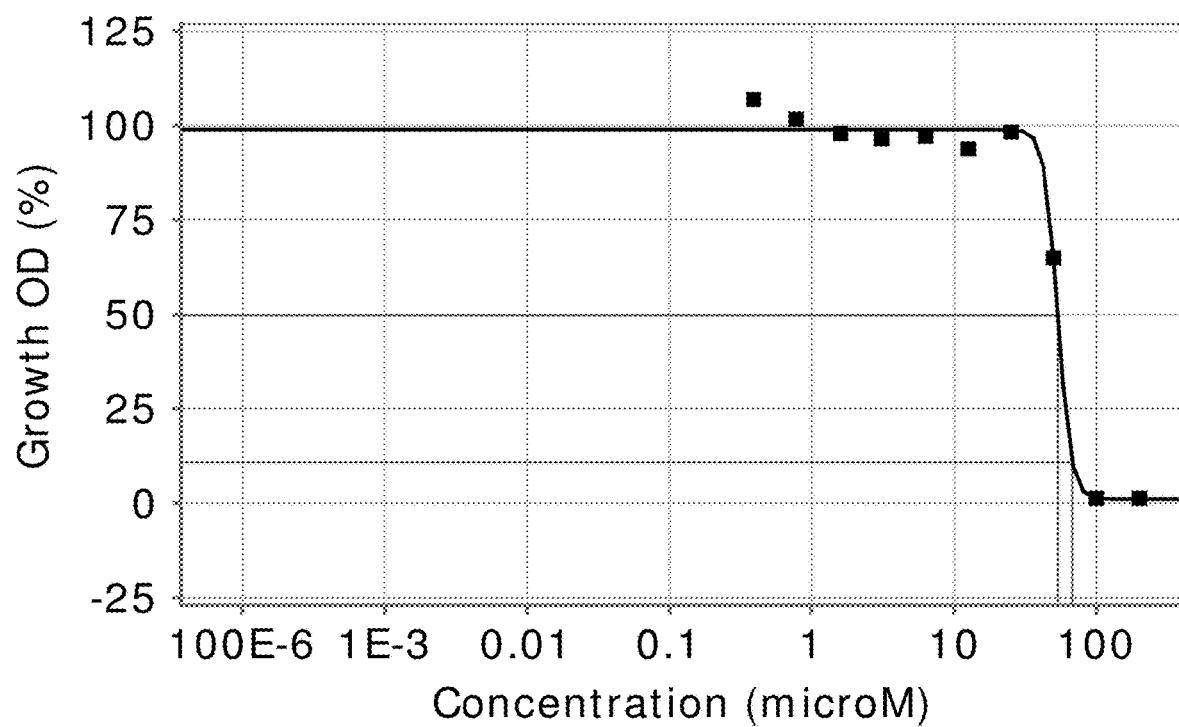
FIG. 10B shows the dose-response curve for compound 506c.
Figure 10C:
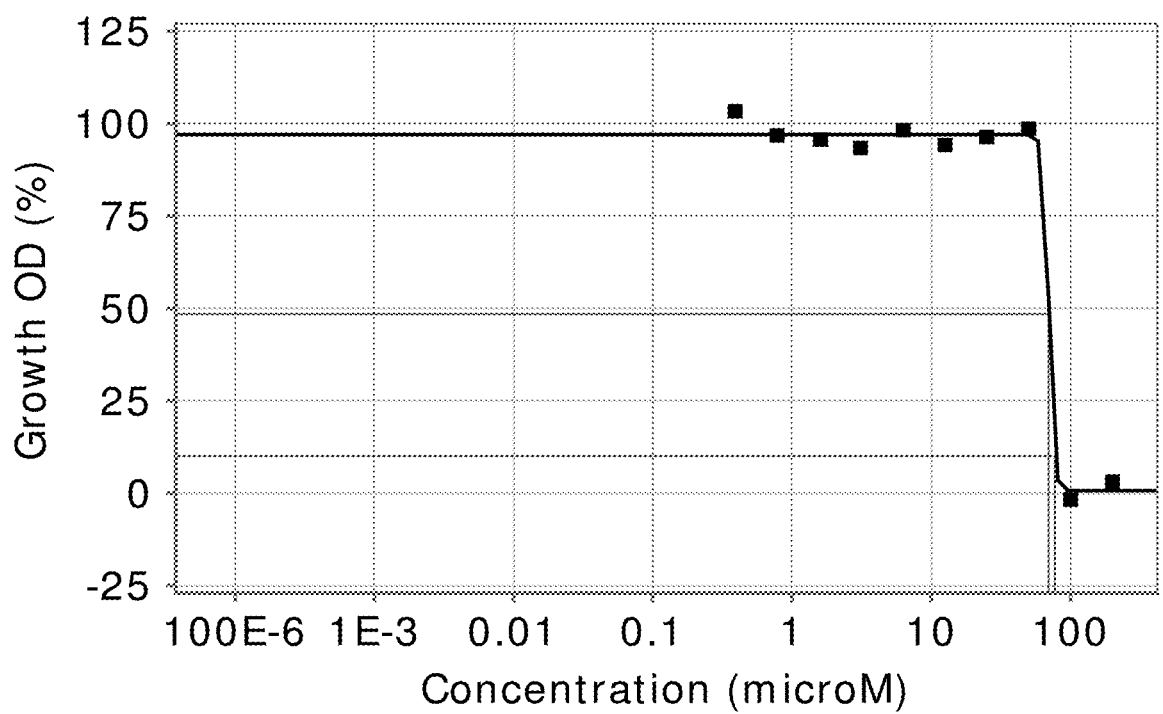
FIG. 10C shows the dose-response curve for compound 506b.
Figure 10D:
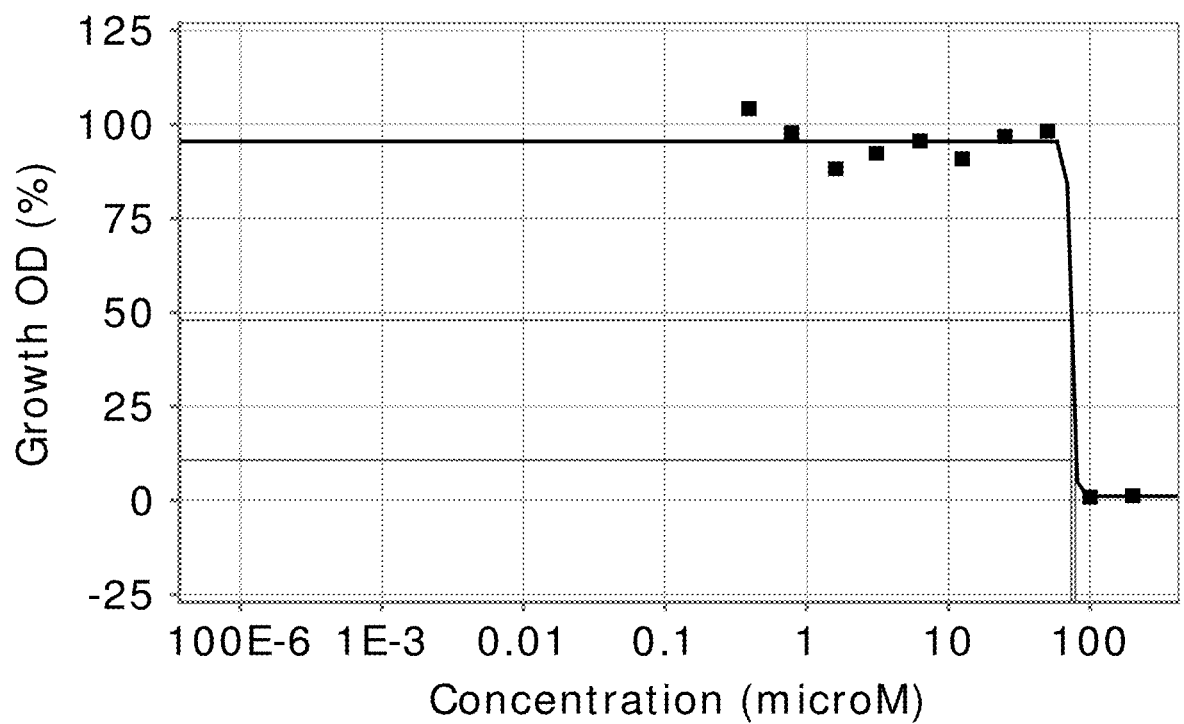
FIG. 10D shows the dose-response curve for compound 506d.
Figure 10E:
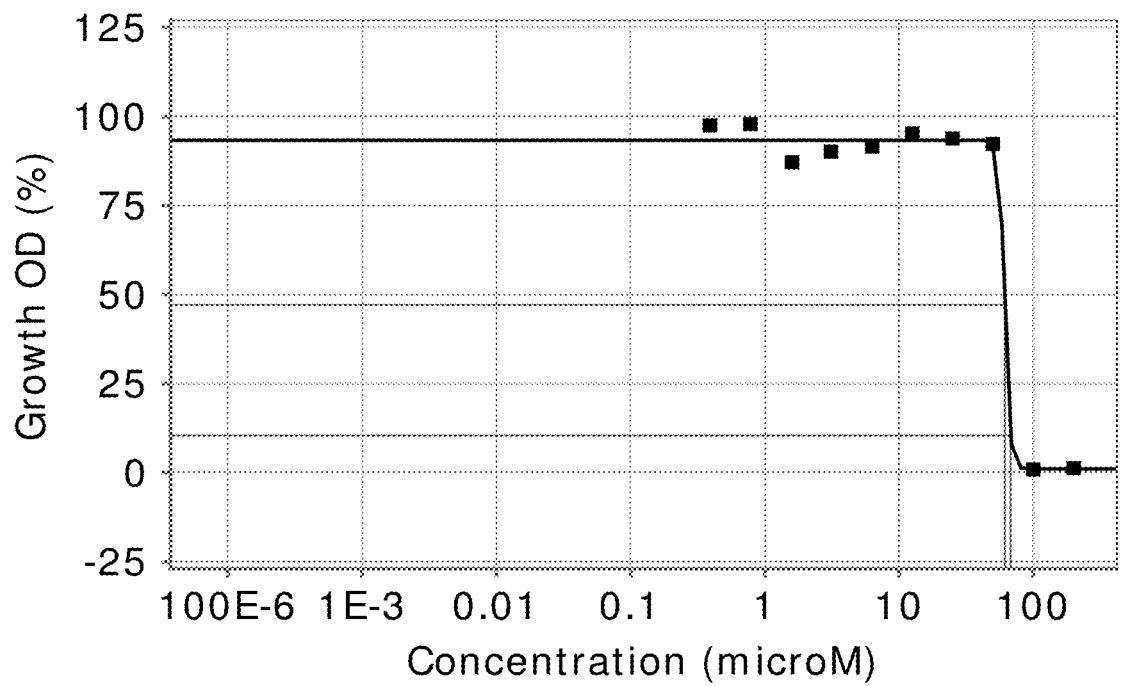
FIG. 10E shows the dose-response curve for compound 506e.
Figure 10F:
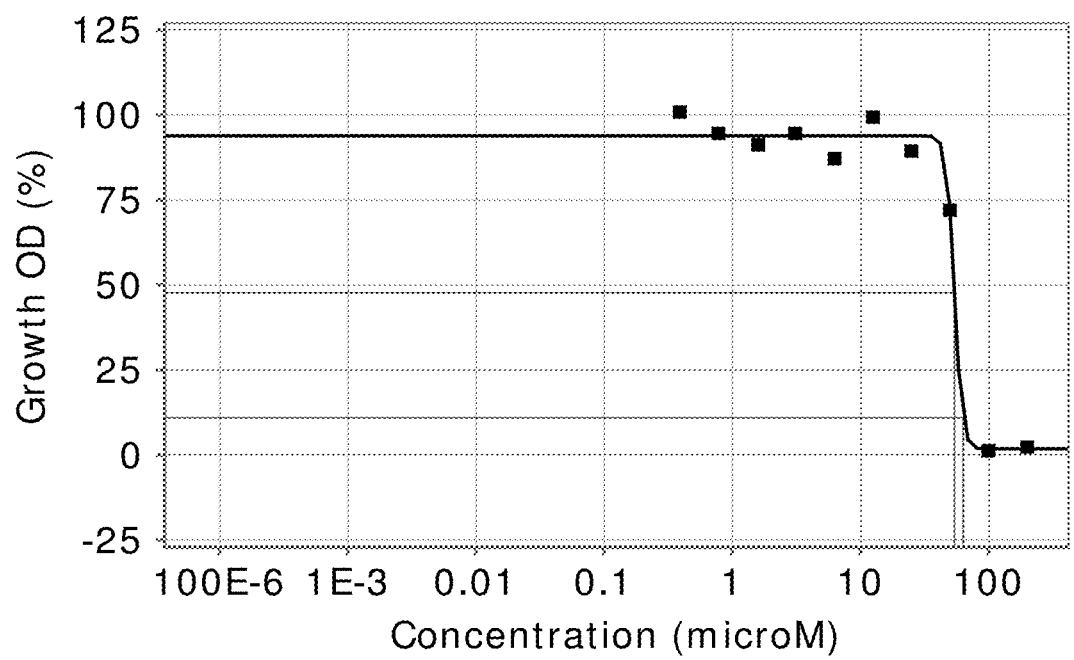
FIG. 10F shows the dose-response curve for compound 506f.
Figure 10G:
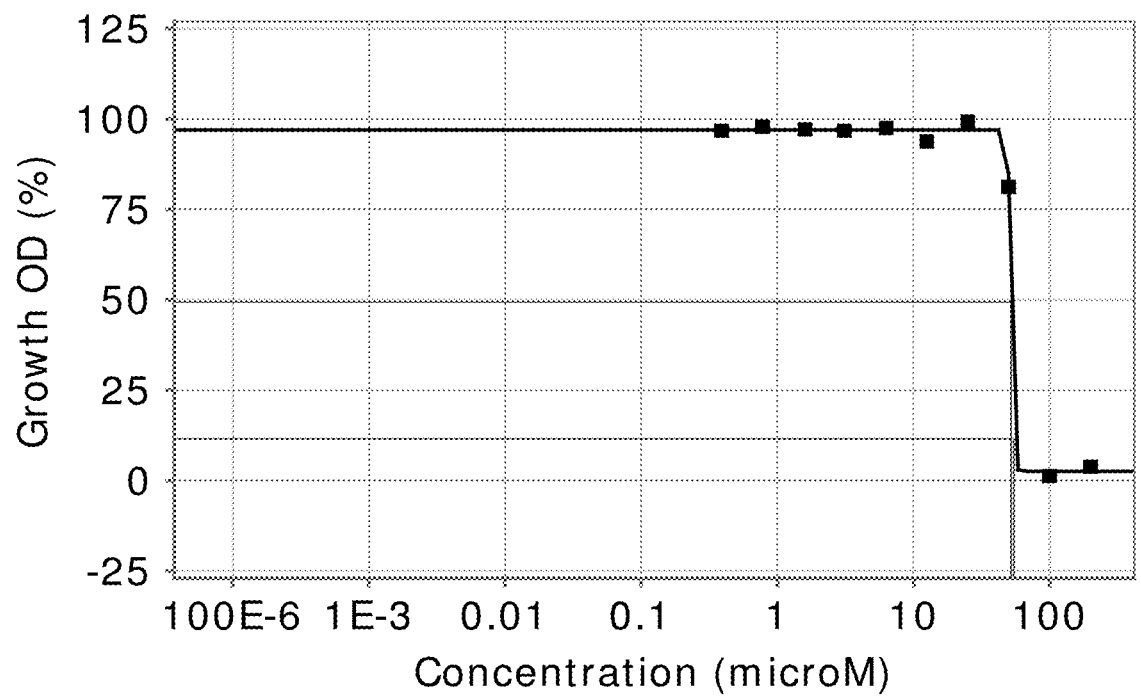
FIG. 10G shows the dose-response curve for compound 506g.
Figure 10H:
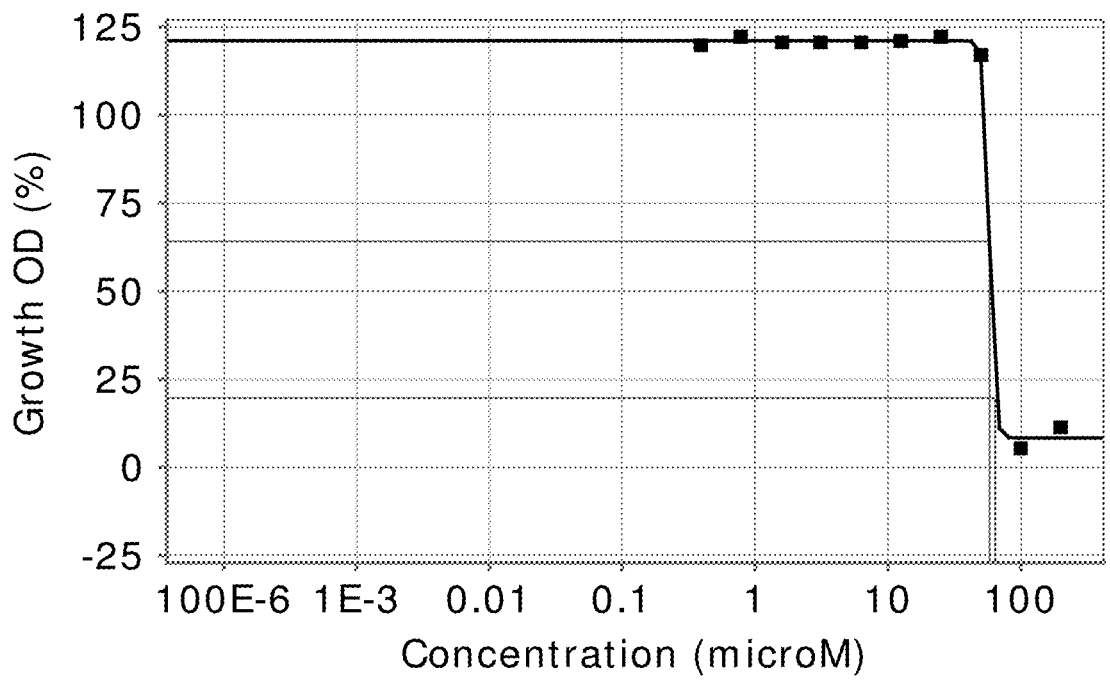
FIG. 10H shows the dose-response curve for compound 506h.
Figure 10I:
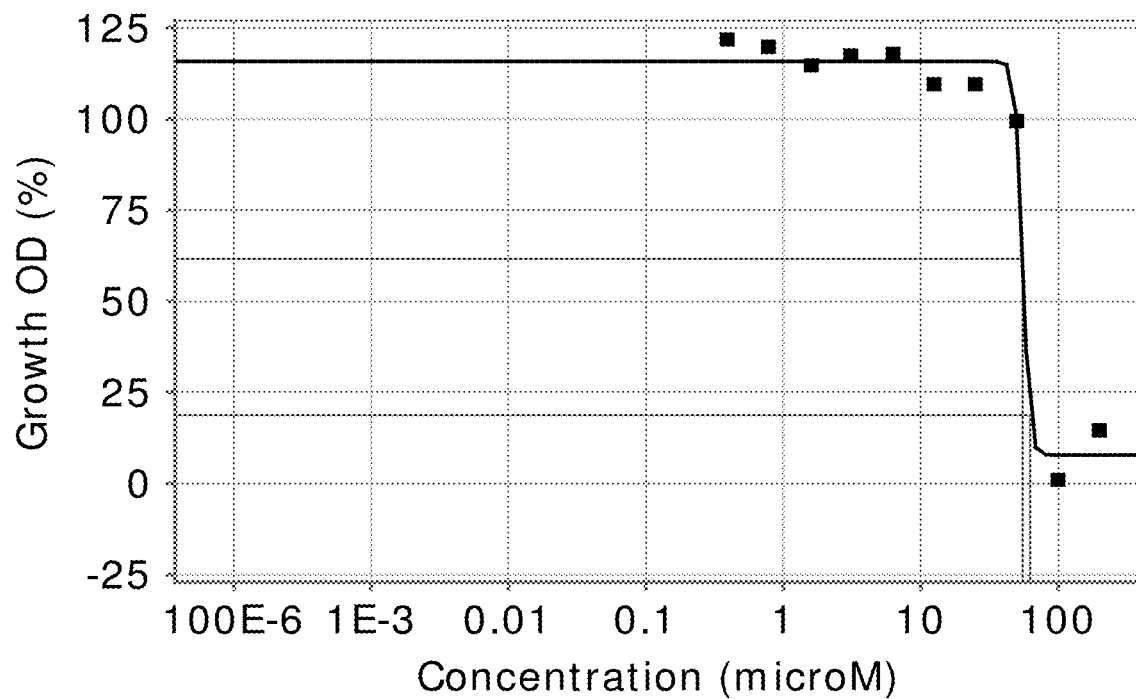
FIG. 10I shows the dose-response curve for compound 506i.
Figure 10J:
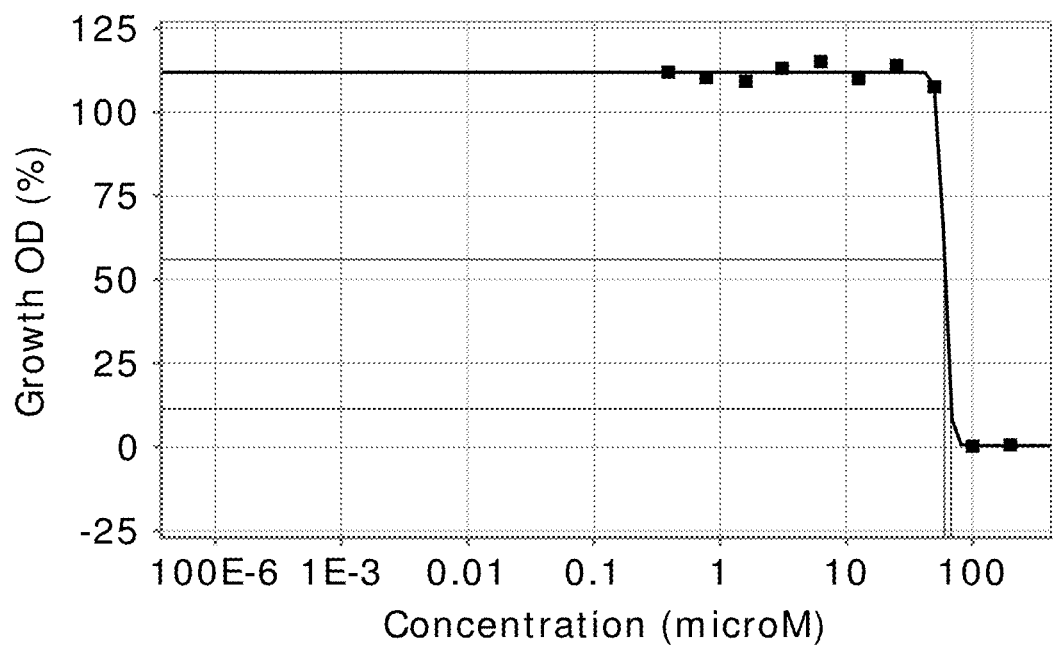
FIG. 10J shows the dose-response curve for compound 506k.
Figure 10K:
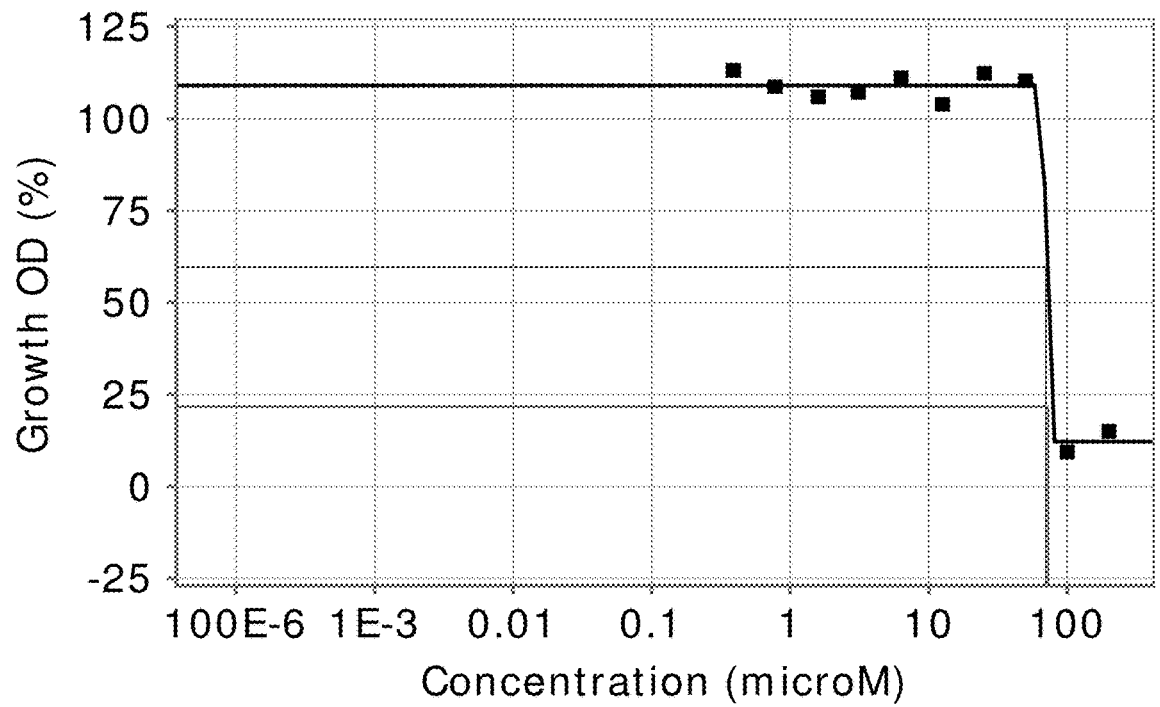
FIG. 10K shows the dose-response curve for compound 506j.
Figure 10L:
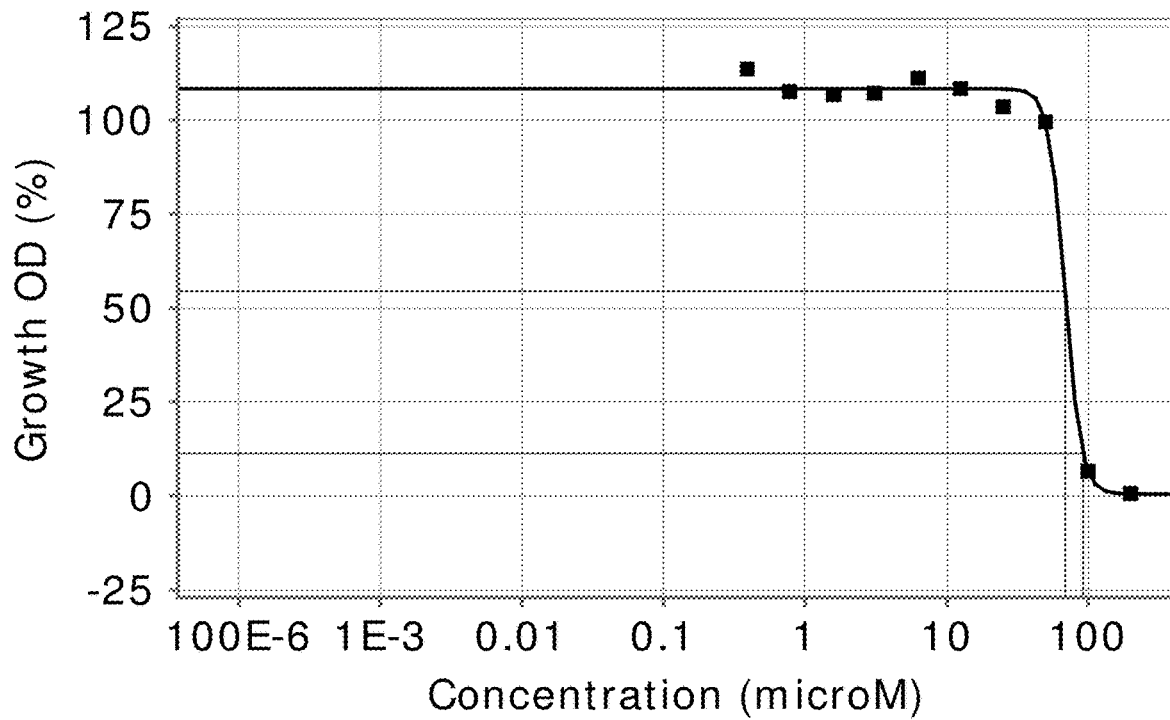
FIG. 10L shows the dose-response curve for compound 506l.
Figure 10M:
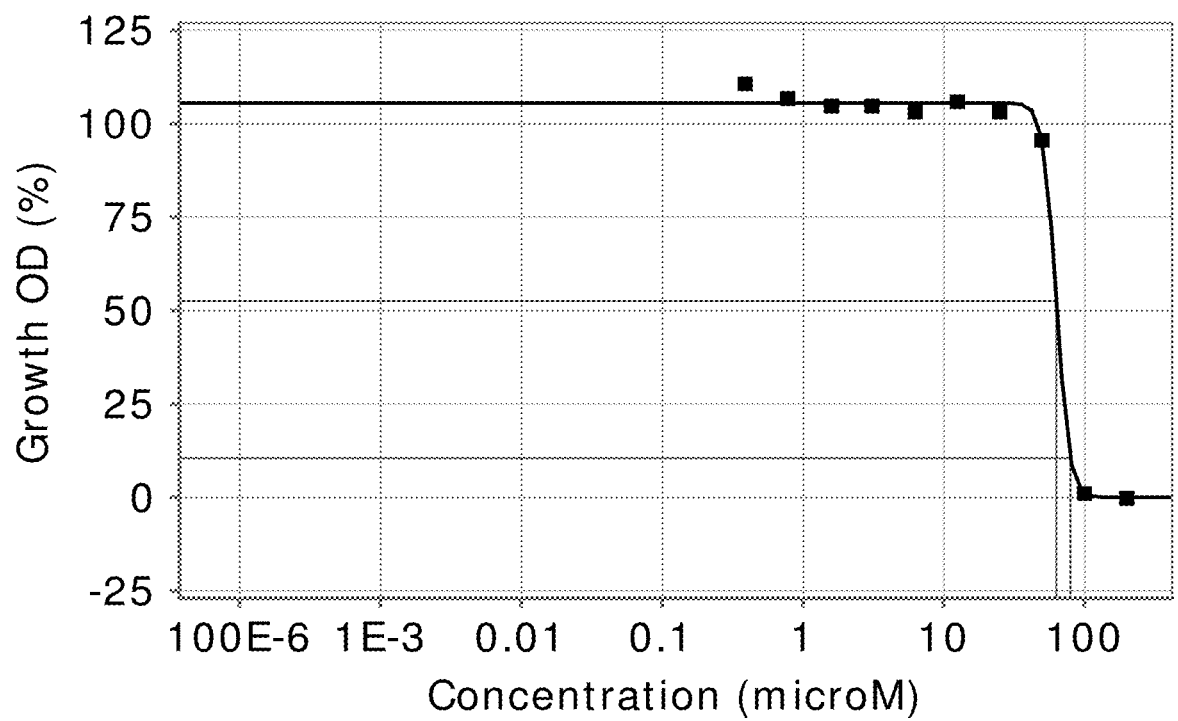
FIG. 10M shows the dose-response curve for compound 506m.
Figure 10N:
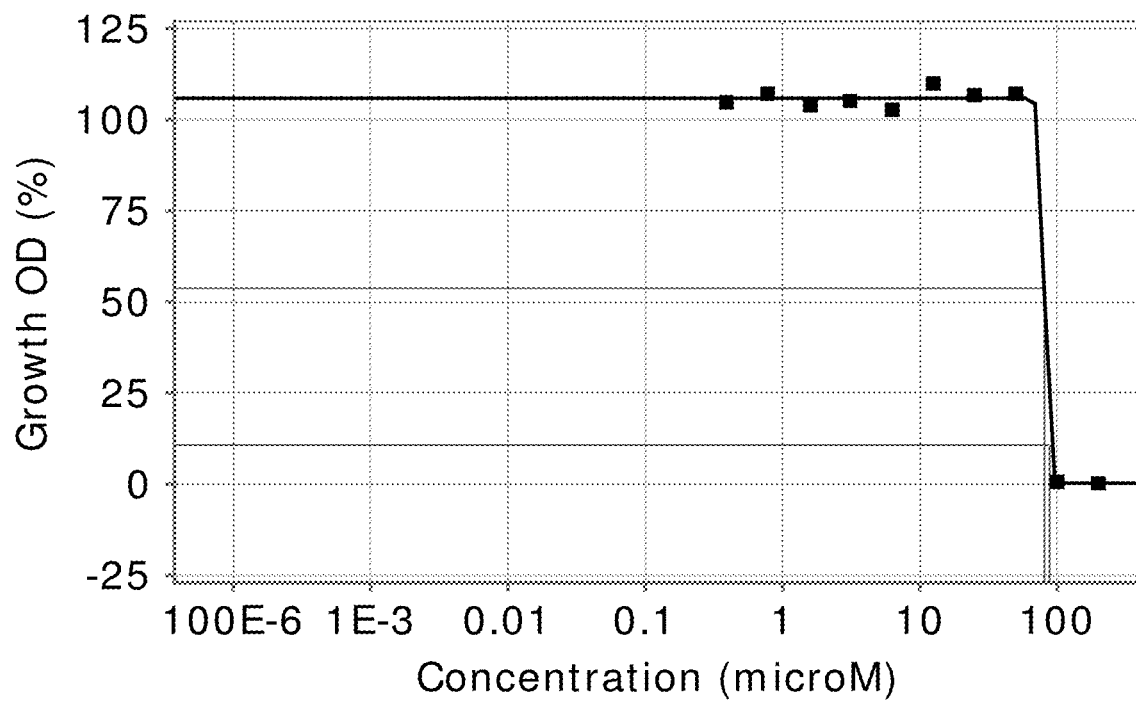

FIGS. 10A-10N show the dose-response curves for compounds 506a-506n against $Mycobacterium$ $tuberculosis$ H37Rv.

The activity of compounds against $Mycobacterium$ $abscessus$ and $Mycobacterium$ $avium$ was assessed under aerobic conditions by determining the minimum inhibitory concentration of compound (MIC). The strains were $M.$ $abscessus$ subsp. $bollettii$ 103 and $M.$ $avium$ subsp. $avium$ 2285 (S). The assay was based on measurement of growth in liquid medium of each strain where the readout is optical density (OD) or metabolic activity (using Alamar blue).

The MIC of compound was determined by measuring bacterial growth in the presence of test compounds. Compounds were prepared as 20-point two-fold serial dilutions in DMSO and diluted into 7H9-Tw-OADC medium in 96-well plates with a final DMSO concentration of 2%. The highest concentration of compound was 200 μM where compounds were soluble in DMSO at 10 mM. Each plate included assay controls for background (medium/DMSO only, no bacterial cells), 2 μM rifampicin, and maximum growth (DMSO only), as well as a rifampicin dose response curve.

For $Mycobacterium$ $abscessus$, plates were inoculated with $M.$ $abscessus$ and incubated for 3 days at 37° C.; growth was measured by $OD_{590}$. The dose response curve was plotted as % growth and fitted to the Gompertz model. The MIC was defined as the minimum concentration at which growth was completely inhibited and was calculated from the inflection point of the fitted curve to the lower asymptote. In addition, dose response curves were generated using the Levenberg-Marquardt algorithm and the concentrations that resulted in 50% and 90% inhibition of growth were determined ($IC_{50}$ and $IC_{90}$, respectively).

For $Mycobacterium$ $avium$, plates were inoculated with $M.$ $avium$, incubated for 5 days at 37° C. and Alamar blue was added to each well (10 μL of Alamar blue to 100 μL culture) and incubated for 24 h at 37° C. Plates were visually inspected and the color was recorded for each well. MIC was defined as the lowest concentration at which no metabolic activity was seen (blue well).

Figure 12A:
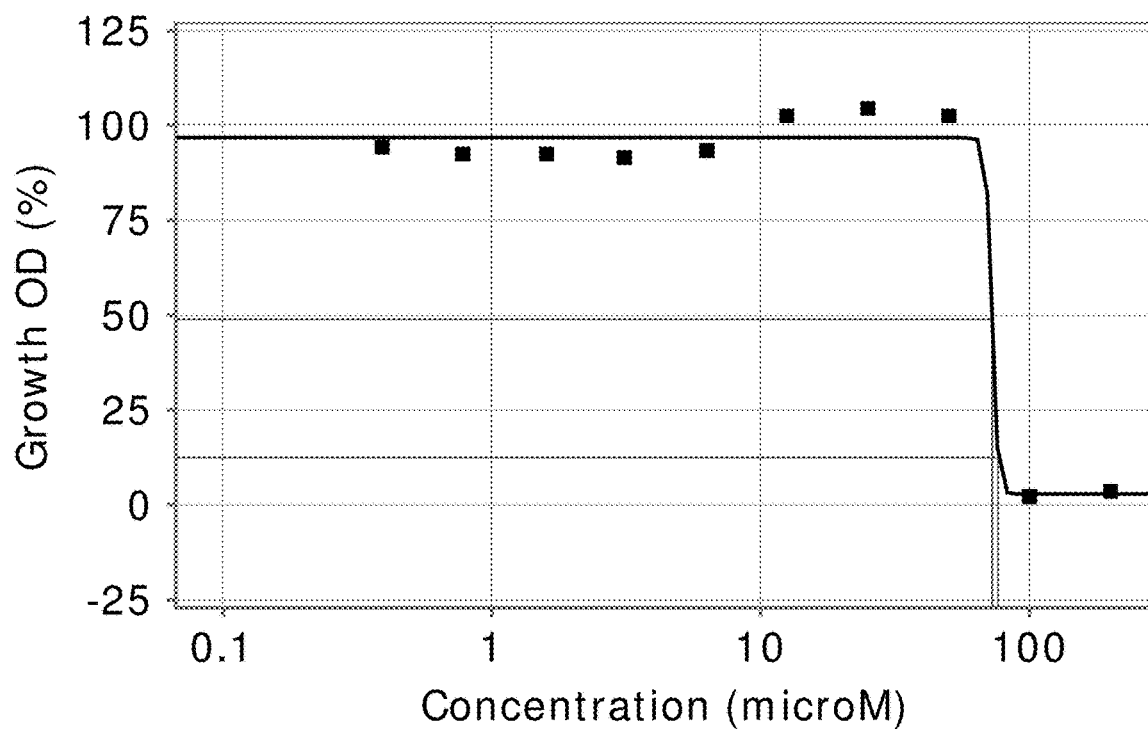
FIGS. 12A-12N: Dose-response curves for compounds 506a-506n against *Mycobacterium abscessus*.
Figure 12B:
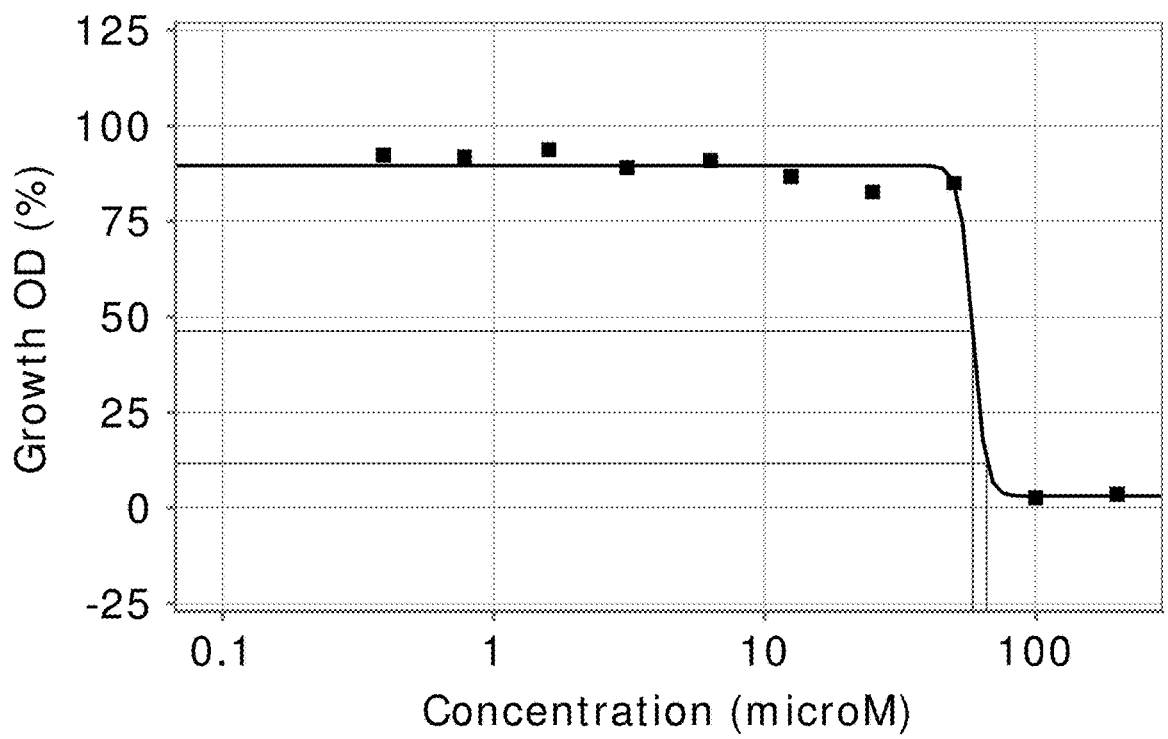
FIG. 12B shows the dose-response curve for compound 506c.
Figure 12C:
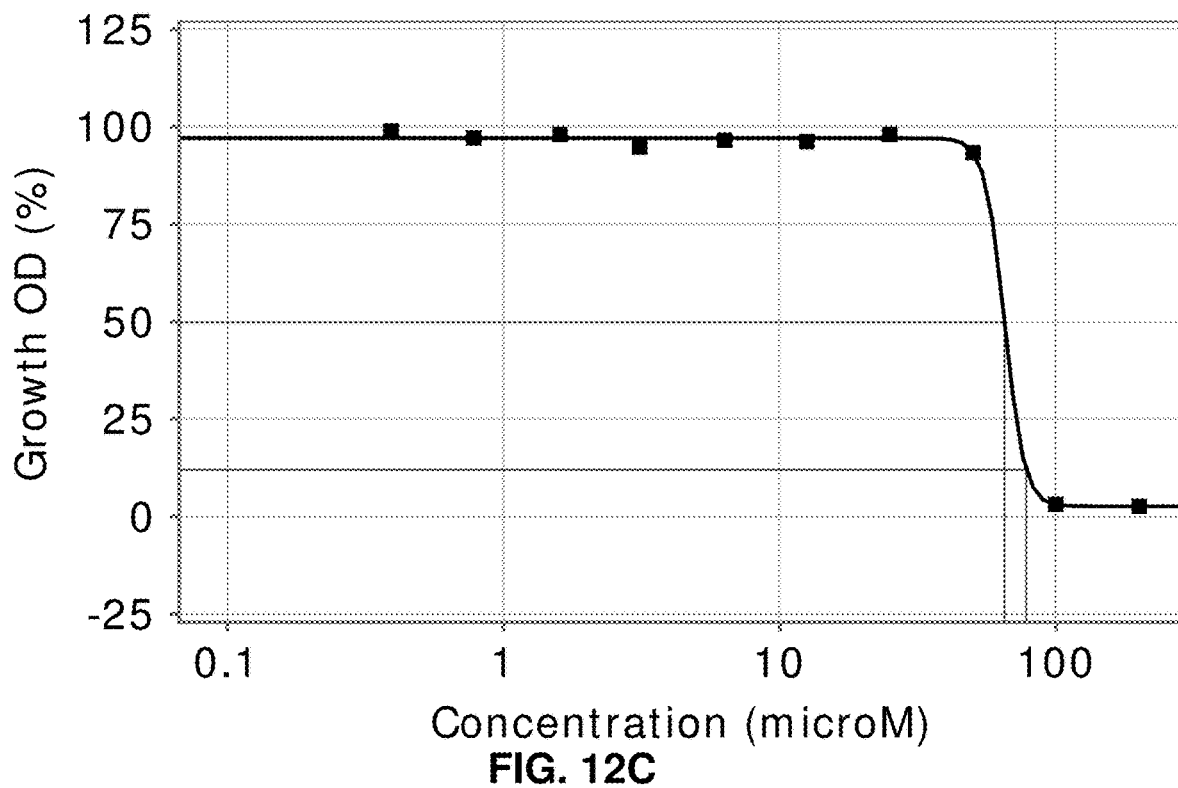
FIG. 12C shows the dose-response curve for compound 506b.
Figure 12D:
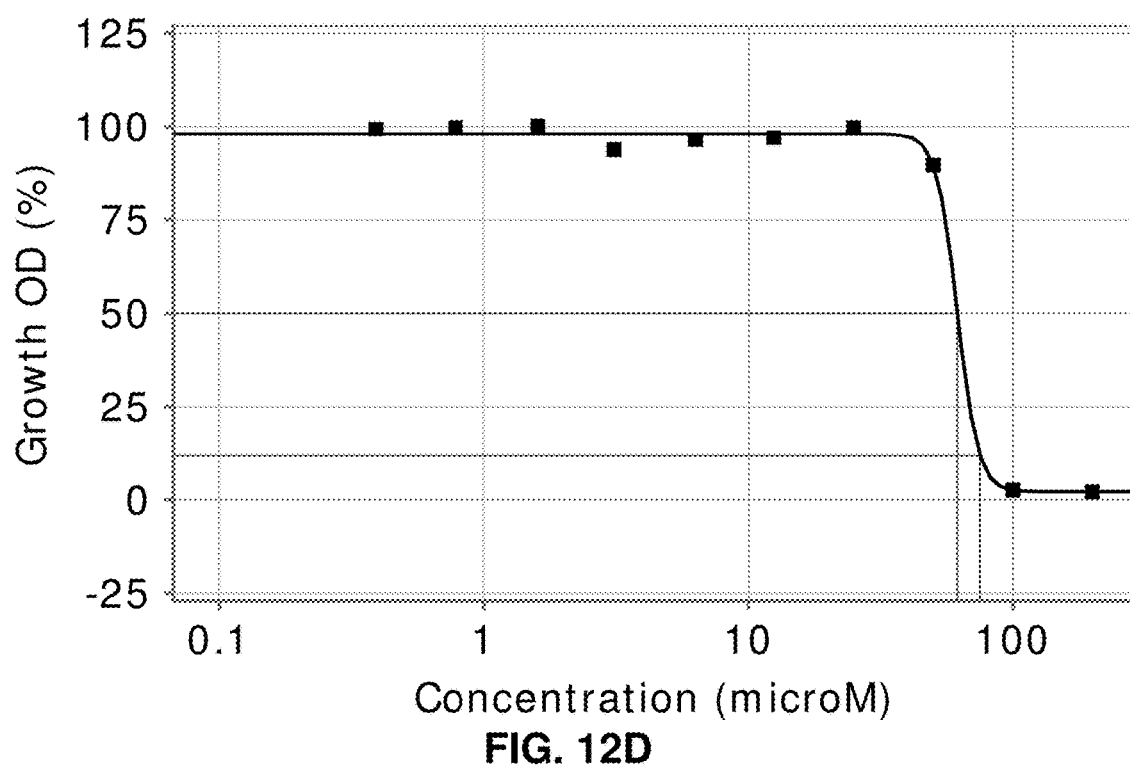
FIG. 12D shows the dose-response curve for compound 506d.
Figure 12E:
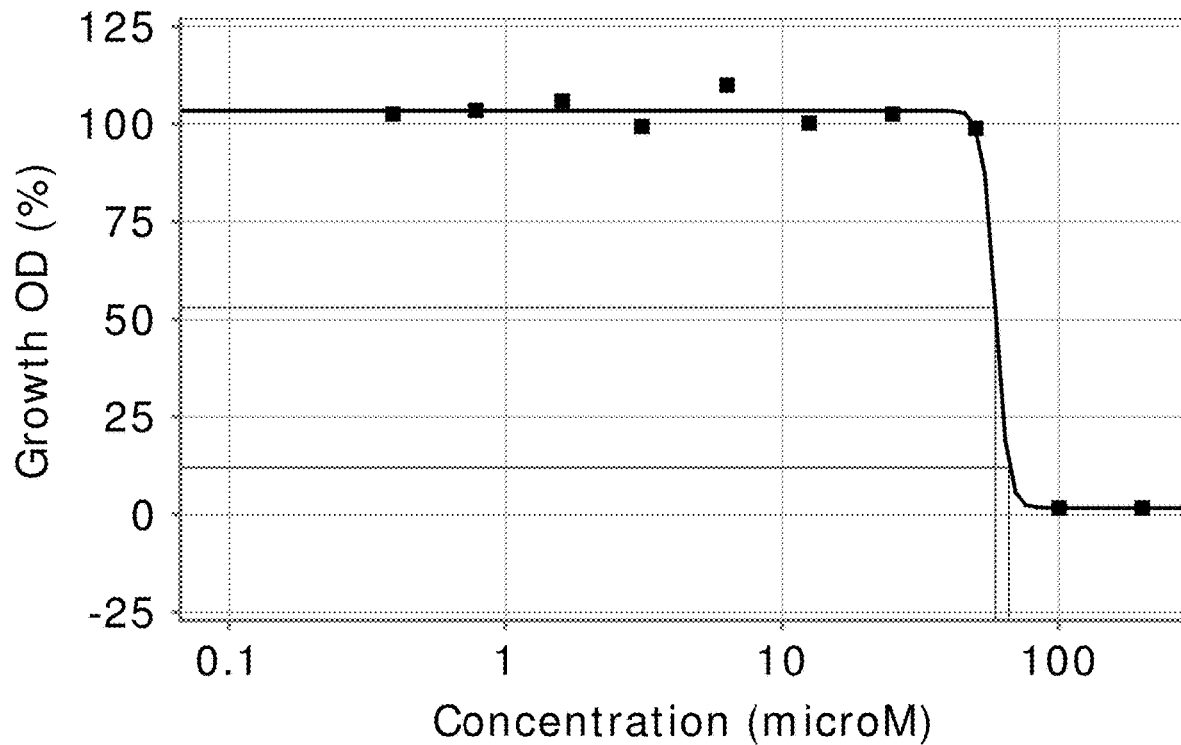
FIG. 12E shows the dose-response curve for compound 506e.
Figure 12F:
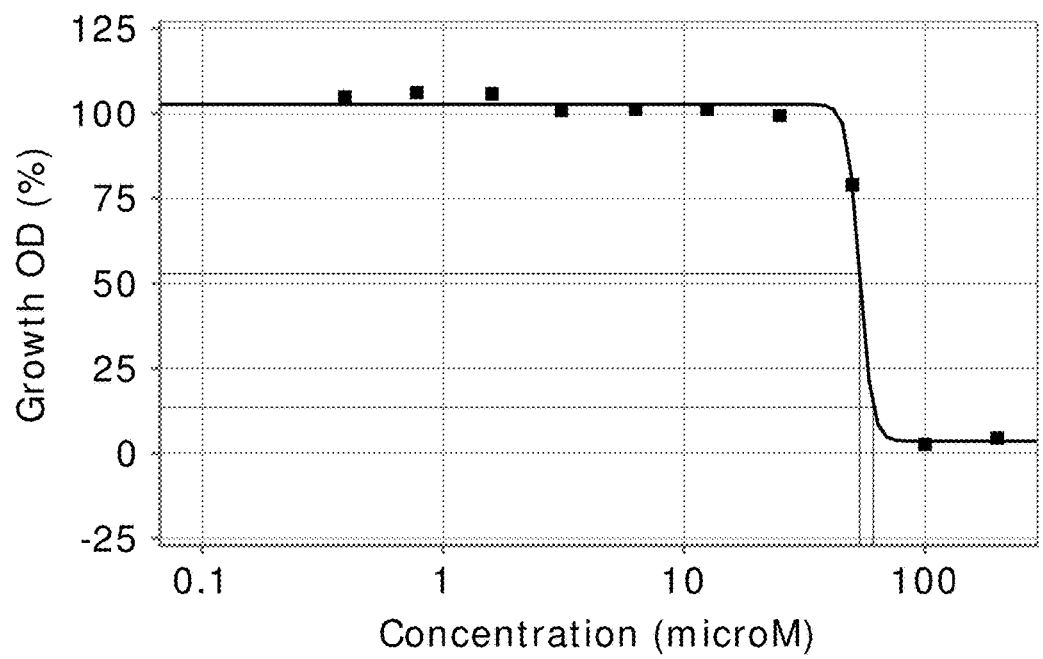
FIG. 12F shows the dose-response curve for compound 506f.
Figure 12G:
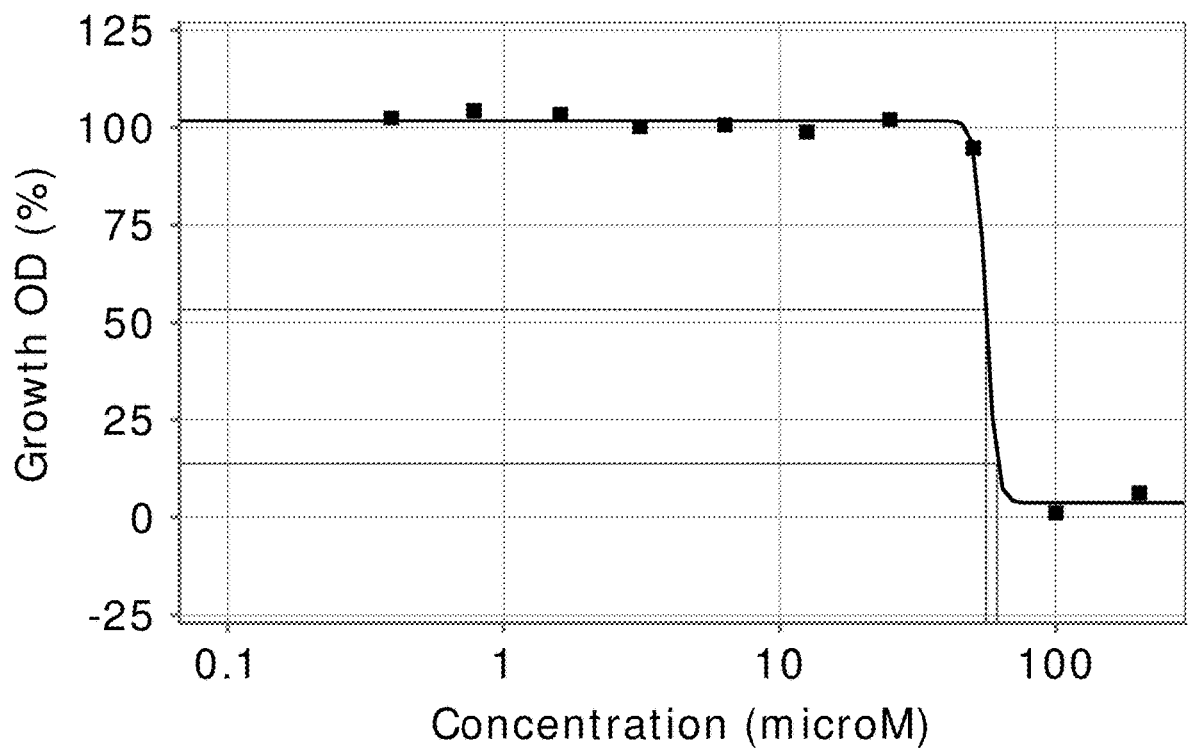
FIG. 12G shows the dose-response curve for compound 506g.
Figure 12H:
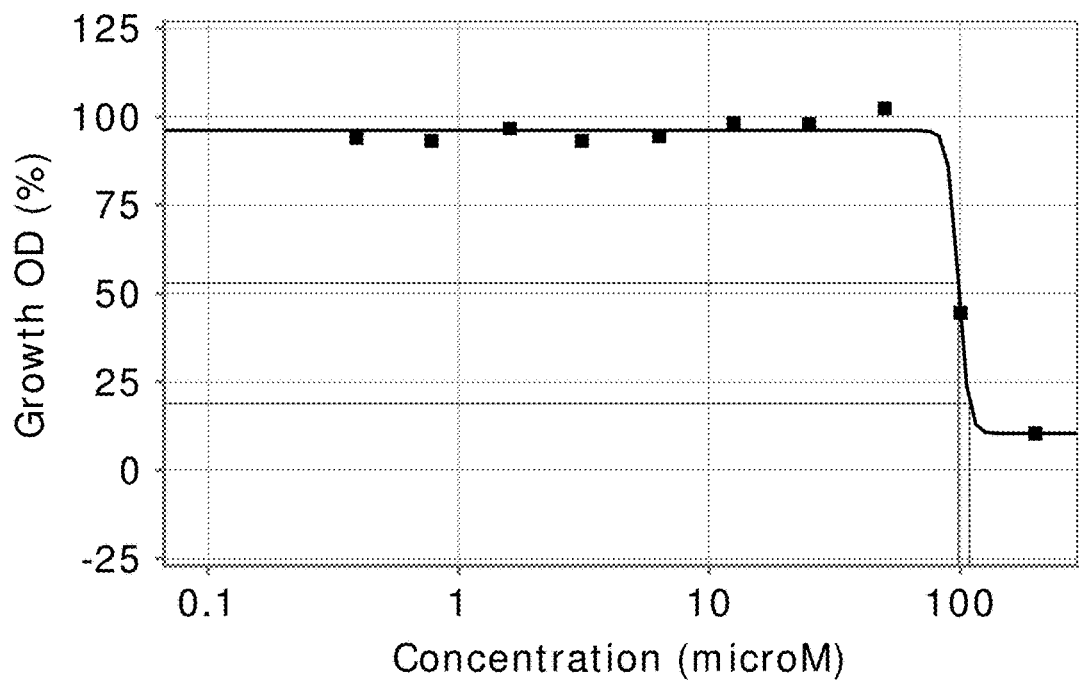
FIG. 12H shows the dose-response curve for compound 506h.
Figure 12I:
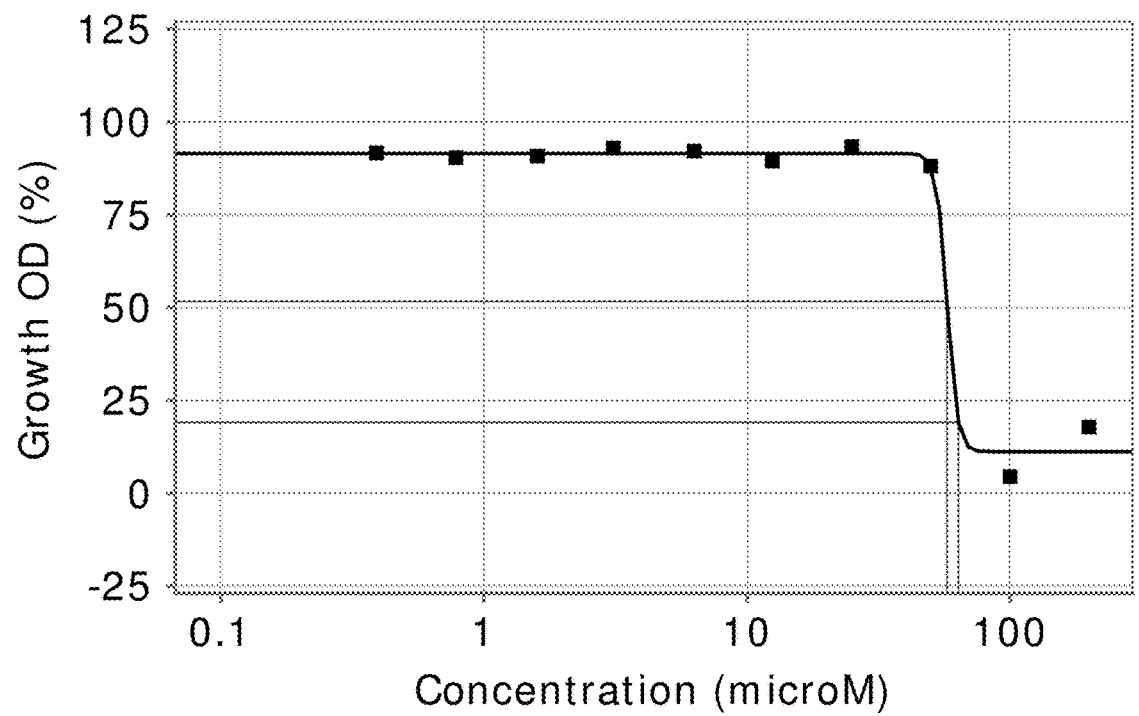
FIG. 12I shows the dose-response curve for compound 506i.
Figure 12J:
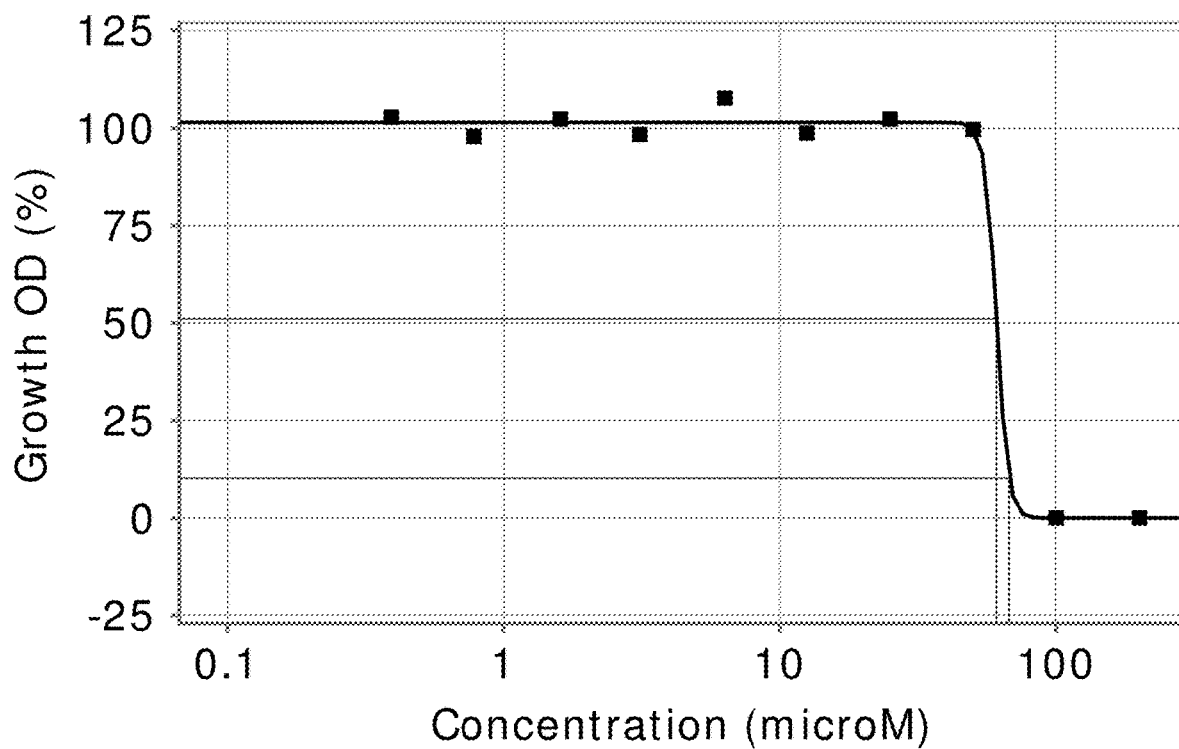
FIG. 12J shows the dose-response curve for compound 506k.
Figure 12K:
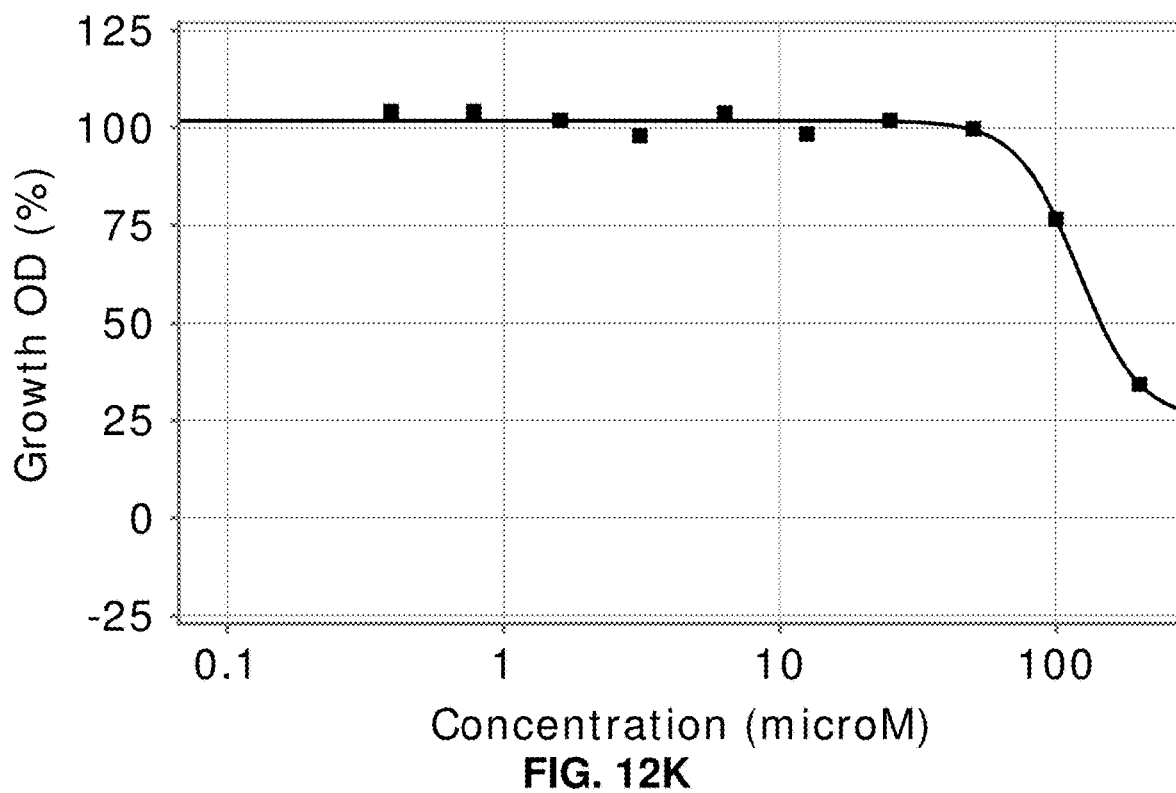
FIG. 12K shows the dose-response curve for compound 506j.
Figure 12L:
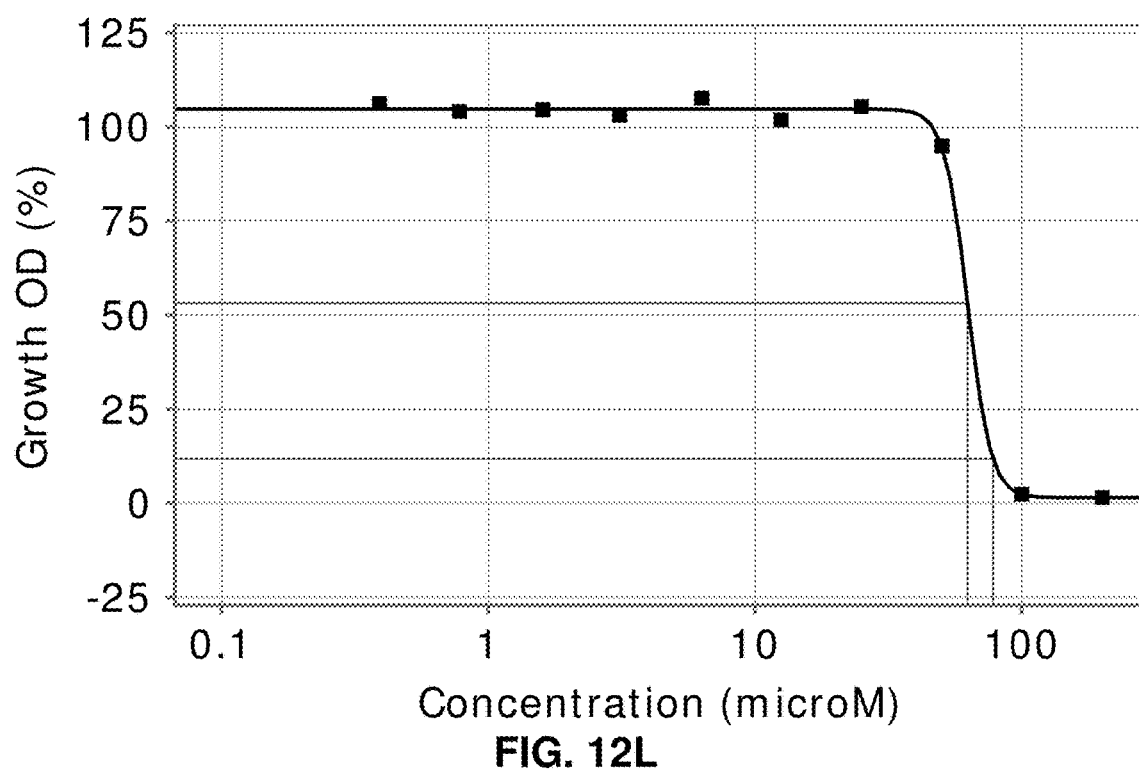
FIG. 12L shows the dose-response curve for compound 506l.
Figure 12M:
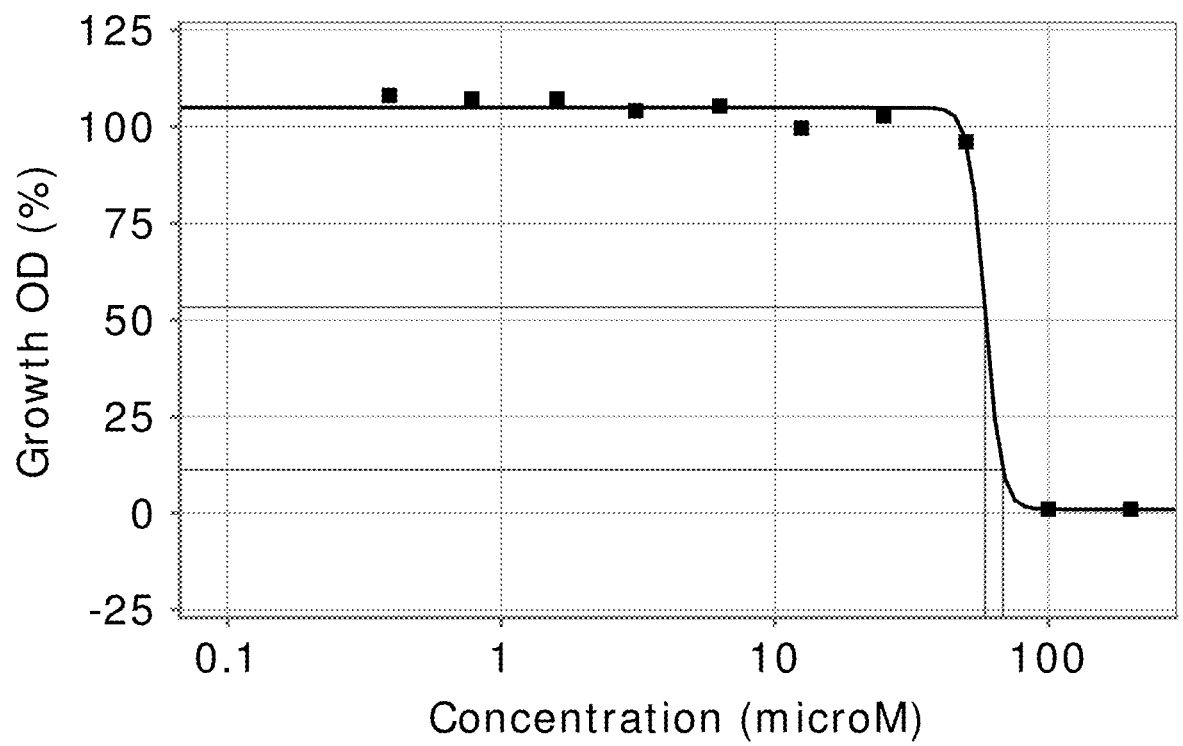
FIG. 12M shows the dose-response curve for compound 506m.
Figure 12N:
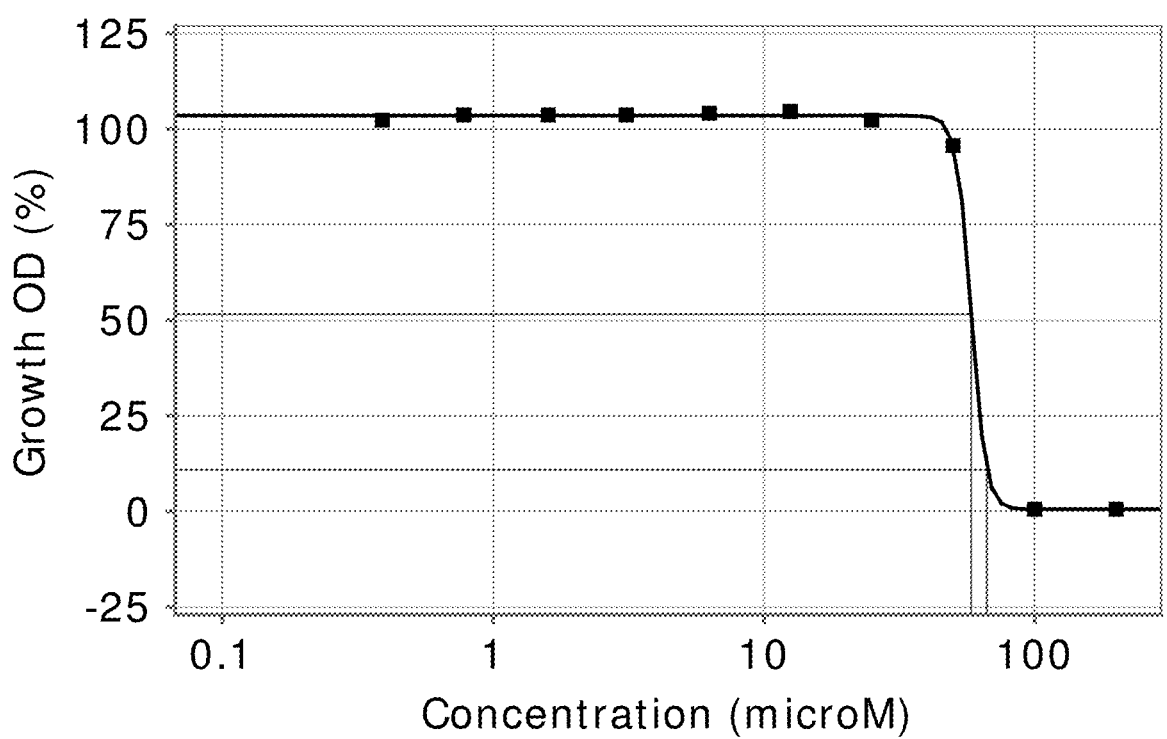

FIG. 11A shows Table 3, summarizing the activity of compounds 506a-506n against $M.$ $abscessus$. FIG. 11B shows Table 4, summarizing activity of compounds 506a-506n against $M.$ $avium$. In both cases, rifampicin was used as a control. FIGS. 12A-12N show the dose-response curves for compounds 506a-506n against $Mycobacterium$ $abscessus$. FIGS. 13A-13B show the raw plate images for activity of compounds 506a-506g (FIG. 13A) and compounds 506h-506n (FIG. 13B) against $Mycobacterium$ $avium$.

General Procedure for Cytoxisity Assay

Figure 14:
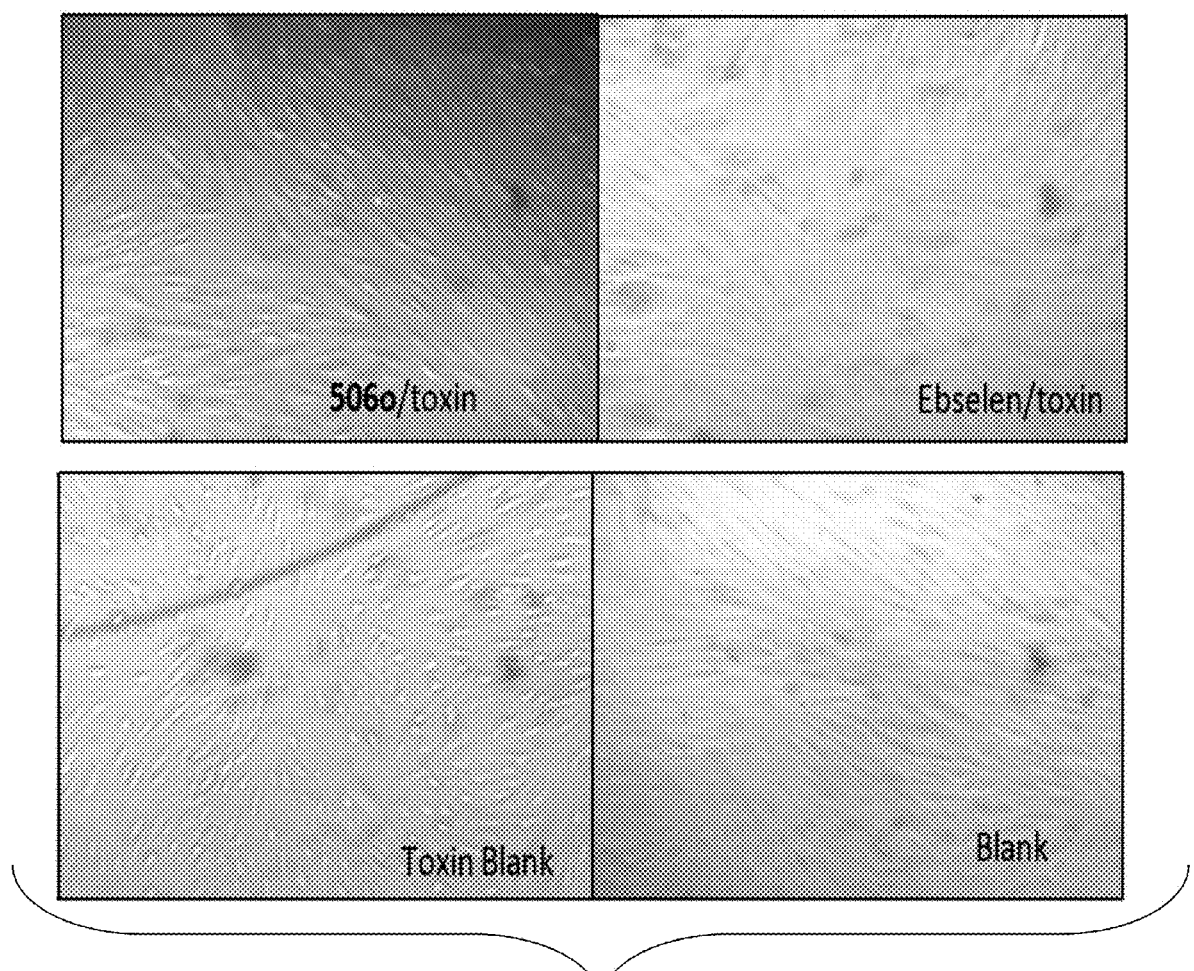
FIG. 14: Inhibition of cell rounding.
Figure 17:
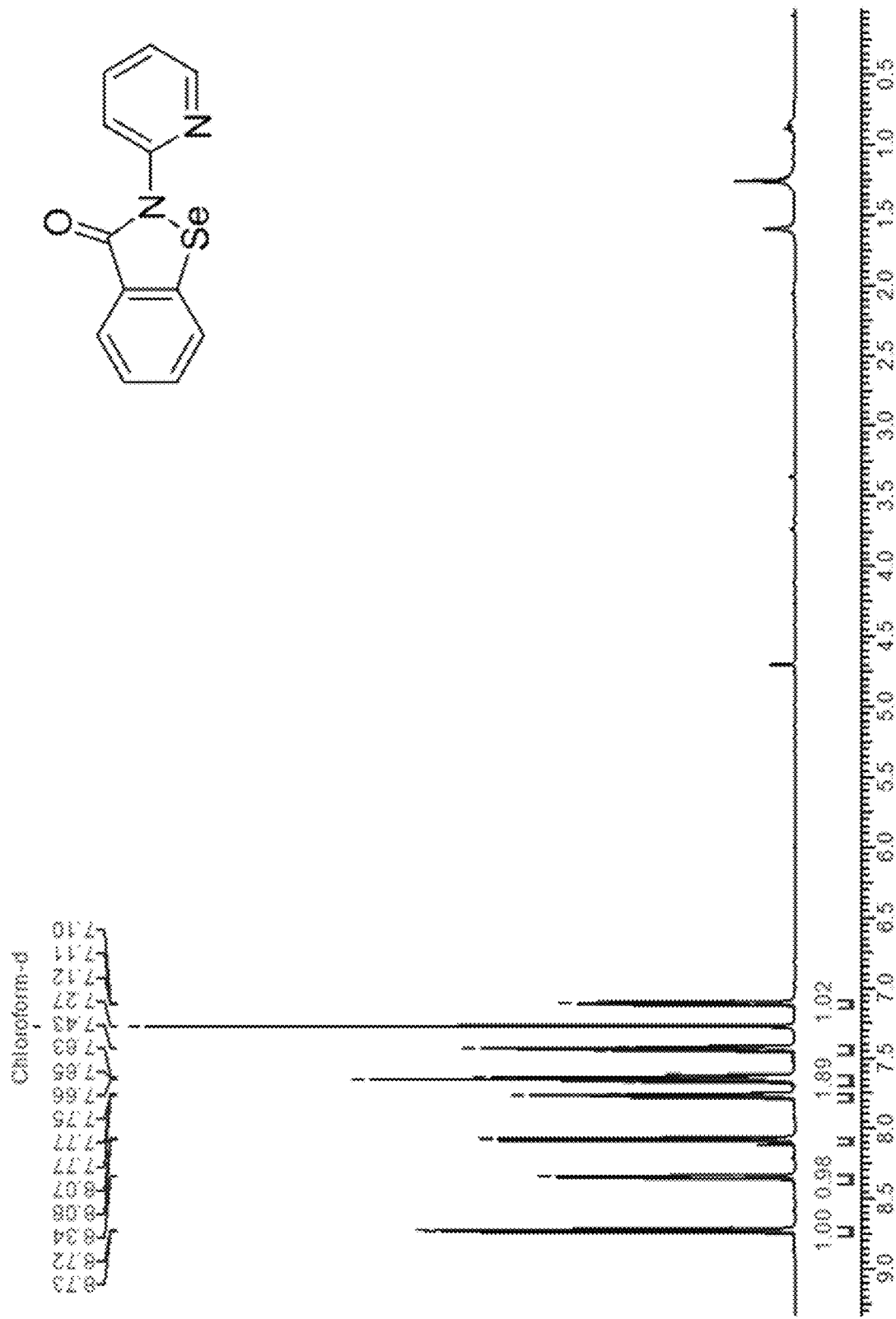
FIG. 17: $^1$H NMR of example 15: 2-(pyridin-2-yl)benzo[d][1,2]selenazol-3(2H)-one (506o).
Figure 18:
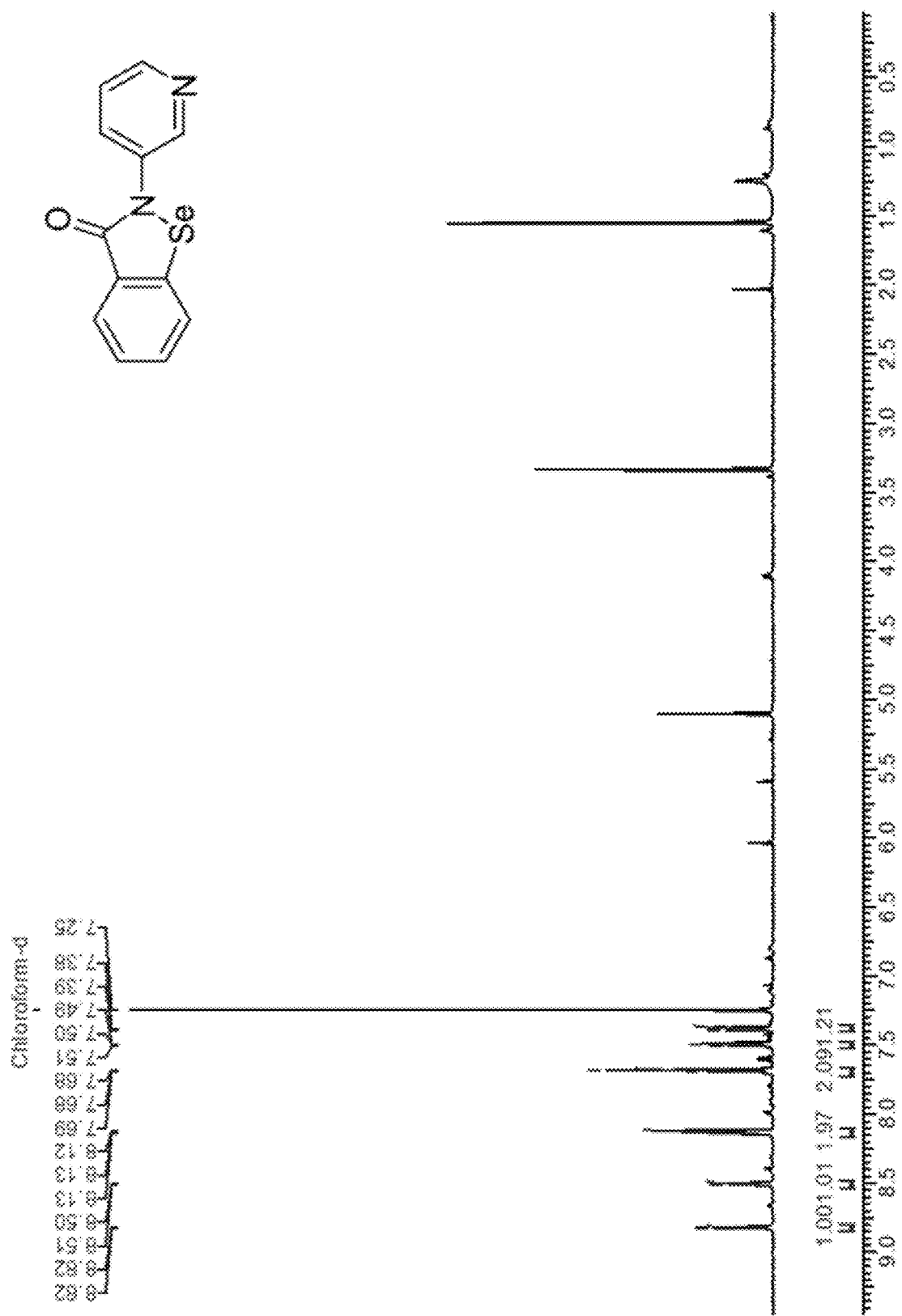
FIG. 18: $^1$H NMR of example 16: 2-(pyridin-3-yl)benzo[d][1,2]selenazol-3(2H)-one (506p).
Figure 19:
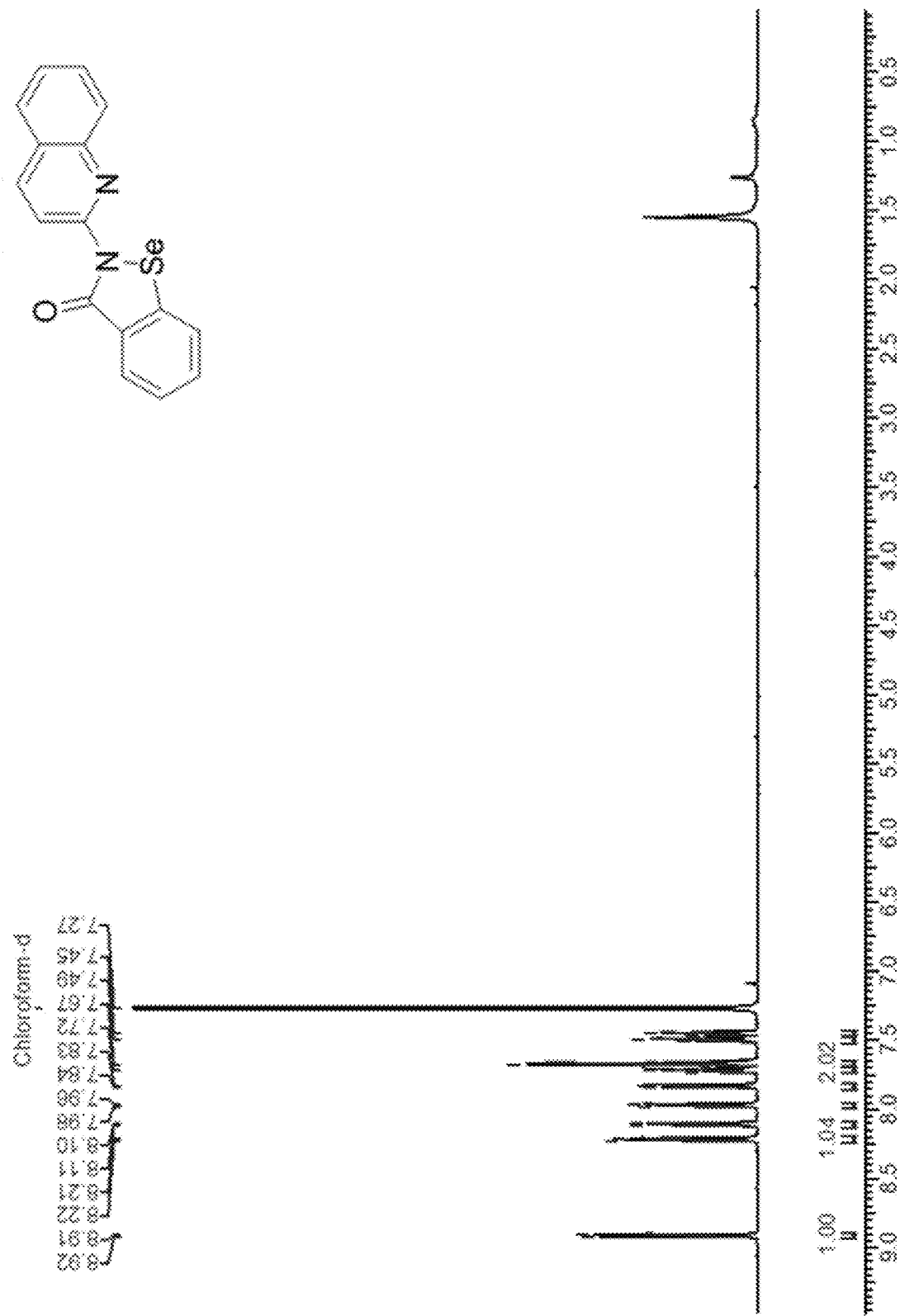
FIG. 19: $^1$H NMR of example 17: 2-(quinolin-2-yl)benzo[d][1,2]selenazol-3(2H)-one (506q).
Figure 20:
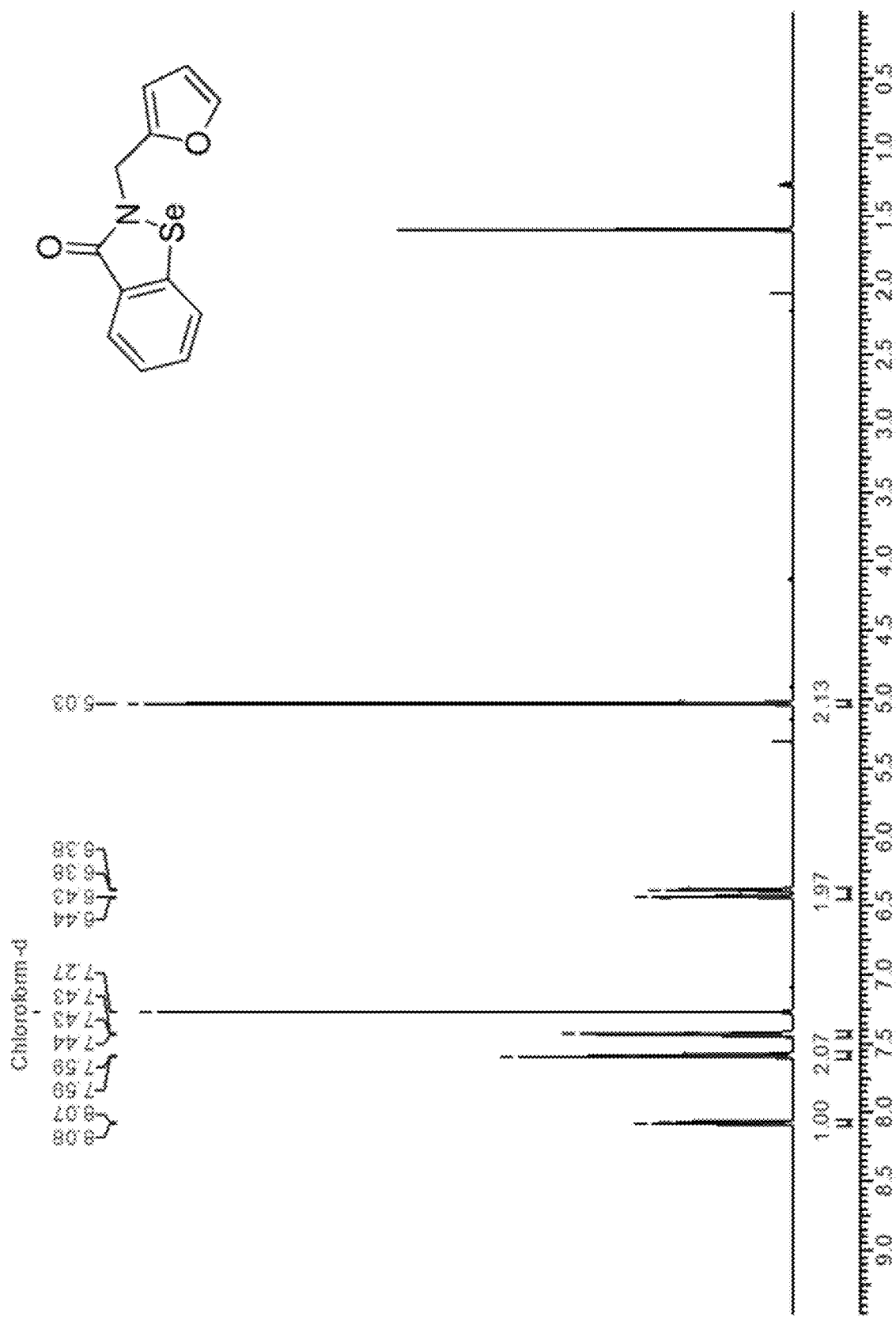
FIG. 20: $^1$H NMR of example 18: 2-(furan-2-ylmethyl)benzo[d][1,2]selenazol-3(2H)-one (506r).
Figure 21:
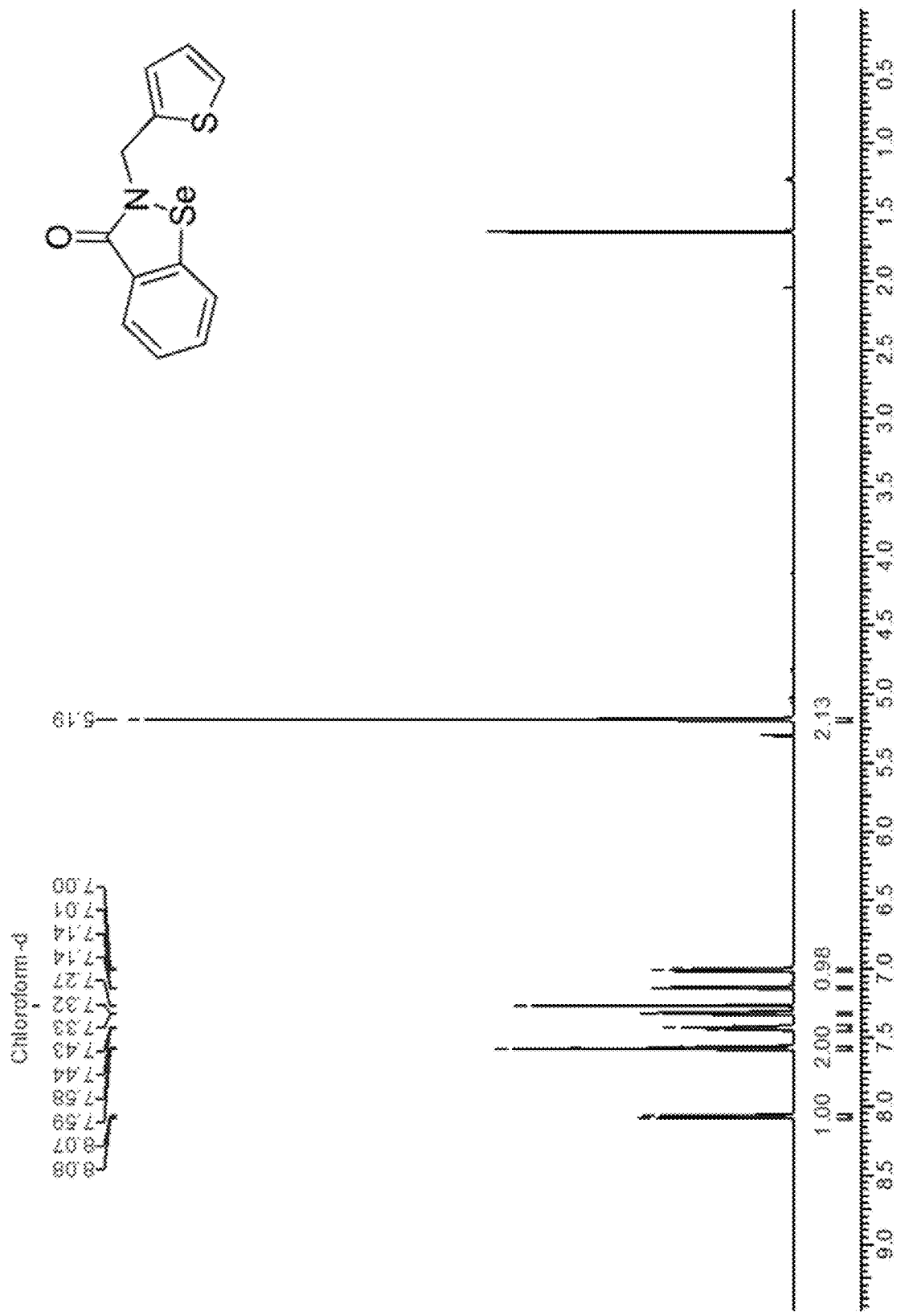
FIG. 21: $^1$H NMR of example 19: 2-(thiophen-2-ylmethyl)benzo[d][1,2]selenazol-3(2H)-one (506s).
Figure 22:
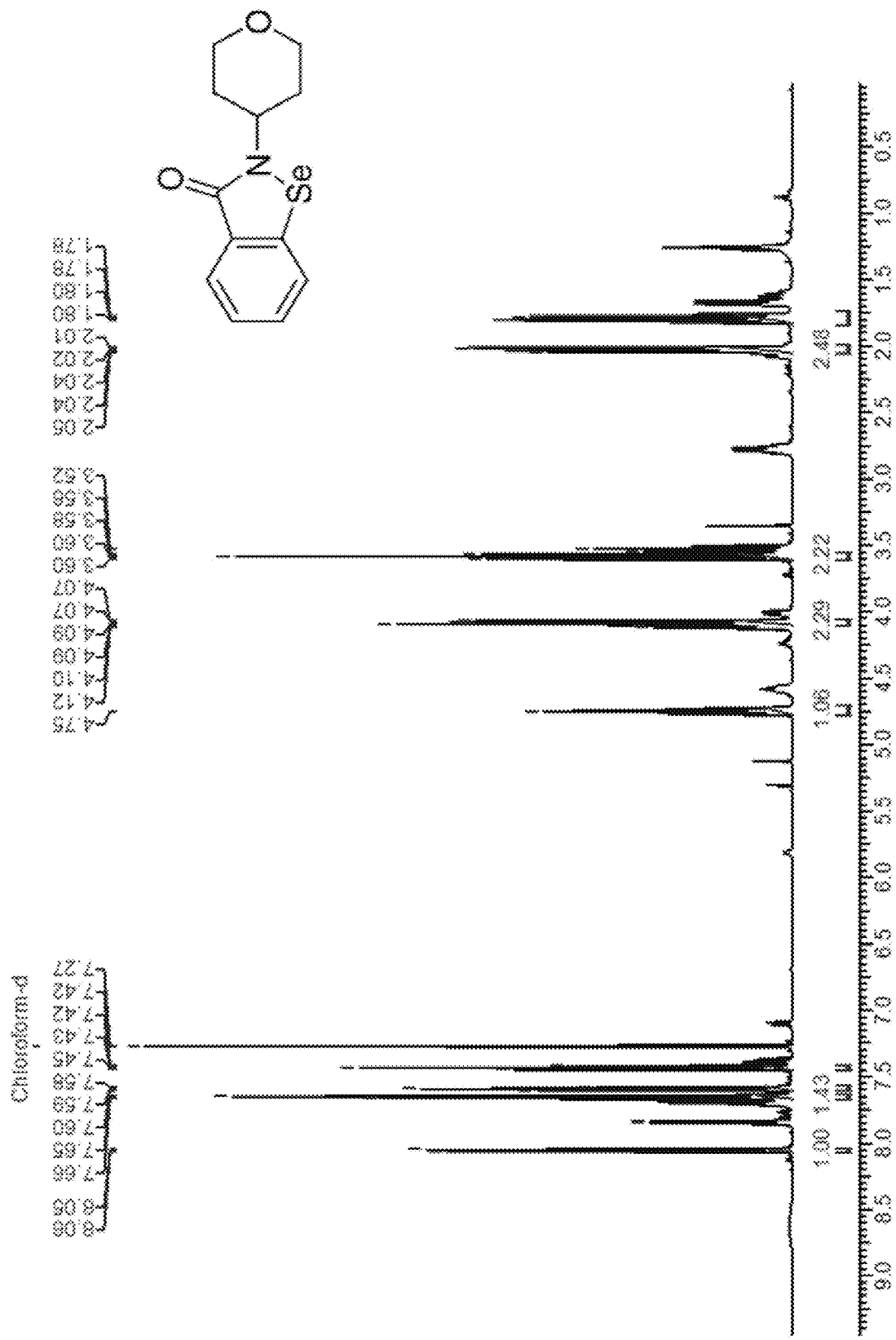
FIG. 22: $^1$H NMR of example 20: 2-(tetrahydro-2H-pyran-4-yl)benzo[d][1,2]selenazol-3(2H)-one (506t).
Figure 23:
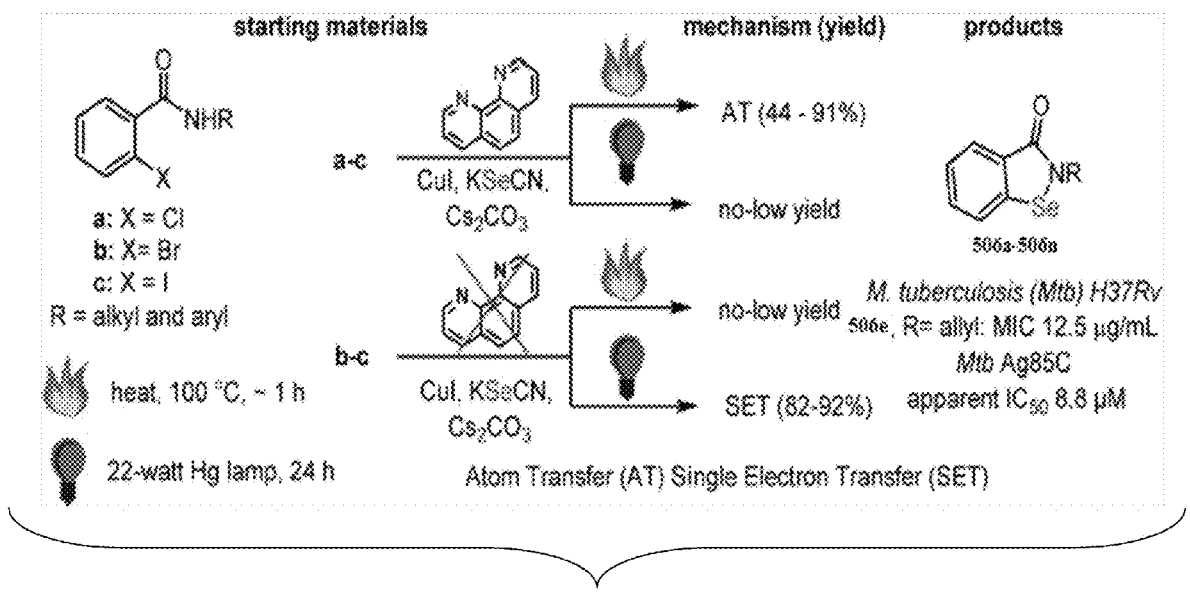
FIG. 23: Non-limiting example scheme showing production of 2-alkyl-1,2,-benzisoselenazol-3(2H)-ones.

Cytotoxicity data was collected using a qualitative assay designed by Quidel to detect TcdB and TcdA presence in patients' stool samples. A solution containing TcdB and TcdA (0.05 mL) was mixed with 0.05 mL of a 40 μM solution of compounds of example 1-15 individually. These solutions were then incubated together for thirty minutes at room temperature. Then the 0.1 ml solutions were used to treat MRHF cells in a twenty four well plate. The cells were then incubated at thirty degrees Celsius under $CO_2$ for two hours. Then, the cells were imaged using a 20× objective on an inverted microscope. FIG. 14 shows inhibition of cell rounding. The cells maintained their string-like appearance when treated with ebselen and the toxin. This is comparable to the cells not treated with toxin. As seen in FIG. 14, compound 506o shows a more intermediate phenotype for the cells, showing the ability to inhibit cell rounding. Thus, compound 506o provides cytoprotection against $Clostridium$ $difficile$ toxins TcdB and TcdA.

FIGS. 15-16 show Tables 9-10, displaying a list of all the compounds prepared in this Example with their structures and chemical names.

Example II—Thermal and Photoinduced Copper-Promoted C—Se Bond Formation: Synthesis of 2-Alkyl-1,2-Benzisoselenazol-3(2H)-Ones and Evaluation Against $Mycobacterium$ $tuberculosis$ 2-Alkyl-1,2-benzisoselenazol-3(2H)-ones, such as ebselen (201a), are useful in medicinal applications. This Example describes both a thermal and photoinduced copper-mediated cross-coupling between potassium selenocyanate (KSeCN) and N-substituted ortho-halobenzamides to form 2-alkyl-1,2-benzisoselenazol-3(2H)-ones containing a C—Se—N bond. The copper ligand (1,10-phenanthroline) facilitates C—Se bond formation during heating via a mechanism that likely involves atom transfer (AT), whereas, in the absence of ligand, photoinduced activation likely proceeds through a single electron transfer (SET) mechanism. A library of 15 2-alkyl-1,2-benzisoselenazol-3(2H)-ones was prepared. One member of the library was azide-containing derivative 506i that was competent to undergo a strain-promoted azide-alkyne cycloaddition. The library was evaluated for inhibition of $Mycobacterium$ $tuberculosis$ (Mtb) growth and Mtb Antigen 85C (Mtb Ag85C) activity. Compound 506e was the most potent with a minimal inhibitory concentration (MIC) of 12.5 μg/mL and an Mtb Ag85C apparent $IC_{50}$ of 8.8 μM.

Figure 24:
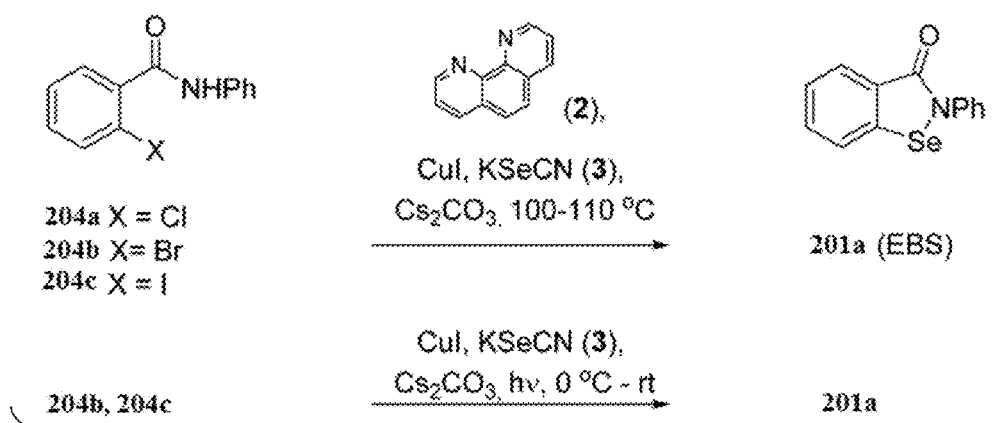
FIG. 24: Thermal (top) and photoinduced (bottom) preparation of ebselen.

2-Phenyl-1,2-benzisoselenazol-3(2H)-one (201a), also called ebselen, EBS, PZ51, and DR3305, is a lipid soluble organo-selenium compound that mimics glutathione peroxidase (GPx) activity and has the ability to inhibit some bacterial thioredoxin reductase systems (FIG. 24). EBS is being studied as a possible therapeutic agent for cancer, bipolar disorder, and for a rapidly expanding list of other indications. Ebselen also has activity against Mtb Ag85C and drug-resistant Mtb. In this Example, an efficient method to prepare libraries of 2-alkyl-1,2-benzisoselenazol-3(2H)-ones was developed, and compounds were evaluated for the treatment of Mtb infection.

Ebselen has been prepared starting from 2-(hydroxyselanyl)cyclohexane-1-carbonyl chloride. Ebselen also also been prepared by converting anthranilic acid to 2,2'-diselanediyldibenzoic acid, followed by elaboration to EBS. Further, N-substituted benzamides have been treated with n-butyl lithium, Se powder, and CuBr to produce this chemotype. EBS has also been accessed using N-substituted ortho-halobenzamides catalytic CuI, 1,10-phenanthroline (2), Se powder, base, and heating for 8-36 h, as well as by using KSeOtBu or lithium diselenide and N-substituted ortho-iodobenzamides. In this Example, EBS and its derivatives were prepared in as little as 1 h using CuI, 1,10-phenanthroline (202), KSeCN (203), and N-substituted orthohalobenzamides (204a-204c) (FIG. 24, top). In addition, a second method is described which is a low temperature photoinduced copper-mediated cross-coupling of (204b-c) with KSeCN (203) to form a C—Se bond, leading to the formation of EBS (FIG. 24, bottom).

Figure 25:
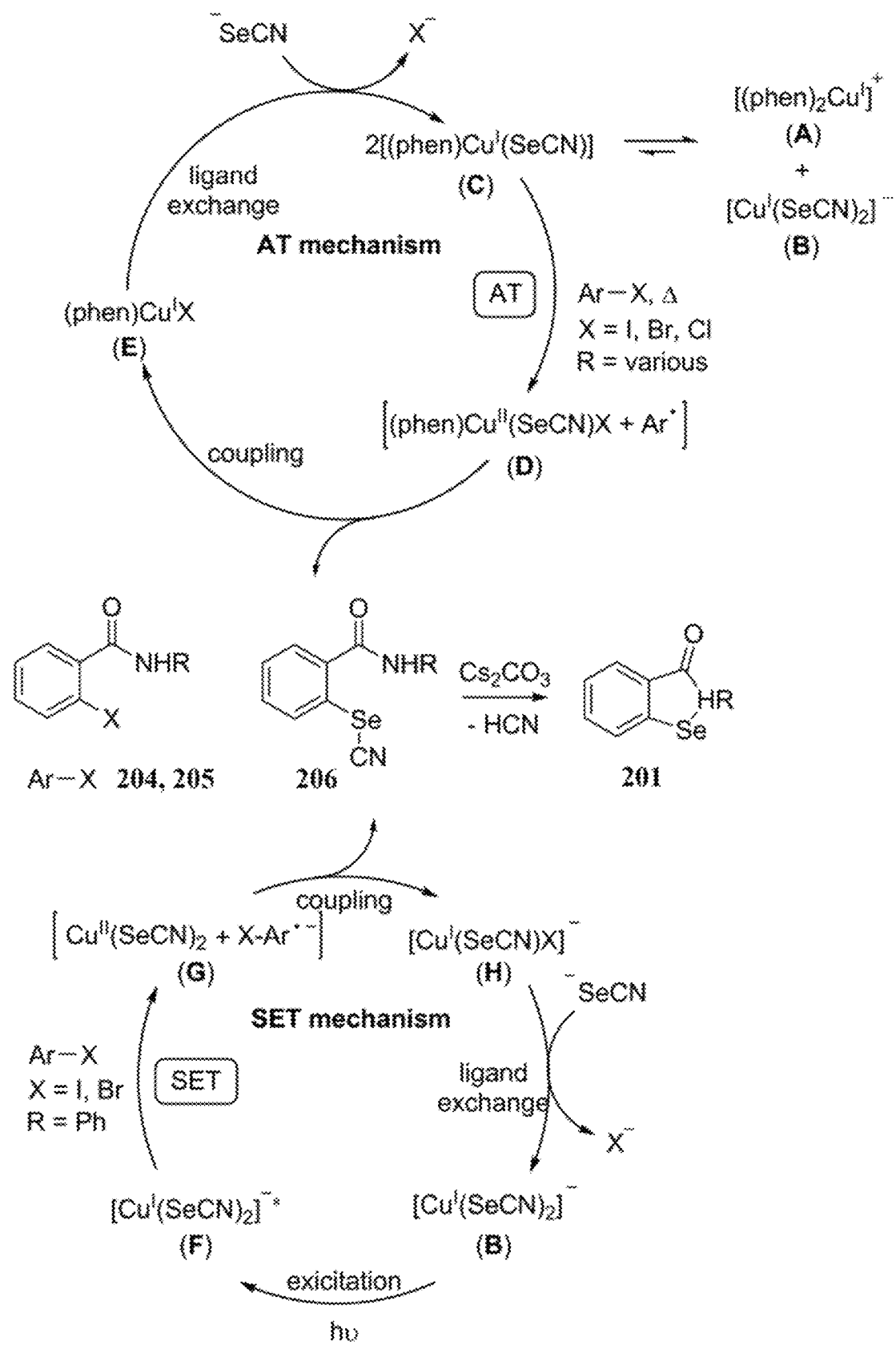
FIG. 25: Scheme showing Cu-promoted mechanisms for thermal and photoinduced synthesis of 2-alkyl-1,2-benzisoselenazol-3(2H)-ones 506a-506n.

This example describes a photoinduced copper-mediated cross-coupling for C—Se bonds. In this process, ligand-directed thermal and photoinduced Cu-promoted cross-coupling methods are utilized to form C—Se bonds in which the presence of ligand favors thermal activation via a putative atom transfer (AT) mechanism, whereas the absence of ligand favors photoinduced activation, which proceeds through a putative single electron transfer (SET) mechanism (FIG. 25). In this Example, the C—Se bond formation results in a putative selenocyanate which cyclizes to the medicinally important ebselen (201a) and its congeners in a single step.

Results

Thermal Activation

Figure 26:
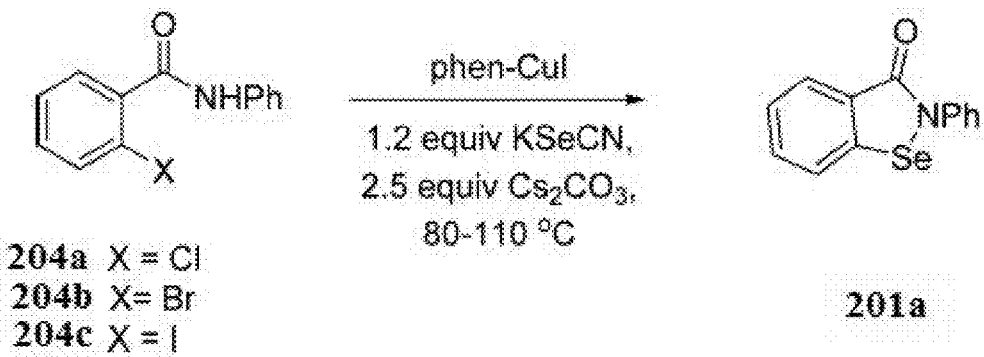
FIG. 26: Table 7, showing the optimization of the thermal method to produce 2-phenyl-1,2-benzisoselenazol-3(2H)-one (201a).

Synthesis of 2-alkyl-1,2-benzisoselenazol-3(2H)-ones was first conducted using known conditions requiring 1,10-phenanthroline(phen)-CuI, Se-powder, potassium carbonate in combination with 204a to afford 201a. However, yields were modest after 30 h of heating (FIG. 26, Table 7, entry 1). The substitution of insoluble selenium power with KSeCN was believed to produce an intermediate selenocyanate 206 that would cyclize to a selenazol-3(2H)-one under base-promoted conditions. Indeed, when aryl bromide 204b, KSeCN, 0.2 equiv of phen-CuI, and 2.5 equiv of $Cs_2CO_3$ were used, similar yields to entry 1 (FIG. 26, Table 7) were obtained with a significantly reduced reaction time (FIG. 26, Table 7, entry 2). Furthermore, the reaction was homogeneous and convenient to work up. Increasing the phen-CuI to 0.30 equiv improved the yield to 34% and 53% at 1 and 12 h reaction times, respectively (FIG. 26, Table 7, entries 3 and 4), while increasing the catalyst loading to 1.0 equiv resulted in a 71% yield in 1 h (FIG. 26, Table 7, entry 5). The chloride 204a was less reactive, producing a 33% yield in 1.5 h under the same conditions (FIG. 26, Table 7, entry 6), while the iodide 204c reacted quickly to produce 201a in 75% yield (FIG. 26, Table 7, entry 7).

Improved yields for 204a were obtained by switching the solvent to acetonitrile (FIG. 26, Table 7, entry 8). Aryl bromide 204b and aryl iodide (FIG. 26, Table 7, entry 11). Further, it was noted that 1,10-phenanthroline could be removed from the reaction to produce 201a; however, the yields were reduced (FIG. 26, Table 7, entry 12).

Figure 27:
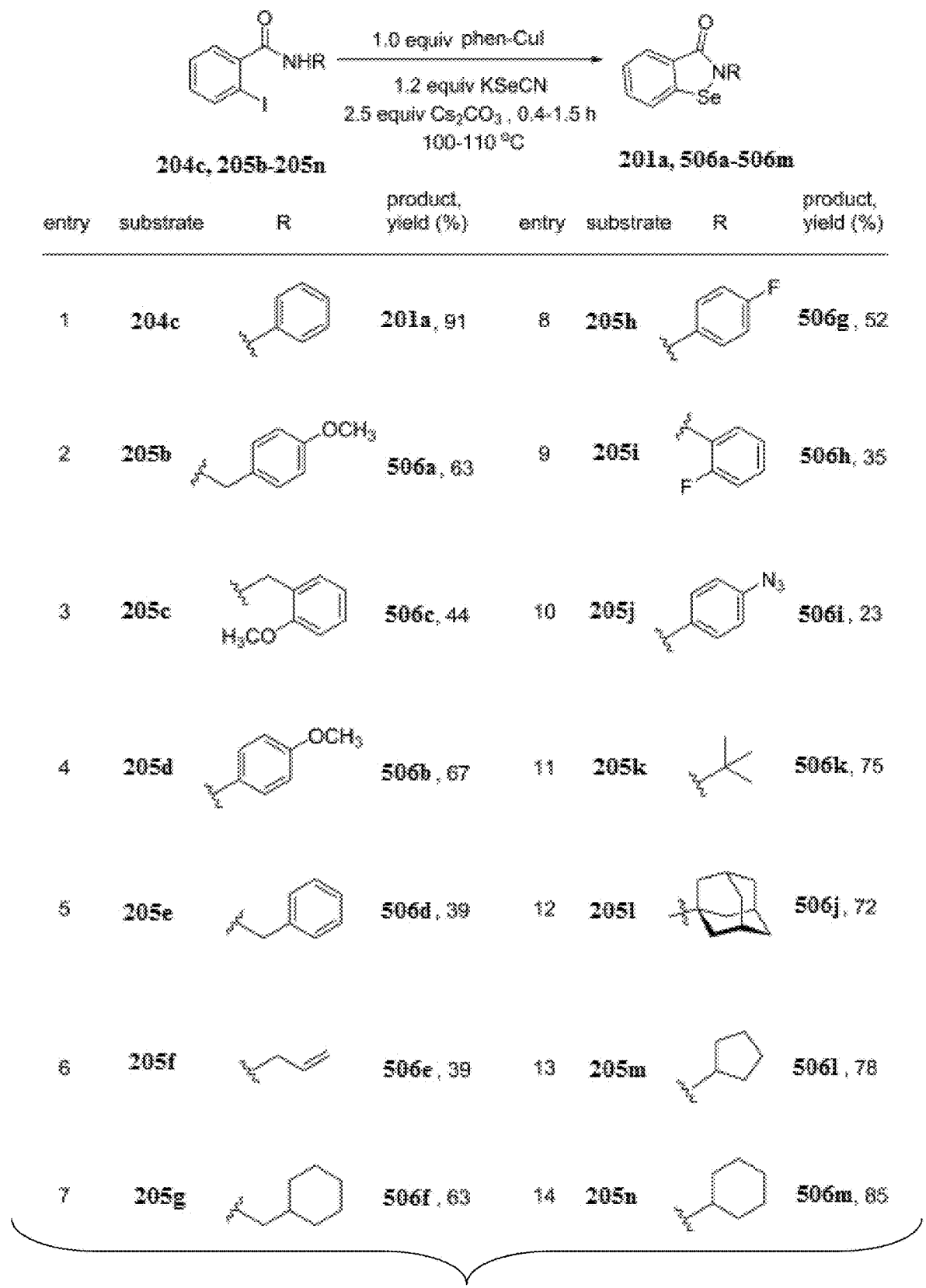
FIG. 27: Table 8, showing thermal synthesis of a 1,2-benzisoselenazol-3(2H)-one library.

A library of 14 1,2-benzisoselenazol-3(2H)-ones was synthesized using this thermal method. The members of the library differ from each other at the nitrogen substituent (FIG. 27, Table 8). Compounds 201a, 506b, 506g, 506h, and 506i were prepared with a phenyl group or an ortho- or para-substituted phenyl group (i.e., substituents=fluoro, methoxy, or azide) as the nitrogen substituent. Compounds 506a, 506c, and 506d contained a benzyl substituent, while compound 506e possessed an allyl substituent. Aliphatic substituents were also tolerated as demonstrated by the preparation of compounds 506f, 506l, and 506m, which contain aliphatic rings. Larger substituents were tolerated such as tertbutyl and adamantyl, as shown by the preparation of compounds 506k and 506j, respectively.

Photoinduced Activation

Figure 28:
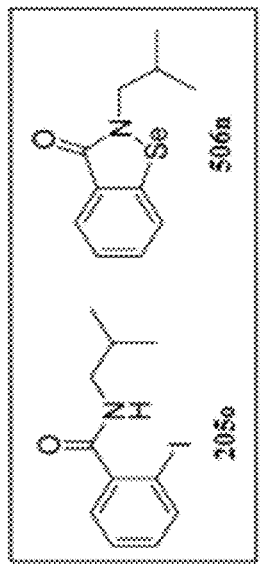
FIG. 28: Table 9, showing optimization of the photoinduced method to produce 2-phenyl-1,2-benzisoselenazol-3(2H)ones. $^a$Unless otherwise stated, KSeCN (2.5 equiv) and Cs$_2$CO$_3$ (1.2 equiv) 24 h, and acetonitrile were used. Reactions were cooled for about 2 h and allowed to warm to room temperature (20° C.). $^b$Thermal activation=phen-CuI (1.0 equiv), KSeCN (1.2 equiv), Cs$_2$CO$_3$ (2.5 equiv), 12 h, 100-110° C. $^c$48 h. $^d$Reaction reached 65-70° C. $^e$NaOtBu (0.1 equiv). N.R.=no reaction. 22 W is a combined wattage of two lamps. $^f$Reaction performed without BLE-8T365 (320-400 nm) lamp; only the 14 W Rayonet RPR-3000A lamp was used.
Figure 29:
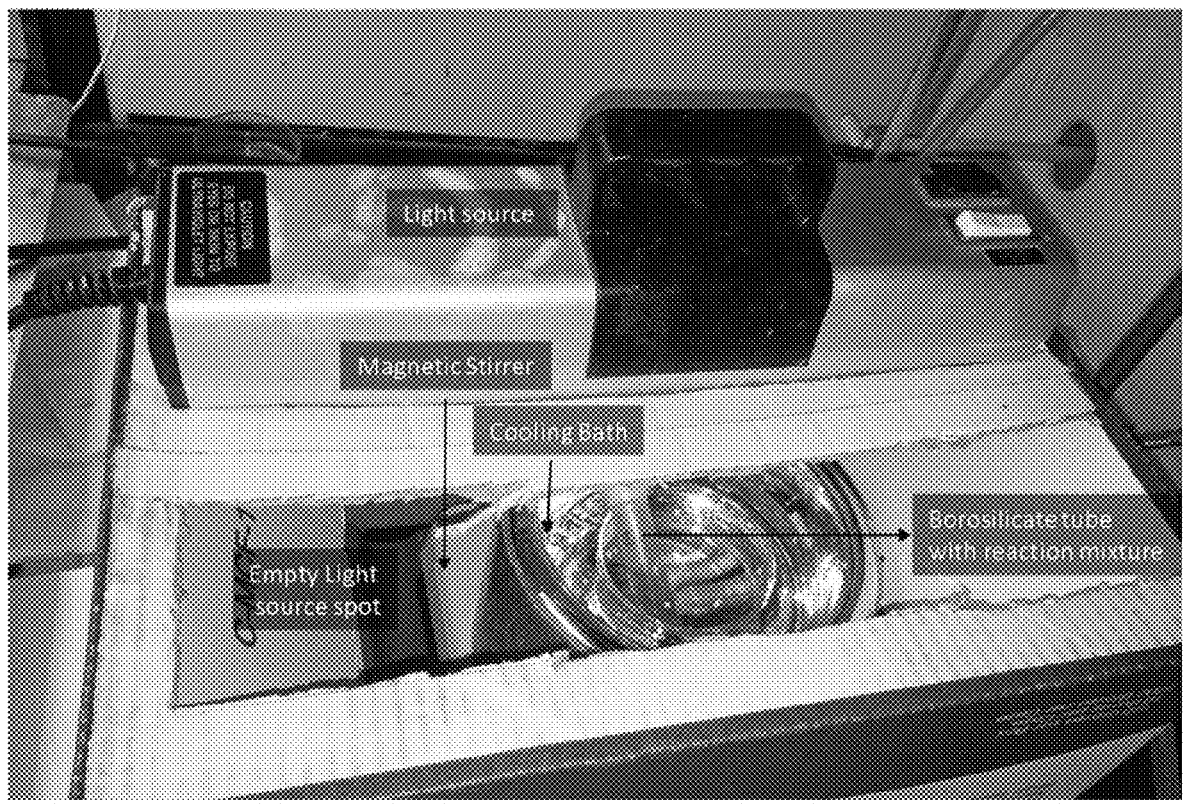
FIG. 29: Photograph showing the photochemical reaction setup used in the Examples herein. The reaction setup was composed of a cardboard box fitted with two light sources with combined output of 22 Watts: (1) 14 watts Rayonet RPR-3000A lamp (spectral energy distribution wavelength range: 250-360 nm); (2) 8 watts Spectronics Corp BLE-8T365 (365 nm).

Ullmann-type reactions occur under photoinduced conditions in the absence of a copper ligand. Therefore, this was explored with KSeCN and aryl halides (204a-204c) to form ebselen (201a). Table 7 (FIG. 28) shows the results using aryl bromide (204b) which affords 201a in 89% using thermal conditions (entry 1). Replacing the heating with a 22 W (combined) Hg lamp (FIG. 29) and cooling with ice for 2 h, following by warming to room temperature, afforded 201a in 31% (FIG. 28, Table 9, entry 2). A significant improvement in the yield to 82% occurred when the 1,10-phenanthroline ligand was removed from the reaction (FIG. 28, Table 9, entry 3). This data supports a mechanism in which a [(phen)CuI—(SeCN)] (C) complex is needed in the thermal activation method, however, not needed in the light activated case. The yield of the photoinduced reaction dropped to 60% and 0% when 10 and 0 mol % CuI were used FIG. 28, Table 9, entries 4 and 5, respectively). These results illustrate the requirement for copper(I). When the phen-free reaction was placed in the dark, a 6% yield was observed (FIG. 28, Table 9, entry 6), indicating the importance of light. Removal of the base (FIG. 28, Table 9, entry 7) resulted in no reaction. Ambient light was sufficient to generate a 21% yield (FIG. 28, Table 9, entry 8). Use of a 250 W IR lamp produced a 63% yield; however, moderate heating (65-70° C.) was also involved (FIG. 28, Table 9, entry 9). Finally, the combination of 10 mol % CuI and NaOtBu afforded a yield of 81%; however, the reaction time was extended to 48 h (FIG. 28, Table 9, entry 10). Iodide 204c was a superior substrate in the reaction; however, chloride 204a was unreactive (FIG. 28, Table 9, entries 11 and 12, respectively). The chemistry was also successful for alkyl amide 205o which afforded ebselen derivative 506n in 85% yield. An additional reaction was conducted using only the shortwave UV light (RPR-3000A lamp, 250-360 nm), indicating that the BLE-8T365 lamp (320-400 nm) was not needed for the reaction (FIG. 28, Table 9, entry 14). In summary, the combination of light, a phen-free Cu(I) source, and base promoted efficient formation of ebselen (201a). Thus, a photoinduced copper-promoted C—Se—N bond forming reaction was used to synthesize ebselen.

Copper Species Evaluation

Figure 30:
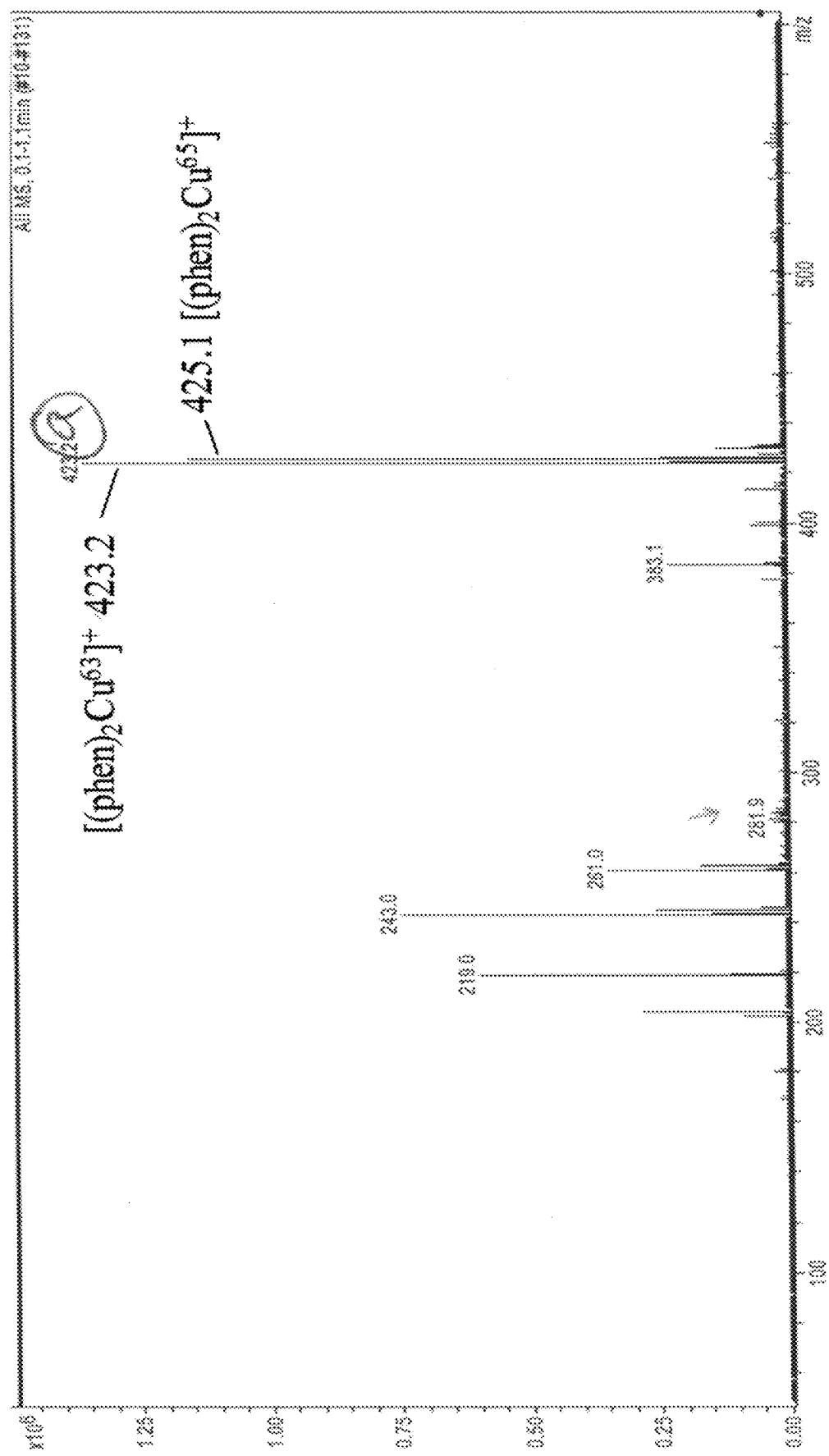
FIG. 30: ESI-MS (positive) of [(phen)$_2$Cu$^I$]$^+$ (A) in CH$_3$CN.
Figure 31:
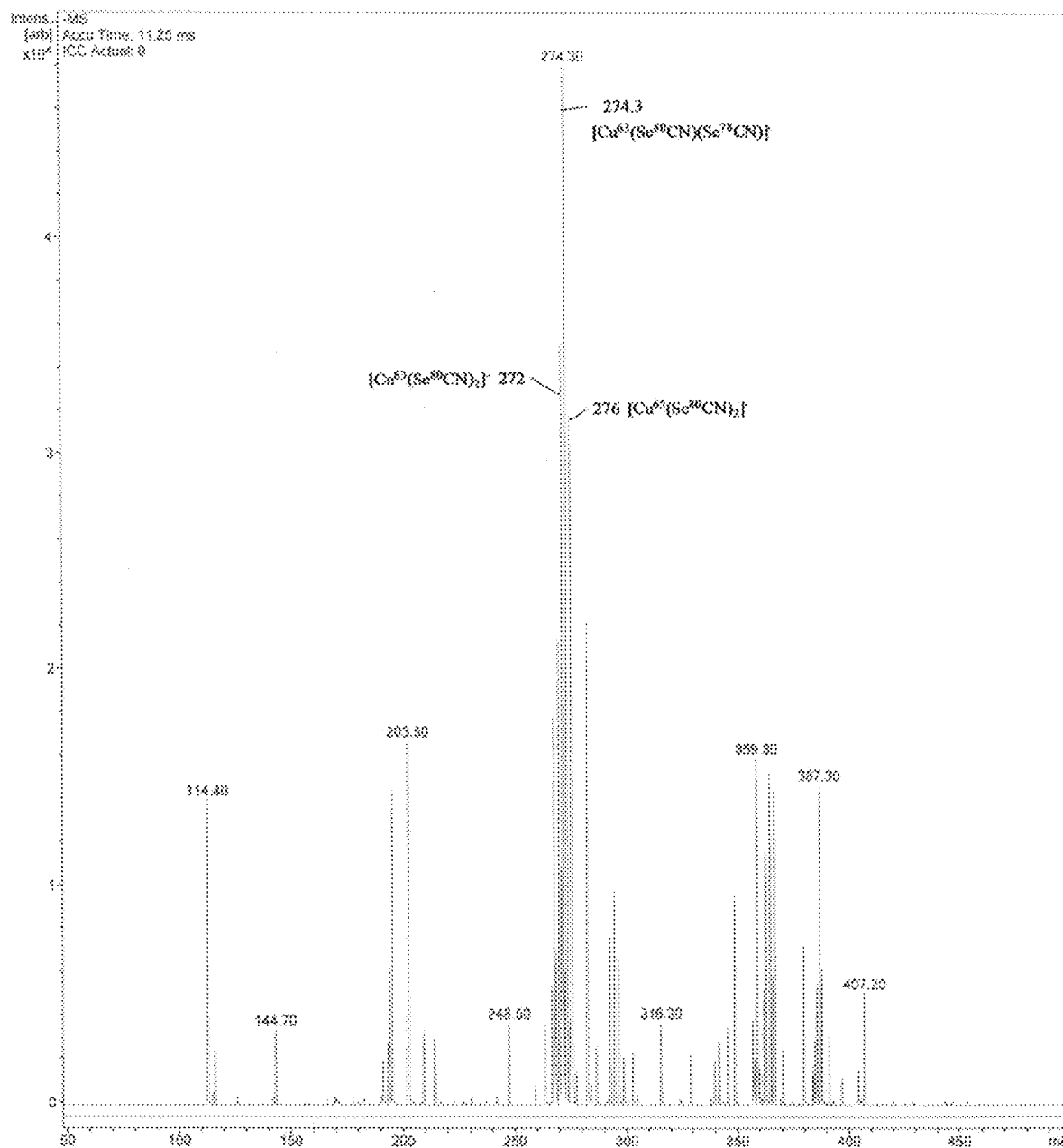
FIG. 31: ESI-MS (negative) of [CuI(SeCN)$_2$]$^-$ (B) in CH$_3$CN.
Figure 32:
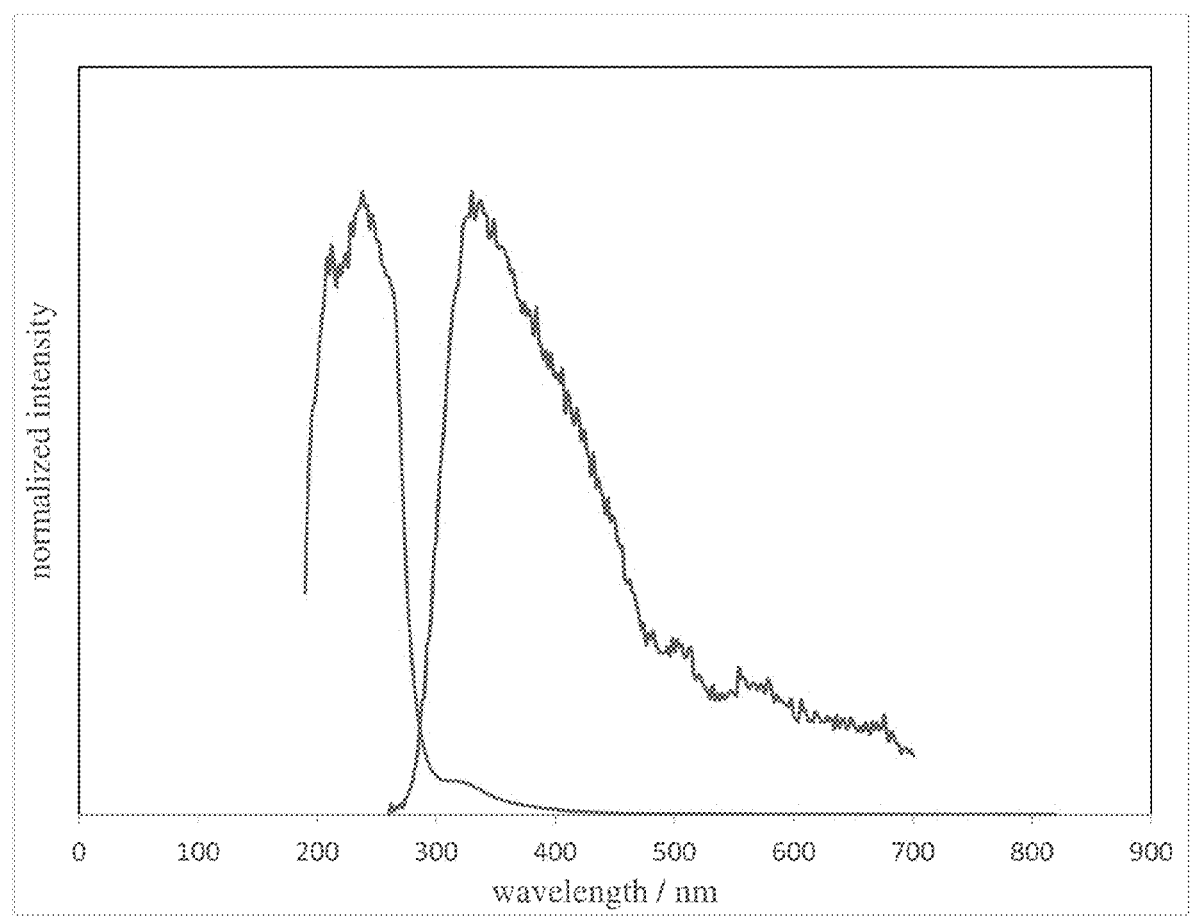
FIG. 32: Absorption spectrum of copper complex B with $\lambda_{max}$=242 nm (Blue) and emission spectrum at 338 (orange) obtained by excitation copper complex B at 242 nm.
Figure 33:
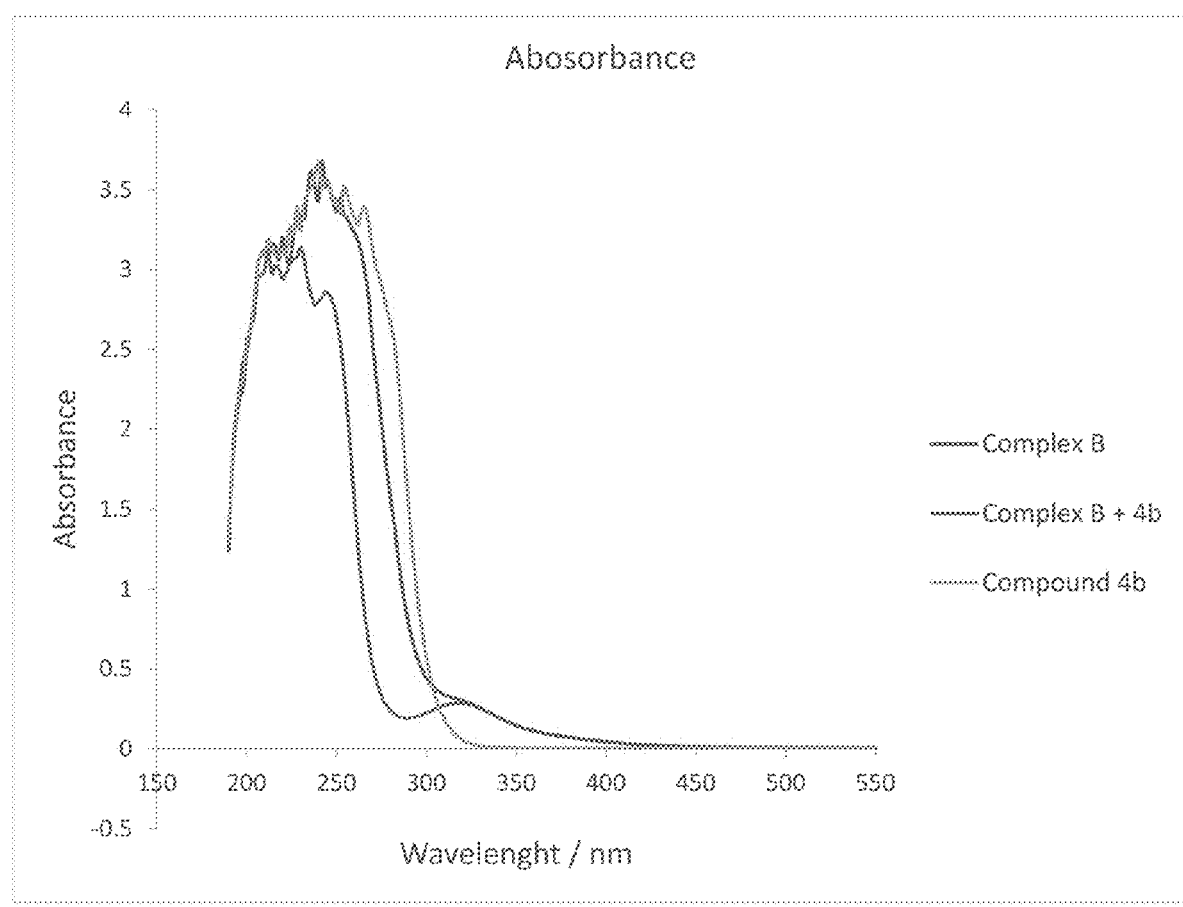
FIG. 33: Absorption spectrum of complex B (0.91 μM, blue), mixture of complex B 0.91 μM+204b 0.91 μM (orange) and compound 204b (0.91 μM, grey)
Figure 35:
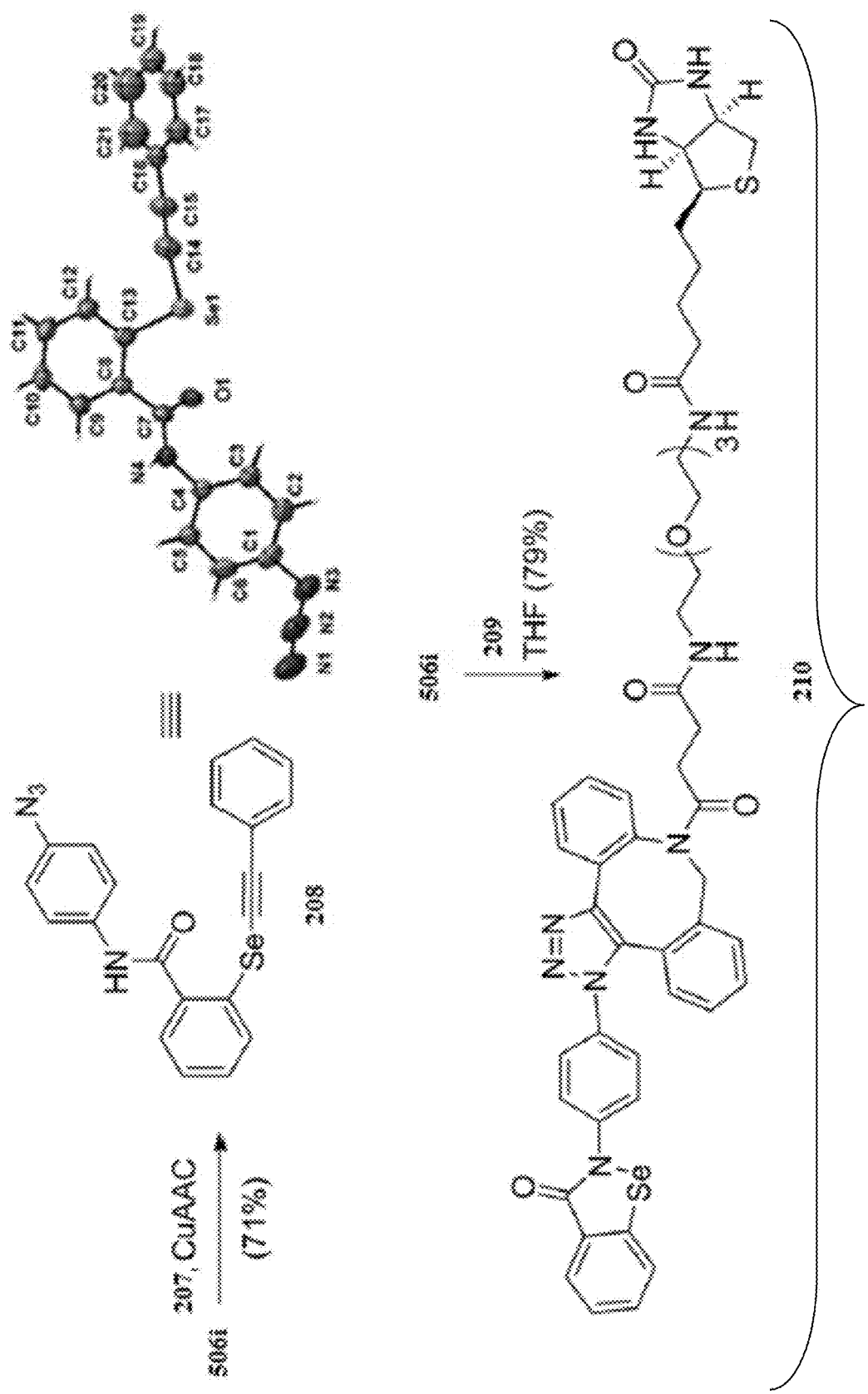
FIG. 35: Scheme showing synthesis of 2-Phenylbiotinyl-1,2-benzisoselenazol-3(2H)-one 210 and X-ray crystal structure of N-(4-azidophenyl)-2-((phenylethynyl)selanyl)benzamide (208).

The identity of possible copper complexes that might be present under thermal conditions was evaluated by electrospray ionization mass spectrometry (ESIMS). For the thermal case, a mixture of CuI, phen, KSeCN, and $Cs_2CO_3$ (1.0:1.0:1.2:2.5) in acetonitrile was heated to 70-80° C. for 1 h, followed by ESI-MS. Major cationic species were detected at m/z: 423.2 and 425.1, which correspond to [(phen)$_2$Cu$_{63}$]+ and [(phen)$_2$Cu$_{65}$]+(A), respectively (FIG. 30). ESI-MS in the negative ion mode was inconclusive. For the photoinduced case, a mixture of CuI, KSeCN, and Cs$_2$CO$_3$ (1.0:2.2:1.2) in acetonitrile, which lacks phen, was irradiated with a 22 W (combined) Hg lamp at room temperature for 1 h. ESI-MS was inconclusive in the positive ion mode; however, the negative ion mode revealed major masses at m/z: 272, 274, and 276 that were assigned to the isotope envelope of [Cu(SeCN)$_2$]$^-$, i.e., [Cu$_{63}$(Se$_{80}$CN)$_2$]$^-$, [Cu$_{63}$(Se$_{80}$CN)(Se$_{78}$CN)]$^-$, and [Cu$_{65}$(Se$_{80}$CN)$_2$]$^-$ (B), respectively (FIG. 31). The absorption spectrum of the CuI, KSeCN, and Cs$_2$CO$_3$ (1.0:2.2:1.2) mixture was recorded after irradiation. The sample had a strong absorption band at 242 nm, and the sample exhibited a strong fluorescence emission at 338 nm after excitation at 242 nm (FIG. 32). The absorption spectra of a mixture of complex B (0.91 μM)+204b (0.91 μM) and compound 4b (0.91 μM) alone were obtained for characterization purposes (FIG. 33). To provide evidence of that photoexcited complex B can transfer energy to the substrate, substrate 204b was titrated into complex B and the luminescence recorded, revealing strong concentration-dependent fluorescence quenching (FIG. 35).

Synthesis of Biotinylated
1,2-Benzisoselenazol-3(2H)-ones

Ebselen has a cysteine-reactive nature against an Mtb Ag85C and other cysteine-containing enzymes. New tools are needed to identify other possible cysteine-reactive targets within Mtb and other organisms. The method in this Example provides for accessing 506i, which may be used in combination with click chemistry as part of a long-term goal to identify cysteine-reactive enzymes and proteins. Once in hand, it was investigated whether azide 506i would undergo the copper-promoted azide-alkyne Huisgen cycloaddition (CuAAC). Thus, azide 506i was treated with phenylacetylene (207) understandard CuAAC conditions. However, instead of forming the 1,2,3-triazole, phenylacetylene opened the selenazol-3(2H)-one ring to afford the isobaric dialkyl selenide (208). The formation of compound 208 was confirmed by X-ray crystallography (FIG. 35). The adduct 208 is a Cu-acetylide. These intermediates can attack the Se atom in 1,2-benzisoselenazol-3(2H)-ones. To circumvent this problem, 506i was treated with dibenzocyclooctyne-PEG3-biotin (209) in THF to afford triazole 10 in 79% yield. Compound 210 may serve as a useful affinity-based tool for identification of enzymes with solvent exposed cysteines.

Mtb Growth and Enzyme Inhibition Studies

Figure 36:
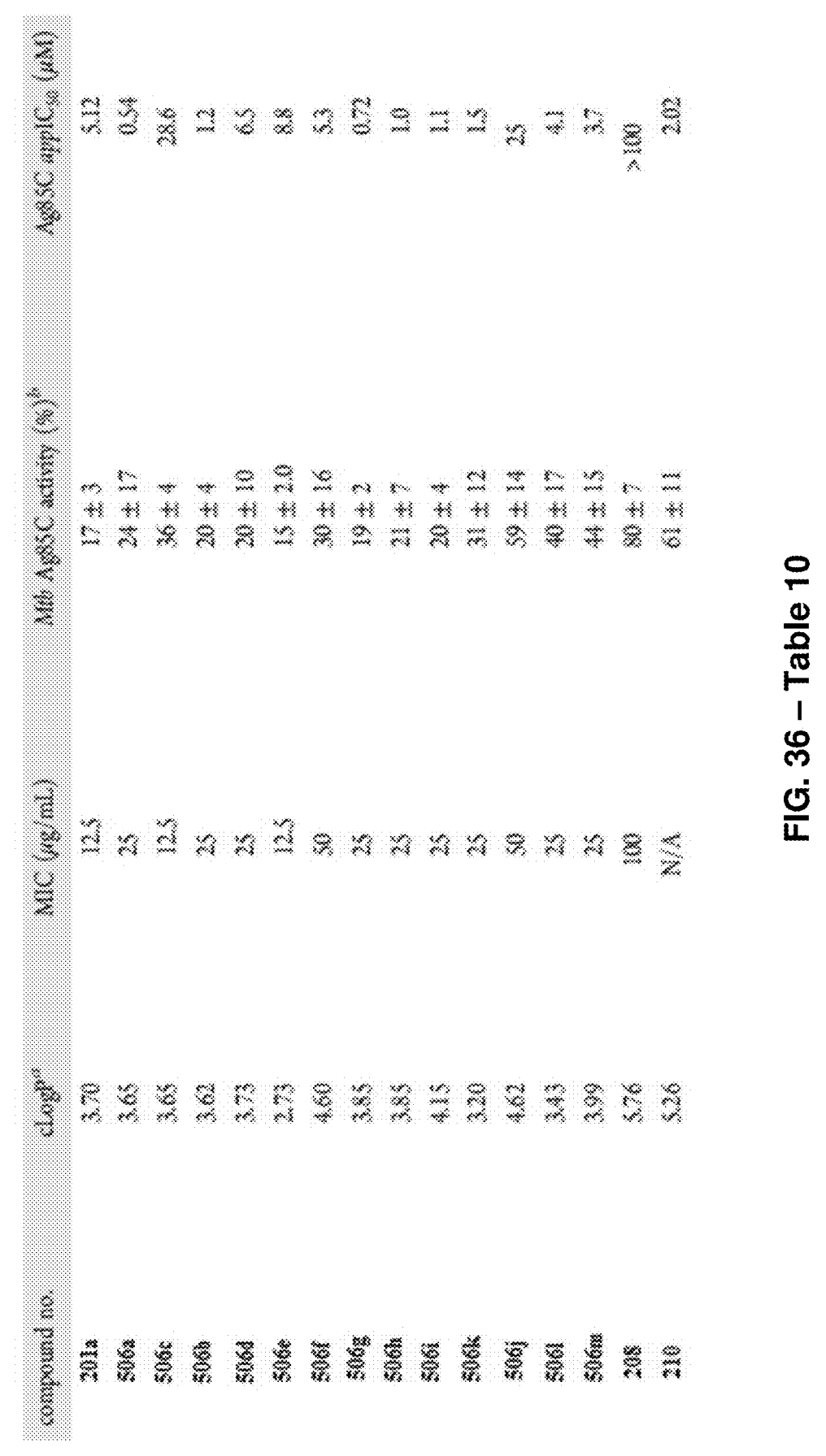
Figure 37:
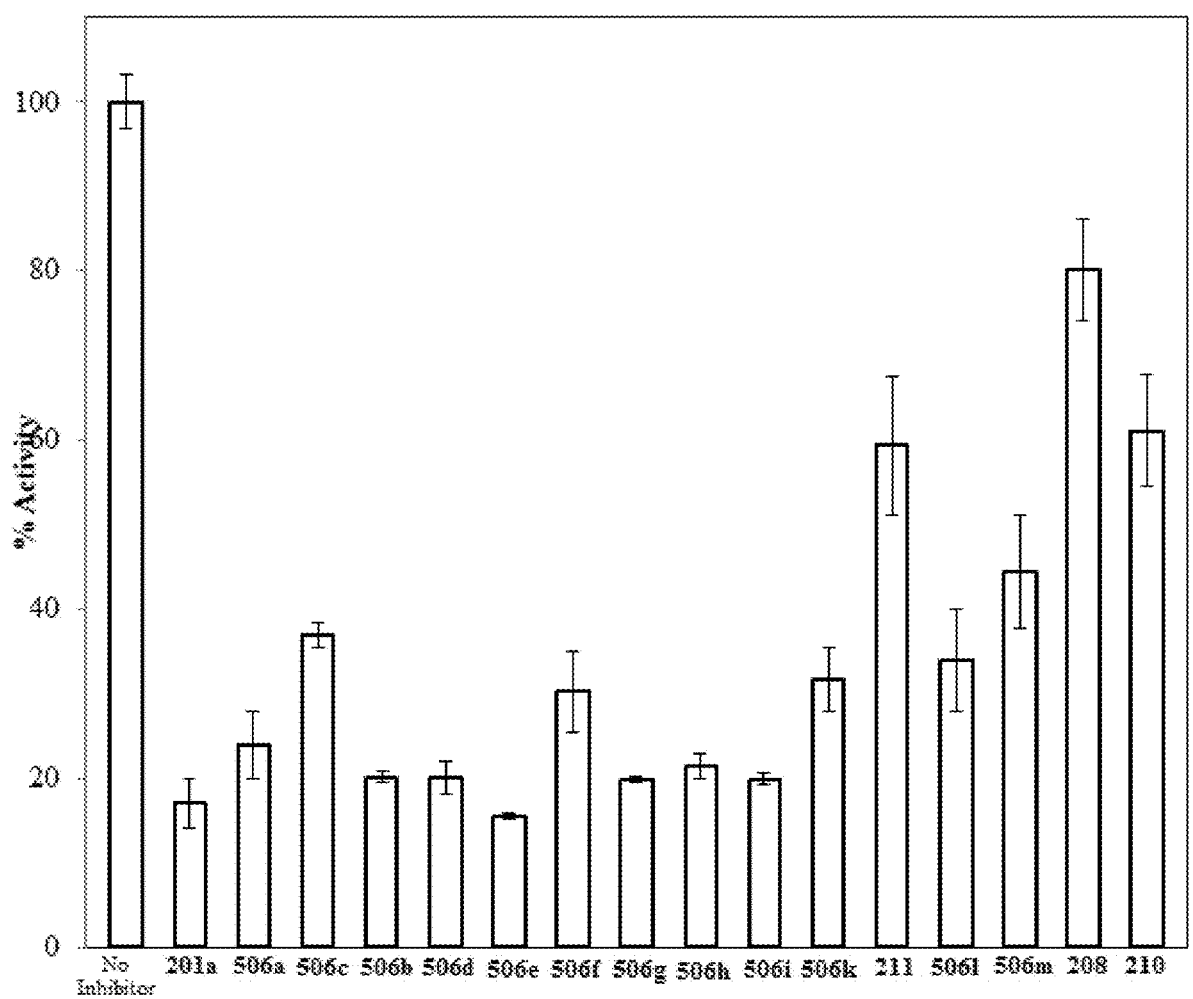
FIG. 37: The enzymatic activity of Mtb Ag85C was evaluated after 40 min of incubation with 5 μM 2-alkyl-1,2-benzisoselenazol-3(2H)-one 201a, 506a-506m, 208, and 210. Enzyme activity was normalized to the control reaction that contained no inhibitor. The error bars were calculated by performing each experiment in triplicate.
Figure 38A:
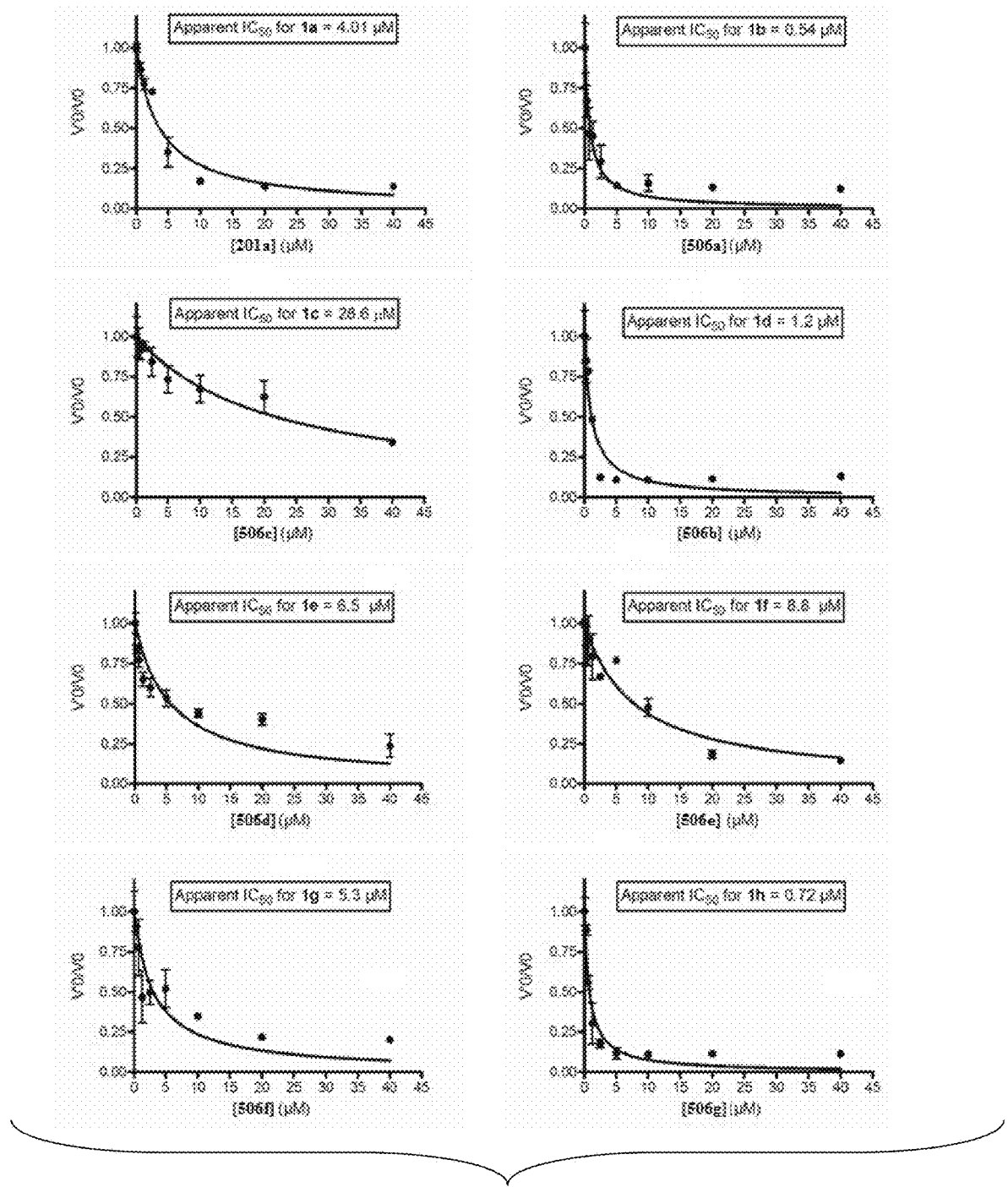
FIGS. 38A-38B: Apparent IC$_{50}$ for 1,2-benzisoselenazol-3(2H)-ones. Error bars are calculated by performing each experiment in triplicate.
Figure 38B:
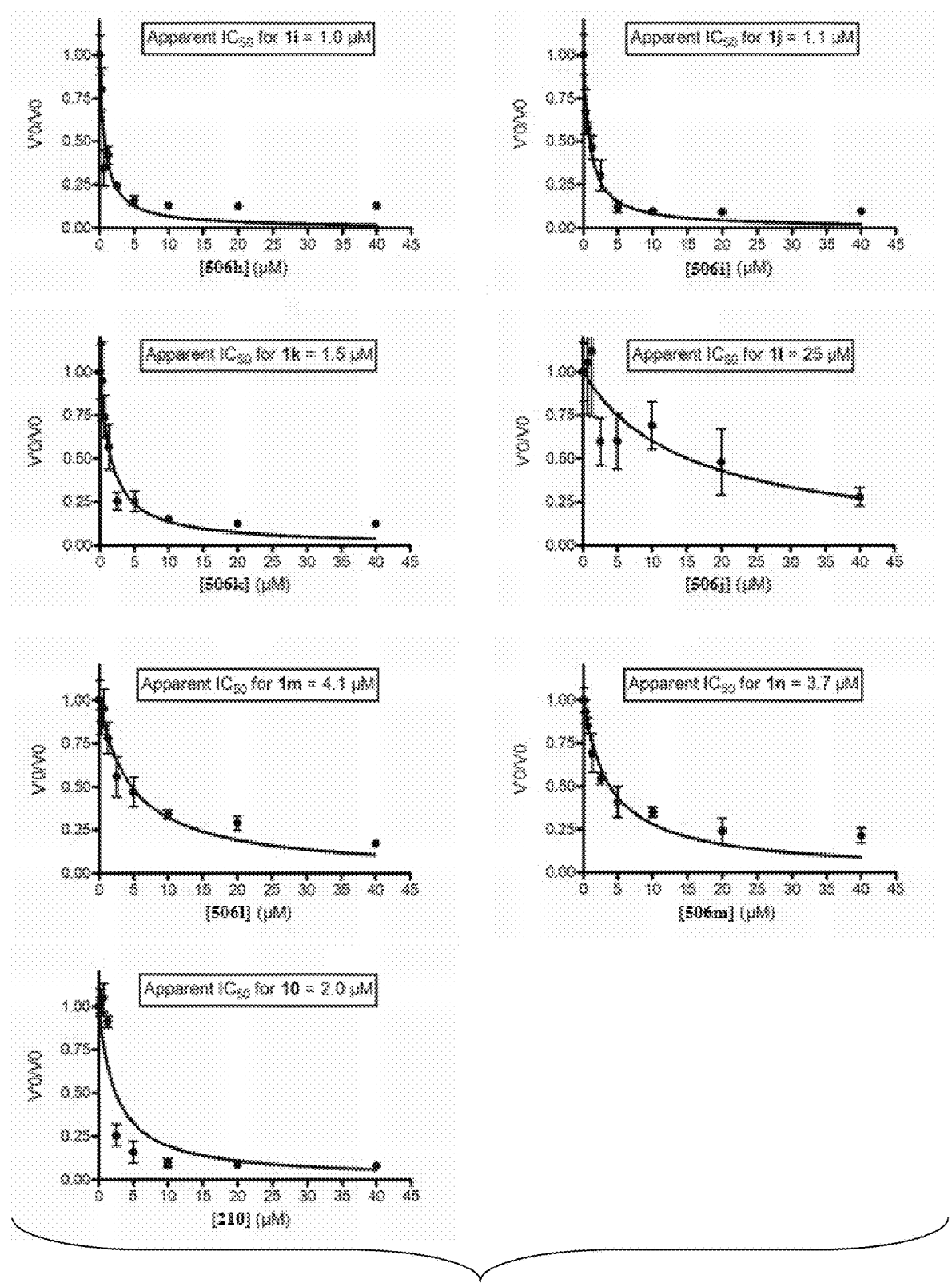
Figure 39A:
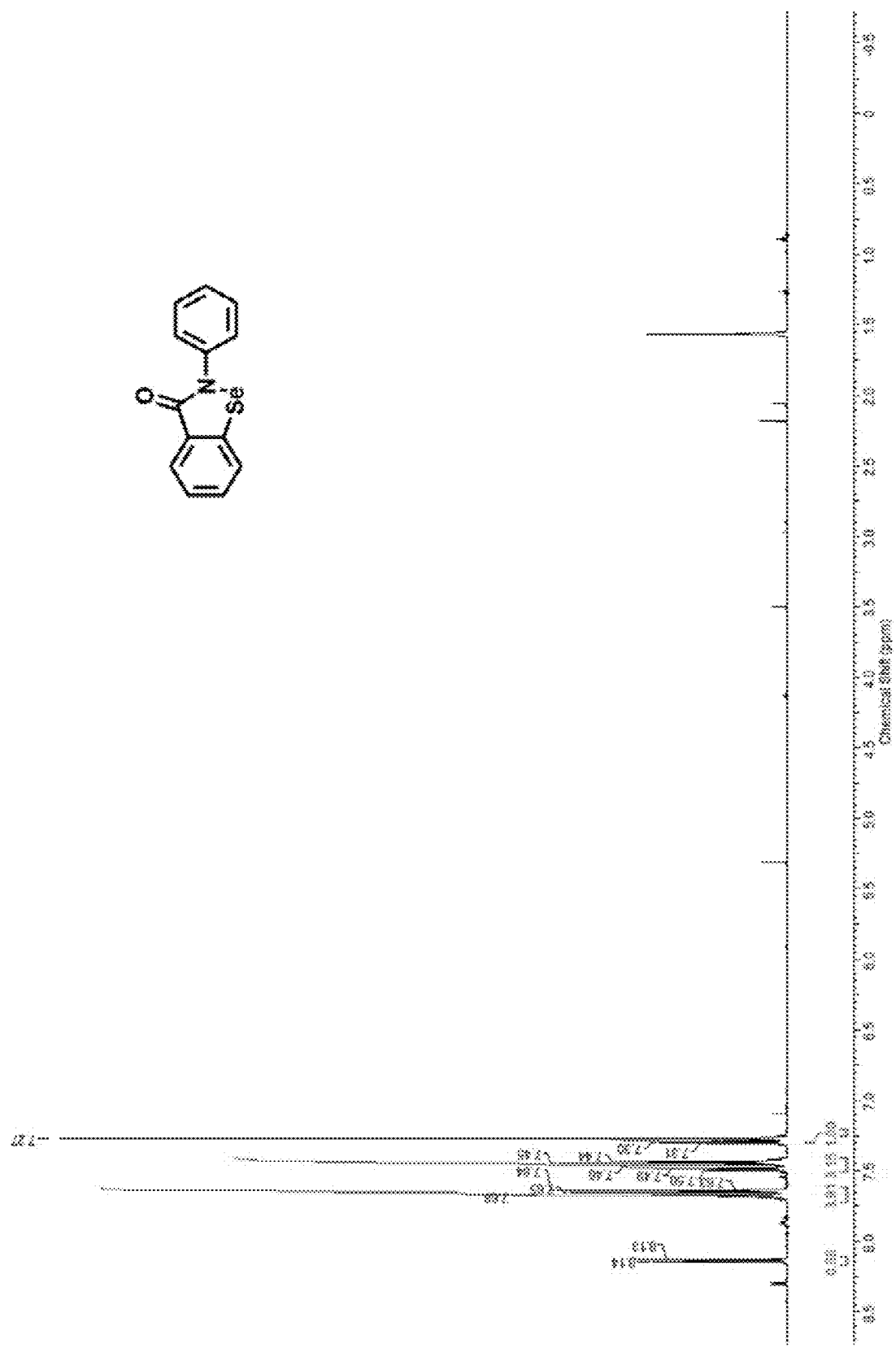
Figure 40A:
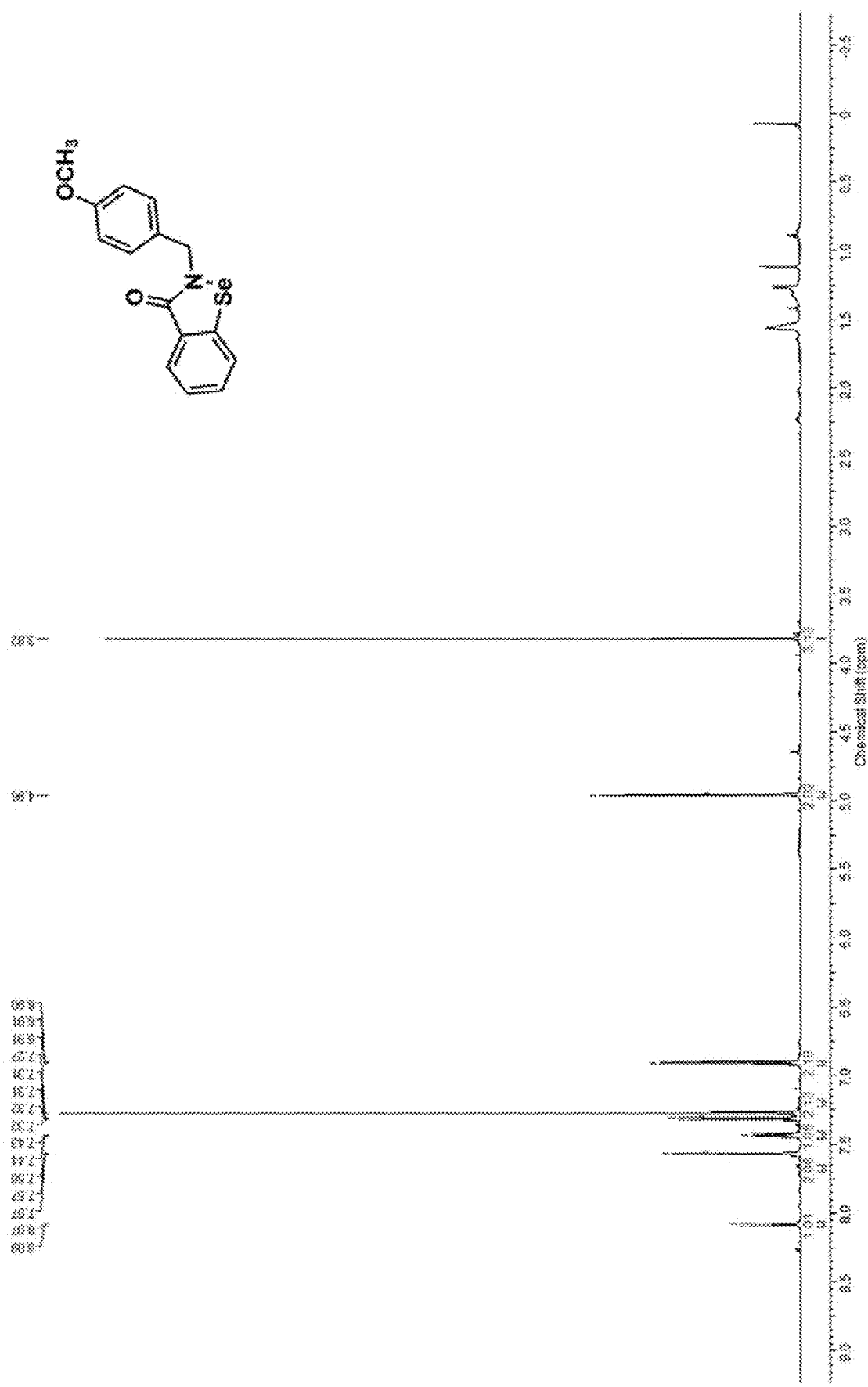
FIGS. 40A-40B: $^1$H (FIG. 40A) and $^{13}$C NMR (FIG. 40B) spectra of 2-(4-methoxybenzyl)benzo[d][1,2]selenazol-3(2H)-one (506a).
Figure 40B:
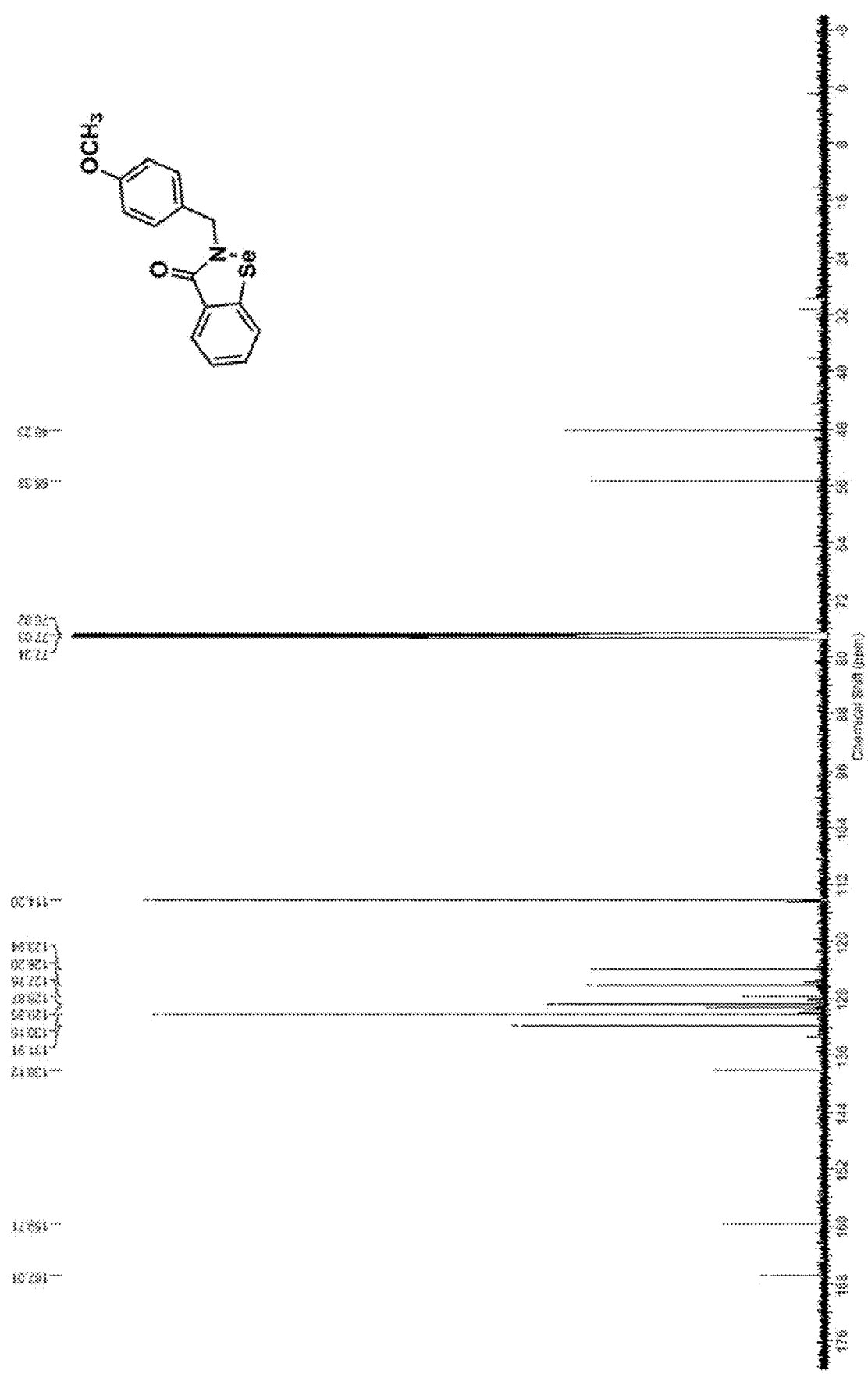
Figure 41A:
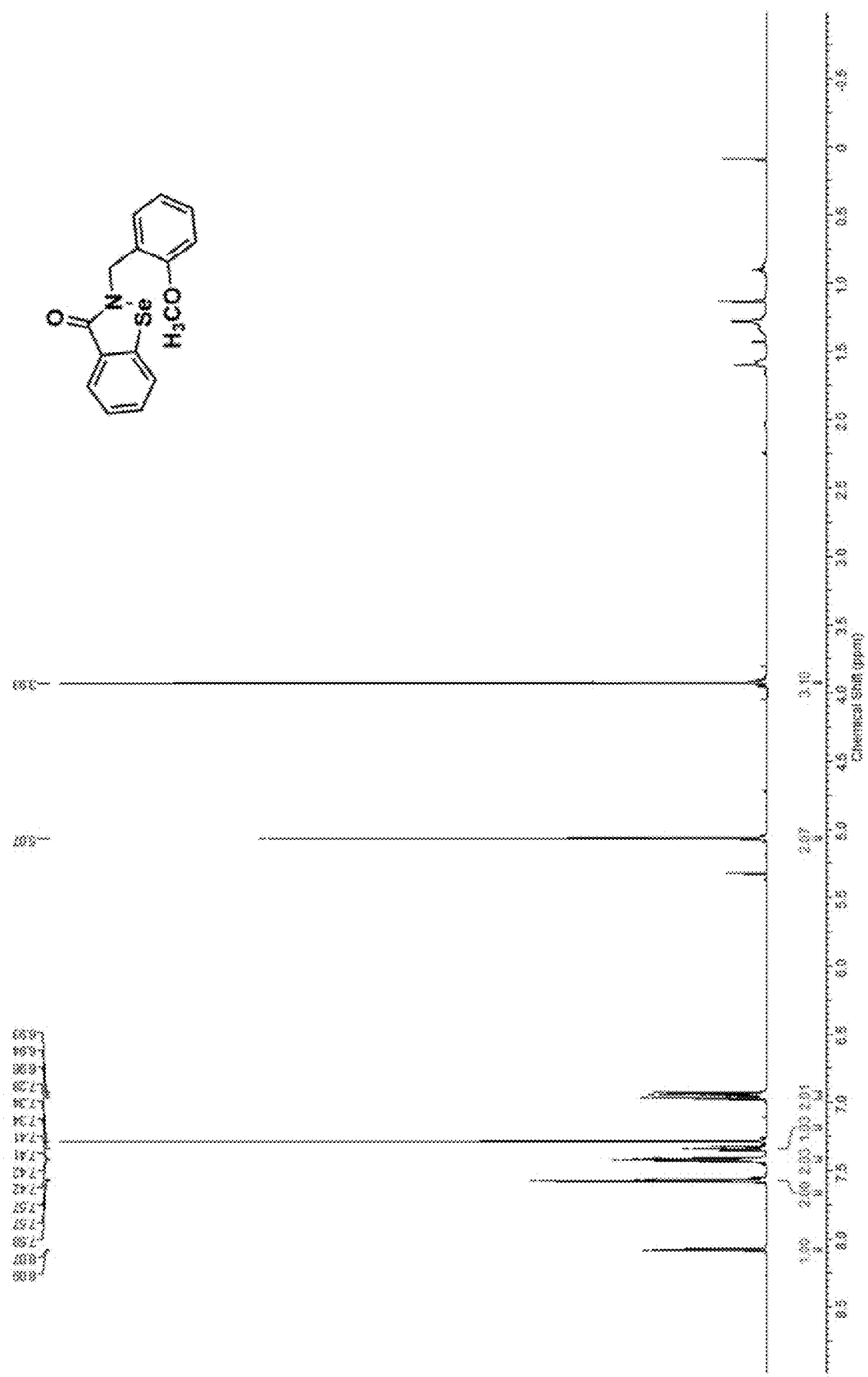
FIGS. 41A-41B: $^1$H (FIG. 41A) and $^{13}$C NMR (FIG. 41B) spectra of 2-(2-methoxybenzyl)benzo[d][1,2]selenazol-3(2H)-one (506c).
Figure 41B:
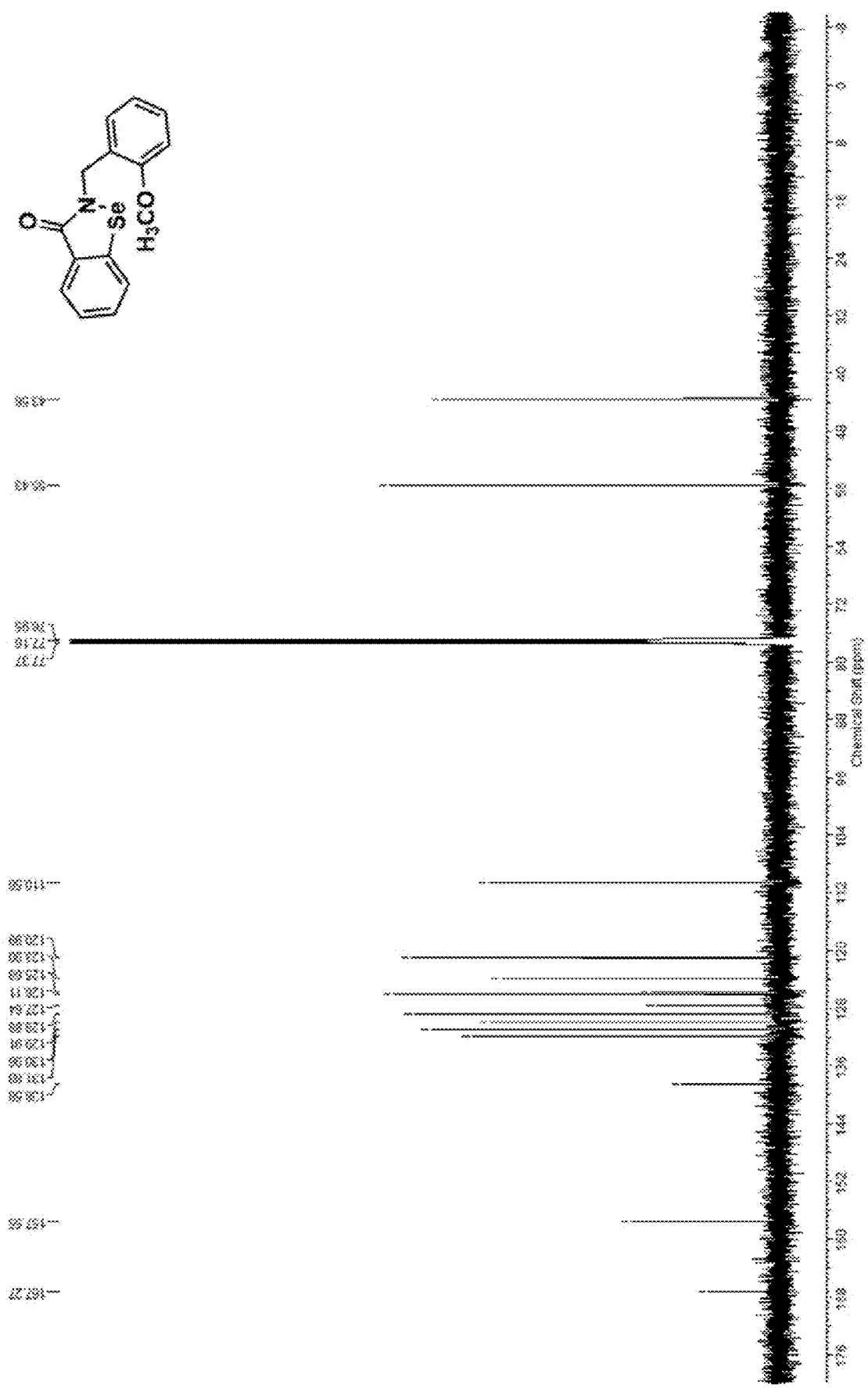
Figure 42A:
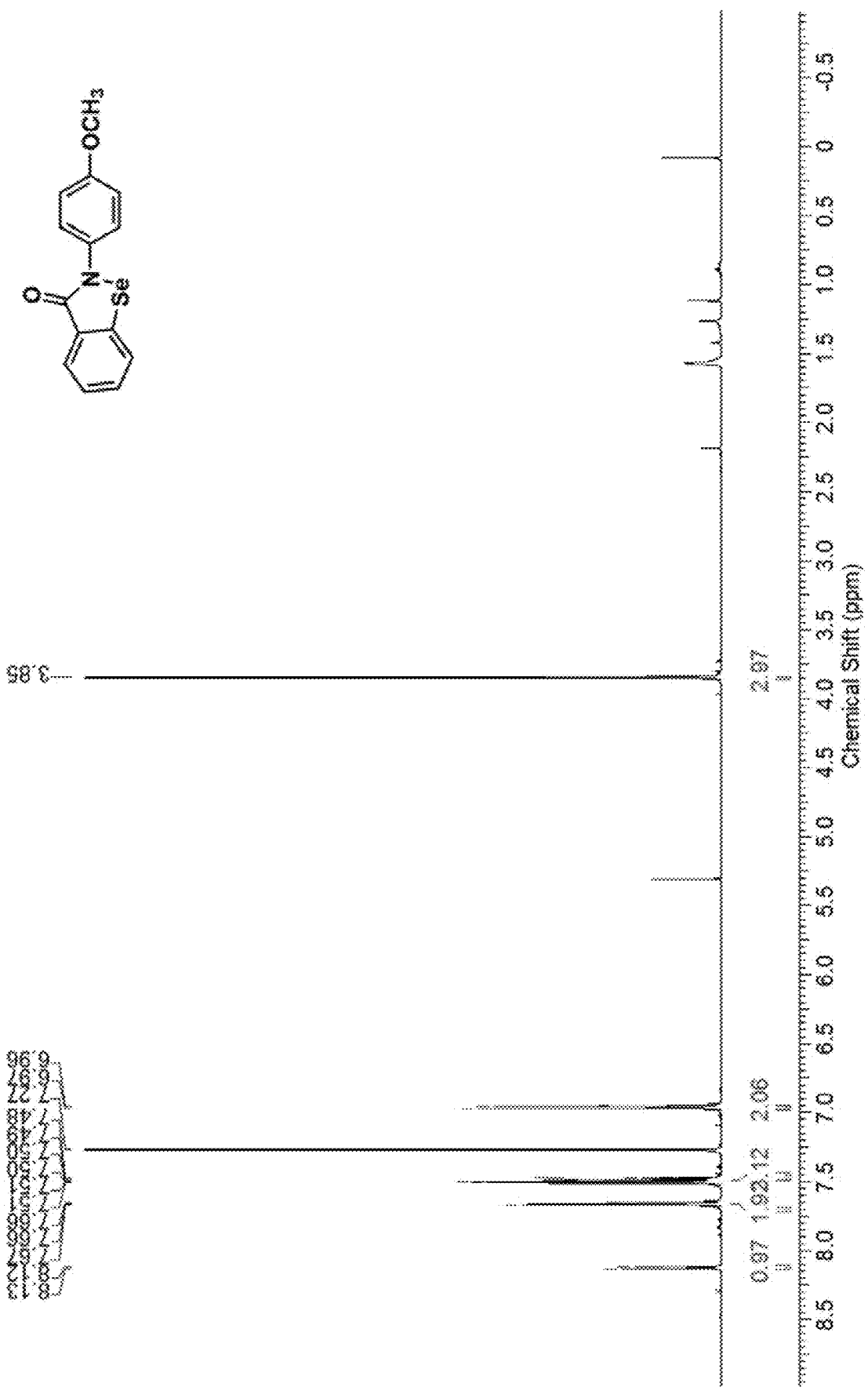
FIGS. 42A-42B: $^1$H (FIG. 42A) and $^{13}$C NMR (FIG. 42B) spectra of 2-(4-methoxyphenyl)benzo[d][1,2]selenazol-3(2H)-one (506b).
Figure 42B:
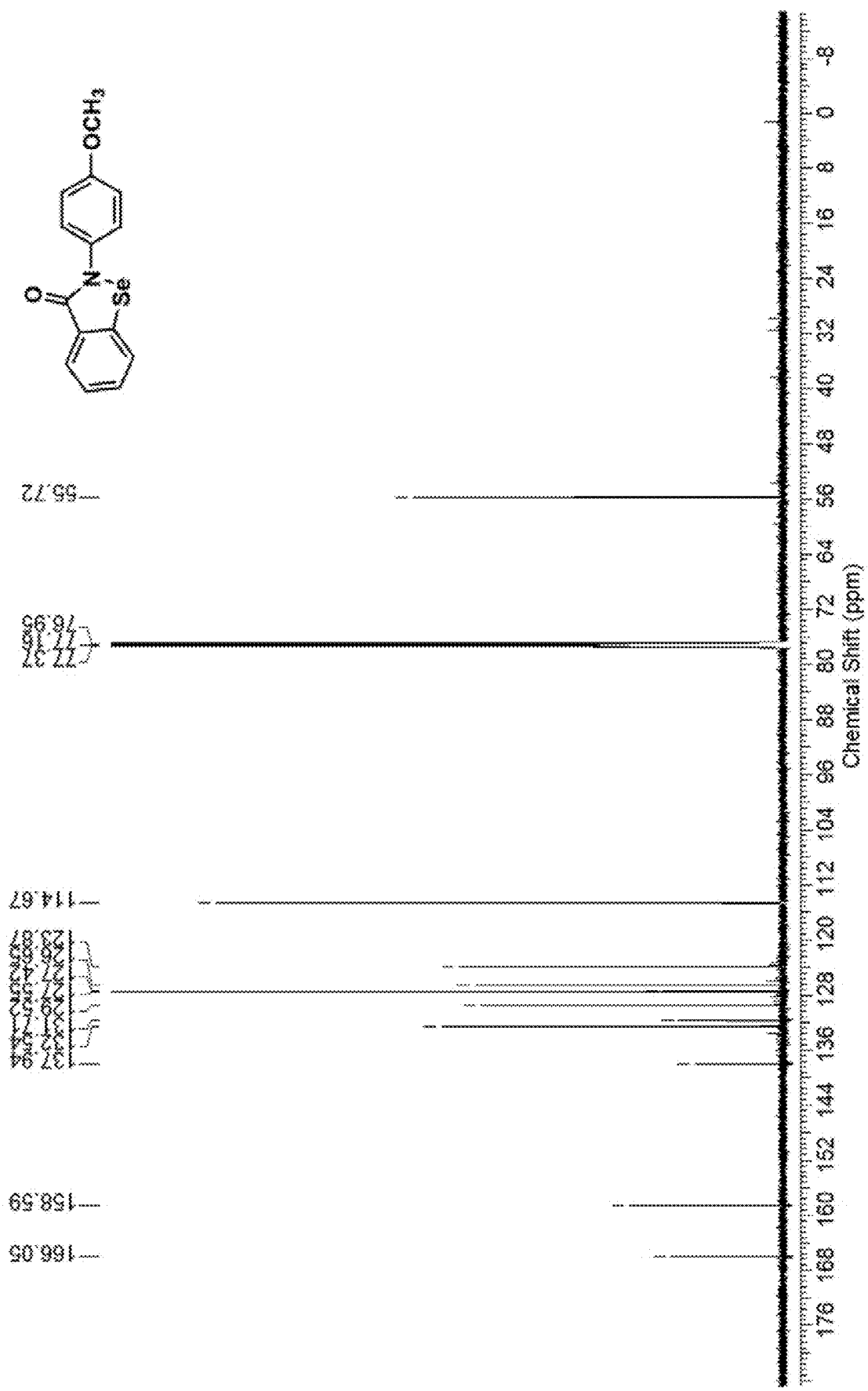
Figure 43A:
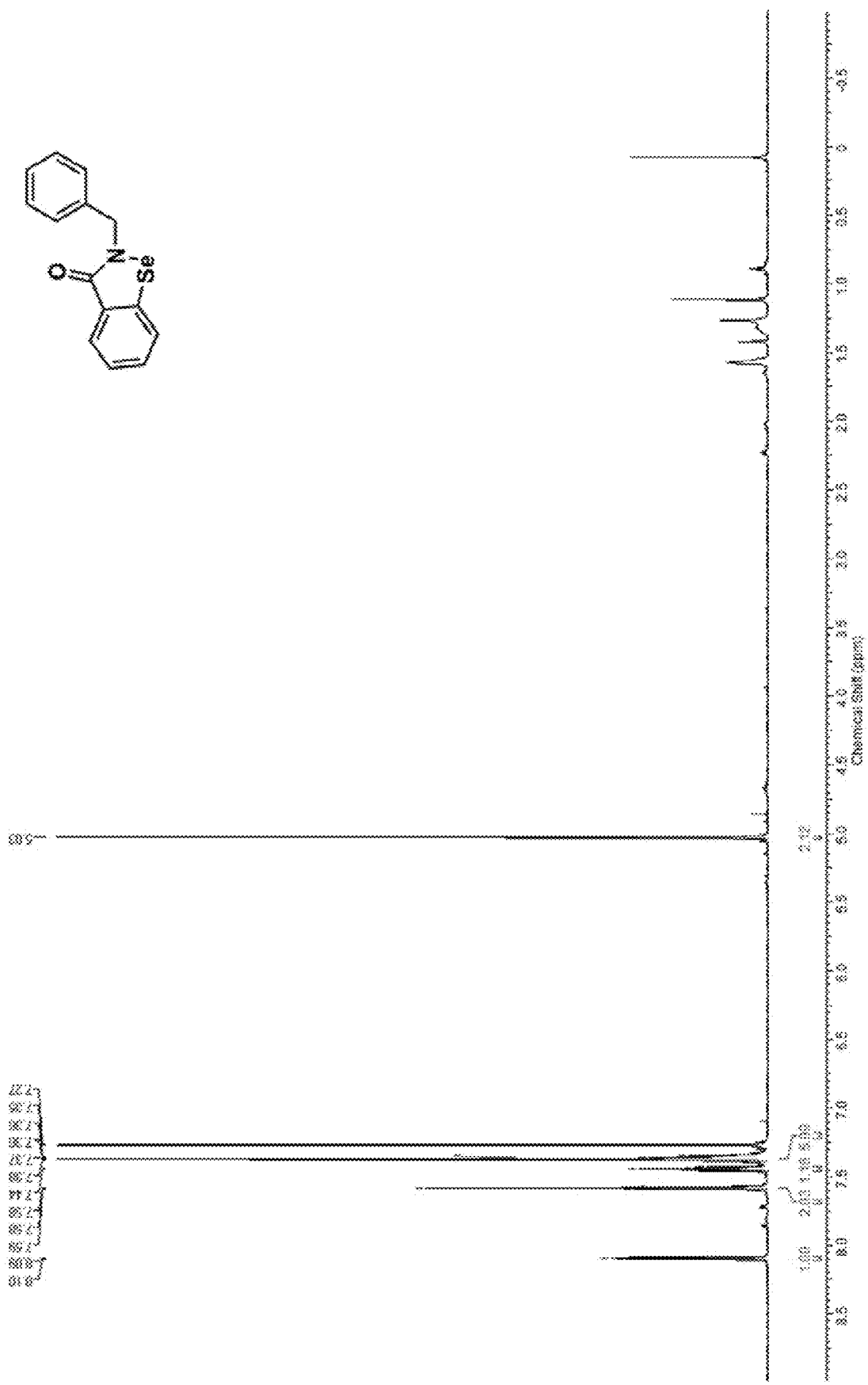
FIGS. 43A-43B: $^1$H (FIG. 43A) and $^{13}$C NMR (FIG. 43B) spectra of 2-benzylbenzo[d][1,2]selenazol-3(2H)-one (506d).
Figure 43B:
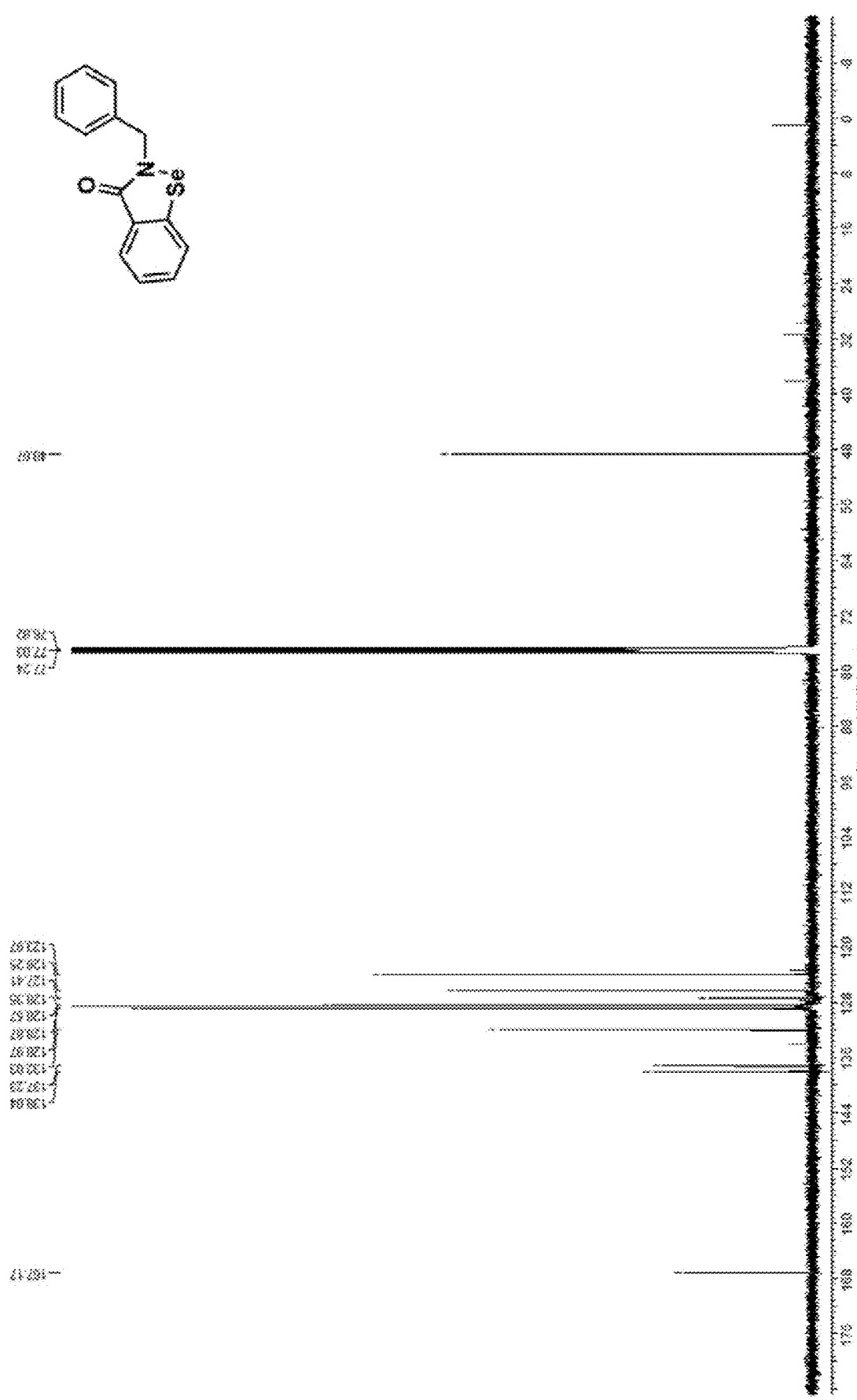
Figure 44A:
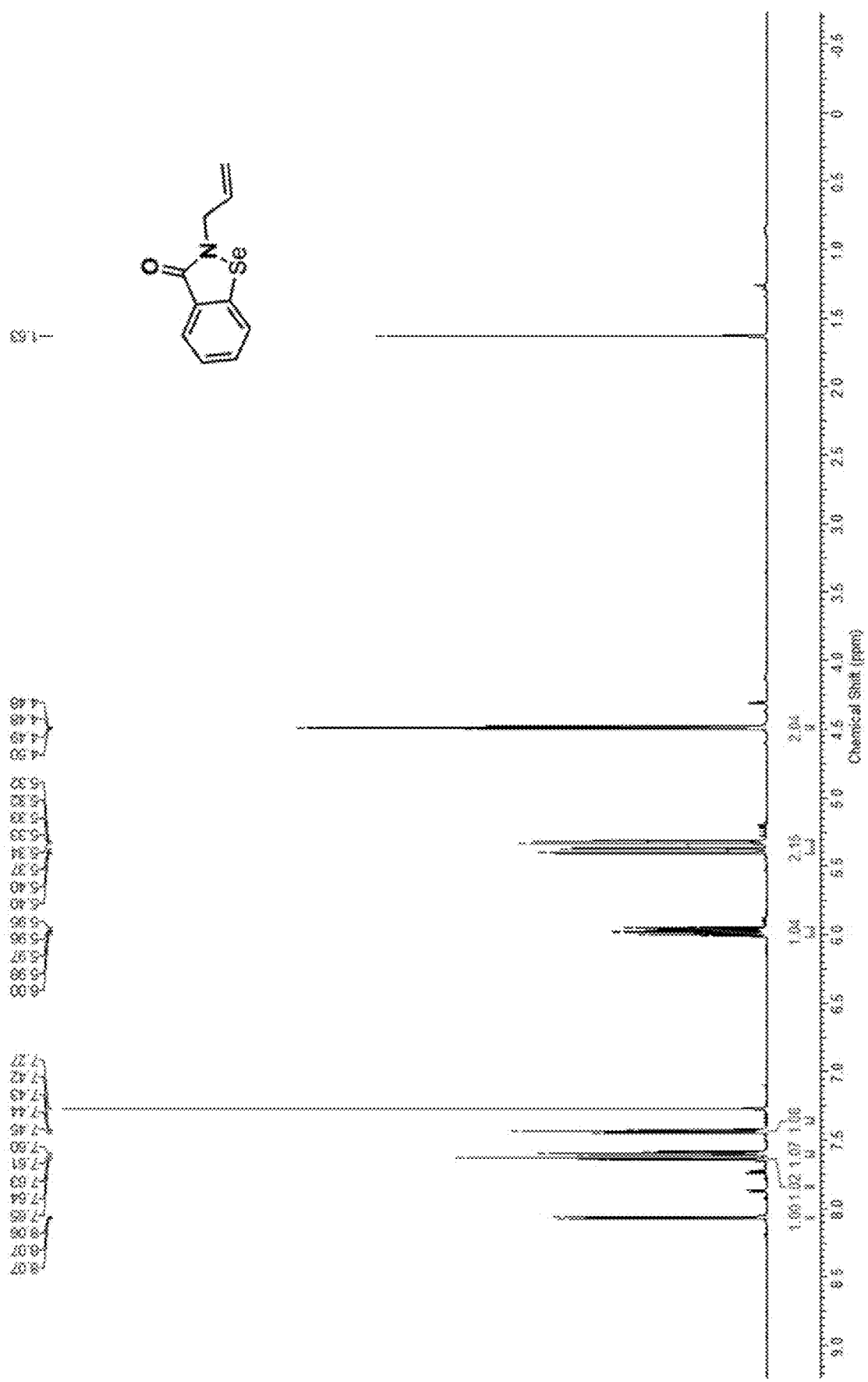
FIGS. 44A-44B: $^1$H (FIG. 44A) and $^{13}$C NMR (FIG. 44B) spectra of 2-allylbenzo[d][1,2]selenazol-3(2H)-one (506e).
Figure 44B:
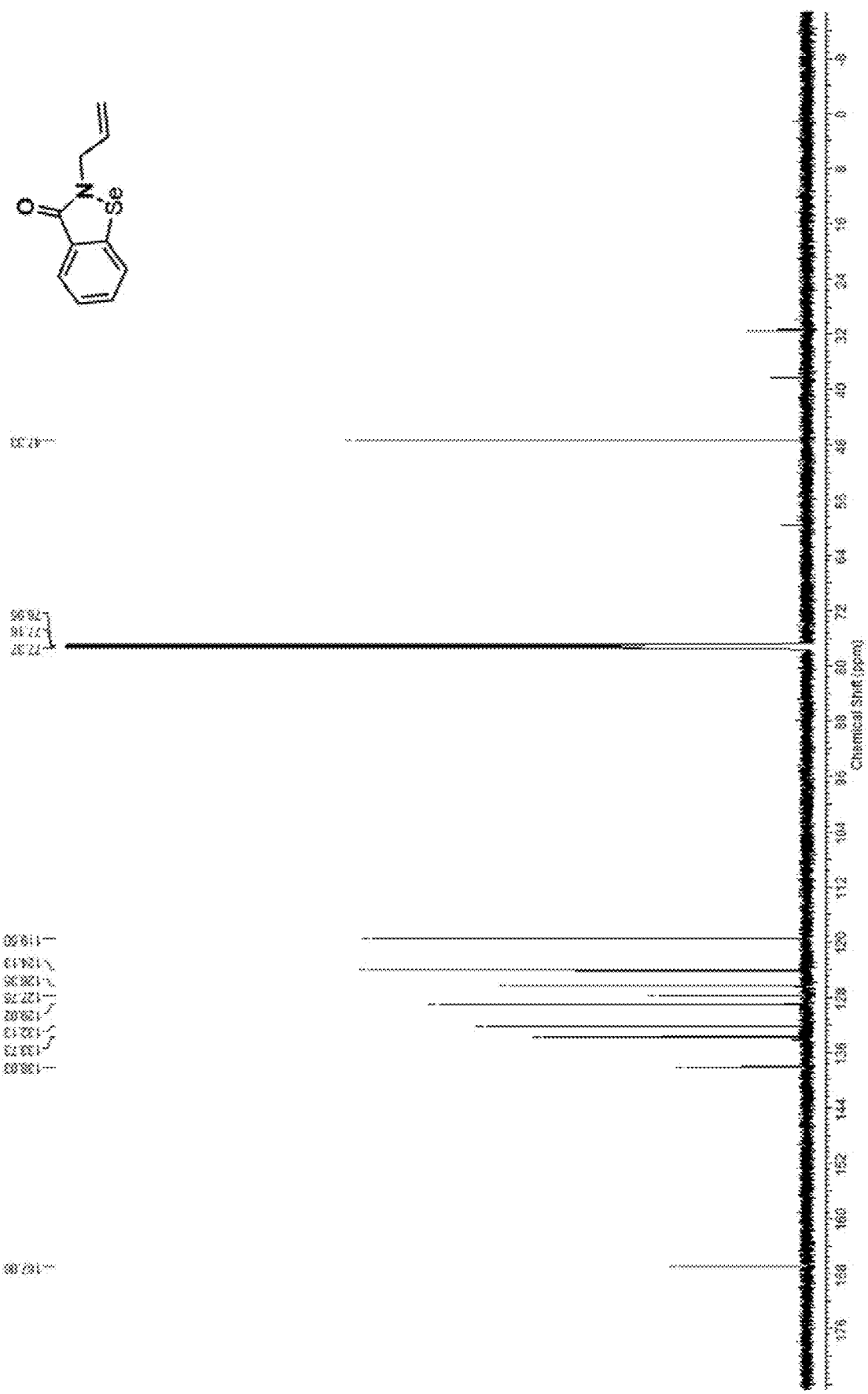
Figure 45A:
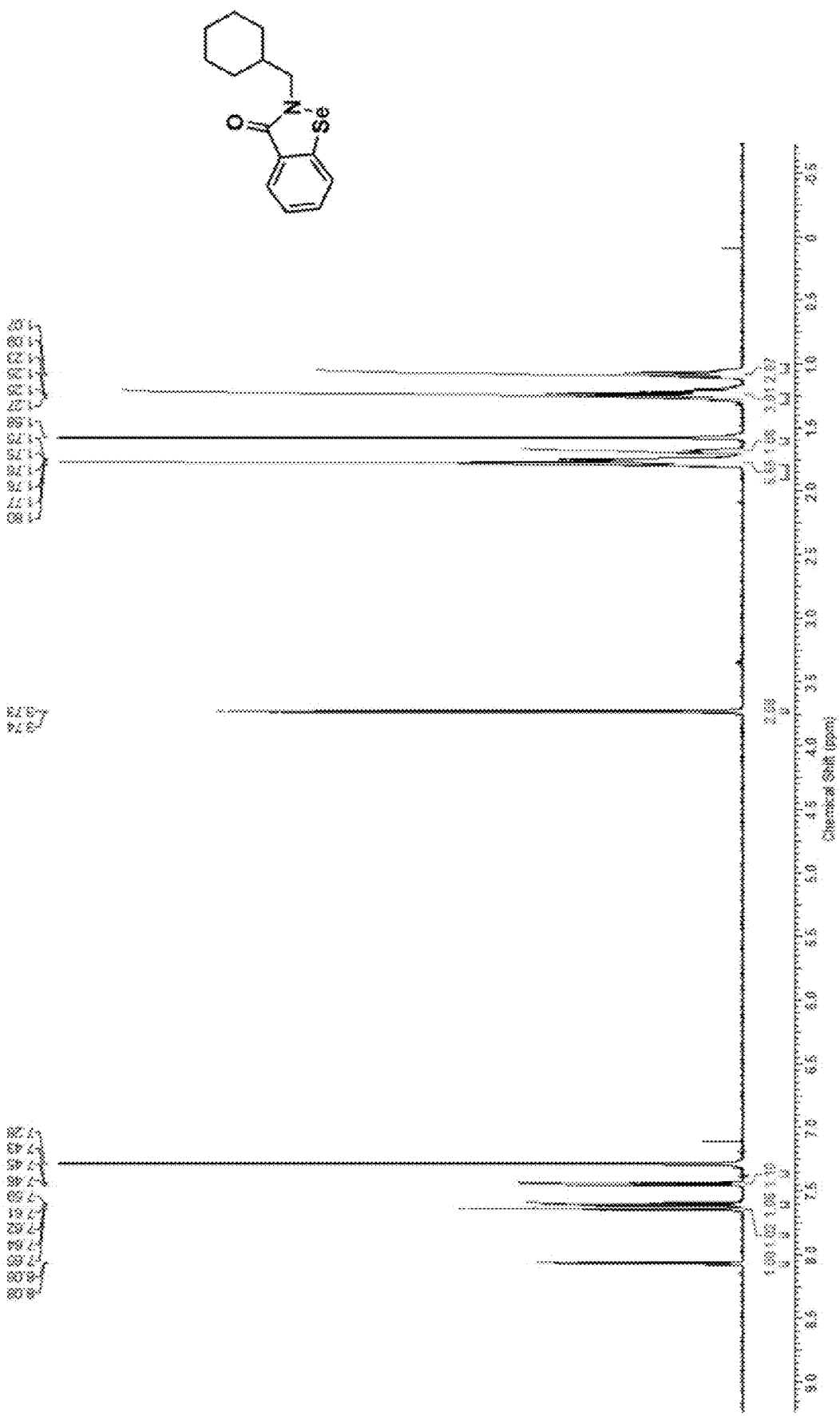
FIGS. 45A-45B: $^1$H (FIG. 45A) and $^{13}$C NMR (FIG. 45B) spectra of 2-(cyclohexylmethyl)benzo[d][1,2]selenazol-3(2H)-one (506f).
Figure 45B:
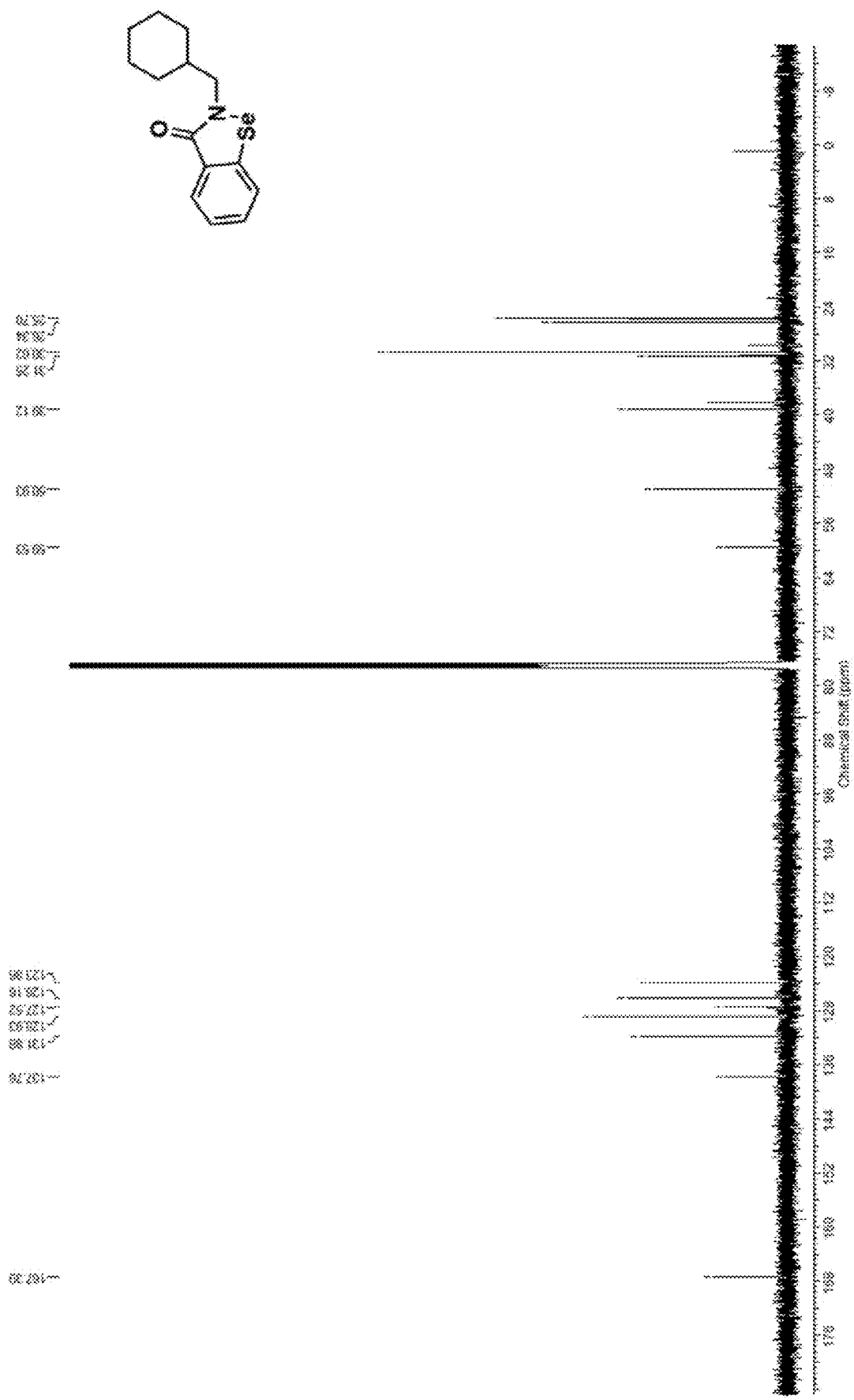
Figure 46B:
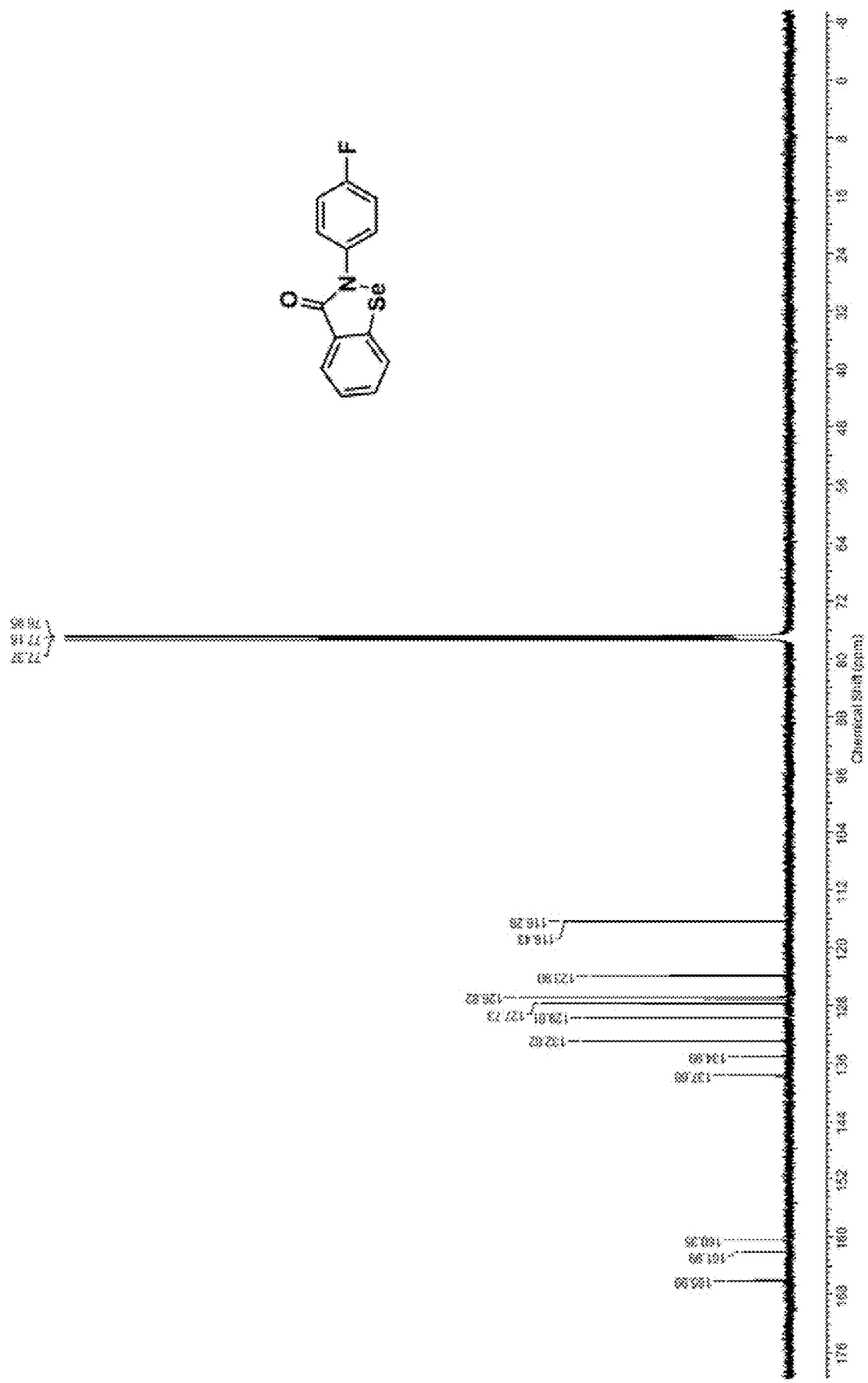
Figure 47B:
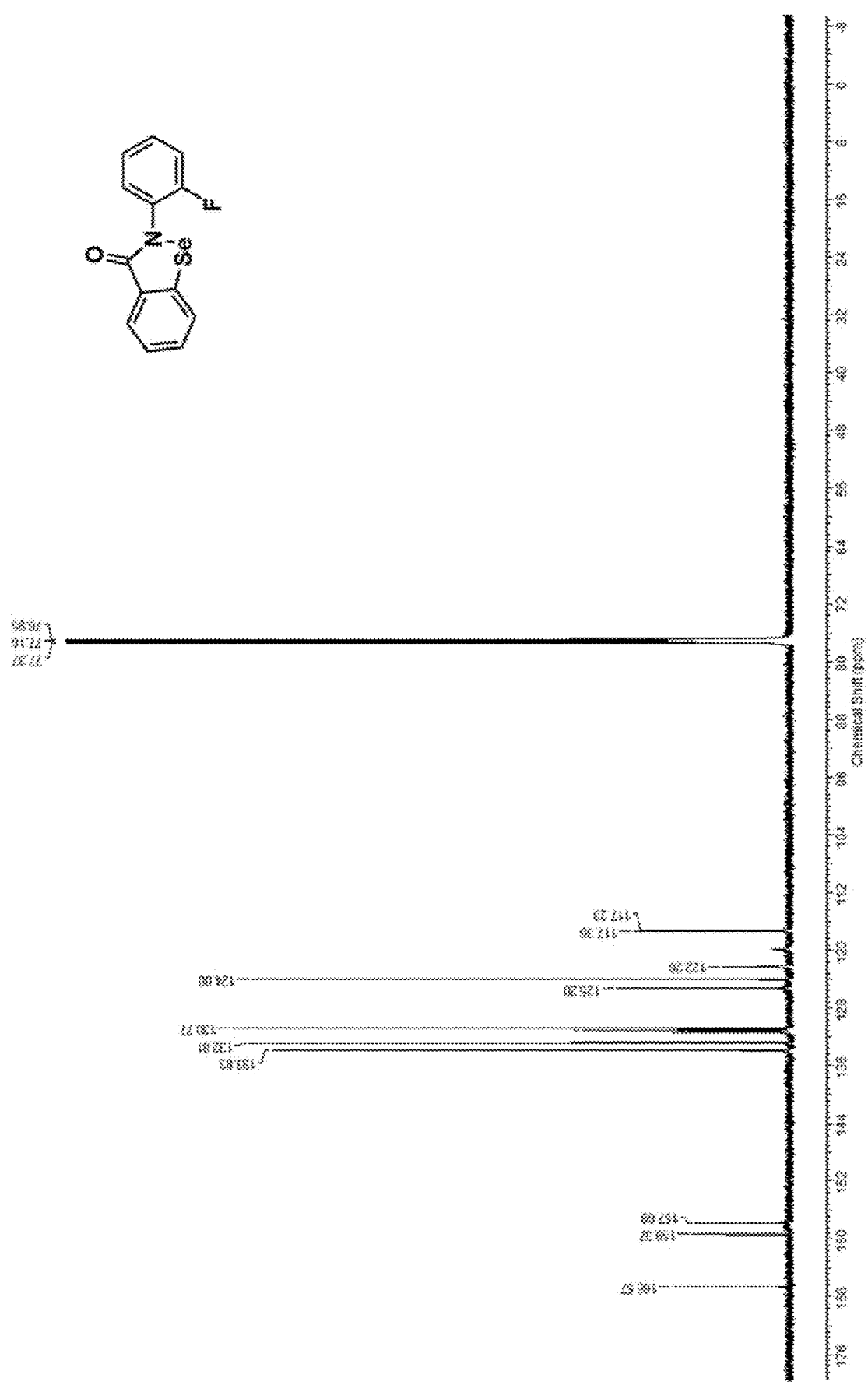
Figure 48A:
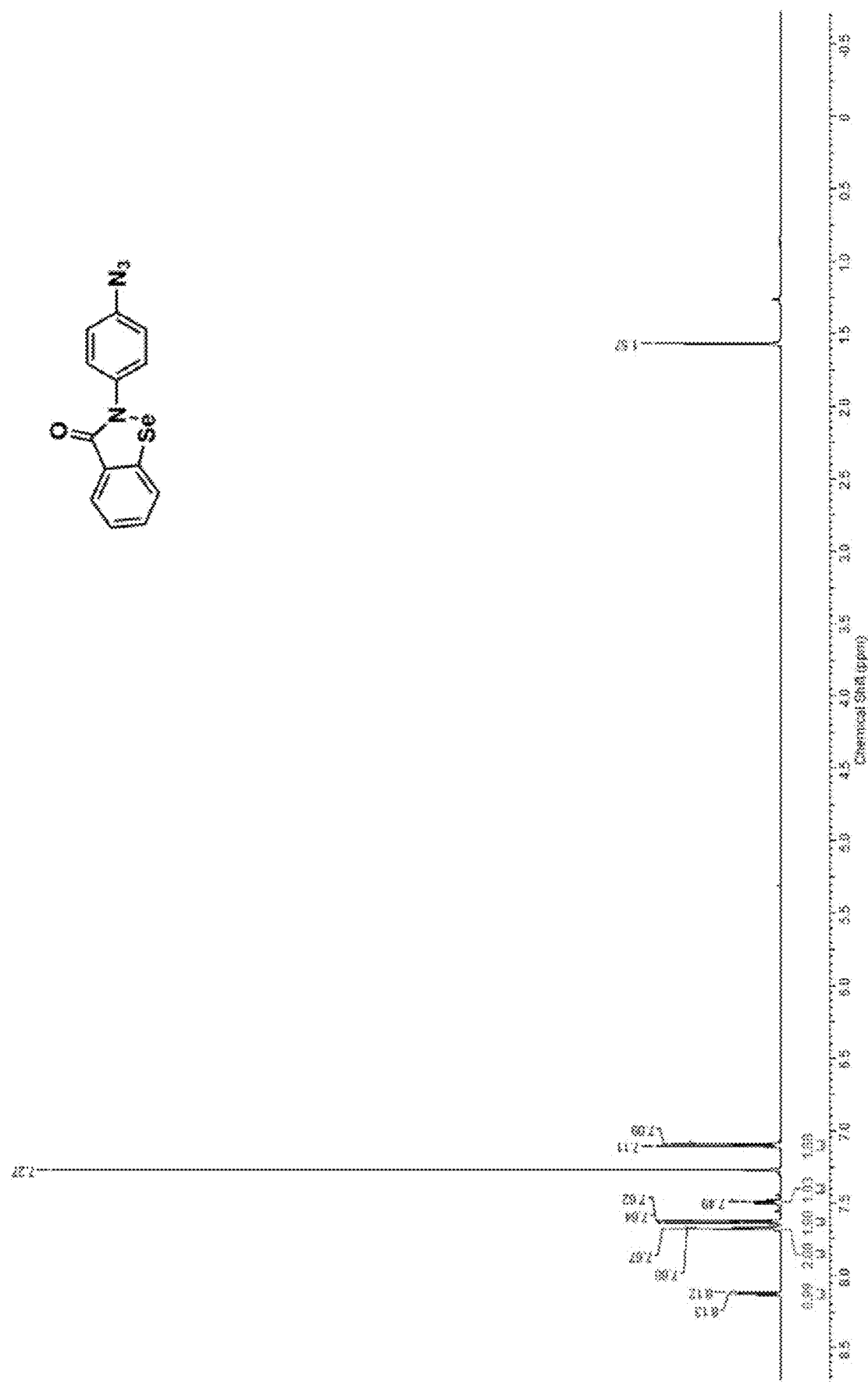
FIGS. 48A-48B: $^1$H (FIG. 48A) and $^{13}$C NMR (FIG. 48B) spectra of 2-(4-azidophenyl)benzo[d][1,2]selenazol-3(2H)-one (506i).
Figure 48B:
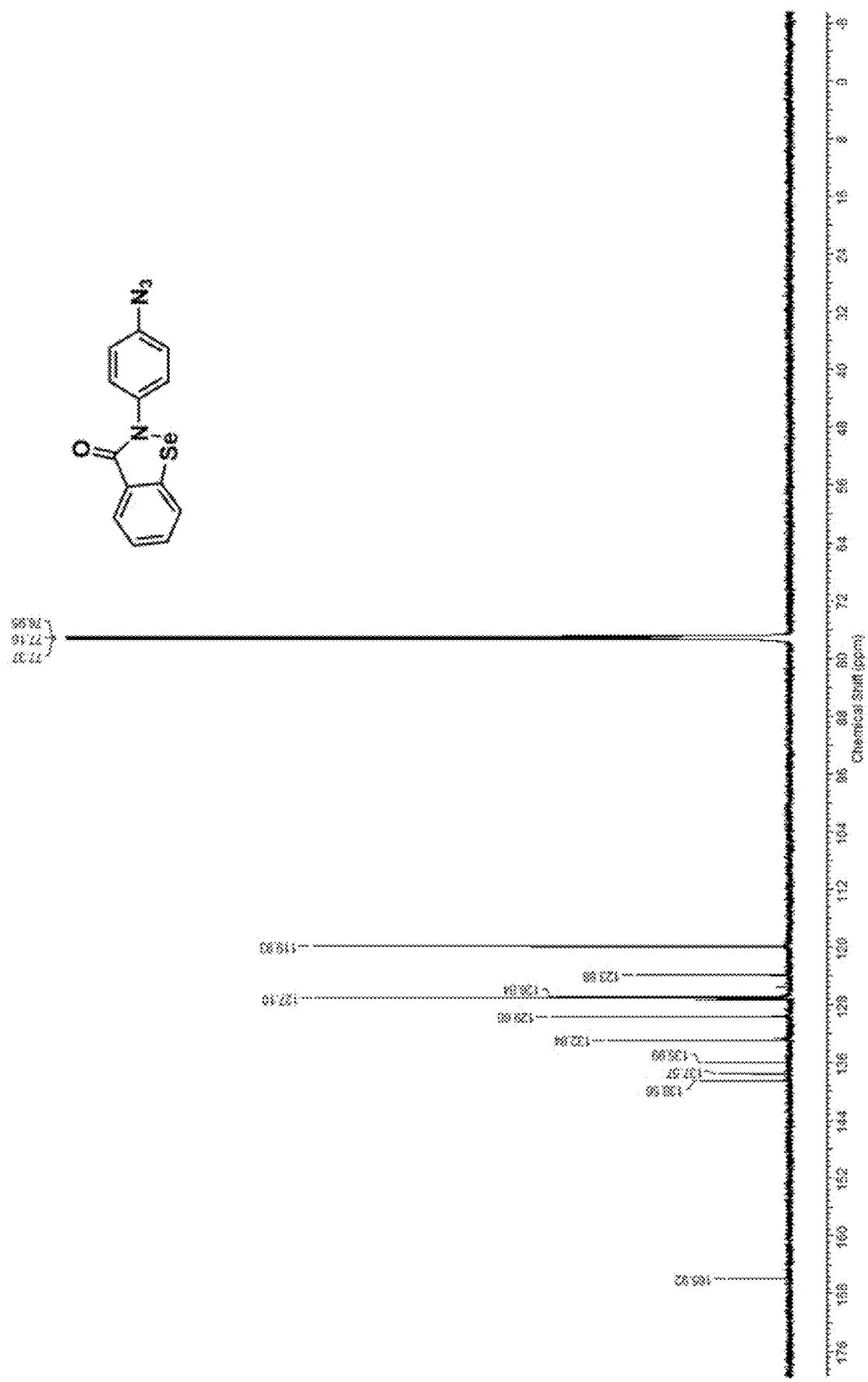
Figure 49A:
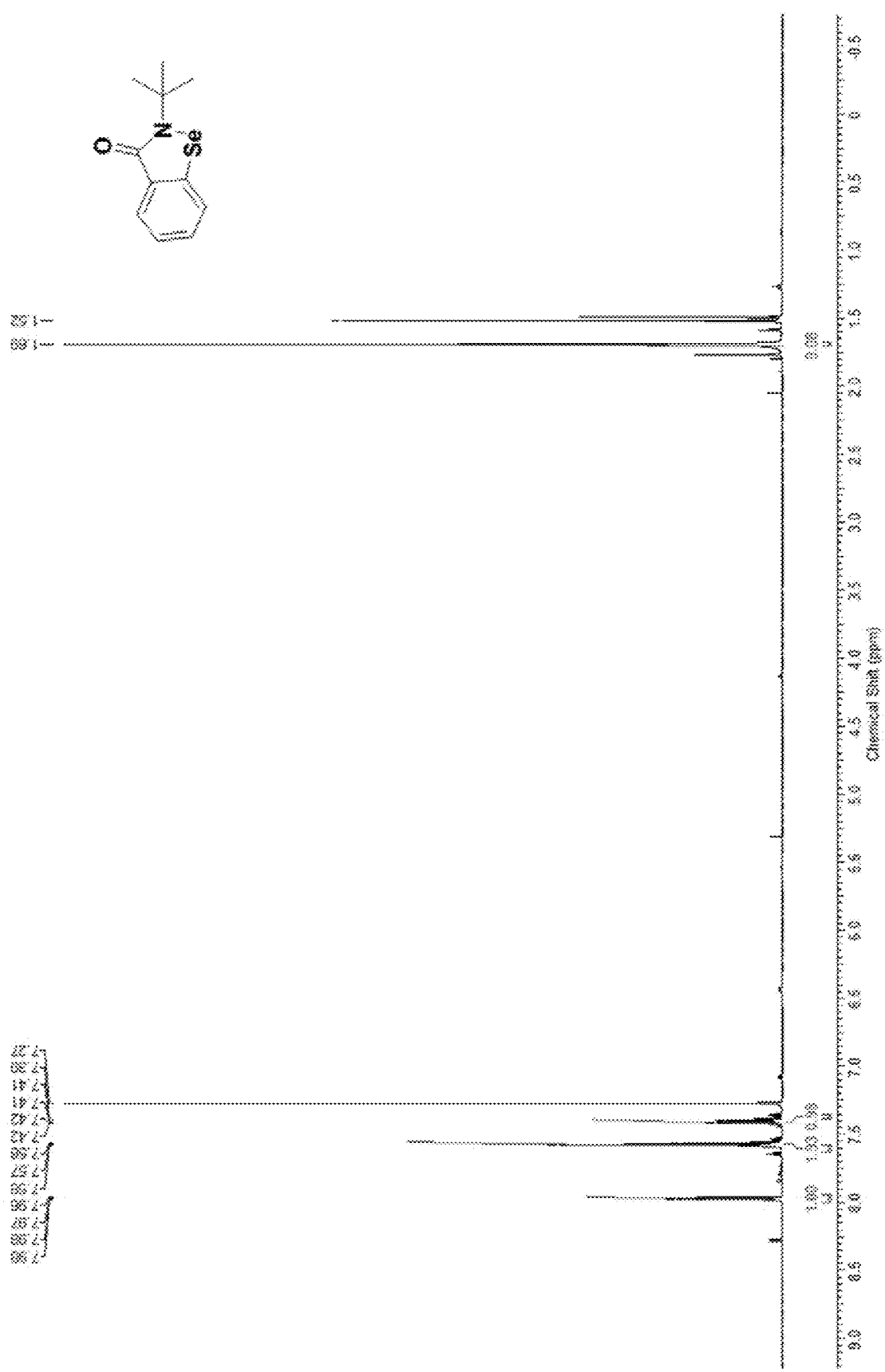
FIGS. 49A-49B: $^1$H (FIG. 49A) and $^{13}$C NMR (FIG. 49B) spectra of 2-(tert-butyl)benzo[d][1,2]selenazol-3(2H)-one (506k).
Figure 49B:
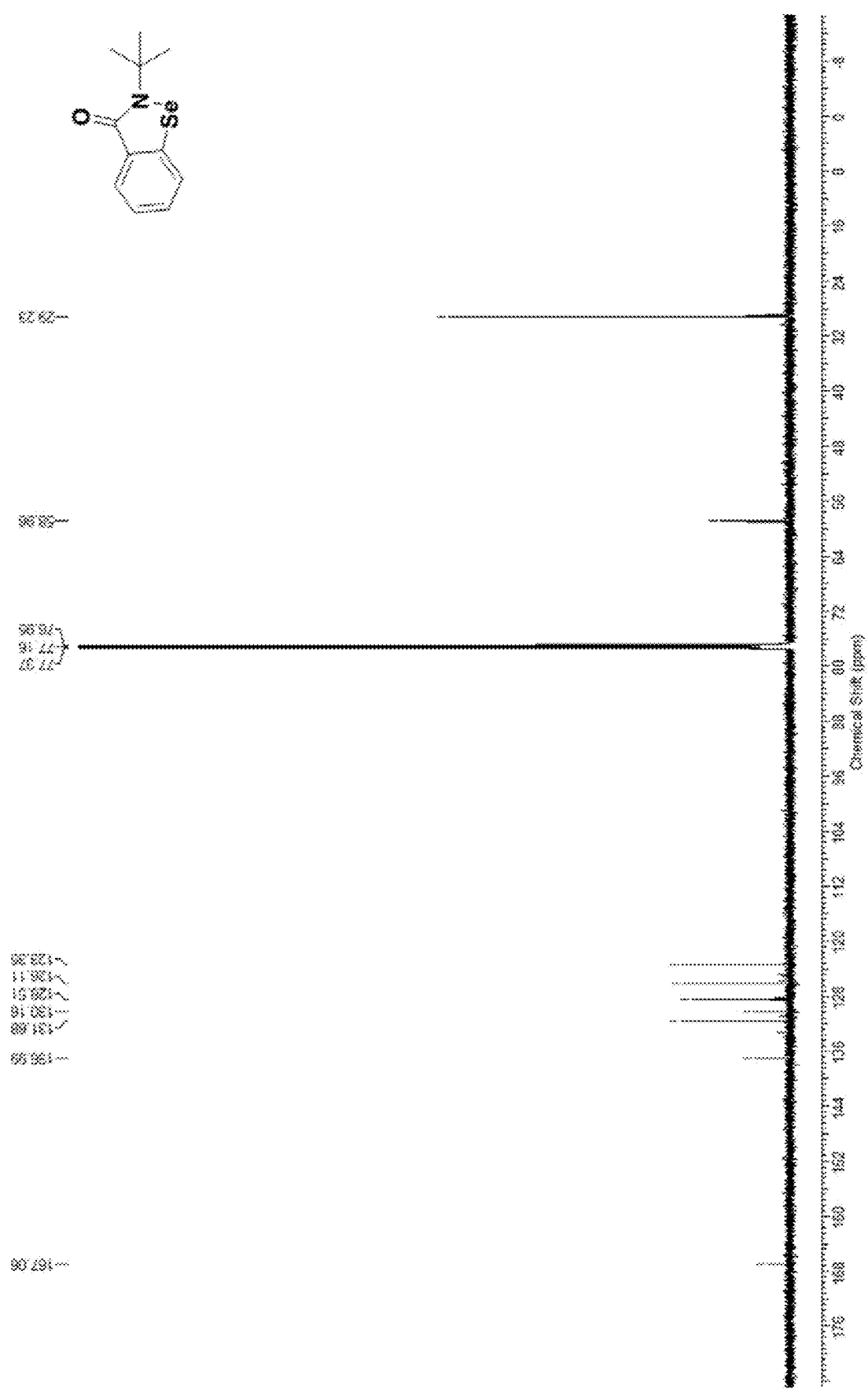
Figure 50A:
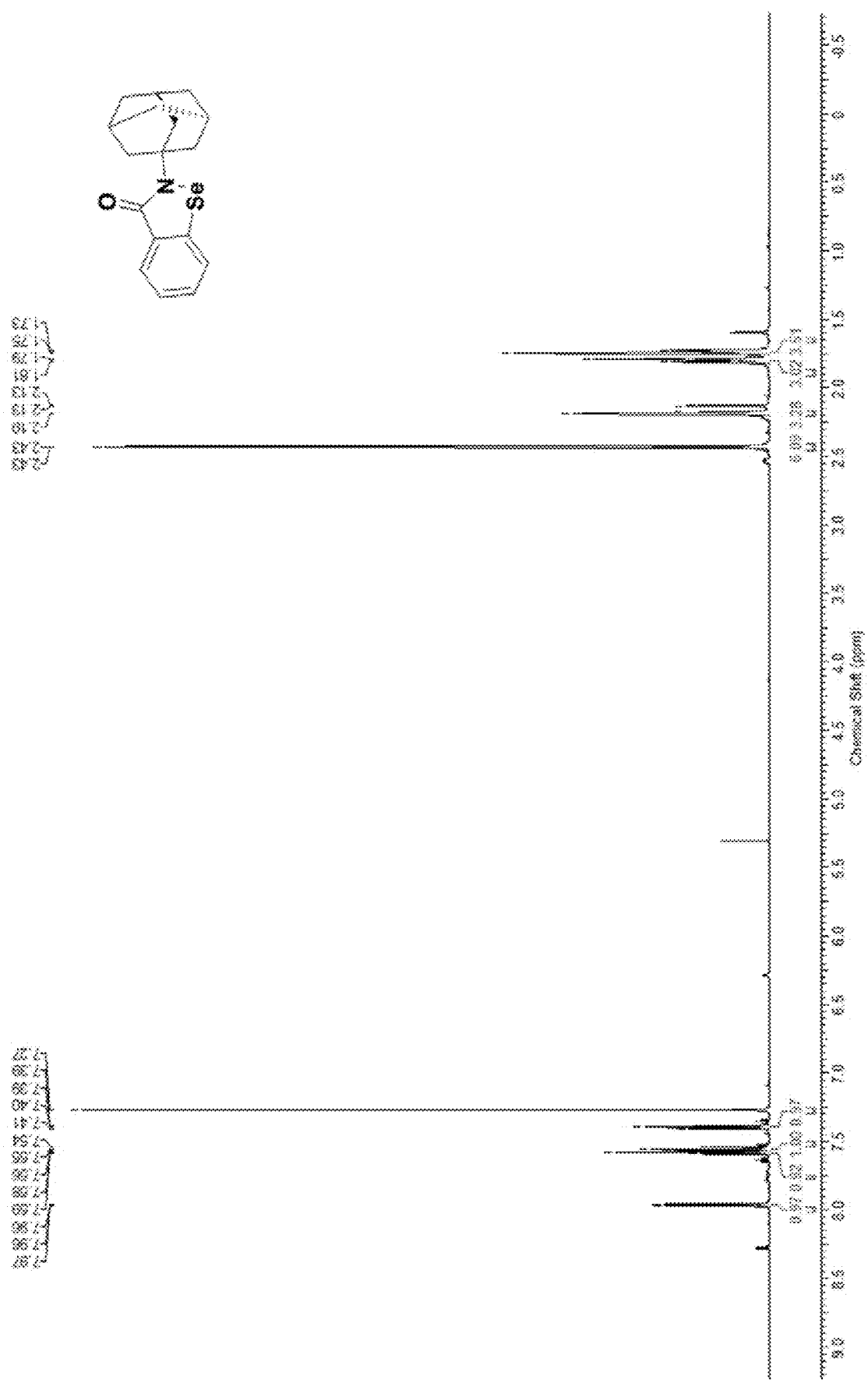
FIGS. 50A-50B: $^1$H (FIG. 50A) and $^{13}$C NMR (FIG. 50B) spectra of 2-((3R,5S)-adamantan-1-yl)benzo[d][1,2]selenazol-3(2H)-one (506j).
Figure 50B:
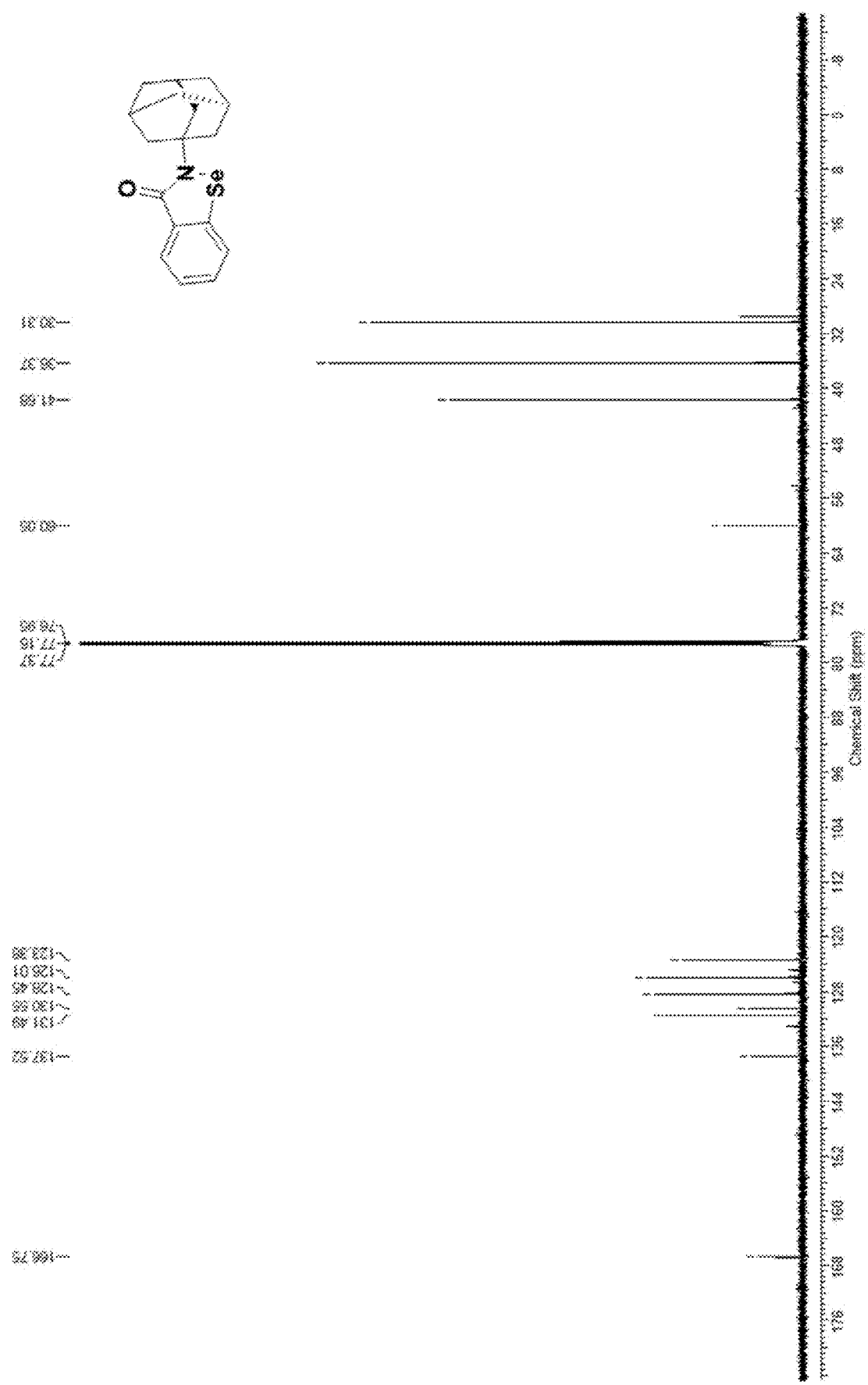
Figure 51A:
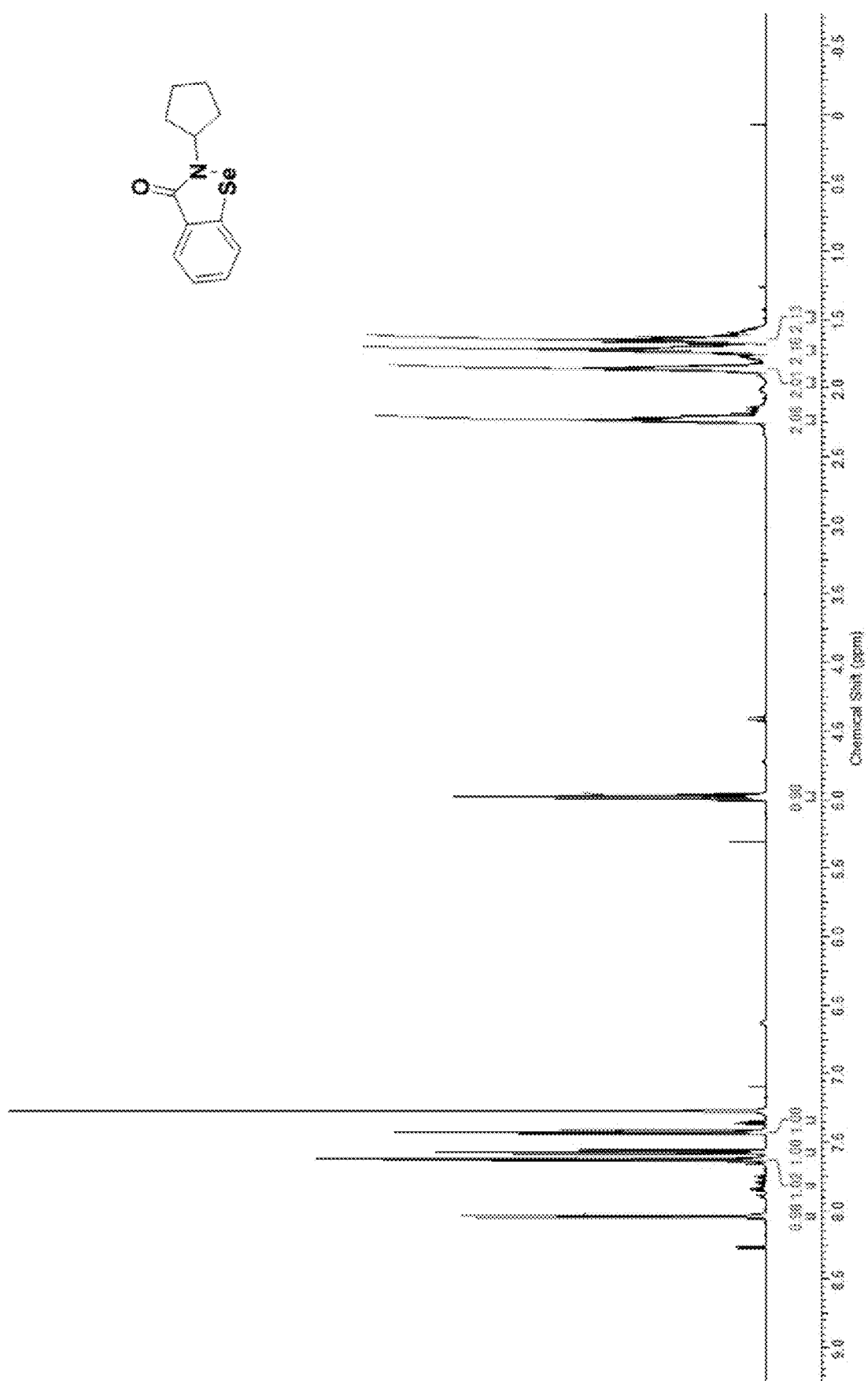
FIGS. 51A-51B: $^1$H (FIG. 51A) and $^{13}$C NMR (FIG. 51B) spectra of 2-cyclopentylbenzo[d][1,2]selenazol-3(2H)-one (506l).
Figure 51B:
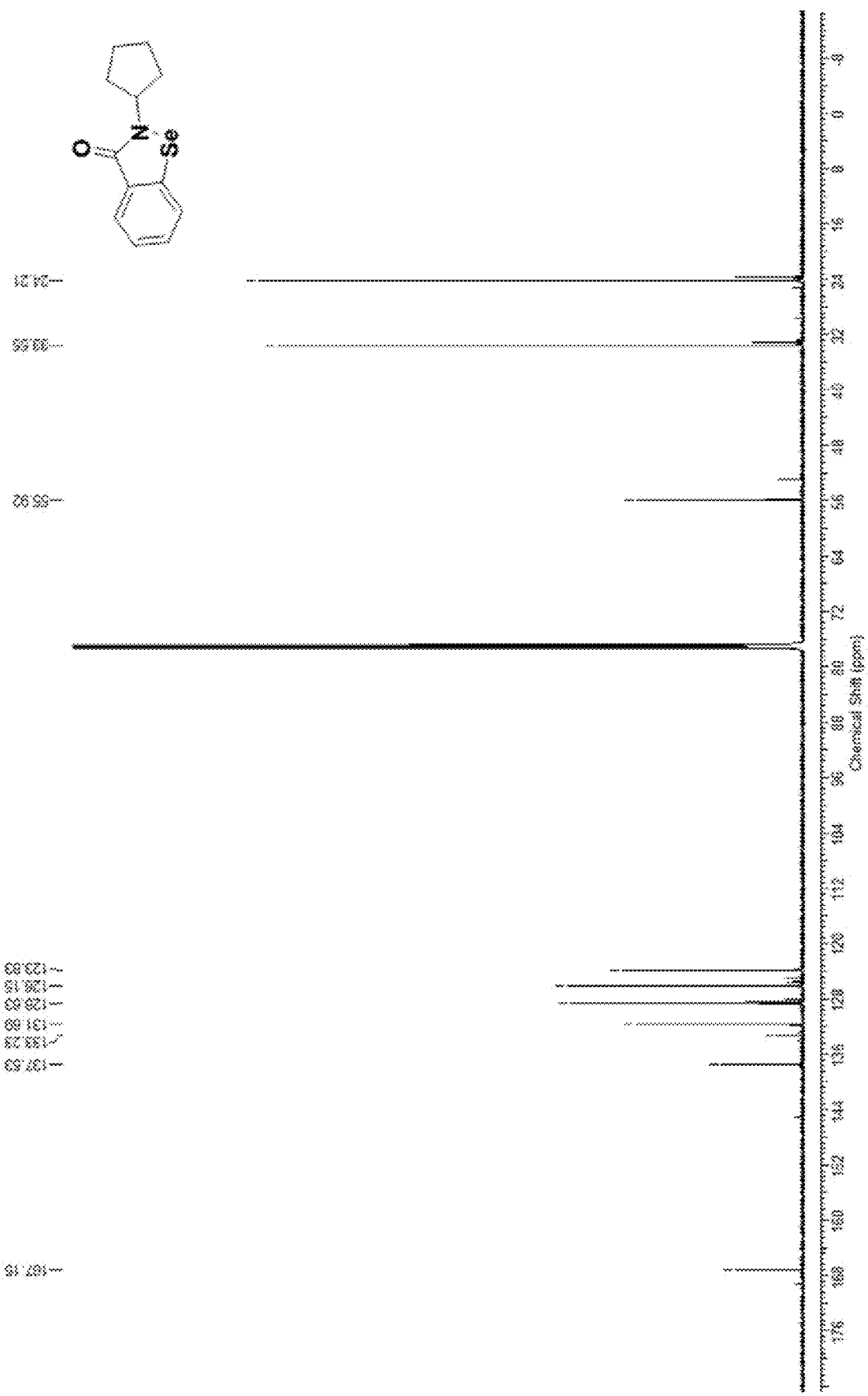
Figure 52B:
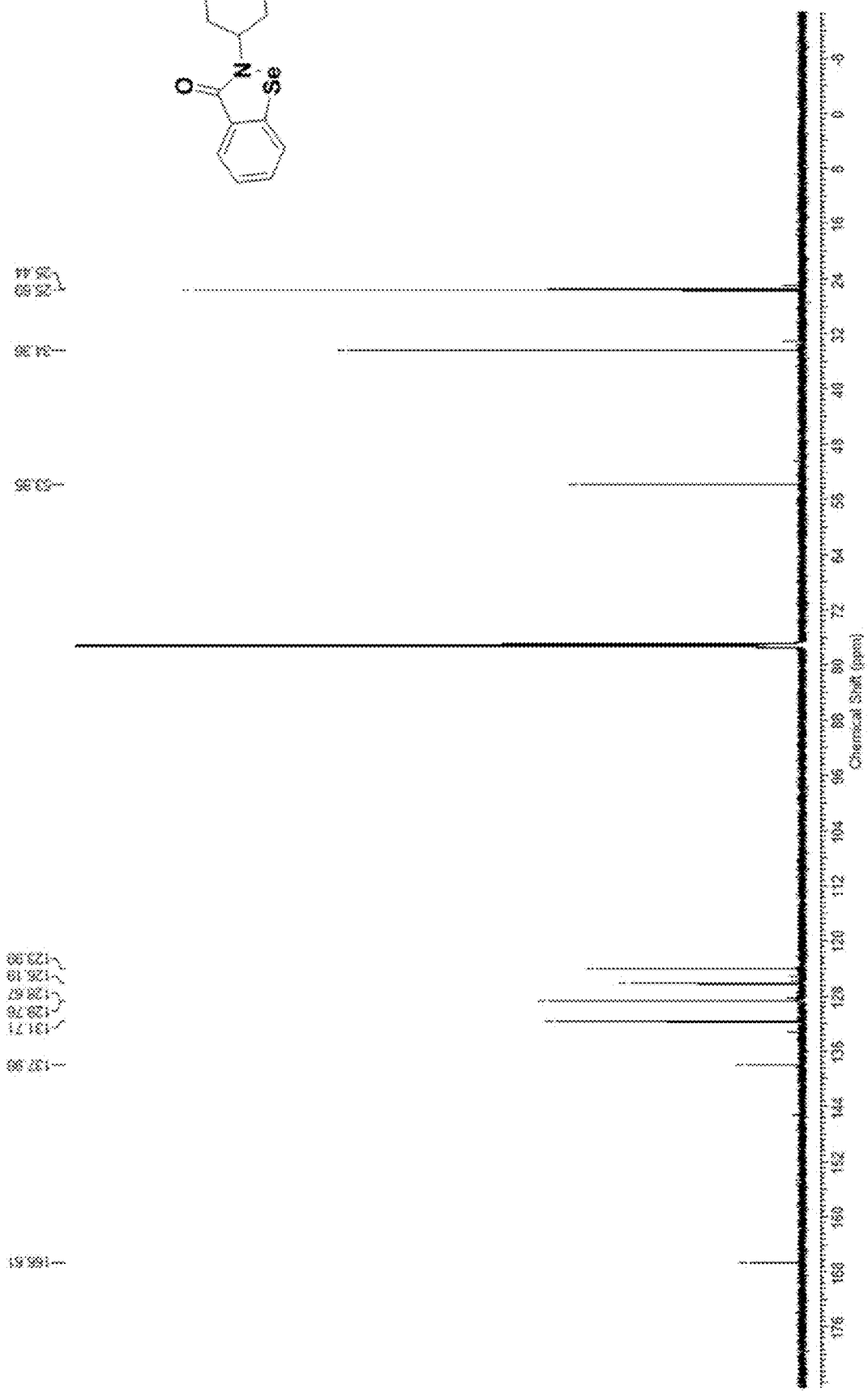
Figure 53A:
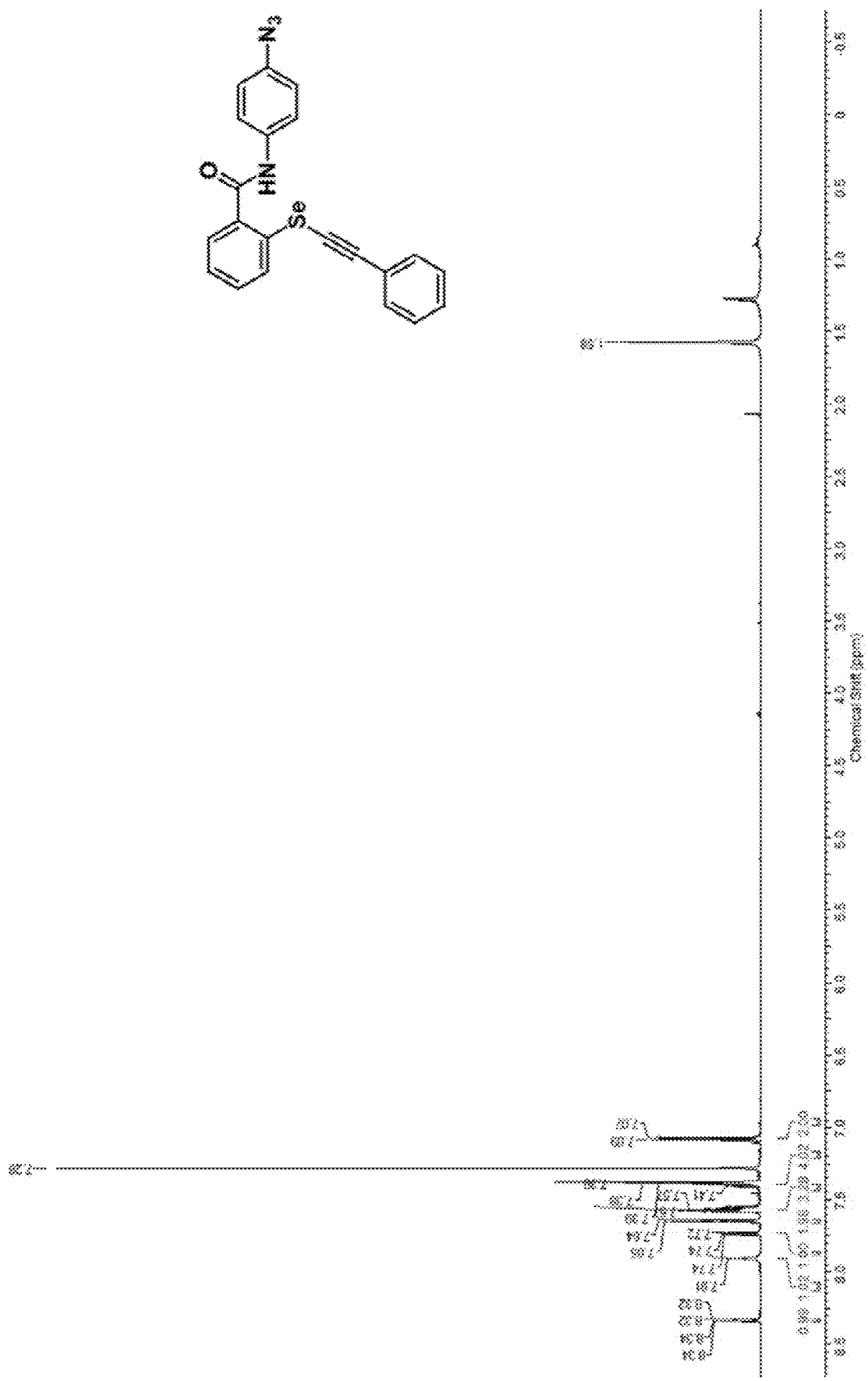
FIGS. 53A-53B: $^1$H (FIG. 53A) and $^{13}$C NMR (FIG. 53B) spectra of N-(4-azidophenyl)-2-((phenylethynyl)selanyl) benzamide (208).
Figure 53B:
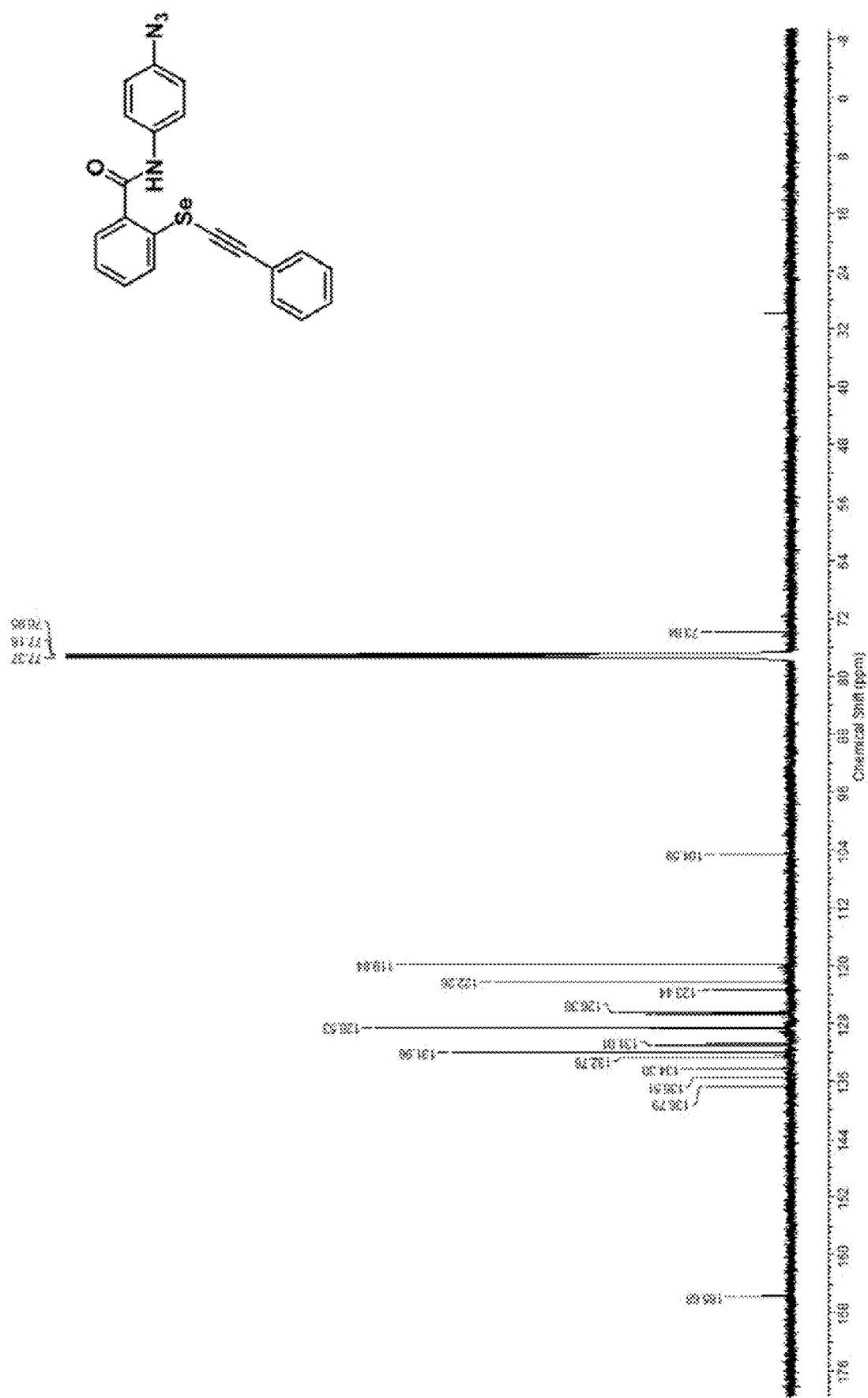
Figure 54A:
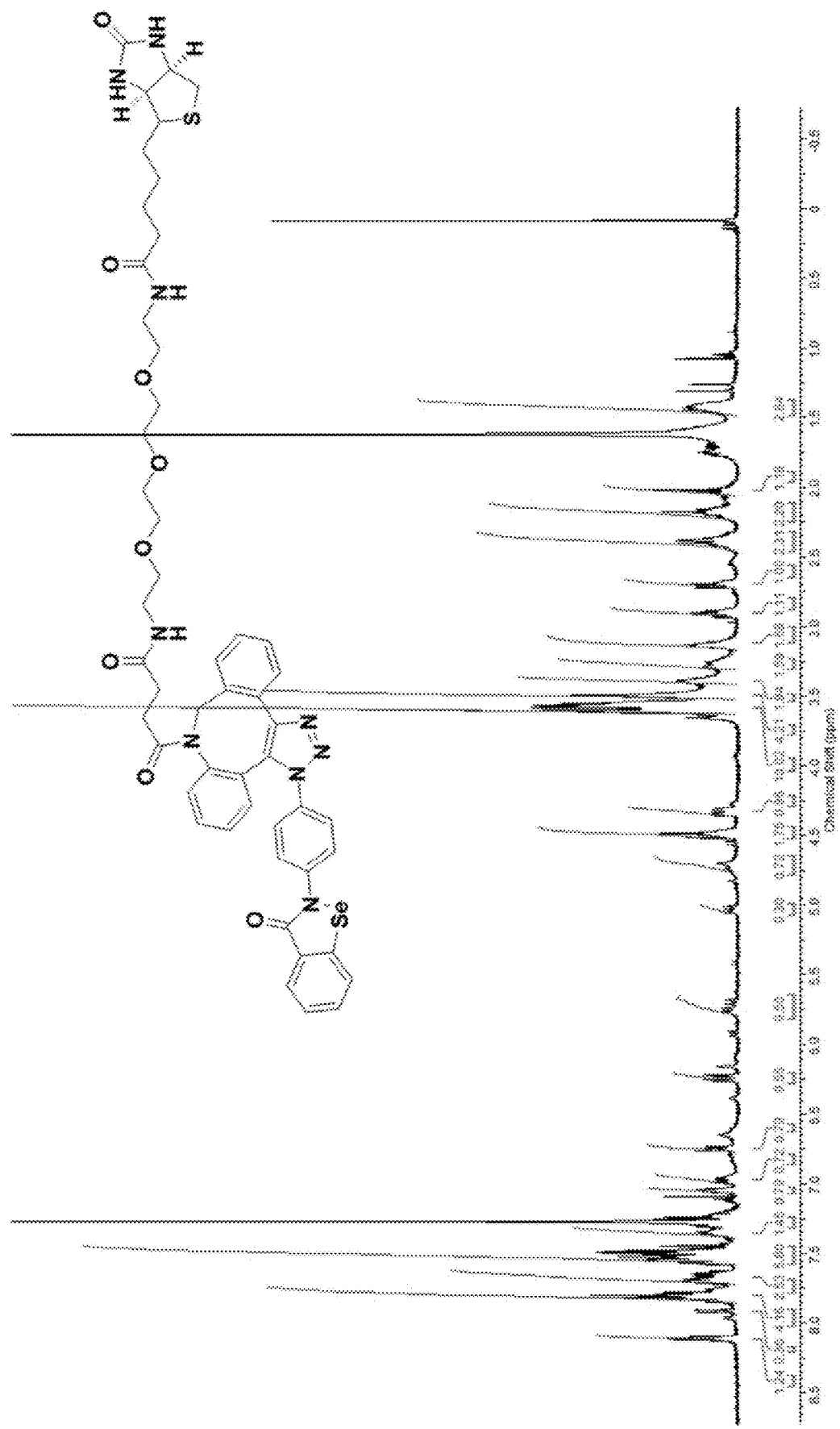
FIGS. 54A-54B: $^1$H (FIG. 54A) and $^{13}$C NMR (FIG. 54B) spectra of N-(13,16-dioxo-16-(3-(4-(3-oxobenzo[d][1,2] selenazol-2(3H)-yl)phenyl)-3,9-dihydro-8H-dibenzo[b,f][1, 2,3]triazolo[4,5-d]azocin-8-yl)-3,6,9-trioxa-12-azahexadecyl)-5-((3aS,6aR)-2-oxohexahydro-1H-thieno[3,4-d] imidazol-4-yl)pentanamide (210).
Figure 54B:
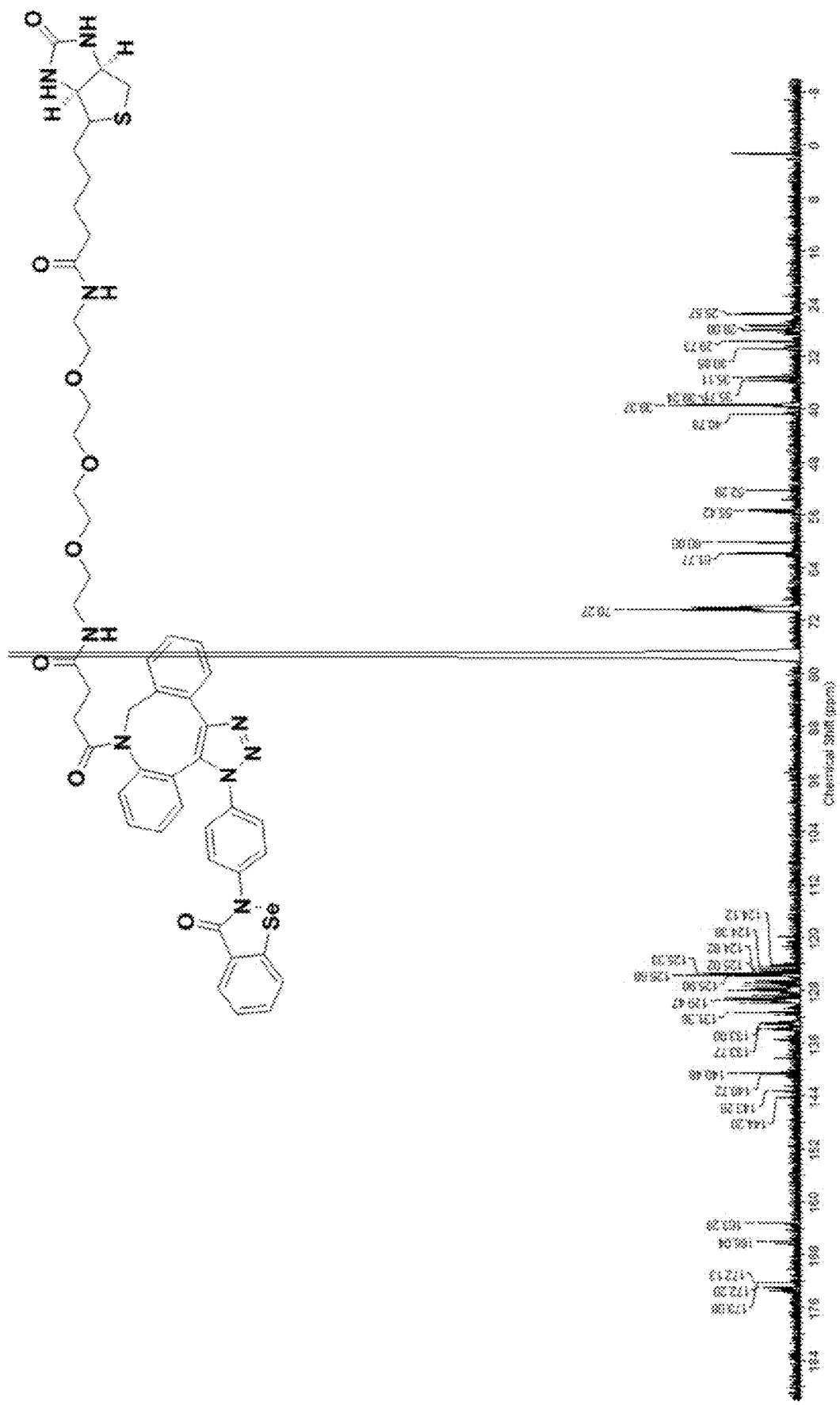
Figure 55A:
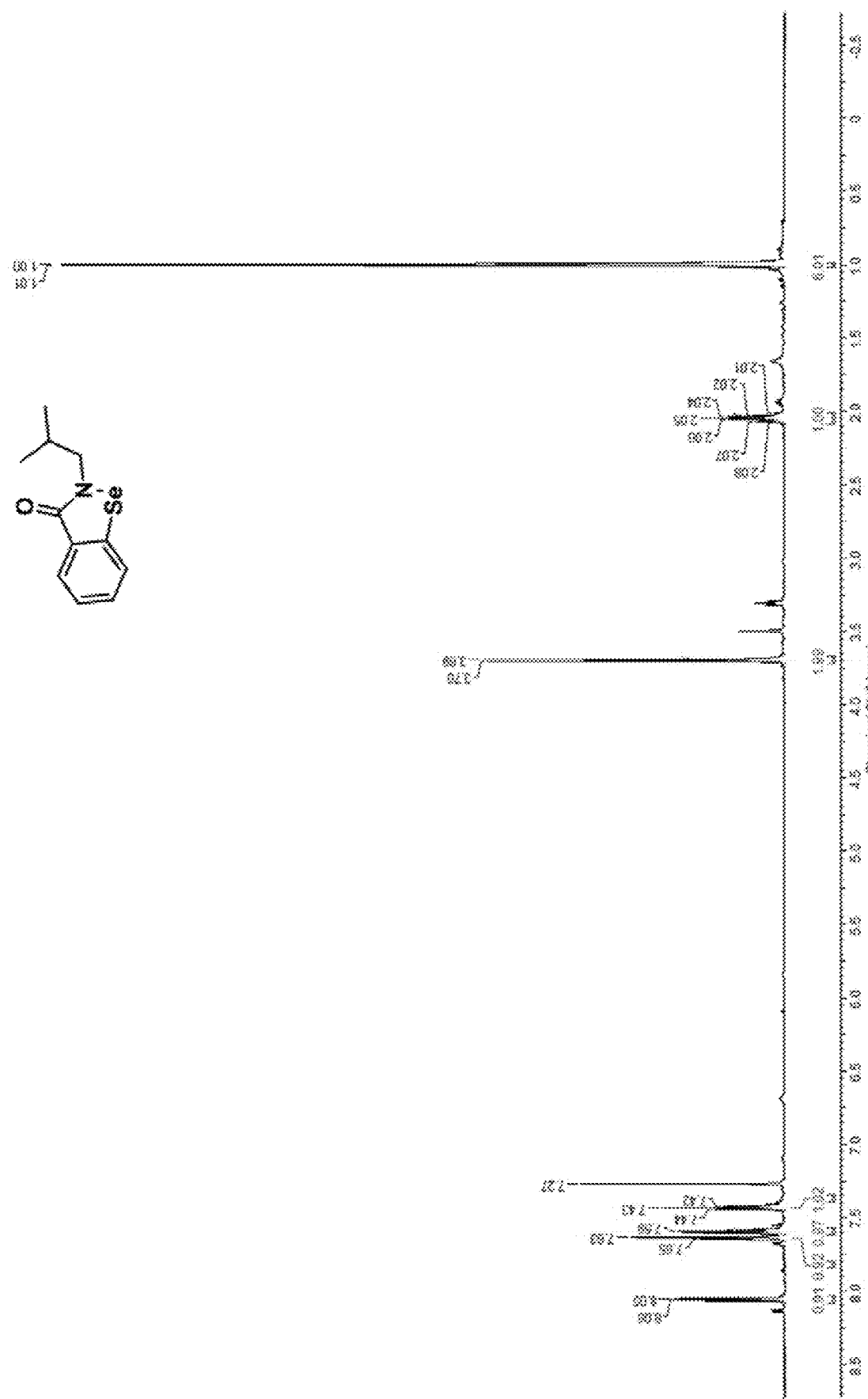
FIGS. 55A-55B: $^1$H (FIG. 55A) and $^{13}$C NMR (FIG. 55B) spectra of 2-isobutylbenzo[d][1,2]selenazol-3(2H)-one (506n).
Figure 55B:
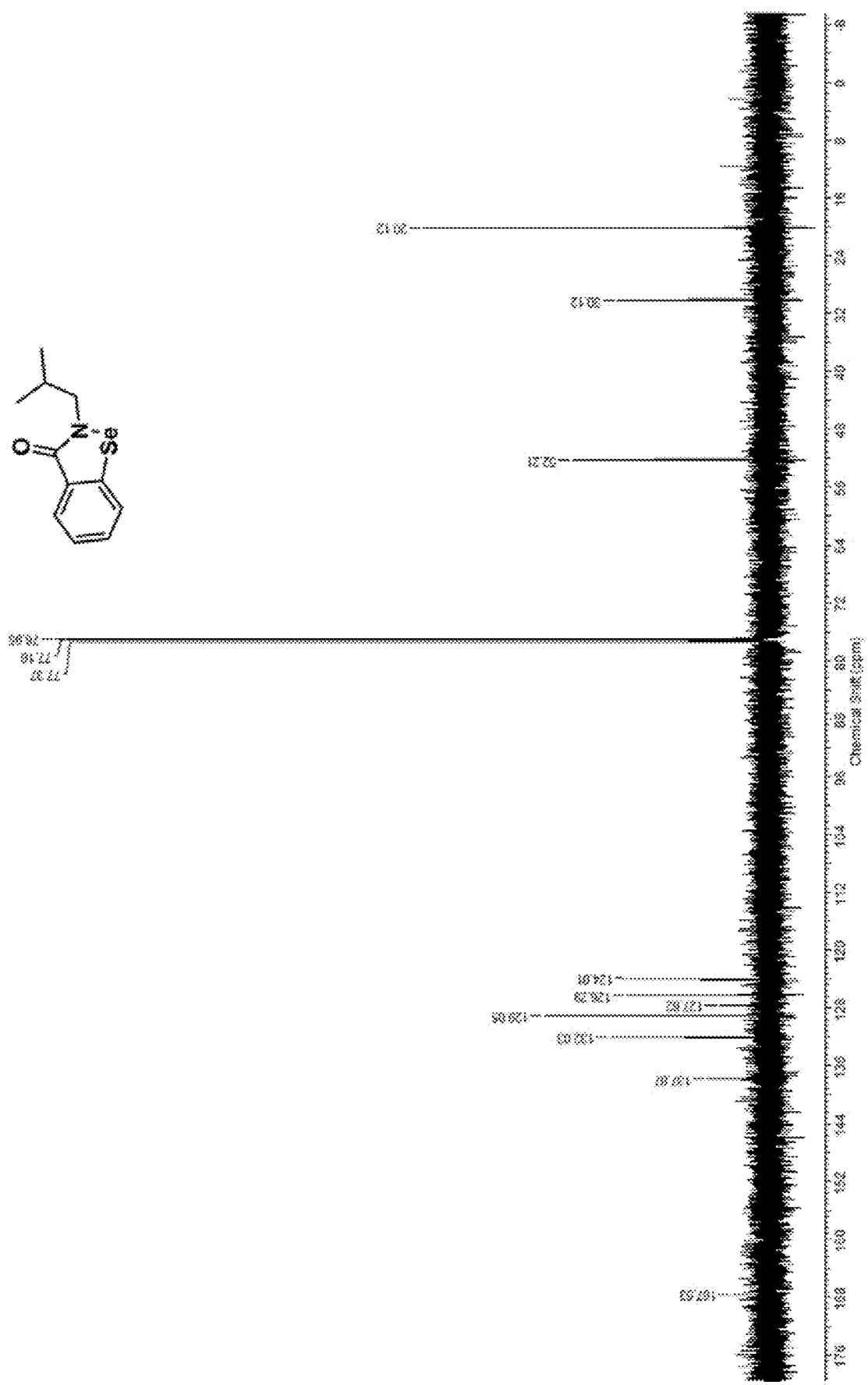

The library of 16 1,2-benzisoselenazol-3(2H)-ones was screened against Mtb H37Rv using a modified 96-well microplate Alamar blue assay (MABA) to determine minimal inhibitor concentrations (MICs). The MICs ranged from 12.5 to 100 μg/mL with the exception of compound 210, which was less active (FIG. 36, Table 10). The library was screened at 5 μM for the ability to covalently inhibit the activity of Mtb Ag85C using a previously reported fluorometric assay. Mtb Ag85C is involved in the biosynthesis of the Mtb cell wall, and EBS has been shown to inhibit Mtb Ag85C by forming a selenenylsulfide bond at Cys209. On the basis of the activity of EBS, it was believed that some members of this library would behave similarly. The percent of Mtb Ag85C activity remaining after 40 min of incubation ranged from 15% to 80% for the library (FIG. 36, Table 10; FIG. 37). The same assay was used to determine the apparent IC$_{50}$ (appIC$_{50}$) for each compound against Mtb Ag85C after 15 min of incubation. This assay revealed appIC$_{50}$ in the range of 0.54 to greater than 100 μM (FIG. 36, Table 10; FIGS. 38A-38B).

Discussion
Chemistry

Different mechanisms have been proposed for the copper-catalyzed Ullmann-type reactions. These include (i) oxidative addition-reductive elimination (OA-RE, Cu(I)/(III)), (ii) single-electron transfer (SET, Cu(I)/(II)), and (iii) atom transfer (AT, Cu(I)/(II)). An OA-RE cycle involves oxidative addition of Ar—X on LCuI(SeCN) to generate an LCuIII(SeCN)ArX intermediate, which undergoes RE to form a C—Se coupled product. The occurrence of Cu(III) species is possible. However, the energies required to access the Cu(III) species in the OA step are prohibitively high in comparison to energies required for key intermediates in SET and AT mechanisms. Therefore, without wishing to be bound by theory, it is believed that the reaction follows the AT and SET mechanisms for the arylselenocyanate formation depicted in FIG. 25. The AT mechanism involves transfer of the halide atom from aryl halide to a (phen)CuI(SeCN) (C) complex, forming caged aryl radical (Ar.) and (phen)CuII(SeCN)X complex (D). Complex (D) couples to afford an arylselenocyanate 206 and (phen)CuIX (E). Intermediate E can undergo ligand exchange to regenerated C, completing the cycle. Arylselenocyanate 206 can cyclize to form 201. A photoinduced SET mechanism requires a radical-nucleophilic aromatic substitution (SRN1) and involves photoexcitation of [CuI(SeCN)$_2$]$^-$ (B) to afford excited species [CuI(SeCN)$_2$]$^-$* (F), which can undergo SET to form a putative caged radical pair comprising [Ar—X.– and CuII(SeCN)$_2$] (G). Intermediate G can couple to form arylselenocyanate 206 and [CuI(SeCN)X]$^-$ (H). Intermediate H can undergo ligand exchange to regenerate B, completing the catalytic cycle. The radicals generated in the SET and AT mechanisms are believed to exist as caged radical pairs which rapidly convert to product and hence are not affected in the presence of radical quenchers. EPR spectroscopy studies on the reaction of haloanthraquinones and aminoethanol have observed the shortlived radical species and Cu(II) species. Similarly, copper(II)-thiolate complexes have been observed during studies on photoinduced cross-coupling between aryl thiols and aryl halides. The order of reactivity of aryl halides for C—Se cross-coupling under the thermal and photoinduced conditions was I>Br>Cl, which parallels the reduction potentials of aryl halides (e.g., PhI –1.91 V, PhBr –2.43 V, PhCl –2.76 V) and is opposite to the reactivity of aromatic nucleophilic substitution reaction. This also indicates that the thermal reaction proceeds through a radical reaction.

The observed and proposed intermediates parallel what has been observed for the Cu-catalyzed cross-coupling of aryl halides with thiols both thermally and photoinduced. For the thermal case, X-ray diffraction and solution phase characterization have been used to observe copper complexes that exist as neutral three-coordinate trigonal planar complexes of [(phen)CuI(phth)] in the solid state and as ionic complexes consisting of [(phen)$_2$CuI]$^+$ and [Cu(phth)$_2$]$^-$ in solution. Ionic complexes (e.g., [(Me$_2$phen)$_2$Cu]$^+$ and [Cu(OPh)$_2$]$^-$) have been isolated in the copper-catalyzed etherification of aryl halides and it has been observed that the concentration of ionic complexes is higher in polar solvents. Without wishing to be bound by theory, it is believed that the presence of a related neutral [(phen)CuI(SeCN)] (C) intermediate in the thermally activated copper-promoted cross-coupling to form C—Se bonds. This adduct can form from the disproportionation reaction of [(phen)$_2$CuI]$^+$ (A) and [CuI(SeCN)$_2$]$^-$ (B) complexes. The evidence for this intermediate is indirectly supported by the observation that addition of ligand increases the yield from 44% to 89% (FIG. 26, Table 7, entries 11 and 9). Only the addition of ligand would allow for formation of a [(phen)CuI(SeCN)] (C) or a related neutral (phen) complex. For the photoinduced case, the cross-coupling between and thiols and aryl halides has been investigated and it has been shown that the [Cu(SAr)$_2$]$^-$ anion is the lone and active intermediate. Similarly, the related [Cu(SeCN)$_2$]$^-$ (B) anion was observed in this Example. Prior EPR studies on the photoinduced Cu-catalyzed cross-coupling of haloanthraquinones and aminoethanol have identified short-lived radical species and Cu(II) species. Similarly, copper(II)-thiolate complexes (analogous to complex G) have been observed during studies on photoinduced cross-coupling between and thiols and aryl halides. Experiments with and without 1,10-phenanthroline ligand were set up in this Example. Under photoinduced activation, addition of ligand decreases yield from 82% to 31% (FIG. 36, Table 10, entries 3 and 2), which is likely a result of a decrease in [CuI(SeCN)$_2$]$^-$ concentration, indicating [CuI(SeCN)$_2$]$^-$ as active catalyst. These observations indicate that the photoinduced Cu-promoted cross-coupling of arylhalides and KSeCN proceeds through an SET mechanism.

Biological

Among the library, compound 201a, 506c, and 506e showed the lowest MICs=12.5 µg/mL against Mtb H$_{37}$Rv and shared calculated Log P (c Log P) values in the range of 2.73-3.70. Compounds 506f, 208, and 210 showed MIC≥50 µg/mL and shared c Log P values ≥4.60. The remainder of the compounds shared intermediate MICs and c Log P values. It is believed that the most active compounds had c Log P values ideal for cell wall diffusion. Compounds 201a, 506c, and 506e reduced Mtb Ag85C activity to 17%, 36%, and 15%, respectively, after 40 min of enzyme incubation (FIG. 36, Table 10). Compounds 506f, 211, 506l, 506m, and 210 reduced Mtb Ag85C activity to 30%, 59%, 40%, 44%, and 61%, respectively. This reduction in compound activity between the two groups loosely correlates with the replacement of the phenyl group with an alkyl or the large biotinyl moiety in the case of 210. The data indicate all the compounds were reacting with the exposed cysteine 209 on Mtb Ag85C; however, the phenyl-containing compounds accessed the reactive site better. This conclusion is supported by the appIC$_{50}$ data which show all the compounds with the exception of 208 rapidly inactivate the enzyme at low concentrations. The results are significant in light of limited progress that has been made identifying inhibitors of Ag85s. The few classes of compounds have been described which inhibit the Ag85s include thiophenes, phosphonates, sulfonates, and derivatives of trehalose and arabinosides. These earlier inhibitors demonstrated IC$_{50}$s in the mid to low µM range, whereas, in the current Example, inhibitors in the nM range have been identified.

Conclusions

An efficient Cu-promoted synthesis of 2-alkyl-1,2-benzisoselenazol-3(2H)-ones is described that involves the use of 1,10-phenanthroline, KSeCN, and ortho-halobenzamides. The method affords the products in as little as 1 h, which is significantly faster than similar chemistry using Se powder. As part of this Example, a photoinduced Cu-promoted C—Se bond forming reaction is described that enabled the synthesis of ebselen (201a) at low temperatures upon irradiation with a 22 W (combined) Hg lamp. An atom transfer step and a 1,10-phenanthroine-Cu complex is described in the thermal mechanism, and a single electron transfer step is described for the photoinduced mechanism. The mechanisms are supported by the ESI-MS detection of [(phen)$_2$CuI]$^+$ (A) and [CuI(SeCN)$_2$]$^-$ (B) complexes. A library of 14 1,2-benzisoselenazol-3(2H)-ones was prepared in good yield using the thermal method. The library was evaluated for anti-Mtb H37Rv activity and the ability to inhibit a cysteine-containing Mtb Ag85C demonstrating different aspects of utility for the chemotype. As a result, Mtb growth and enzyme inhibitors were identified. Due to the rapidly expanding medical applications for 2-alkyl-1,2-benzisoselenazol-3(2H)-ones, these methods may be used to facilitate the synthesis of new therapeutics.

Experimental

General Information

All the starting materials were obtained from Acros Organics or Sigma-Aldrich. Unless specified, all the reactions were carried out under an atmosphere of nitrogen using a nitrogen balloon. All solvents were purchased form Fisher Scientific or Sigma-Aldrich. The solvents were purified by distillation and other standard methods. Reactions were monitored using thin-layer chromatography (TLC silica gel 62 F254), and spots were observed by UV light. All photochemical reactions were carried out in a handmade cardboard box fitted with two bulbs with a combined output of 22 W (14 W Rayonet RPR-3000A lamp (spectral energy distribution wavelength range: 250-360 nm)+8 W Spectronics Corp. BLE-8T365 (365 nm)). An Aminco Bowman II luminescence spectrometer was used for fluorimetry experiments. $^1$H NMR and $^{13}$C NMR and G-COSY were carried out using a Bruker Avance III 600 MHz or Varian Inova 600 MHz spectrometers. $^1$H NMR and $^{13}$C NMR were referenced to the CDCl$_3$ peak at 7.27 and 77.16, respectively. High resolution mass spectroscopy (HRMS) was performed on a micro mass Q-TOF2 instrument. General Procedure for Thermal Activated Synthesis of Benzo-1,2-selenazol-3(2H)-one compounds, Table 7 (FIG. 26). The starting benzamide (1 equiv), copper(I) iodide (1 equiv), 1,10-phenanthroline (1 equiv), cesium carbonate (2.5 equiv), and potassium selenocyanate (1.2 equiv) were suspended in solvent N,N-dimethylmethanamide or acetonitrile. The resulting red colored mixture was heated to 95-100° C. for 0.6-12 h. The reaction was cooled, diluted with 20.0 mL of ethyl acetate, and filtered, and the residue was washed with ethyl acetate. To the filtrate was added cold H$_2$O (20.0 mL), followed by extraction with 20.0 mL of ethyl acetate. This process was repeated thrice. The combined ethyl acetate extracts were dried over anhydrous Na$_2$SO$_4$, filtered, and concentrated to obtain a solid which was purified by flash column chromatography on silica gel (ethyl acetate-hexane) to obtain product 1,2-benzisoselenazol-3(2H)-one derivative.

Synthesis of 2-Phenylbenzo[d][1,2]selenazol-3(2H)-one (201a)

2-Iodo-N-phenylbenzamide (400 mg, 1.24 mmol), copper (I) iodide (236 mg, 1.24 mmol), 1,10-phenanthroline (223 mg, 1.24 mmol), cesium carbonate (1011 mg, 3.10 mmol), potassium selenocyanate (214 mg, 1.49 mmol), and N,N-dimethylmethanamide (4.0 mL), 45 min, 100° C. Purified by flash column chromatography on silica gel (35% ethyl acetate-hexanes) to obtained pure 2-phenylbenzo[d][1,2] selenazol-3(2H)-one 201a. Yield 75% (256.2 mg), white solid; silica gel TLC Rf=0.37 (3:7 ethyl acetate-hexanes); mp 182-183° C.; $^1$H NMR (600 MHz, CDCl$_3$) δ 8.13 (d, J=7.7 Hz, 1H), 7.70-7.62 (m, 4H), 7.49 (ddd, J=2.3, 5.8, 7.9

Hz, 1H), 7.47-7.42 (m, 2H), 7.32-7.28 (m, J=1.0, 1.0 Hz, 1H); $^{13}$C NMR (150.2 MHz, MeoD) δ 166.6, 139.7, 139.0, 132.2, 129.0, 128.0, 127.9, 126.7, 126.1, 125.5, 124.8; HRMS (ESI-TOF) m/z: [M+Na]+ Calcd for $C_{13}H_{17}NO_3Na$ 297.9747; Found 297.9748.

Synthesis of 2-(4-Methoxybenzyl)benzo[d][1,2]selenazol-3(2H)-one (506a)

2-Iodo-N-(4-methoxybenzyl)benzamide (400 mg, 1.08 mmol), copper(I) iodide (207 mg, 1.08 mmol), 1,10-phenanthroline (196 mg, 1.08 mmol), cesium carbonate (888 mg, 2.72 mmol), potassium selenocyanate (188 mg, 1.30 mmol), and N,Ndimethylmethanamide (4.0 mL), 1 h, 100° C. Purified by flash column chromatography on silica gel (35% ethyl acetate-hexane) to obtain pure 2-(4-methoxybenzyl)benzo[d][1,2]selenazol-3(2H)-one (506a). Yield 63% (220.5 mg), white solid; silica gel TLC Rf=0.1 (3:7 ethyl acetate-hexanes); mp 139-141° C.; $^1$H NMR (600 MHz, CDCl$_3$) δ 8.08 (d, J=7.9 Hz, 1H), 7.59-7.54 (m, 9H), 7.43 (ddd, J=2.6, 5.6, 7.9 Hz, 1H), 7.33-7.30 (m, J=8.6 Hz, 8H), 6.92-6.89 (m, 2H), 4.96 (s, 2H), 3.82 (s, 3H); $^{13}$C NMR (150.2 MHz, CDCl$_3$) δ 167.1, 159.8, 139.3, 132.0, 130.3, 129.5, 129.0, 127.9, 126.3, 124.1, 114.3, 55.5, 48.4; HRMS (ESI-TOF) m/z: [M+Na]+ Calcd for $C_{15}H_{13}NO_2SeNa$ 342.0004; Found 342.0016.

2-(2-Methoxybenzyl)benzo[d][1,2]selenazol-3(2H)-one (506c)

2-Iodo-N-(2-methoxybenzyl)benzamide (370 mg, 1.01 mmol), copper(I) iodide (192 mg, 1.01 mmol), 1,10-phenanthroline (182 mg, 1.01 mmol), cesium carbonate (821 mg, 2.52 mmol), potassium selenocyanate (174 mg, 1.20 mmol), and N,N-dimethylmethanamide (4.0 mL), 1 h, 100° C. Purified by flash column chromatography on silica gel (25% ethyl acetate-hexane) to obtain pure product 2-(2-methoxybenzyl)benzo[d][1,2]selenazol-3(2H)-one (506c). Yield 44% (141 mg), white solid; silica gel TLC $R_f$=0.24 (3:7 ethyl acetate-hexanes); mp 169-170° C.; $^1$H NMR (600 MHz, CDCl$_3$) δ 8.08 (d, J=7.9 Hz, 5H), 7.58-7.56 (m, 10H), 7.44-7.40 (m, J=1.7 Hz, 11H), 7.34 (dt, J=1.7, 7.8 Hz, 6H), 6.99-6.91 (m, J=0.9, 7.4, 7.4 Hz, 11H), 5.07 (s, 2H), 3.93 (s, 3H); $^{13}$C NMR (150.2 MHz, CDCl$_3$) δ 167.3, 157.6, 138.6, 131.9, 131.0, 130.0, 128.9, 127.6, 126.1, 125.7, 123.9, 121.0, 110.6, 55.4, 43.6; HRMS (ESI-TOF) m/z: [M+Na]+ Calcd for $C_{15}H_{13}NO_2SeNa$ 342.0009; Found 342.0017.

Synthesis of 2-(4-Methoxyphenyl)benzo[d][1,2]selenazol-3(2H)-one (506b)

2-Iodo-N-(4-methoxyphenyl)benzamide (400 mg, 1.13 mmol), copper(I) iodide (216 mg, 1.13 mmol), 1,10-phenanthroline (204 mg, 1.33 mmol), cesium carbonate (922 mg, 2.83 mmol), potassium selenocyanate (196 mg, 1.30 mmol), and N,Ndimethylmethanamide (4.0 mL), 1 h, 100° C. Purified by flash column chromatography on silica gel (35% ethyl acetate-hexane) to obtain pure product 2-(4-methoxyphenyl)benzo[d][1,2]selenazol-3(2H)-one (506b). Yield 67% (231 mg), pale yellow solid; silica gel TLC Rf=0.25 (3:7 ethyl acetate-hexanes); mp 170-171° C.; 1H NMR (600 MHz, CDCl$_3$) δ 8.12 (td, J=0.9, 7.7 Hz, 1H), 7.65-7.68 (m, 2H), 7.46-7.53 (m, 3H), 6.94-6.98 (m, 2H), 3.85 (s, 3H); $^{13}$C NMR (150.2 MHz, CDCl$_3$) δ 166.1, 158.6, 137.9, 132.5, 131.7, 129.5, 127.6, 127.4, 126.6, 132.9, 114.7, 55.7; HRMS (ESI-TOF) m/z: [M+Na]+ Calcd for $C_{14}H_{11}NO_2SeNa$ 327.9847; Found 327.9858.

Synthesis of 2-Benzylbenzo[d][1,2]selenazol-3(2H)-one (506d)

N-Benzyl-2-iodobenzamide (276 mg, 0.88 mmol), copper (I) iodide (156 mg, 0.82 mmol), 1,10-phenanthroline (148 mg, 0.82 mmol), cesium carbonate (667 mg, 2.04 mmol), potassium selenocyanate (142 mg, 1.20 mmol), and N,N-dimethylmethanamide (4.0 mL), 1 h, 100° C. Purified by flash column chromatography on silica gel (25% ethyl acetate-hexane) to obtain pure product 2-benzylbenzo[d][1,2]selenazol-3(2H)-one (506d). Yield 39% (90 mg), white solid; silica gel TLC Rf=0.28 (3:7 ethyl acetate-hexanes); mp 130-132° C.; $^1$H NMR (600 MHz, CDCl$_3$) δ 8.10 (d, J=7.9 Hz, 1H), 7.56-7.60 (m, J=0.7 Hz, 2H), 7.44 (ddd, J=2.7, 5.4, 7.9 Hz, 1H), 7.33-7.39 (m, 5H), 5.03 (s, 2H); $^{13}$C NMR (150.2 MHz, CDCl$_3$) δ 167.2, 138.0, 137.2, 132.0, 129.0, 128.9, 128.6, 128.4, 127.4, 126.3, 124.0, 49.0; HRMS (ESI-TOF) m/z: [M+Na]+ Calcd for C14H11NOSeNa 311.9898; Found 311.9914.

Synthesis of 2-Allylbenzo[d][1,2]selenazol-3(2H)-one (506e)

2-Iodo-N-allylbenzamide (400 mg, 1.39 mmol), copper(I) iodide (267 mg, 1.39 mmol), 1,10-phenanthroline (251 mg, 1.39 mmol), cesium carbonate (1.135 g, 3.48 mmol), potassium selenocyanate (241 mg, 1.67 mmol), and N,N-dimethylmethanamide (4.0 mL), 1.5 h, 100° C. Purified by flash column chromatography on silica gel (25% ethyl acetate-hexane) to obtain pure product 2-allylbenzo[d][1,2]selenazol-3(2H)-one (506e). Yield 39% (90 mg), white solid; silica gel TLC Rf=0.28 (3:7 ethyl acetate-hexanes); mp 124-126° C.; $^1$H NMR (600 MHz, CDCl$_3$) δ 8.08 (qd, J=0.7, 7.9 Hz, 1H), 7.67-7.64 (m, 1H), 7.63-7.59 (m, 1H), 7.45 (ddd, J=1.0, 7.0, 7.9 Hz, 1H), 5.99 (tdd, J=6.3, 10.2, 16.9 Hz, 1H), 5.44-5.31 (m, 2H), 4.50 (td, J=1.3, 6.4 Hz, 2H); $^{13}$C NMR (150.2 MHz, CDCl$_3$) δ 167.1, 138.0, 133.7, 132.1, 129.0, 127.8, 126.3, 124.1, 119.5, 47.3; HRMS (ESI-TOF) m/z: [M+Na]+ Calcd for $C_{10}H_9NOSeNa$ 261.9742; Found 261.9755.

Synthesis of 2-(Cyclohexylmethyl)benzo[d][1,2]selenazol-3(2H)-one (506f)

N-(Cyclohexylmethyl)-2-iodobenzamide (200 mg, 0.58 mmol), copper(I) iodide (110 mg, 0.58 mmol), 1,10-phenanthroline (105 mg, 0.58 mmol), cesium carbonate (474.66 mg, 1.45 mmol), potassium selenocyanate (100 mg, 0.70 mmol), and N,Ndimethylmethanamide (4.0 mL), 1.5 h, 100° C. After flash column chromatography on silica gel using 20% ethyl acetate in hexanes as mobile phase, pure product 2-(cyclohexylmethyl)benzo[d][1,2]-selenazol-3(2H)-one (506f) was obtained. Yield 63% (110 mg), offwhite solid; silica gel TLC Rf=0.59 (1:1 ethyl acetate-hexanes); mp 151-152° C.; $^1$H NMR (600 MHz, CDCl3) δ 8.07 (d, J=7.9 Hz, 1H), 7.66-7.59 (m, 2H), 7.47-7.43 (m, 1H), 3.73 (d, J=7.0 Hz, 2H), 1.82-1.73 (m, 5H), 1.69 (d, J=9.0 Hz, 1H), 1.31-1.18 (m, 3H), 1.12-1.03 (m, 2H); $^{13}$C NMR (150.2 MHz, CDCl$_3$) δ 167.4, 137.8, 131.9, 128.9, 127.5, 126.2, 123.9, 59.5, 50.9, 39.1, 31.3, 30.6, 26.3, 25.7; HRMS (ESI-TOF) m/z: [M+Na]+ Calcd for $C_{14}H_{17}NOSeNa$ 318.0368; Found 318.0381.

Synthesis of 2-(4-Fluorophenyl)benzo[d][1,2]selenazol-3(2H)-one (506g)

N-(4-Fluorophenyl)-2-iodobenzamide (400 mg, 1.17 mmol), copper(I) iodide (335 mg, 1.76 mmol), 1,10-phenanthroline (317 mg, 1.79 mmol), cesium carbonate (995.56 mg, 2.93 mmol), potassium selenocyanate (203 mg, 1.40 mmol), and N,Ndimethylmethanamide (4.0 mL), 1 h, 100° C. After flash column chromatography on silica gel using 20% ethyl acetate in hexanes as mobile phase, pure product 2-(4-fluorophenyl)benzo [d][1,2]-selenazol-3(2H)-one (506g) was obtained. Yield 52% (180 mg), white solid; silica gel TLC Rf=0.15 (3:7 ethyl acetate-hexanes); mp 176-177° C.; 1H NMR (600 MHz, CDCl$_3$) δ 8.13 (d, J=7.9 Hz, 1H), 7.68 (d, J=3.7 Hz, 2H), 7.56-7.61 (m, 2H), 7.46-7.52 (m, 1H), 7.11-7.18 (m, J=8.6 Hz, 1H); 13C NMR (151 MHz, CDCl$_3$) δ 165.8, 160.94 (d, J=247.6 Hz), 137.47, 134.77 (d, J=3.30 Hz), 132.6, 129.4, 127.49 (d, J=7.7 Hz), 127.0, 126.6, 123.7, 116.2 (d, J=22.0 Hz); HRMS (ESI-TOF) m/z: [M+Na]+ Calcd for C$_{13}$H$_8$FNOSeNa 315.9647; Found 315.9657.

Synthesis of 2-(2-Fluorophenyl)benzo[d][1,2]selenazol-3(2H)-one (506h)

N-(2-Fluorophenyl)-2-iodobenzamide (400 mg, 1.17 mmol), copper(I) iodide (335 mg, 1.76 mmol), 1,10-phenanthroline (317 mg, 1.79 mmol), cesium carbonate (995.56 mg, 2.93 mmol), potassium selenocyanate (203 mg, 1.40 mmol), and N,Ndimethylmethanamide (4.0 mL), 1 h, 100° C. After flash column chromatography on silica gel using 20% ethyl acetate in hexanes as mobile phase, pure product 2-(2-fluorophenyl)benzo [d][1,2]-selenazol-3(2H)-one (506h) was obtained. Yield 35% (120 mg), offwhite solid; silica gel TLC Rf=0.24 (3:7 ethyl acetate-hexanes); mp 156-158° C.; $^1$H NMR (600 MHz, CDCl$_3$) δ 8.04-7.97 (m, J=7.3 Hz, 2H), 7.82-7.73 (m, 2H), 7.54-7.49 (m, J=1.7 Hz, 1H), 7.43-7.39 (m, J=1.7 Hz, 1H), 7.38-7.31 (m, J=1.2, 7.6 Hz, 2H); 13C NMR (151 MHz, CDCl$_3$) δ 117.18 (d, J=19.8 Hz), 122.1, 123.9, 125.11 (d, J=3.3 Hz), 130.7, 130.9, 131.13 (d, J=6.6 Hz), 132.7, 133.7, 158.44 (dd, J=250.8, 1.0 Hz), 166.4; HRMS (ESI-TOF) m/z: [M+Na]+ Calcd for C$_{13}$H$_8$FNOSeNa 315.9647; Found 315.9657.

Synthesis of 2-(4-Azidophenyl)benzo[d][1,2]selenazol-3(2H)-one (506i)

N-(4-Azidophenyl)-2-iodobenzamide (500 mg, 1.37 mmol), copper(I) iodide (262 mg, 1.37 mmol), 1,10-phenanthroline (247 mg, 1.37 mmol), cesium carbonate (1118 mg, 3.43 mmol), potassium selenocyanate (237 mg, 1.40 mmol), and N,N-dimethylmethanamide (5.0 mL), 1 h, 90° C. After flash column chromatography on silica gel using 20% ethyl acetate in hexanes as mobile phase, pure product 2-(4-azidophenyl)benzo[d][1,2]selenazol-3(2H)-one (506i) was obtained. Yield 20% (90 mg), brown solid; silica gel TLC Rf=0.24 (3:7 ethyl acetate-hexanes); mp 169-170° C.; $^1$H NMR (600 MHz, CDCl$_3$) δ 8.14 (td, J=0.9, 7.9 Hz, 1H), 7.71-7.67 (m, 2H), 7.66-7.63 (m, J=8.8 Hz, 2H), 7.51 (ddd, J=3.7, 4.5, 7.9 Hz, 1H), 7.14-7.09 (m, J=8.8 Hz, 2H); $^{13}$C NMR (150.2 MHz, CDCl$_3$) δ 165.8, 138.4, 137.4, 135.9, 132.7, 129.5, 127.2, 127.0, 126.7, 123.8, 119.8; HRMS (ESI-TOF) m/z: [M+Na]+ Calcd for C$_{13}$H$_8$N$_4$OSeNa 338.9756; Found 338.9763.

Synthesis of 2-(tert-Butyl)benzo[d][1,2]selenazol-3(2H)-one (506k)

N-(tert-Butyl)-2-iodobenzamide (200.0 mg, 0.66 mmol), copper(I) iodide (126 mg, 0.66 mmol), 1,10-phenanthroline (119 mg, 0.66 mmol), cesium carbonate (538 mg, 1.65 mmol), potassium selenocyanate (114 mg, 0.79 mmol), and N,N-dimethylmethanamide (2.0 mL), 1 h, 90° C. After flash column chromatography on silica gel using 20% ethyl acetate in hexanes as mobile phase, pure product 2-(tert-butyl)benzo[d][1,2]selenazol-3(2H)-one (506k) was obtained. Yield 75% (125 mg), white solid; silica gel TLC Rf=0.43 (3:7 ethyl acetate-hexanes); mp 137-139° C.; $^1$H NMR (600 MHz, CDCl$_3$) δ 7.97 (td, J=1.1, 7.8 Hz, 1H), 7.56-7.60 (m, 2H), 7.40 (ddd, J=1.7, 6.3, 8.0 Hz, 1H), 1.69 (s, 9H); $^{13}$C NMR (151 MHz, CDCl$_3$) δ 167.1, 137.0, 131.7, 130.2, 128.5, 126.1, 123.3, 59.0, 29.2; HRMS (ESI-TOF) m/z: [M+H]+ Calcd for C$_{11}$H$_{14}$NOSe 256.0235; Found 256.0233.

Synthesis of 2-((3R,5S)-Adamantan-1-yl)benzo[d][1,2]-selenazol-3(2H)-one (506j)

N-((3R,5S)-Adamantan-1-yl)-2-iodobenzamide (400.0 mg, 1.04 mmol), copper(I) iodide (200 mg, 1.04 mmol), 1,10-phenanthroline (189 mg, 1.04 mmol), cesium carbonate (855 mg, 2.62 mmol), potassium selenocyanate (182 mg, 1.26 mmol), and N,N-dimethylmethanamide (4.0 mL), 1 h, 90° C. After flash column chromatography on silica gel using 20% ethyl acetate in hexanes as mobile phase, pure product 2-((3R,5S)-adamantan-1-yl)benzo[d][1,2]selenazol-3(2H)-one (506j) was obtained. Yield 72% (250 mg), white solid; silica gel TLC Rf=0.51 (3:7 ethyl acetate-hexanes); mp 215-217° C.; $^1$H NMR (600 MHz, CDCl$_3$) δ 7.97 (d, J=7.9 Hz, 1H), 7.59-7.58 (m, 1H), 7.57-7.54 (m, 1H), 7.41-7.38 (m, 1H), 2.43 (d, J=2.4 Hz, 6H), 2.19 (s, 3H), 1.81-1.79 (m, 3H), 1.75-1.73 (m, 3H); $^{13}$C NMR (150.2 MHz, CDCl$_3$) δ 166.8, 137.5, 131.5, 130.5, 128.5, 126.0, 123.4, 60.1, 41.7, 36.4, 30.3; HRMS (ESI-TOF) m/z: [M+H]+ Calcd for C$_{17}$H$_{20}$NOSe 334.0705; Found 334.0722.

Synthesis of 2-Cyclopentylbenzo[d][1,2]selenazol-3(2H)-one (506l)

N-Cyclopentyl-2-iodobenzamide (350.0 mg, 1.11 mmol), copper(I) iodide (211.6 mg, 1.11 mmol), 1,10-phenanthroline (200.2 mg, 1.11 mmol), cesium carbonate (905 mg, 2.77 mmol), potassium selenocyanate (192.1 mg, 1.33 mmol), and N,N-dimethylmethanamide (3.0 mL), 1 h, 90° C. After flash column chromatography on silica gel using 20% ethyl acetate in hexanes as mobile phase, pure product 2-cyclopentylbenzo[d][1,2]selenazol-3(2H)-one (506l) was obtained. Yield 78% (232 mg), white solid; silica gel TLC Rf=0.23 (3:7 ethyl acetate-hexanes); mp 119-120° C.; $^1$H NMR (600 MHz, CDCl$_3$) δ 8.03-8.05 (m, 1H), 7.62-7.64 (m, 1H), 7.57 (dt, J=1.4, 7.6 Hz, 1H), 7.42 (ddd, J=1.0, 7.1, 7.9 Hz, 1H), 4.98 (quin, J=7.8 Hz, 1H), 2.17-2.27 (m, J=1.6, 2.8 Hz, 2H), 1.81-1.90 (m, 1H), 1.69-1.75 (m, 2H), 1.61-1.68 (m, 2H); $^{13}$C NMR (151 MHz, CDCl$_3$) δ 167.2, 137.5, 133.2, 131.7, 128.6, 126.2, 123.8, 55.9, 33.5, 24.2; HRMS (ESI-TOF) m/z: [M+Na]+ Calcd for C$_{12}$H$_{13}$NOSeNa 290.0055; Found 290.0058.

Synthesis of 2-Cyclohexylbenzo[d][1,2]selenazol-3(2H)-one (506m)

N-Cyclohexyl-2-iodobenzamide (400.0 mg, 1.21 mmol), copper(I) iodide (231.6 mg, 1.22 mmol), 1,10-phenanthroline (219.1 mg, 1.21 mmol), cesium carbonate (990.3 mmol), potassium selenocyanate (210.2 mg, 1.45 mmol), and N,N-dimethylmethanamide (4.0 mL), 1 h, 90°

C. After flash column chromatography on silica gel using 20% ethyl acetate in hexanes as mobile phase, pure product 2-cyclohexylbenzo[d][1,2]selenazol-3(2H)-one (506m) was obtained. Yield 85% (290 mg), white solid; silica gel TLC Rf=0.27 (3:7 ethyl acetate-hexanes); mp 157-158° C.; $^1$H NMR (600 MHz, CDCl$_3$) δ 8.10-7.99 (m, 1H), 7.64 (d, J=7.9 Hz, 1H), 7.57 (s, 1H), 7.42 (s, 1H), 4.53-4.45 (m, 1H), 2.11 (dd, J=2.0, 12.7 Hz, 2H), 1.87 (d, J=13.9 Hz, 2H), 1.77-1.70 (m, 1H), 1.50 (d, J=13.0 Hz, 2H), 1.40 (dd, J=3.7, 11.7 Hz, 2H), 1.25-1.16 (m, 1H); $^{13}$C NMR (151 MHz, CDCl$_3$) δ 166.6, 137.9, 137.9, 131.7, 128.8, 126.2, 124.0, 53.8, 34.4, 25.6. HRMS (ESI-TOF) m/z: [M+H]+ Calcd for C$_{13}$H$_{16}$NOSe 282.0392; Found 282.0392.

Synthesis of N-(4-Azidophenyl)-2-((phenylethynyl) selanyl)-benzamide (208)

2-(4-Azidophenyl)benzo[d][1,2]selenazol-3(2H)-one (100.0 mg, 0.32 mmol), copper(I) iodide (60.27 mg, 0.32 mmol), 1,10-phenanthroline (57.0 mg, 0.32 mmol), cesium carbonate(257.8 mg, 0.79 mmol), potassium selenocyanate (54.7 mg, 0.38 mmol), and N,N-dimethylmethanamide (1.5 mL), 1 h, 90° C. After flash column chromatography on silica gel using 35% ethyl acetate in hexanes as mobile phase, pure product N-(4-azidophenyl)-2-((phenylethynyl) selanyl)benzamide (8) was obtained. Yield 71% (93.7 mg), brown solid; silica gel TLC Rf=0.26 (3:7 ethyl acetate-hexanes); $^1$H NMR (600 MHz, CDCl$_3$) 8.33 (dd, J=0.9, 8.1 Hz, 1H), 7.91 (s, 1H), 7.73 (dd, J=1.3, 7.70 Hz, 1H), 7.62-7.67 (m, 2H), 7.55-7.59 (m, 3H), 7.37-7.42 (m, 4H), 7.05-7.10 (m, 2H); $^{13}$C NMR (151 MHz, CDCl$_3$) δ 165.7, 136.8, 135.5, 134.3, 132.8, 132.0, 131.0, 130.7, 128.7, 128.5, 126.7, 126.4, 123.4, 122.3, 119.8, 104.5, 73.8; HRMS (ESI-MS) m/z: [M+Na]+ Calcd for C$_{21}$H$_{14}$N$_4$OSeNa 441.02; Found 441.02.

Synthesis of N-(13,16-Dioxo-16-(3-(4-(3-oxobenzo [d][1,2]-selenazol-2(3H)-yl)phenyl)-3,9-dihydro-8H-dibenzo[b,f][2,3]-triazolo[4,5-d]azocin-8-yl)-3,6,9-trioxa-12-azahexadecyl)-5-((3aS,6aR)-2-oxohexahydro-1H-thieno[3,4-d]imidazol-4-yl)-pentanamide (210)

In a dried round-bottom flask, 2-(4-azidophenyl) benzo[d][1,2]selenazol-3(2H)-one (10.0 mg, 0.032 mmol) was dissolved in dry THF (0.5 mL) under a N$_2$ atmosphere and stirred for 5.0 min. Then, the solution of dibenzocyclooctyne-PEG3-biotin (209, 22.32 mg, 0.032 mmol) was added and the reaction mixture was stirred at room temperature for 12.0 h. After reverse phase column chromatography using H2O as mobile phase, pure product compound 210 was obtained. Yield 79% (25.6 mg), ash color solid. Note: $^1$H NMR integration values were not clear due to the complexity of the molecule, but C13 and HRMS were clear. $^1$H NMR (600 MHz, CDCl$_3$) δ 8.08-8.15 (m, 1H), 7.74-7.87 (m, 4H), 7.61-7.72 (m, 2H), 7.42-7.59 (m, 6H), 7.30-7.39 (m, 2H), 7.02-7.07 (m, 1H), 6.92-7.01 (m, 1H), 6.75 (s, 1H), 6.20-6.28 (m, 1H), 5.66-5.79 (m, 1H), 4.97-5.08 (m, 1H), 4.45-4.52 (m, 2H), 4.29-4.38 (m, 1H), 3.61 (br. s., 4H), 3.53-3.59 (m, 6H), 3.46-3.52 (m, 4H), 3.35-3.42 (m, 2H), 3.23-3.32 (m, 2H), 3.06-3.18 (m, 2H), 2.85-2.96 (m, 1H), 2.65-2.75 (m, 1H), 2.33-2.46 (m, 2H), 2.13-2.25 (m, 2H), 2.02 (s, 1H), 1.37-1.50 (m, 2H); $^{13}$C NMR (151 MHz, CDCl$_3$) δ 173.0, 172.1, 172.0, 165.9, 163.1, 144.1, 143.2, 140.6, 140.3, 133.7, 132.9, 131.6, 131.2, 129.8, 129.3, 129.1, 128.7, 127.9, 127.8, 127.6, 127.5, 127.2, 126.7, 125.8, 125.5, 125.2, 124.9, 124.7, 124.2, 124.0, 70.3, 61.7, 59.9, 55.2, 52.2, 40.6, 39.3, 39.2, 39.2, 39.1, 35.6, 35.0, 30.7, 29.6, 27.9, 27.2, 25.4. HRMS (ESITOF) m/z: [M+Na]+ Calcd for C$_{50}$H$_{55}$N$_9$O$_8$SSeNa 1044.2952; Found 1044.2976.

General Procedure for Photoinduced Synthesis of Benzo-1,2-selenazol-3(2H)-ones A borosilicate tube under an atmosphere of nitrogen was charged with aryl halide (1.0 equiv), CuI (1.0 equiv), KSeCN (2.5 equiv), Cs$_2$CO$_3$ (1.2 equiv), and acetonitrile (3.0 mL). The tube was sealed with a rubber septum, and the heterogeneous reaction mixture was cooled to 0° C. with vigorous stirring. The cooled tube was irradiated by the 22 W Hg lamps for 12-24 h. After the reaction was complete, it was filtered through Celite, and washed with ethyl acetate. The filtrate was concentrated under reduced pressure, and the crude product was purified by flash column chromatography on silica gel, 30% ethyl acetate in hexanes.

Photoinduced Synthesis of 2-Phenylbenzo[d][1,2] selenazol-3(2H)-one (201a)

Using 2-iodo-N-phenylbenzamide (100 mg, 0.31 mmol), copper(I) iodide (59.0 mg, 0.31 mmol), cesium carbonate (121 mg, 0.37 mmol), potassium selenocyanate (112 mg, 0.78 mmol), and acetonitrile (3.0 mL), 16 h, 0° C. to room temperature. Purified by flash column chromatography on silica gel (35% ethyl acetate-hexane) to obtain pure 2-phenylbenzo[d][1,2]selenazol-3(2H)-one (201a). Yield 92% (78.3 mg); silica gel TLC Rf=0.37 (3:7 ethyl acetate-hexanes). Using 2-bromo-N-henylbenzamide (4b, 100 mg, 0.36 mmol), copper(I) iodide (69.2 mg, 0.36 mmol), cesium carbonate (142 mg, 0.44 mmol), potassium selenocyanate (131 mg, 0.91 mmol), and acetonitrile (3.0 mL), 16 h, 0° C. to room temperature. Purified by flash column chromatography on silica gel (35% ethyl acetate-hexane) to obtain pure 2-phenylbenzo[d][1,2]-selenazol-3(2H)-one (201a). Yield 87% (87.2 mg); silica gel TLC Rf=0.37 (3:7 ethyl acetate-hexanes). Using 2-chloro-N-phenylbenzamide (4a, 100 mg, 0.31 mmol), copper(I) iodide (59.0 mg, 0.31 mmol), cesium carbonate (121 mg, 0.37 mmol), potassium selenocyanate (112 mg, 0.78 mmol), and acetonitrile (3.0 mL), 16 h, 0° C. to room temperature. Purified by flash column chromatography on silica gel (35% ethyl acetate-hexane) to obtain pure 2-phenylbenzo[d][1,2]-selenazol-3(2H)-one (201a). Yield <5; silica gel TLC Rf=0.37 (3:7 ethyl acetate-hexanes).

Photoinduced Synthesis of 2-Isobutylbenzo[d][1,2]-selenazol-3(2H)-one (506n)

2-Iodo-N-isobutylbenzamide (200 mg, 0.66 mmol), copper(I) iodide (126 mg, 0.66 mmol), cesium carbonate (258 mg, 0.79 mmol), potassium selenocyanate (237 mg, 1.65 mmol), and acetonitrile (3.0 mL), 32 h, 0° C. to room temperature. Purified by flash column chromatography on silica gel (30% ethyl acetate-hexane) to obtain pure 2-isobutylbenzo[d][1,2]selenazol-3(2H)-one (506n). Yield 85% (143.8 mg), white solid; silica gel TLC Rf=0.39 (3:7 ethyl acetate-hexanes); mp 114-116° C.; $^1$H NMR (600 MHz, CDCl$_3$) δ 8.06 (d, J=7.6 Hz, 1H), 7.62-7.66 (m, 1H), 7.57-7.62 (m, 1H), 7.43 (t, J=7.3 Hz, 1H), 3.70 (d, J=7.3 Hz, 2H), 2.05 (quind, J=6.8, 13.7 Hz, 1H), 1.00 (d, J=6.6 Hz, 6H); $^{13}$C NMR (151 MHz, CDCl$_3$) δ 167.5, 137.9, 132.0, 129.0, 127.6, 126.3, 124.0, 52.2, 30.1, 20.1; HRMS (ESI-MS) m/z: [M+Na]+ Calcd for C$_{11}$H$_{14}$NOSe 256.0235; Found 256.0240.

Synthesis of Thermal Activated Copper Complex [(phen)2-CuI]+ [CuI(SeCN)2]− (A and B)

A 50.0 mL round-bottom flask (RBF) was charged with CuI (50 mg, 0.26 mmol), phen (47.3 mg, 0.26 mmol), KSeCN (95 mg, 0.65 mmol), $Cs_2CO_3$ (102.64 mg, 0.31 mmol), and acetonitrile (2.0 mL) under an atmosphere of $N_2$. The resulting red colored reaction mixture was heated to 80° C. for 1.0 h, and then it was filtered through a plug of Celite to obtain copper complex A and B.

Synthesis of Copper Complex [CuI(SeCN)2]− (B)

A borosilicatetube was charged with CuI (50 mg, 0.26 mmol), KseCN (95 mg, 0.65 mmol), $Cs_2CO_3$ (102.64 mg, 0.31 mmol), and acetonitrile (2.0 mL) under an atmosphere of $N_2$. The tube was sealed with a rubber septum, and the heterogeneous mixture was cooled to 0° C. The cooled tube with reaction mixture was irradiated with a 22 W Hg lamp for 1 h, and then it was filtered through a short plug of Celite to obtain copper complex B.

Steady-State Fluorimetry Experiment on Copper Complex B

A 26 μM solution of complex B in acetonitrile was excited using a Xe arc lamp (500 W) at 242 nm, and the right angle emission was detected at 338 nm (FIG. 32).

Absorption Spectrum of Complex B, Mixture of B and 204b, and Compound 204b

Copper complex [CuI(SeCN)2]− (B) at 5.25 μM, complex B (5.25 μM) plus 4b (0.91 μM), and compound 4b (0.91 μM, alone) were prepared. The absorption spectra were then recorded (FIG. 33).

Figure 34:
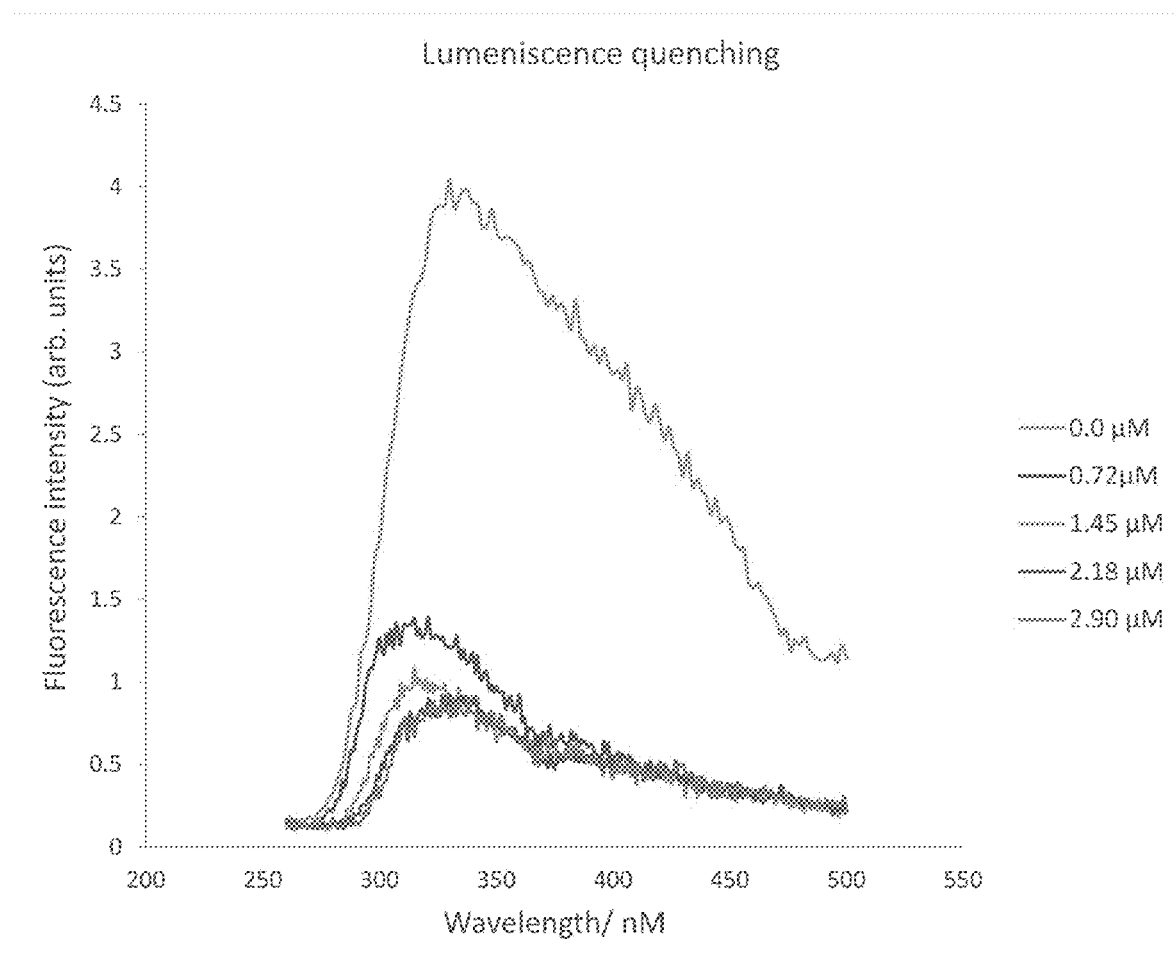
FIG. 34: Effect of aryl halide (204b) on emission spectra of copper complex B (5.25 μM) in acetonitrile. Excitation wavelength: 242.

Luminescence Quenching of Complex B. 2.0 mL of 5.25 μM copper complex [CuI(SeCN)2]− (B) in acetonitrile was transferred into a standard quartz cuvette. The cuvette was placed in an Aminco Bowman II Spectrofluorometer, and complex B was excited at a wavelength of 242 nm. The emission spectrum was recorded, revealing an emission at 338 nm. Compound 204b was added to the cuvette at concentrations of 0.72, 1.45, 2.18, and 2.90 μM, and the change in intensity of the emission spectra was recorded (FIG. 34).

Procedure to Determine Percent Mtb A85C Active after 40 Min of Incubation with Inhibitors Ag85C was expressed and purified as previously described. The enzyme was reacted with 5 μM of 1,2-benzisoselenazol-3(2H)-one 1a-1n, 8, and 10 (10 mM DMSO stock) for 40 min at room temperature. The enzymatic activity of Ag85C, covalently modified with these analogues, was evaluated using a fluorometric assay previously described (FIG. 37). Briefly, resorufin butyrate was used as an acyl donor while trehalose was utilized as the acyl acceptor. All reactions were performed in 50 mM sodium phosphate (pH 7.5). Trehalose was dissolved in the reaction buffer to produce a 500 mM stock, while a 10 mM stock solution of resorufin butyrate was prepared using DMSO. The reactions were performed in triplicate at 37° C. on a Synergy H4 Hybrid Reader (BioTek) using 500 nM Ag85C, 4 mM trehalose, and 100 μM resorufin butyrate. Reactions were initiated through the addition of resorufin butyrate. Analysis of the data was carried out using Prism 5 software (FIG. 37).

Procedure to Determine Apparent $IC_{50}$ of 1,2-Benzisoselenazol-3(2H)-ones Against Mtb Ag85C An apparent $IC_{50}$ value for each 1,2-benzisoselenazol-3 (2H)-one was obtained for Mtb Ag85C by varying the concentration of inhibitor, ranging from 40.0 μM to 312.0 nM (FIGS. 38A-38B). Compounds were incubated with Ag85C for 15 min at room temperature. Enzymatic activity was assessed using the resourifin butyrate assay previously described. The apparent $IC_{50}$ was calculated using the following equation: $IC_{50}=[(50-A)(B-A)]\times(D-C)+C$, where points were expressed in percent inhibition: (i) A=the point on the curve that is less than 50%, (ii) B=the point on the curve that is greater than or equal to 50%, (iii) C=the concentration of inhibitor that gives the A % inhibition, and (iv) D=the concentration of inhibitor that gives the B % inhibition (FIGS. 38A-38B).

In Vitro Mtb Alamar Blue Assay (MABA)

Mtb H37Rv is a drug sensitive laboratory reference strain used in the MIC studies. The bacteria were grown at 37° C. in Difco 7H9 Middlebrook liquid media(BD Biosciences, 271310) supplemented with 10% Middlebrook OADC Enrichment, 0.05% Tween (G-Biosciences, 786-519) and 0.2% Glycerol. A modified 96-well microplate Alamar Blue assay (MABA) was used to establish MIC values. Briefly, compounds were solubilized in DMSO and were 2-fold serially diluted in 7H9 media (DMSO< or equal to 0.02% DMSO). Bacteria were grown to mid-log growth, diluted, and added to the wells with compounds. Cell and media controls were included in each plate. The plates were incubated at 37° C. for 6 days when Alamar blue was added to each well, and then the plate was incubated overnight (Alamar blue final concentration 0.001%). On day seven, the last well that showed no sign of growth and remained blue was considered the MIC for that compound.

NMR Spectra

FIGS. 39-55 show $^{1}H$ NMR and $^{13}C$ NMR spectra for compounds 201a, 506a-506n prepared as described in this Example.

Certain embodiments of the compounds, compositions, and methods disclosed herein are defined in the above examples. It should be understood that these examples, while indicating particular embodiments of the invention, are given by way of illustration only. From the above discussion and these examples, one skilled in the art can ascertain the essential characteristics of this disclosure, and without departing from the spirit and scope thereof, can make various changes and modifications to adapt the compositions and methods described herein to various usages and conditions. Various changes may be made and equivalents may be substituted for elements thereof without departing from the essential scope of the disclosure. In addition, many modifications may be made to adapt a particular situation or material to the teachings of the disclosure without departing from the essential scope thereof.

What is claimed is:

1. A compound of Formula III:

Formula III 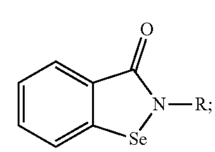 wherein R is a $C_1$-$C_8$ alkenyl, quinoline; furan; thiophene; tetrahydropyran; or, a Y-substituted Ph group;

wherein Y is $N_3$, 1,2,3-triazole, $C_1$-$C_8$ acyloxy, amino, $C_1$-$C_8$ alkoxy Ph, vinyl, $CO_2H$, or $CO_2R_6$; and, wherein $R_6$ is furan, thiophene, Ph, or a $C_1$-$C_8$ alkyl optionally substituted with one or more of the following: F, Cl, hydroxy, $C_1$-$C_8$ alkoxy, $C_1$-$C_8$ acyloxy, amino, $C_1$-$C_8$ alkylamino, $C_1$-$C_8$ dialkylamino, O—$CH_2$-Ph, Ph, or vinyl.

2. The compound of claim 1, having a structure of 506a, 506c, 506i-506j, or 506q-506u:

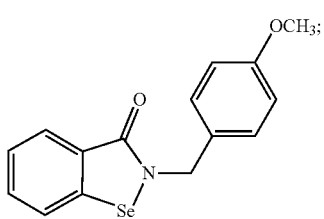
(506a)

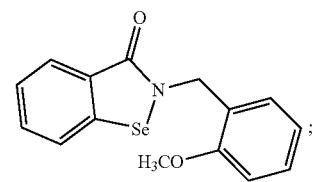
(506c)

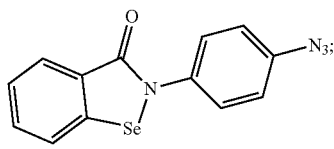
(506i)

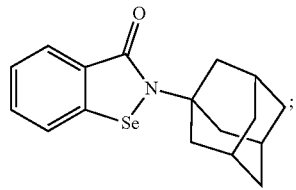
(506j)

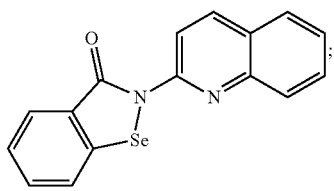
(506q)

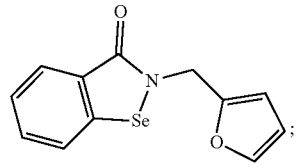
(506r)

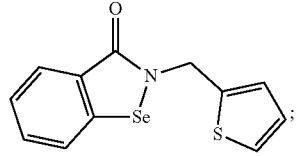
(506s)

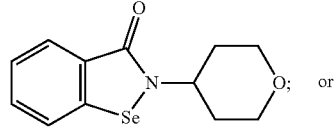
(506t)

or

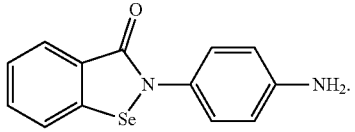
(506u)

* * * * *